US010192025B2

(12) United States Patent
Dormitzer et al.

(10) Patent No.: US 10,192,025 B2
(45) Date of Patent: Jan. 29, 2019

(54) ROTAVIRUS PARTICLES WITH CHIMERIC SURFACE PROTEINS

(71) Applicants: Novartis AG, Basel (CH); Children's Medical Center Corporation, Boston, MA (US); Brandeis University, Waltham, MA (US)

(72) Inventors: Philip R. Dormitzer, Cambridge, MA (US); Nikolaus Grigorieff, Leesburg, VA (US); Stephen Harrison, Boston, MA (US); Junhua Pan, Brookline, MA (US); Ethan Settembre, Cambridge, MA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/900,829

(22) PCT Filed: Jul. 8, 2014

(86) PCT No.: PCT/EP2014/064652
§ 371 (c)(1),
(2) Date: Dec. 22, 2015

(87) PCT Pub. No.: WO2015/004158
PCT Pub. Date: Jan. 15, 2015

(65) Prior Publication Data
US 2016/0188790 A1  Jun. 30, 2016

(30) Foreign Application Priority Data
Jul. 8, 2013 (EP) .................................... 13175637

(51) Int. Cl.
| | |
|---|---|
| *G06F 19/16* | (2011.01) |
| *C07K 14/14* | (2006.01) |
| *C07K 14/005* | (2006.01) |
| *C12N 7/00* | (2006.01) |
| *C12Q 1/02* | (2006.01) |
| *G06F 19/12* | (2011.01) |

(52) U.S. Cl.
CPC ............ *G06F 19/16* (2013.01); *C07K 14/005* (2013.01); *C07K 14/14* (2013.01); *C12N 7/00* (2013.01); *C12Q 1/02* (2013.01); *G06F 19/12* (2013.01); *C07K 2319/42* (2013.01); *C07K 2319/50* (2013.01); *C07K 2319/70* (2013.01); *C07K 2319/73* (2013.01); *C07K 2319/735* (2013.01); *C12N 2720/12321* (2013.01); *C12N 2720/12323* (2013.01); *C12N 2720/12351* (2013.01)

(58) Field of Classification Search
CPC ............ A61K 2039/523; A61K 39/385; A61K 2039/5258; C07K 14/005; C07K 2319/00; C07K 14/14; C07K 2319/73; C07K 2319/735; C12N 15/62; C12N 2720/12323; C12N 2770/32122; G06F 19/16
See application file for complete search history.

(56) References Cited

U.S. PATENT DOCUMENTS

| | | | |
|---|---|---|---|
| 8,685,411 B2 * | 4/2014 | Dormitzer ............ | C07K 14/005 424/186.1 |
| 2008/0293039 A1 | 11/2008 | Paik et al. | |

FOREIGN PATENT DOCUMENTS

| | | |
|---|---|---|
| CN | 102465137 A | 5/2012 |
| EP | 0235754 A2 | 9/1987 |
| WO | 1989001514 A1 | 2/1989 |
| WO | 2007030803 A2 | 3/2007 |

OTHER PUBLICATIONS

Tan et al. J. Virol. Jan. 2011 vol. 29 (44), 7670-7677.*
Shane et al. Journal of Virology, 2006, vol. 80, (22), pp. 11293-11304.*
Peralta et al. Virology Journal. 2009 vol. vol. 6m, Issue 1, pp. 1-9.*
Reddy et al. Virology 1992, vol. 189, pp. 423-434.*
International Search Report dated Oct. 17, 2014 from corresponding PCT Application No. PCT/EP2014/064652.
Huang et al, "Spike Protein VP8 of Human Rotavirus Recognizes Histo-Blood Group Antigens in a Type-Specific Manner," Journal of Virology, 86:4833-4843 (2012).
Aoki et al., "Cross-Linking of Rotavirus Outer Capsid Protein VP7 by Antibodies or Disulfides Inhibits Viral Entry," Journal of Virology, 85:10509-10517 (2011).
Trask et al., "A Rotavirus Spike Protein Conformational Intermediate Binds Lipid Bilayers," Journal of Virology, 84:1764-1770 (2010).
Kim et al., "Effect of Mutations in VP5 Hydrophobic Loops on Rotavirus Cell Entry," Journal of Virology, 84:6200-6207 (2010).
Trask et al., "Assembly of Highly Infectious Rotavirus Particles Recoated with Recombinat Outer Capsid Proteins," Journal of Virology, 80:11293-11304 (2006).
Ludert et al., "Antiboides to Rotavirus Outer Capsid Glycoprotein VP7 Neutralize Infectivity by Inhibiting Virion Decapsidation," Journal of Virology, 76:6643-6651 (2002).
Chan et al., "Core Structure of GP41 from the HIV Envelope Glycoprotein," Cell, 89:263-273 (1997).
Extended European Search Report received in European Application No. 13175637.1, dated Dec. 11, 2013; 12 pages.

(Continued)

*Primary Examiner* — Bao Q Li
(74) *Attorney, Agent, or Firm* — McDermott Will & Emery LLP

(57) ABSTRACT

The present invention relates to the use of rotavirus particles for displaying a heterologous protein, alone or in complex with another molecule. The invention further relates to methods that employ these modified rotavirus particles to rapidly determine the structure of the heterologous protein or the complex using cryo-electron microscopy (cryo-EM). The invention also relates to a method of immunizing a patient, wherein said method comprises administering to the patient the modified rotavirus particles of the invention.

14 Claims, 8 Drawing Sheets
Specification includes a Sequence Listing.

(56) References Cited

OTHER PUBLICATIONS

Choi et al., Synthesis of a ricin toxin B subunit-rotavirus VP7 fusion protein in potato. Mol Biotechnol. Feb. 2006;32(2):117-28.
Fuentes-Panana et al., Mapping the hemagglutination domain of rotaviruses. J Virol. Apr. 1995;69(4):2629-32.
Gonzalez et al., Immunological characterization of a rotavirus-neutralizing epitope fused to the cholera toxin B subunit. Gene. Nov. 15, 1993;133(2):227-32 (Abstract Only).
Ye et al., Antigenic properties of a transport-competent influenza HA/HIV Env chimeric protein. Virology. Aug. 15, 2006;352(1):74-85.
Ye et al., Induction of HIV neutralizing antibodies against the MPER of the HIV envelope protein by HA/gp41 chimeric protein-based DNA and VLP vaccines. PLoS One. 2011;6(5):e14813.
Arnold et al., Culturing, storage, and quantification of rotaviruses. Curr Protoc Microbiol. Nov. 2009:Chapter 15:Unit 15C.3.
Greenberg et al., Rescue of noncultivatable human rotavirus by gene reassortment during mixed infection with ts mutants of a cultivatable bovine rotavirus. Proc Natl Acad Sci U S A. Jan. 1981;78(1):420-4.
Kim et al., Production of hybrid double- or triple-layered virus-like particles of group A and C rotaviruses using a baculovirus expression system. Virology. Oct. 10, 2002;302(1):1-8.
First Office Action dated Sep. 27, 2018 in Chinese Patent Application No. 201480049500.2, and English translation thereof (13 pages).
Office Action dated Jul. 24, 2018 in Russian Patent Application No. 2016103770, and English translation thereof (12 pages).

\* cited by examiner

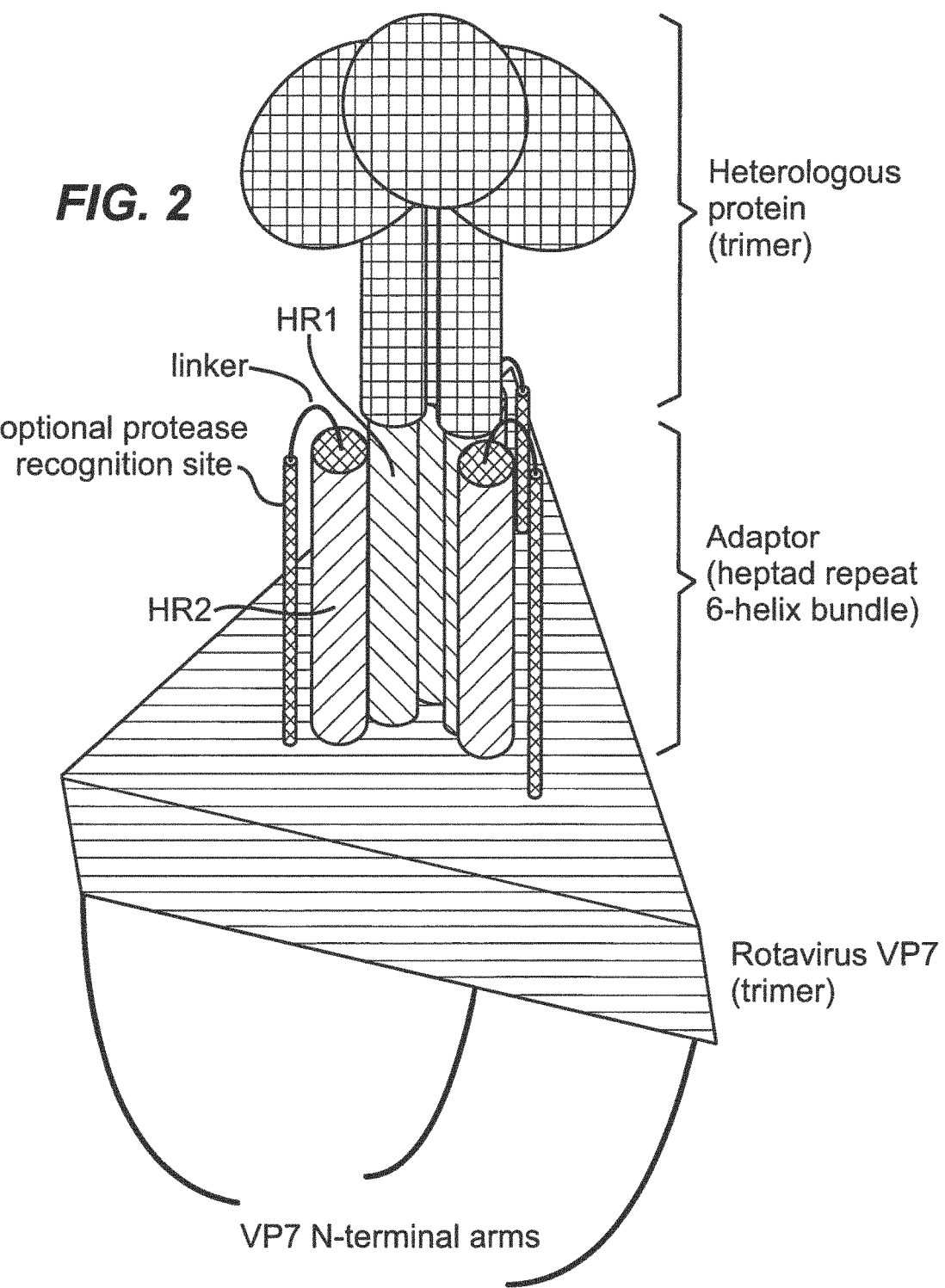

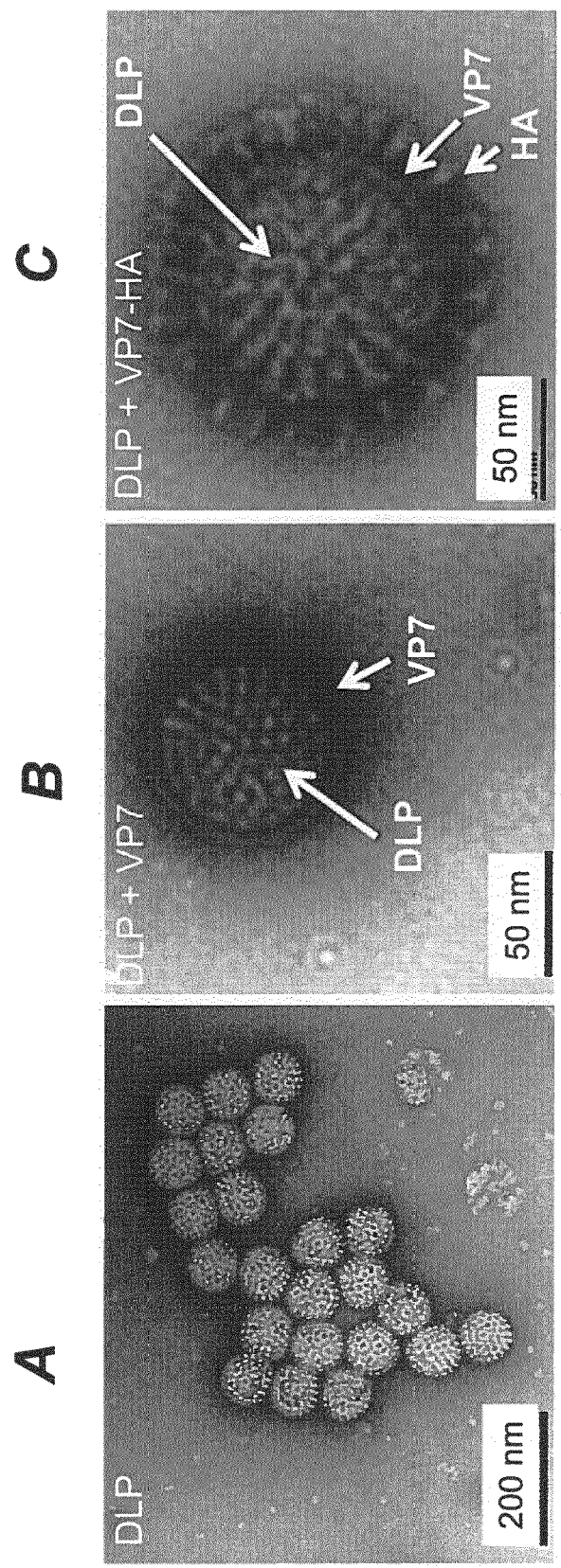

FIG. 5

A: DLP + VP7-HA

B: DLP + VP7-HA-CR6261ScFv

C: DLP + VP7-HA-CR6261Fab

US 10,192,025 B2

ROTAVIRUS PARTICLES WITH CHIMERIC SURFACE PROTEINS

GOVERNMENT S sequence. In some embodiments, the adapter polypeptide comprises a heptad repeat sequence. A cell containing a nucleic acid of the invention is also provided. The nucleic acids and cells containing the same may be used to prepare the chimeric surface proteins of the invention.

The invention further relates to a kit comprising the first and second nucleic acid sequences of the invention. In some embodiments, a kit according to the invention may comprise a first nucleic acid encoding a modified rotavirus surface protein comprising a rotavirus surface protein and a first adapter polypeptide, and a second nucleic acid comprising a nucleotide sequence encoding a second adapter polypeptide and a multiple cloning site, whereby insertion of a coding region for a heterologous protein in the multiple cloning site yields an open reading frame encoding a fusion protein comprising the heterologous protein and the second adapter polypeptide, wherein the first adapter polypeptide and the second adapter polypeptide are able to form a stable complex. The kits of the invention may further comprise a rotavirus particle. The rotavirus particle can be derived from the same species of rotavirus from which the rotavirus surface protein was derived or from a different species. For example, rhesus rotavirus VP7 can be used to recoat DLPs prepared from bovine rotavirus and vice versa.

Rotavirus particles comprising a chimeric surface protein can be prepared by various methods. A preferred method of the invention involves propagating a native rotavirus particle comprising an outer layer in a cell grown in a culture medium, purifying the particles from the culture medium, removing the outer layer from the particle to obtain a rotavirus DLP, and recoating the rotavirus DLP with a one or more chimeric surface proteins to form a rotavirus particle comprising the chimeric surface protein or proteins. A native rotavirus particle is a triple-layered particle, wherein the outermost third layer forms the outer shell of the rotavirus particle.

In a particular aspect, the invention relates to a first fusion protein comprising a trimer-forming rotavirus surface protein, a heptad repeat sequence, and optionally a linker sequence. The invention further provides a second fusion protein comprising a trimer-forming heterologous protein, a heptad repeat sequence, and optionally a linker sequence. The first fusion protein and the second fusion protein are able to form a stable complex via the heptad repeat sequences comprised in each of them. In some embodiments, the invention provides a chimeric surface protein formed by the first fusion protein and the second fusion protein. The chimeric surface protein may be displayed on the surface of a rotavirus particle.

In one aspect of the invention, rotavirus particles comprising a chimeric surface protein are used for determining the structure of a heterologous protein that forms a portion of the chimeric surface protein. For example, the invention provides a method for obtaining a three-dimensional model of a chimeric surface protein, wherein the method comprises the steps of (i) recoating a rotavirus DLP with a chimeric surface protein comprising all or part of a heterologous protein to yield a suspension of rotavirus particles displaying the chimeric surface protein, (ii) freezing the suspension, (iii) imaging the rotavirus particles using cryo-EM to obtain a plurality of micrographs, and (iv) analysing the plurality of micrographs to obtain a three-dimensional model of the chimeric surface protein. In some embodiments, step (i) may be subdivided into two steps, namely (a) a recoating step in which the rotavirus DLP is recoated with a rotavirus surface protein comprising a first adapter to form rotavirus particles and (b) a binding step in which the recoated rotavirus DLP is incubated in the presence of a heterologous protein comprising a second adapter whereby a complex is formed between the first adapter and the second adapter resulting in a chimeric surface protein being displayed on the rotavirus particles. In some instances, the method can be modified to determining the structure of a heterologous protein bound to a molecule that specifically binds to the heterologous protein. The modified method comprises the steps of (i) recoating a rotavirus DLP with a chimeric surface protein comprising all or part of a heterologous protein to yield a suspension of rotavirus particles displaying the chimeric surface protein, (ii) adding to the suspension a molecule that specifically binds to the heterologous protein, wherein the molecule forms a complex with the chimeric surface protein, (iii) freezing the suspension, (iv) imaging the rotavirus particles using cryo-EM to obtain a plurality of micrographs, and (v) analysing the plurality of micrographs to obtain a three-dimensional model of the chimeric surface protein complexed to the molecule. The molecule may a proteinaceous molecule. For example, the proteinaceous molecule may be all or part of a receptor or antibody that specifically binds the heterologous protein. Alternatively, the proteinaceous molecule may be a polypeptide or peptide that specifically binds to the heterologous protein. In other embodiments, the molecule is a non-proteinaceous molecule. For instance, the non-proteinaceous molecule may be a nucleic acid.

In a further aspect, the rotavirus particles prepared in accordance with the invention are used as a medicament. In one embodiment, the invention relates to an immunogenic composition comprising a rotavirus particle that comprises the chimeric surface protein of the invention. The invention further relates to a method of treating a patient in need thereof comprising administering to said patient the rotavirus particle of the invention, e.g. in form of an immunogenic composition of the invention.

The underlying concept of the invention can be extended to other (trimeric or non-trimeric) heterologous proteins and other viruses (in particular reoviruses) or assemblies (e.g. virus-like particles, ferritin cages, etc.) by adapting the methods described herein.

DETAILED DESCRIPTION OF THE INVENTION

Viral Particles

Rotavirus is a genus of double-stranded RNA viruses in the family Reoviridae comprising five known types (Rotaviruses A-E). Rotaviruses are a major cause of childhood gastroenteritis. Rotavirus is a non-enveloped, triple-layered icosahedral particle. An infectious triple-layered particle (TLP) or virion is formed from a non-infectious double layered particle (DLP) by coating the DLP with the shell protein VP7 and the spike protein VP4. VP7 is a trimer, and 260 such trimers decorate the outside of the coated particle. The DLP, which is composed of concentric VP2 and VP6 icosahedral protein layers, is about 700 Å in diameter and encapsidates 11 double-stranded RNA genome segments, the viral polymerase (VP1), and a capping enzyme (VP3). During the infection of a cell, the VP4 and VP7 proteins, which form the outer layer of the rotavirus particle, dissociate from the DLP in a low-calcium environment (probably in the endosomal compartment)—a process referred to as "uncoating"—and deliver the DLP containing the viral RNA transcription machinery into the cytoplasm. There, the DLP synthesizes, caps and releases copies of the 11 mRNA species.

Dissociation or "uncoating" of VP4 and VP7 from a rotavirus particle can be performed in vitro by incubating rotavirus particles in the presence of a calcium chelator such as EDTA or EGTA or by heat shock. The resulting DLPs can be recoated in vitro with recombinantly expressed VP4 and VP7 to form fully infectious rotavirus particles. Particles recoated in this way are very well ordered and give high-resolution cryo-EM images and density maps. Using in vitro reconstituted TLPs, cryo-EM has been used to study the molecular interactions in rotavirus assembly and uncoating at a resolution comparable with that of X-ray crystallography (see references 1 and 2).

The inventors demonstrate herein that a heterologous trimeric protein (such as influenza hemagglutinin) can be attached to the trimeric VP7 protein, thus forming a chimeric surface protein that can project from the surface of a suitably recoated rotavirus DLP, therefore making it possible to determine the structure of the heterologous protein with the same cryo-EM methods that have previously provided near-atomic resolution structures of rotavirus and its subparticles. The method makes it possible for the first time to develop a high-throughput assay for the structure determination of antigen-antibody complexes. This was previously not possible due to the constraints of X-ray crystallography, which has been the method of choice to determine the structure of antigen-antibody complexes.

In principle, any non-enveloped icosahedral virus particle comprising an inner layer and an outer layer can be used to practise the methods of the invention. For example, displaying a chimeric surface protein comprising all or part of a heterologous protein is easily possible using any icosahedral virus for which a reverse genetics system for the production of virus particles has been established. A plasmid-based reverse genetics system consisting of ten reovirus cDNA constructs has been established for the mammalian reoviruses (see reference 3). The octameric symmetry of ferritin cages also has 3-fold axes of symmetry and is suitable for the practice of this invention. Other proteins that assemble into particulate, regular structures with three-fold axes of symmetry may be suitable for the practice of this invention.

Ideally, the outer layer of the virus particle of a non-enveloped icosahedral virus can be removed or stripped, e.g. by protease treatment or under low-calcium conditions, to yield subviral particles that comprise the inner layer(s) only and can be recoated with recombinantly produced outer layer proteins. In vitro reassembly or recoating of subviral particles to complete viral particles by addition of recombinantly expressed outer layer protein(s) is particularly advantageous in cases where the presence of the chimeric surface protein would interfere with the proper assembly of the virus propagated in cell culture using a reverse genetics approach. In addition, only expression vectors for the outer layer proteins need to be constructed, removing the need for an efficient plasmid-based reverse genetics system to be in place. Native virus can simply be propagated in tissue culture cells, and viral particles can be stripped of the outer layer and reassembled in vitro using recombinantly expressed outer layer proteins. Thus, using a method that relies on in vitro recoating of subviral particles to complete viral particles eliminates the need for transfecting large numbers of plasmids and removes the additional propagation step typically needed to yield large numbers of virus particles from plasmid-based reverse genetics system, making such a method more amiable for high-throughput applications.

According to the inventors' knowledge, all known non-enveloped icosahedral viruses where the outerlayer of the virus particle can be stripped and the subviral particle can be recoated with recombinantly expressed outer layer proteins to form infectious virus particles belong to the family of Reoviridae. This family is subdivided into two subfamilies, Sedoreovirinae and Spinareovirinae, which comprise six and nine genera, respectively. The subfamily Sedoreovirinae comprises the genera Cardoreovirus, Mimoreovirus, Orbivirus, Phytoreovirus, Rotavirus, and Seadornavirus. The subfamily Spinareovirinae comprises the genera Aquareovirus, Coltivirus, Cypovirus, Dinovernavirus, Fijivirus, Idnoreovirus, Mycoreovirus, Orthoreovirus, and Oryzavirus.

In addition to rotaviruses, mammalian orthoreoviruses may be useful in practising the invention. For these viruses, suitable conditions for the complete in vitro assembly of the outer capsid and the use of cryo-EM are well established (see references 1, 2, 4 and 5). Other orthoreoviruses (e.g. baboon or avaian orthoreoviruses), oryzavirus (e.g. rice ragged stunt virus) and aquareoviruses for which cryo-EM has been used and for which structural information is already available (see references 6, 7 and 8) may also suitable for practising the invention.

Cypoviruses and dinovernaviruses have the equivalent of an inner capsid only and therefore are typically not considered suitable for practicing the invention and are therefore considered less preferable. In certain embodiments, the non-enveloped icosahedral viruses for use in the invention do not include cypoviruses and dinovernaviruses. In a preferred embodiment, the viruses of the invention can be manipulated at biosafety level 2 or lower (see reference 9).

Preferably, the virus particle used in practising the invention has three or fewer outer layer proteins. More preferably, the outer layer of the virus particle can be formed by a single outer layer protein, which is the outer surface protein used in preparation of the chimeric surface protein. A low number of outer layer proteins is advantageous because fewer proteins need to be expressed recombinantly to recoat the subviral particles after stripping.

For example, rotavirus has two outer layer proteins, VP4 and VP7, but only VP7 is a shell protein that is required to form the outer layer of a rotavirus particle. In most instances, only recoating of rotavirus DLPs with one outer layer protein, VP7, is sufficient in order to practice the invention.

Chimeric Surface Protein

In one aspect, the invention relates to a chimeric surface protein comprising a rotavirus surface protein covalently linked to a heterologous protein. The rotavirus surface protein may be linked to the heterologous protein via a linker sequence. In a specific embodiment, the heterologous protein is inserted in a flexible loop of the rotavirus surface protein which is the outer surface-exposed portion. In some instances, portions of the rotavirus surface protein are deleted to better accommodate the linker sequence and/or the heterologous protein. For examples, short N-terminal and C-terminal truncations (<10 amino acids) typically do not affect the ability of the rotavirus VP7 protein to recoat rotavirus DLPs. In addition, amino acid sequences that form surface loops that extend from away from the virus particle when the VP7 protein has been used to recoat DLPs are dispensable. Whether a deletion affect the ability of the VP7 protein to recoat DLPs can be assessed by incubating recombinantly expressed VP7 protein in the presence of DLPs and observe the formation of recoated virus particles.

In another aspect of the invention, the rotavirus surface protein is non-covalently linked to the heterologous protein via an adapter system. In a preferred aspect of the invention, the heterologous protein is non-covalently bound to the rotavirus surface protein by a two-part adapter system, where one part of the adapter system is linked to the rotavirus surface protein and the other part of the adapter system is linked to the heterologous protein, whereby both parts of the adapter system form a stable complex thus non-covalently attaching the heterologous protein to the rotavirus surface protein. The adapter system is typically composed of a first adapter polypeptide and a second adapter polypeptide. The first adapter polypeptide is fused to the rotavirus surface protein, optionally via linker sequence. The second adapter polypeptide is fused to the heterologous protein, optionally via a linker sequence. The first and second adapter polypeptides interact with each other to form a stable complex therefore non-covalently attaching the rotavirus surface protein to the heterologous protein, thus forming the chimeric surface protein.

Viral Surface Protein

The outer layer of a virus particle suitable for practising the invention typically comprises several different outer surface proteins. The main surface protein is particularly suitable for displaying a heterologous protein, as it covers most of the virus particle's surface. For example, the outer surface of rotavirus (excluding the spikes) is formed by 780 copies of the VP7 protein, which forms homotrimers. Choosing a viral particle with a major surface protein that forms homotrimers is particularly preferred for practising the invention.

In one specific embodiment, the viral surface protein is a rotavirus surface protein. In another specific embodiment, the viral surface protein is a glycoprotein.

Examples of other viruses with viral surface proteins that may be suitable for practising the invention include the orthoreoviruses. For example, the outer viral capsid of aquareovirus is formed by 200 trimers of a protein designated VP5. In mammalian orthoreoviruses, the outer layer of an infectious reoviral particle contains 600 copies of the trimeric membrane penetration protein μ1, which is studded with the chaperone protein σ3 (also present in 600 copies) thus forming a heterohexamer.

Heterologous Protein

Many heterologous proteins can be displayed using a trimeric rotavirus surface protein, provided a linker of appropriate length and/or an appropriate insertion site within the surface protein is chosen to avoid steric hindrance between monomers during assembly of the timer. No upper size limit for the heterologous protein exists as long as the heterologous protein does not form a volume that overlaps with the neighbouring volumes of other mounted heterologous proteins. Preferably an adapter system is used to display the heterologous protein on the trimeric rotavirus surface protein. Heterologous proteins that are not soluble, form higher-order oligomers or aggregate are typically not considered suitable in practising the invention.

Any size constraints due to steric hindrance may be overcome by choosing an appropriate linker or adapter system.

In the context of the heterologous protein, the term "heterologous" typically means that the protein is not a rotavirus protein. In some embodiments, the expression "heterologous protein" may mean that the protein is not derived from the same rotavirus strain that is used to display the protein.

Trimeric surface proteins are particularly suitable for displaying trimeric heterologous proteins. Examples of trimeric heterologous proteins include trimeric viral cell entry proteins and other trimeric viral surface proteins, in particular those that are targeted by neutralizing antibodies. Specific examples are the influenza haemagglutinin (HA), human immunodeficiency virus (HIV) gp140, the Ebola virus glycoprotein, rabies virus glycoprotein (RVG), the Env protein of caprine arthritis encephalitis virus, the F protein of respiratory syncytial virus (RSV), the gB protein and its complexes found in human herpes simplex viruses and human cytomegalovirus (HCMV) etc.

In some embodiments, the rotavirus surface protein and/or the heterologous protein include(s) a trimerization tag to aid in the assembly of the heterohexamer complex formed by the trimeric rotavirus surface protein and the trimeric heterologous protein. The trimerization tag, particularly coiled-coil based trimerization tags (e.g. GCN4, [10]), can also serve as structural modules to extend the space available for a heterologous protein which is displayed on the surface of a rotavirus particle recoated with a modified rotavirus VP7 protein. Another suitable trimerization tag can be derived from bacteriophage T4 fibritin [11].

In certain embodiments, heterologous proteins that are not trimeric can interact with a trimerization tag present on the rotavirus surface proteins. As an example, if the heterologous protein has an accessible α-helix that could interact with α-helices of a coiled-coil-based trimerization tag, that heterologous protein could bind the trimerization tag. If there is no steric hindrance, up to three such heterologous proteins could bind the trimerization tag simultaneously, forming a six-helix bundle. If fewer than three such heterologous proteins bound, the six-helix bundle would be incomplete, containing the inner three helices contributed by the trimerization tag present on the rotavirus protein but only one or two of the outer helices of the bundle. The non-trimeric heterologous protein could have 1, 2, 4, or more subunits (i.e. be a monomer, dimer, tetramer, or other oligomer), provided that at least one of the subunits had an α-helix that could interact with the trimerization tag present on the rotavirus surface protein.

In certain embodiments, a monomeric heterologous protein can include multiple α-helices arranged such that more than one helix could interact with the α-helices of the trimerization tag present on the rotavirus surface protein, forming a complete or partial six-helix bundle. In certain embodiments, tetramers (or higher order structures) wherein at least three of the monomers contain suitably arranged α-helices could associate with the trimerization tag attached to the rotavirus surface protein to form a six-helix bundle. In certain embodiments, tetramers (or higher order structures), wherein at least two of the monomers contain suitably arranged α-helices, could associate with the trimerization tag associated with the rotavirus surface protein to form a partial six-helix bundle, missing one of the outer helices. The subunits of the heterologous protein may be identical (i.e. a homodimer, homotrimer, homotetramer, etc.) or may not be identical (i.e. a heterodimer, heterotrimer, heterotetramer, etc.).

If the trimerization tag present on the rotavirus surface protein is not an α-helical coiled-coil, the interacting structural element on the heterologous protein could have a secondary structure that binds the trimerization tag but is not α-helical.

Preferably, the heterologous protein is not an antibody which specifically binds to a rotavirus surface protein.

Adapter System

In some embodiments of the invention, an adapter system is used to display the heterologous protein on a rotavirus particle. The adapter system is typically composed of two adapter molecules. The first adapter molecule is covalently linked to the rotavirus surface protein that was chosen to display a heterologous protein. The second adapter molecule is covalently linked to the heterologous protein. The first adapter molecule and the second adapter molecule interact with each other to form a stable complex.

Adapter systems typically are composed of two adapter polypeptides. The first adapter polypeptide is fused to the rotavirus surface protein that was chosen to display a heterologous protein. The second adapter polypeptide is fused to the heterologous protein. The first adapter polypeptide and the second adapter polypeptide can interact with each other to form a stable complex.

Many polypeptides are known that associate which each other to form a stable complex. In some instances, these polypeptides will be derived from different proteins, e.g. a receptor and a ligand or an antibody and an antigen. In other instances, these polypeptides can be derived from the same protein such as the two heptad repeat sequences of HIV gp41.

Suitable adapter systems that do not rely on interactions between two adapter polypeptides can also be envisioned. For example, the rotavirus surface protein may be modified to include a specific glycosylation site, and the heterologous protein can be modified to include a lectin domain that specifically recognises the glycan at the glycosylation site. Examples of lectins that recognise specific glycan structures are well-known in the art.

Another suitable adapter system that does not rely on interactions between two adapter polypeptides is the streptavidin-biotin system. Monomeric streptavidin which has been mutated to prevent tetramer formation and to enhance solubility is preferably used [12]. The monomeric streptavidin can be fused to the rotavirus surface protein that was chosen to display a heterologous protein. For complex formation to occur, the heterologous protein is biotinylated. Enzymatic biotinylation is preferred as it allows biotin to be linked specifically to an amino acid residue present in the protein that is to be biotinylated. For example, the heterologous protein may be modified by insertion of an "AviTag" or "Acceptor Peptide" (AP), which can be specifically biotinylated by a biotin ligase (e.g., BirA) in the presence of biotin and ATP (see reference 13 for details).

Another adapter system that does not rely on interactions between two adapter polypeptides can include an antibody bound to a hapten (e.g., diethylene triamine pentaacetic acid (DTPA), 1,4,7,10-tetraazacyclododecane-1,4,7,10-tetraacetic acid (DOTA)). Alternatively, the chelators DTPA and DOTA can be coordinated with metal ions to form complexes.

Use of an adapter system is not essential for practising the invention. However, use of an adapter system may be preferred to optimally preserve the structural features of the heterologous protein, in particular of trimeric surface proteins of other viruses that are to be displayed on a rotavirus particle. The use of an adapter system is particularly advantageous because a rotavirus surface protein which has been modified to contain a first adapter needs to be prepared only once and can subsequently be used with any heterologous protein that has been modified to contain a compatible second adapter.

A further advantage of using an adapter system is that expression and purification can be optimised separately for each of the components of the chimeric surface protein. In most instances, the insertion of an adapter polypeptide sequence will not change those characteristics of the viral surface protein or of the heterologous protein which are relevant for their expression or purification. Thus existing expression systems and purification methods can typically be used without modification to prepare large quantities of the viral surface protein comprising the first adapter polypeptide and the heterologous protein comprising the second adapter polypeptide. In contrast, a chimeric surface protein composed of a viral surface protein covalently linked to a heterologous protein will likely have characteristics that differ substantially from the characteristics of the viral surface protein or the heterologous protein each by itself.

The rotavirus surface proteins and many reoviral surface proteins form trimers. Thus, in one aspect of the invention, the adapter system of choice preferably forms a trimeric complex. Particularly preferred are adapter systems wherein the first adapter polypeptide and the second adapter polypeptide comprise heptad repeat sequences and form α-helical structures that allow the formation of six-helix bundles. Most preferably, three copies of the second adapter polypeptide form an interior coiled-coil trimer, while three copies of the first adapter polypeptide pack into grooves on the surface of this trimer completing the six-helix bundle. However, the inverse may also be possible, in which case three copies of the first adapter polypeptide form an interior coiled-coil trimer, while three copies of the second adapter polypeptide pack into grooves on the surface of this trimer. Various polypeptide pairs that comprise heptad repeat sequences and form six-helix bundles are known in the art. These are typically derived from viral fusion proteins. Because of the rotational symmetry and stability of their six-helix bundles, viral fusion proteins are the preferred source for adapter polypeptide sequences.

One of the most thoroughly studied viral fusion proteins is the envelope glycoprotein of human immunodeficiency virus 1 (HIV-1). The ectodomain of HIV-1 envelope glycoprotein consists of gp120 and gp41. gp41 mediates fusion between viral and cellular membranes. gp41 comprises two heptad repeat sequences, "helical region 1" (HR1) and "helical region 2" (HR2), which can form a six-helix bundle in the native protein [14]. In a preferred embodiment, the first adapter polypeptide and the second adapter polypeptide of the adapter system correspond to gp41 HR2 (SEQ ID NO: 1) and gp41 HR1 (SEQ ID NO: 2), respectively. In a further preferred embodiment, the first adapter polypeptide and the second adapter polypeptide of the adapter system correspond to Nipah virus F protein HR2 (SEQ ID NO: 3) and HR1 (SEQ ID NO: 4), respectively. However, various other viral fusion proteins are known that may be a source of interacting HR1 and HR2 polypeptides that can be used to prepare the first and second adapter polypeptides. These include the influenza hemagglutinin 2 (HA2), the transmembrane (TM) subunit of Moloney murine leukemia virus (Mo-MLV), the paramyxovirus F protein (including avian paramyxovirus F protein, e.g. Hendra virus F protein) e.g. from respiratory syncytial virus (RSV) and Newcastle disease virus (NDV), the spike protein of coronavirus (e.g. the spike proteins of mouse hepatitis virus and SARS-CoV), the ZEBRA protein of Epstein-Barr virus, simian virus 5 fusion protein etc. (see references 14, 15, 16 and 17).

Where the heterologous protein itself comprises heptad repeat sequences and these sequences are compatible with the heptad repeat sequence comprised in a modified rotavirus surface protein, the addition of heptad repeat sequences to the heterologous protein may not be necessary. In such a case, the native heptad repeat sequences of the heterologous protein may form a six-helix bundle with the heptad repeat sequence of the modified rotavirus surface protein and the heterologous protein may not need to be modified by the addition of a heptad repeat sequence that is foreign to the heterologous protein.

For example, any of the above listed viral fusion proteins contain interacting heptad repeat sequences, and these native heptad repeat sequences may be able to interact with the heptad repeat sequences in a rotavirus surface protein modified to contain heptad repeat sequences. In some embodiments, it may be preferred to rely on heptad repeat sequences heterologous to the viral fusion protein, in particular where the two-part adapter system is chosen to allow for a modular approach where the same modified rotavirus surface protein is used to display various different heterologous proteins.

Other protein domains comprising heptad repeat sequences that form six-helix bundles are known. These include the CARD domain of human Apaf-1 and RAIDD, death effector domain of FADD and the death domain of p75 and Fas. Other sources of six-helix bundle-forming peptide sequences include the SNAREs and GCN4-pII. Any of these domains or peptide sequences may likewise be adapted for use in the present invention. For example, the three N-terminal helices and the three C-terminal helices of the CARD domain may be used for the first adapter polypeptide and the second adapter polypeptide, respectively, to form an adapter system suitable for monomeric or dimeric surface proteins.

Other peptide-based adapter systems can also be used. For example, an antibody or antigen binding portion thereof (e.g., a Fab fragment, an scFv, a domain antibody (DAb)) which binds the heterologous protein that one wishes to display on the virus surface can be inserted into the rotavirus surface protein. The antibody or antigen binding portion thereof may recognise a specific epitope that either can be inserted into the heterologous protein (e.g., in form of a peptide tag) or may naturally be present in the heterologous protein.

In some embodiments, a suitable two-part adapter system requires modification of the heterologous protein only. For example, in one embodiment of the invention, the rotavirus surface protein is a glycoprotein. In such a case, a heterologous protein may be modified to contain a lectin domain that specifically binds the glycan in the glycoprotein. For example, the rotavirus VP7 protein can be modified by the introduction of a single glycosylation sites in the surface-exposed portion of the protein so that the lectin domain of the modified heterologous protein specifically binds to the glycan in the modified VP7 protein.

Alternatively, the heterologous protein may be modified to contain an antigen-binding domain of an antibody that is specific for an epitope on the rotavirus surface antigen. For example, the heterologous protein may be fused to a Fab fragment of an antibody that binds the rotavirus surface antigen with high affinity.

Linker Sequence

Linker sequences separate domains derived from different proteins and allow these domains to fold properly. Many linker sequences are known in the art (see reference 18). A linker sequence may be included to separate the rotavirus surface protein and/or the heterologous protein from the adapter sequence. Alternatively, where the rotavirus surface protein and the heterologous protein form two parts of the same protein, both parts may be separated from each other by a linker sequence.

Both rigid and flexible linkers are known. A typical sequence of a flexible linker is composed of repeats of the amino acids G and S. For instance, the linker may have the following sequence: GS, GSG, SGG, GGSGG (SEQ ID NO: 5) or GSGSGSGT (SEQ ID NO: 6). In some embodiments, the same sequence is repeated multiple times (e.g. two, three, four, five or six times) to create a longer linker. In other embodiments, a single amino acid such as S or G can be used as a linker. A rigid linker may be composed of several repeats of the amino acid sequence EAAAR (SEQ ID NO: 7).

When choosing a linker sequence, care should be taken to select a hydrophilic linker to avoid aggregation of the modified rotavirus surface protein or heterologous protein.

Typically, the linker is protease-insensitive but in some embodiments the linker contains a protease cleavage site. Protease cleavage sites may be useful to remove tags that are included for detection/purification of e.g. a modified rotavirus surface protein of the invention. Protease cleavage sites may also be useful for exposing an amino acid sequence that has been inserted in a modified rotavirus surface protein so that the amino acid sequence becomes more accessible on the outer surface of the modified rotavirus surface protein after cleavage with a site-specific protease. For example, a protease cleavage site may be used to expose an adapter polypeptide for improving its binding to the corresponding adapter polypeptide of a two-part adapter system which has been fused to a heterologous protein that is to be displayed on the surface of a rotavirus particle. In some instances, the use of a protease cleavage to expose an adapter polypeptide which forms part of a modified rotavirus surface protein may obviate the need for additional linker sequences and thus reduce the number of additional amino acid sequences that need to be inserted into a modified rotavirus surface protein in order to form a stable complex with a heterologous protein.

Protease cleavage sites for a specific protease can be found in a number of proteins. For example, the blood-clotting cascade and the complementation cascade contains a number of very specific proteases that recognise cleavage sites in proteins further downstream in the cascade. Usually, the enzymes at the early stages of a cascade are more specific than are the later ones. For example, Factor X is more specific than thrombin. If thrombin is used, the most preferred thrombin-sensitive cleavage sites are those found in fibrinogen, Factor XIII, and prothrombin. Further examples of proteases of the blood clotting cascade, their target proteins and specific cleavage sites are listed in Table 1 below. The underlined portion of the sequence shown in Table 1 is the minimal cleavage site that needs to be included for the protease to recognise the target.

TABLE 1

| Protease | Target | Cleavage Site(s) |
|---|---|---|
| Human factor XI | Human factor IX | QT<u>SKLTR</u>AEAVF (SEQ ID NO: 8) and SF<u>NDFTR</u>VVGGE (SEQ ID NO: 9) |
| Human kallikrein | Human factor XII | LF<u>SSMTR</u>VVGGLV (SEQ ID NO: 10) |

TABLE 1-continued

| Protease | Target | Cleavage Site(s) |
|---|---|---|
| Human facor XII | Human factor IX | KIKPRIVGGT (SEQ ID NO: 11) |

Other proteases that have been used to cleave fusion proteins include enterokinase, collagenase, chymosin, urokinase, renin, Rhinovirus 3C protease, Tobacco Etch Virus (TEV) protease, factor Xa, thrombin, furin, and certain signal peptidases (see e.g. reference 19).

Preferably the cleavage site is positioned in such a way in the final construct that any tag that has been added to the rotavirus surface protein or the heterologous protein can easily be removed.

In some embodiments, the linker contains a tag for detection and/or purification. Many tags to facilitate the detection of proteins are known in the art. Frequently used peptide tags include FLAG-tag (DYKDDDDK; SEQ ID NO: 12), HA-tag (YPYDVPDYA; SEQ ID NO: 13), His-tag (e.g. HHHHHH; SEQ ID NO: 14), Myc-tag (EQKLISEEDL; SEQ ID NO: 15), Strep-tag I (AWRHPQFGG; SEQ ID NO: 16), Strep-tag II (NWSHPQFEK; SEQ ID NO: 17), and protein C-tag (EDQVDPRLIDGK; SEQ ID NO: 18). His-tags are preferred as they allow easy detection by anti-His antibodies and permit purification of the tagged protein using a nickel-column. Strep-tag II allows simple and easy purification of recombinantly expressed proteins using streptavidin columns. In some cases, protein tags are used. For example, a glutathione-S-transferase-tag may be included to allow for the easy purification of a protein of the invention using a column comprising immobilized glutathione. A green fluorescent protein-tag can be used if easy detection by fluorescence microscopy is required.

In some embodiments of the invention, a tag (e.g. a protein C tag) is included as part of the linker sequence because tags typically used e.g. for protein detection and purification do not interfere with the function and folding of the tagged protein and are generally surface exposed. Therefore a tag may provide advantageous properties over other, artificially designed linker sequences.

In other embodiments, a linker sequence may comprise an epitope sequence. Including an epitope sequence can be useful for packing antibody fragments recognising said epitope to further stabilise the complex formed by a modified rotavirus surface protein and a heterologous protein via two-part adapter system. Stabilising the complex may be particularly important for achieving high resolution images for structural studies.

Signal Peptide

In some embodiments of the invention, the rotavirus surface protein and the heterologous protein are further modified to comprise a heterologous signal peptide sequence, preferably replacing the native signal peptide sequence. The use of a heterologous signal peptide may be advantageous for achieving higher expression levels in the expression system used to prepare large amounts of the modified rotavirus surface protein and the heterologous protein for recoating rotavirus DLPs. Accordingly, the heterologous signal peptide will be derived from a protein that is known to be expressed in high levels in the chosen expression system. For example, the HIV consensus signal sequence or signal peptide of human tissue plasminogen activator (tPA) are particular suitable for expression in human cells. For expression in insect cells, the Baculovirus gp64 signal peptide or the honeybee melittin signal sequence may be used. Typically, a linker is placed after the heterologous signal peptide sequence in order to guarantee efficient signal peptide cleavage. Generally, the signal peptide is removed by a signal peptidase endogenous to the chosen expression system so that it is not present in the final protein (i.e. rotavirus surface protein and the heterologous protein recovered from the expression system).

Nucleic Acids

The invention also relates to nucleic acids comprising an open reading frame encoding a chimeric surface protein of the invention operationally linked to a promoter sequence such that the chimeric surface protein is expressed in large amounts in an expression system.

The invention also relates to a nucleic acid construct that encodes a modified rotavirus surface protein, that comprises all or a portion of a rotavirus surface protein, a first adapter polypeptide and, optionally, a linker sequence. The invention further relates to a nucleic acid comprising an open reading frame encoding a fusion protein comprising a heterologous protein, a second adapter polypeptide, and, optionally, a linker sequence, wherein the open reading frame is operationally linked to a promoter sequence such that the fusion protein is expressed in large amounts in an expression system. In one embodiment, the invention relates to a nucleic acid construct that comprises a nucleotide sequence encoding a second adapter polypeptide, optionally, a linker sequence and a multiple cloning site, wherein insertion of a coding region for a heterologous protein in the multiple cloning site yields an open reading frame encoding a fusion protein comprising the heterologous protein and the second adapter polypeptide. The nucleic acid construct further comprises a promoter sequence that can drive expression of the fusion protein comprising the heterologous protein and the second adapter polypeptide in an expression system.

The first adapter polypeptide and the second adapter polypeptide form part of a two-part adapter system so that the fusion protein comprising the heterologous protein and the second adapter polypeptide and the modified rotavirus surface protein comprising the first adapter polypeptide form a stable complex with each other.

Expression Systems

The invention also relates to expression systems for expressing the proteins encoded by the nucleic acids of the invention.

In one embodiment, a first expression system is used to express a modified rotavirus surface protein comprising all or a portion of a rotavirus surface protein, a first adapter polypeptide and, optionally, a linker sequence. A second expression system is used to express a fusion protein comprising a heterologous protein, a second adapter polypeptide, and, optionally, a linker sequence. Optionally, a third expression system is used to express one or more rotavirus protein(s) that, together with the rotavirus surface protein, form(s) the outer layer of a rotavirus particle. The first and second adapter polypeptides interact with each other to form a stable complex. The first expression system comprises a first nucleic acid construct comprising an open reading frame encoding the modified rotavirus surface protein, wherein the open reading frame is operationally linked to a promoter sequence. The second expression system comprises a second nucleic acid construct comprising an open reading frame encoding the fusion protein, wherein the open reading frame is operationally linked to a promoter sequence. The third expression system comprising one or more expression vector(s) for the one or more rotavirus protein(s). The modified rotavirus surface protein and the fusion protein and optionally the one or more rotavirus protein(s) are then purified. The modified rotavirus surface protein and the fusion protein can be mixed in appropriate ratios to form a chimeric surface protein. The chimeric surface protein and optionally the one or more rotavirus protein(s) are then used to recoat rotavirus DLPs to form rotavirus particles displaying the heterologous protein on their surface. Alternatively, rotavirus DLPs are recoated with the modified rotavirus surface protein and optionally the one or more rotavirus protein(s) to form rotavirus particles. The rotavirus particles can then be mixed with the fusion protein to allow the formation of a complex between the first adapter polypeptide and the second adapter polypeptide yielding a chimeric surface protein so that the heterologous protein is displayed on the surface of the rotavirus particles.

In another embodiment, the invention relates to an expression system comprising (i) a first nucleic acid construct comprising an open reading frame encoding a modified rotavirus surface protein that comprises all or a portion of a rotavirus surface protein, a first adapter polypeptide and, optionally, a linker sequence, wherein the open reading frame is operationally linked to a promoter sequence, and (ii) a second nucleic acid construct comprising an open reading frame encoding a fusion protein comprising a heterologous protein, a second adapter polypeptide, and, optionally, a linker sequence, wherein the open reading frame is operationally linked to a promoter sequence. In some instances, the expression system further comprises an expression vector for one or more rotavirus protein(s) that, together with the rotavirus surface protein, form(s) the outer layer of the rotavirus particle.

The expression system can be a bacterial cell, a yeast cell, a protozoan cell, an insect cell or a mammalian cell. The use of bacterial cells or yeast cells as expression systems is less preferred, in particular where proper glycosylation of the expressed proteins is desired.

Kits

The invention further provides kits comprising a first nucleic acid construct encoding a modified rotavirus surface protein that comprises all or a portion of a rotavirus surface protein and a first adapter polypeptide, and a second nucleic acid construct, wherein the second nucleic acid construct comprises a nucleotide sequence encoding a second adapter polypeptide and a multiple cloning site, and wherein insertion of a coding region for a heterologous protein in the multiple cloning site yields an open reading frame encoding a fusion protein comprising the heterologous protein and a second adapter polypeptide, wherein the first adapter polypeptide of the chimeric fusion protein and the second adapter polypeptide of the fusion protein interact with each other to form a stable complex.

The invention further relates to kits comprising a first nucleic acid construct encoding a modified rotavirus surface protein comprises all or a portion of rotavirus surface protein and a first adapter polypeptide, and a second nucleic acid construct encoding a fusion protein comprising all or a portion of a heterologous protein and a second adapter polypeptide, wherein the first adapter polypeptide of the modified rotavirus surface protein and the second adapter polypeptide of the fusion protein interact with each other to form a stable complex, thus yielding a chimeric surface protein.

Kits may further comprise a rotavirus particle. The rotavirus particle can be either from the same species from which the rotavirus surface protein was derived or from a different species. For example, rhesus rotavirus VP7 can be used to recoat DLPs prepared from bovine rotavirus and vice versa. The rotavirus can be uncoated and recoated with the chimeric surface protein. Alternatively, kits may comprise DLPs for recoating with the chimeric surface protein. Rotavirus DLPs can be prepared by uncoating native rotavirus particles or by recombinantly expressing the rotavirus inner shell proteins VP2 and VP6.

Recombinant Expression of Outer Layer Proteins

Recoating of rotavirus DLPs requires only one or two recombinant viral proteins, the outer layer protein VP7 or the outer layer protein VP7 together with the outer layer spike protein VP4. The expression and purification of VP4 and VP7 are described in detail in references 20 and 21, respectively.

The outer layer proteins including the chimeric surface protein of the invention can be produced using conventional expression systems known to the skilled person. In order to guarantee correct folding, and in some instances proper glycosylation, expression systems other than prokaryotic or yeast expression systems are preferred. For example, mammalian cells such as CHO cells or 293 cells may be used to overexpress the outer layer proteins needed for recoating of the rotavirus DLPs. Alternatively, the protozoan *Leishmania tarentolae* may be used to express the outer layer proteins. Insect cell systems are also suitable for the expression of the outer layer proteins. For example, the insect cell lines Sf9, Sf21 and Hi-5 are suitable for the overexpression of glycosylated proteins. In some instances, baculovirus-based insect cell systems are preferred. The expression systems described in references 2, 4 and 5 are particularly suitable in practising the invention.

Various ways of recovering and purifying the overexpressed outer layer proteins are known in the art. Typically a series of chromatographic steps is used to purify the overexpressed proteins from cytoplasmic extracts or the supernatant of the cells which were used as the expression system. For example lectin affinity, immunoaffinity and size exclusion chromatography may be used. If the outer shell protein has been tagged with a peptide- or protein tag, this tag may advantageously be used for purification. If a protease cleavage site is present in the sequence preceding the tag, the tag may be removed after purification using a protease that specifically recognises the protease cleavage site.

In some instances, a crude preparation of the recombinantly expressed outer layer proteins can be used for the recoating reaction. For example, lysates of cells used for expressing the outer layer proteins can be prepared using a lysis buffer and/or mechanical disruption of the cells (e.g., by scraping or sonicating the cells). Any cell debris is removed by centrifugation, and the supernatant containing a crude preparation of the recombinant outer layer proteins can be used in a recoating reaction. The crude preparation may be concentrated using ultrafiltration prior to being used in a recoating reaction.

In those aspects of the invention where a heterologous protein is non-covalently bound to a rotavirus surface protein by a two-part adapter system comprising a first adapter polypeptide and a second adapter polypeptide, the rotavirus surface protein fused to the first adapter polypeptide and the heterologous protein fused to the second adapter polypeptide are expressed separately in different cells. Separate expression may be preferable because both proteins can be purified separately using known purification protocols for each of the proteins. After purification, the proteins can be mixed in the appropriate ratios required for recoating of rotavirus DLPs. For example, the molar ratio of VP7 and VP4 in the outer layer of rotavirus is 13:1. The molar ratio of the modified VP7 protein comprising the first adapter polypeptide and the heterologous protein comprising the second adapter polypeptide is typically 1:1. Alternatively, DLPs are recoated with the rotavirus outer layer protein to form rotavirus particles. The rotavirus particles are then mixed with the heterologous protein to allow the formation of a complex between the first adapter polypeptide and the second adapter polypeptide so that the heterologous protein is displayed on the surface of the rotavirus particles.

Alternatively, both the rotavirus surface protein and the heterologous protein may be expressed in the same cell. Co-expression results in formation of a stable complex of the rotavirus surface protein and the heterologous protein mediated by the two-part adapter system (see above for details). Where the linker sequence connecting the adapter sequence to the rotavirus surface protein or to the heterologous protein contains a tag, this tag may be used to purify the complex from the cells/cell supernatant of the expression system.

To be able to recoat a reoviral core particle with a chimeric surface protein comprising all or part of a heterologous protein, not all proteins need to be provided to form an outer layer. For example, the outer layer of a mammalian reovirus is formed of μ1, σ1 and σ3. In order to recoat reoviral core particles for the purposes of the invention, typically providing a recombinant version of μ1 is sufficient to form viral particles. Optionally, recombinant versions of σ1 and σ3 can also be provided. The recombinant proteins can be prepared with one of the expression systems mentioned above and can then be purified using known protocols.

Propagation of Viral Particles

Rotaviruses have been found in a large number of animal species including cattle, pigs, horses, rabbits, mice, dogs, cats, birds and exotic animal species such as addax, saiga, white-tailed gnu, grizzly bear, and red kangaroo. Accordingly, the suitability of a certain cell type for their propagation depends on the host-range of the chosen virus. Preferably, a virus is chosen that allows high-yield propagation in established cell culture systems.

For example, the cell line MA104 can be used to propagate rhesus rotavirus. Rotavirus can be recovered by lysing infected cells, e.g. by freeze-thawing infected MA104 cells in medium. Cell debris is cleared from the lysates by low-speed centrifugation, and the viral particles are concentrated by pelleting them using ultracentrifugation or by ultrafiltration. The concentrated suspension of viral particles can be further purified using CsCl gradient centrifugation [2]. A suitable buffer for preparation of the CsCl gradient is TNC (20 mM Tris pH 8.0, 100 mM NaCl, 1 mM $CaCl_2$).

Preferably a well-characterised cell is used for the propagation of rotavirus. Human, bovine and rhesus monkey rotaviruses can be propagated in Vero cells. A suitable Vero cell line (CCL81) can be obtained from the American Type Culture Collection (ATCC).

Similarly, members of the family Reoviridae have been isolated from a wide range of mammals, birds, reptiles, fish, crustaceans, insects, ticks, arachnids, plants and fungi. Culture systems have also been established for other viruses in the family Reoviridae. For instance, Rice ragged stunt virus (RRSV) can be prepared in sufficient amounts from infected rice leaves [7]. C6/36 cells can be used to propagate Banna virus (BAV) [22]. Mouse L-cells, in particular the cell line L929, and murine erythroleukemia (MEL) cells can be used to propagate mammalian reovirus strains type 1 Lang (T1L) and type 3 Dearing (T3D) [5]. Grass carp aquareovirus (GCRV) can be propagated in *Ctenopharyngodon idellus* kidney (CIK) cell culture [8].

Virus particles can typically be recovered from cell supernatants or lysed cells. For examples, any cell debris can be removed by low-speed centrifugation, and viral particles are pelleted from the supernatant using ultracentrifugation. The pellets contain virus particles that can be further purified if needed.

DLP Preparation

Rotavirus DLPs are prepared by removing the outer layer proteins from purified rotavirus particles.

Rotavirus particles can be uncoated by incubating virus particles in the presence of a calcium chelator such as EDTA or EGTA. A suitable buffer for uncoating rotavirus particles contains 20 mM Tris, pH8, 100 mM NaCl and 1 mM EDTA [2]. Rotavirus particles may also be uncoated by heat shock. The resulting DLPs can be purified by banding on two successive preformed CsCl gradients (p=1.25 to 1.50 $g/cm^3$).

The method of choice for removing the outer layer proteins depends on the chosen viral particle. For example, mammalian reovirus particles can be stripped to the core by incubating the particle with α-chymotrypsin (CHT) for two hours at 37° C. [4].

The above methods may be adapted to other viruses in the family Reoviridae depending on the sensitivity of their outer layer proteins to protease treatment or low-calcium conditions.

In some instances, subviral particle can be recovered by lysing the cells that were used to propagate the virus. The subviral particle can then be recovered from the cell lysates, e.g., by a CsCl gradient as described for Banna virus [22].

Alternatively, DLPs or subviral particles may be prepared by recombinantly expressing the relevant viral proteins in one of the expression systems described above. For example, the rotavirus inner shell proteins VP2 and VP6 can be expressed recombinantly to from virus-like particles that resemble DLPs.

Recoating

Recoating of rotavirus DLPs occurs at a pH range including pH 4.5 and 6.5, but is most efficient between pH 5 and 5.5 (preferably pH 5.2). Recoating occurs at temperatures including 4° C. and 37° C., but is more efficient between 4° C. and 30° C. than at 37° C.

The recoating of reoviral core particles can typically be done under conditions that mimic the conditions under which the assembly of the viral particles occurs in the cell. For example, mammalian orthoreovirus core particles can be recoated at 37° C. However, individual parameters such as pH and temperature may require further optimisation for efficient reassembly of viral particles from purified viral cores and recombinantly expressed outer layer proteins.

Recoated virus particles can be recovered by CsCl gradient centrifugation. CsCl gradient purification can be repeated a second time to increase the purity of the recovered virus particles.

Where an adapter system is used to display a heterologous protein on the surface of a recoated rotavirus particle, the rotavirus DLPs can be recoated with a rotavirus surface protein comprising a first adapter polypeptide. The heterologous protein comprising a second adapter polypeptide, which forms a stable complex with the first adapter polypeptide, can subsequently be added to the recoated virus particles. This may be advantageous where recoating with the complex formed by the heterologous protein and the rotavirus surface protein would be less efficient, e.g. due the size of the heterologous protein. Alternatively, a complex between the heterologous protein and the rotavirus surface protein via the adapter polypeptides may be formed first, and this complex may be added to rotavirus DLPs for recoating.

Complex Formation

In some aspects of the invention, the chimeric surface protein is used to study the structure of complexes formed between the heterologous protein which forms part of the chimeric surface protein (e.g. by being non-covalently bound to a rotavirus surface protein via a two-part adapter system) and a molecule that specifically binds to the heterologous protein.

In one aspect of the invention, the molecule is a proteinaceous molecule. The proteinaceous molecule typically is another protein such as a receptor or ligand that interacts with the heterologous protein or an antibody or antibody fragment that recognises an epitope found on the surface of the heterologous protein.

For example, a hexameric complex of a trimeric rotavirus surface protein bound to a trimeric viral cell entry protein (e.g., HIV gp140 or RSV F protein) which is displayed on the surface of a rotavirus particle may be used to study interaction between the viral cell entry protein and its host cell surface receptor.

The optimal conditions for complex formation between the heterologous protein and the proteinaceous molecule depend on the nature of the interaction. Receptor-ligand interactions may require different conditions from antibody-antigen interactions. Typically, complex formation is performed at room temperature in a buffered solution (e.g., phosphate-buffered saline).

In one embodiment, the proteinaceous molecule is added to a suspension of recoated rotavirus particles displaying the chimeric surface protein. The buffered solution may contain additional components such as $Ca^{2+}$ to prevent uncoating of the rotavirus particles and optionally one or more protease inhibitors to block degradation of the proteins. After incubation of the proteinaceous molecule in the presence of the recoated rotavirus particles, the newly formed complexes of the proteinaceous molecules bound to the rotavirus particles can be separated from any unbound proteinaceous molecules by centrifugation or ultrafiltration. However, removal of unbound proteinaceous molecules may not be necessary if the recoated rotavirus particles are used for cryo-EM analysis.

Alternatively, the proteinaceous molecule and the chimeric surface protein are incubated together to allow complex formation to occur. First, the heterologous protein and the rotavirus surface antigen may be incubated together to form the chimeric surface protein. Once the chimeric surface protein has formed, the proteinaceous molecule is added. The complex of the proteinaceous molecule and the chimeric surface protein can then be added to rotavirus DLPs to form rotavirus particles, optionally in the presence of any additional rotavirus proteins that, together with the rotavirus surface protein, form the outer layer of a native rotavirus particle.

In a particular aspect of the invention, the chimeric surface protein of the invention is used to determine the structure of an antigen-antibody complex. In this aspect of the invention, the heterologous protein may be derived from a pathogen such as a virus or a bacterium. For example, an immunodominant antigen may be chosen as the heterologous protein to study which parts of the protein are targeted by antibodies during an immune response against the antigen. Preferably, the heterologous protein is a trimeric viral surface protein such as influenza virus haemagglutinin, respiratory syncytial virus F, or HIV gp140. To determine the structure of an antigen-antibody complex, the use of a Fab fragment in place of the full-length antibody is typically preferred to avoid steric hindrance between neighbouring chimeric surface proteins and to guarantee maximal occupancy of the epitope found on the heterologous protein.

In another aspect of the invention, complex formation between a heterologous protein and a non-proteinaceous molecule may be studied. A non-proteinaceous molecule may be a nucleic acid (e.g., RNA or DNA), a polysaccharide or oligosaccharide (e.g., a glycan). For example, the heterologous protein may be a transcription factor or other DNA-binding protein that forms a complex with a specific DNA sequence. Alternatively, the heterologous protein may be a lectin that forms a complex with a glycan.

Cryo-EM

Using cryo-EM for structure determination has several advantages over more traditional approaches such as X-ray crystallography. In particular, cryo-EM places less stringent requirements on the sample to be analysed with regard to purity, homogeneity and quantity. Importantly, cryo-EM can be applied to targets that do not form suitable crystals for structure determination.

A suspension of purified or unpurified recoated rotavirus particles, either alone or in complex with a proteinaceous molecule such as an antibody or non-proteinaceous molecule such as a nucleic acid, can be applied to carbon grids for imaging by cryo-EM. The coated grids are flash-frozen, usually in liquid ethane, to preserve the particles in the suspension in a frozen-hydrated state. Larger particles can be vitrified by cryofixation. The vitrified sample can be cut in thin sections (typically 40 to 200 nm thick) in a cryo-ultramicrotome, and the sections can be placed on electron microscope grids for imaging.

The quality of the data obtained from images can be improved by using parallel illumination and better microscope alignment to obtain resolutions as high as ~3.3 Å. At such a high resolution, ab initio model building of full-atom structures is possible. However, lower resolution imaging might be sufficient where structural data at atomic resolution on the chosen or a closely related rotavirus particle and the selected heterologous protein or a close homologue are available for constrained comparative modelling (see below).

To further improve the data quality, the microscope can be carefully aligned to reveal visible contrast transfer function (CTF) rings beyond ⅓ $Å^{-1}$ in the Fourier transform of carbon film images recorded under the same conditions used for imaging. The defocus values for each micrograph can then be determined using software such as CTFFIND [23]. Final pixel size of the density map can be calibrated using, e.g., Tobacco Mosaic Virus (TMV).

Useful descriptions of applying cryo-EM to structural studies of rotavirus particles are found in references 24 and 25.

Image Analysis and Structure Determination

Images obtained by cryo-EM are analysed to identify micrographs of single particles. Single particle selection can be done with the help of software tools such as SIGNATURE [26]. The astigmatic defocus, specimen tilt axis, and tilt angle for each micrograph can be determined using the computer programme CTFTILT [23]. Obtaining separate defocus values for each particle according to its coordinate in the original image improves the data quality of the cryo-EM density map which is obtained by averaging single-particle micrographs of rotavirus particles.

Fitting of known atomic models within a cryo-EM density map is a common approach for building models of complex structures such as viral particles. A number of computational fitting tools are available which range from simple rigid-body localization of protein structures, such as Situs [27], Foldhunter [28] and Mod-EM [29], to complex and dynamic flexible fitting algorithms like NMFF [30], Flex-EM [31], MDFF [32] and DireX [33, 34], which morph known structures to a density map.

When an atomic model is not known, cryo-EM density maps can be used in building and/or evaluating structural models from a gallery of potential models that are constructed in silico (see references 29, 35, 36, 37 and 38). A related template structure must be known for constrained comparative modelling or, for constrained ab initio modelling, the fold to be modelled must be relatively small. For example, an initial structure may be obtained using IMIRS [39]. Further alignment and reconstruction can be performed with FREALIGN [40] using a known rotavirus structure and a known structure of the heterologous protein or a close homologue as template.

Significant structural and functional information can be obtained directly from the density map itself. For example, at 5-10 Å resolutions, some secondary structure elements are visible in cryo-EM density maps: α-helices appear as cylinders, while β-sheets appear as thin, curved plates. These secondary structure elements can be reliably identified and quantified using feature recognition tools to describe a protein structure or infer the function of individual proteins. At near-atomic resolutions (3-5 Å), the pitch of α-helices, separation of β-strands, as well as the densities that connect them, can be visualized unambiguously (see, e.g., references 41, 42, 43 and 44).

De novo model building in cryo-EM comprises feature recognition, sequence analysis, secondary structure element correspondence, Cα placement and model optimisation. Various software applications can be used, e.g., EMAN for density map segmentation and manipulation [45], SSE-Hunter [46] to detect secondary structure elements, visualization in UCSF's Chimera [47] and atom manipulation in Coot [48,49].

Secondary structure identification programs like SSE-Hunter provide a semi-automated mechanism for detecting and displaying visually observable secondary structure elements in a density map [46]. Registration of secondary structure elements in the sequence and structure, combined with geometric and biophysical information, can be used to anchor the protein backbone in the density map [41, 43]. This sequence-to-structure correspondence relates the observed secondary structure elements in the density to those predicted in the sequence. The modelling toolkit GORGON couples sequence-based secondary structure prediction with feature detection and geometric modelling techniques to generate initial protein backbone models [50]. Automatic modelling methods such as EM-IMO (electron microscopy-iterative modular optimization) can be used for building, modifying and refining local structures of protein models using cryo-EM maps as a constraint [51].

Once a correspondence has been determined using secondary structure element, Cα atoms can be assigned to the density beginning with α-helices and followed by β-strands and loops. For example, by taking advantage of clear bumps for Cα atoms, Cα models can be built using the Baton build utility in the crystallographic programs O [52] and/or Coot [48]. Cα positions can be interactively adjusted such that they fit the density optimally while maintaining reasonable geometries and eliminating clashes within the model. Coarse full-atom models can be refined in a pseudocrystallographic manner using CNS [53]. Models can be further optimized using computational modeling software such as Rosetta [36]. Full-atom models can also be built with the help of other computational tools such as REMO [54]. The quality of a model can be confirmed by visual comparison of the model with the density map. Pseudocrystallographic R factor/Rfree analysis [55] provides a measure of the agreement between observed and computed structure factor amplitudes and may be used to confirm that the obtained atomic model provides a good fit to the cryo-EM density maps. Protein model geometry can be checked by PROCHECK [56].

Screening Methods for Immunogen Design

Using cryo-EM in place of X-ray crystallography facilitates rapid structure determination. In comparison to X-ray crystallography, cryo-EM places less stringent requirements on the purity, homogeneity and quantity of the sample to be analysed. These characteristics make cryo-EM attractive in the context of immunogen design for vaccines, particularly against pathogens that are subject to antigenic drift.

Having more structural information especially about epitopes shared by variants of the same pathogen or closely related pathogens may allow the rational design of immunogens, which can be used in vaccines that provide broad protection against a large number of variants of the same pathogen or closely related pathogens. Such so-called "universal" vaccines are believed to be more cost-effective than traditional vaccines because they would make it superfluous to include various variants of the same pathogen or closely related pathogens in the same vaccine composition (as is the case, e.g., for currently available polio vaccines as well as for streptococcal and meningococcal conjugate vaccines) or to provide new vaccine compositions each year to account for the antigenic drift that occurred in the pathogen population in the previous season (as is the case for influenza vaccines).

Rational design of an immunogen for vaccination against a diverse pathogen involves identification of those regions of an immunodominant protein that are conserved among various variants/subtypes of the same pathogen or among closely related pathogens. The use of rotavirus particles for displaying heterologous proteins on chimeric rotavirus surface proteins makes it possible to rapidly determine a large number of structures in a relatively short time. Therefore the methods of the invention may be particularly useful in the identification of conserved epitopes of immunogenic proteins.

By determining the structure of immunogens in complex with antibodies or corresponding antigen-binding fragments that have been found to be elicited against a number of variants/subtypes of the same pathogen and/or against closely related pathogens, conserved regions in the immunodominant immunogen of this pathogen and/or closely related pathogens can be identified. In one embodiment, the invention therefore relates to a method for obtaining a three-dimensional model of an immunogen complexed to an antibody wherein said method comprises the steps of (i) recoating a rotavirus DLP with a chimeric surface protein comprising the immunogen to yield a suspension of rotavirus particles displaying the chimeric surface protein, (ii) adding to the suspension an antibody or antibody fragment that specifically binds to the immunogen, wherein the antibody or fragment forms a complex with the chimeric surface protein, (iii) freezing the suspension, (iv) imaging the rotavirus particles using cryo-EM to obtain a plurality of micrographs, and (vi) analysing the plurality of micrographs to obtain a three-dimensional model of the immunogen complexed to the antibody. The immunogen is typically heterologous to the rotavirus particle. The three-dimensional model of the immunogen complexed to the antibody can be used to define the epitope on the surface of the immunogen which is recognised by the antibody.

This method can be used to identify the epitope bound by an antibody that has broadly neutralising activity against a number of related pathogens or variants of a pathogen which arise due to antigenic drift. Alternatively, this method can be used to identify the epitope bound by an antibody that may recognise an epitope that interferes e.g. with the function of a viral cell entry protein and may be used to prevent or inhibit virus propagation. An antibody that binds to a specific three-dimensional configuration of a protein may also be useful as a quality control reagent during manufacturing of the protein, e.g. to exclude lots of a manufactured protein that contain a large number of denatured or misfolded copies of this protein. This method may further be employed to identify epitopes that are particularly useful when bound by an antibody that is used as diagnostic reagent (e.g. epitopes that are specific to a particular pathogen in a group of closely related pathogens).

By repeating the method for obtaining a three-dimensional model of an immunogen complexed to an antibody for a panel of antibodies or their corresponding antigen-binding fragments which have been found to be elicited in response to infection by a number of variants/subtypes of the same pathogen and/or against closely related pathogens, the epitope of each antibody on the surface of the immunogen can be identified. Once the epitope of each antibody in the panel has been identified, this information can be used for the rational design of an immunogen. For examples, the method may be used to identify the epitopes of a panel of antibodies which have been found to have neutralising activity against a number of variants/subtypes of the same pathogen and/or against closely related pathogens to design an immunogen that provides broad neutralising activity against a large number of variants/subtypes of the same pathogen and/or closely related pathogens.

Alternatively, the method described above can be employed to map the repertoire of epitopes recognised by antibodies that are elicited in response to immunisation with an existing vaccine. By mapping the eptitopes most commonly recognised by these antibodies, immunodominant epitopes can be identified. This information can be used advantageously to further optimise an existing vaccine. For example, where an existing vaccine is composed of an inactivated pathogen, an optimised version of the vaccine may only include the immunodominant portions of said pathogen (e.g., in form of a subunit vaccine that comprises recombinant versions of the identified immunodominant antigens or epitopes). Understanding of the structural determinants of immunodominant antibody epitopes, obtained using these technique, can be applied to prepare antigens that have been engineered to make the most useful epitopes (such as broadly neutralizing epitopes) immunodominant Examples of epitope mapping to aid in immunogen design are known in the art but generally have been limited to a small number of epitopes on an immunogen because of the efforts involved in getting structural data for immunogen-antibody complexes by X-ray crystallography. Often only a single antibody is tested (see references 57, 58 and 59). The present invention for the first time allows obtaining structural information for immunogen-antibody complexes using a high-throughput approach. The invention is particularly useful for antibodies that only weakly associate with the immunogen and thus present major challenges for crystallization.

Various approaches to design immunogens that are broadly protective against a number of variants of the same pathogen or closely related pathogens are known in the art. In recent years, many efforts have been made to design "universal" vaccines against influenza virus and HIV (see references 60, 61 and 62) Rational design of a modified immunogen has been hampered by the lack of structural data to guide the process. The use of rotavirus particles for displaying heterologous proteins on chimeric rotavirus surface proteins makes it possible to rapidly determine how modifications of the amino acid sequence of a protein affect its three dimensional structure Amino acid modifications that change the structure of a protein may affect its ability to form crystals. Thus, structural information for assessing the impact of these modifications may not easily be available because the modified protein may not crystalize under the same conditions as the unmodified protein. Since the use of cryo-EM does not rely on the formation of crystals for the determination of protein structures and, in addition, does not require any adaptation of the basic experimental set-up for different types of proteins, the rapid structural characterisation of modified proteins is possible.

Once an epitope on an immunogenic protein of a pathogen has been identified that is present in a number of variants/subtypes of the same pathogen and/or in many closely related pathogens, this information can be used to design a universal vaccine. In some instances, this may require modification of the immunogen, particularly where a conserved region which comprises a shared epitope is not easily accessible to antibodies in the native protein, as poor accessibility of the epitope usually translates into poor immunogenicity. By modifying the immunogen in such a way that it retains the native epitope which can be recognised by an antibody, but making the epitope more accessible, the modified immunogen may yield an antibody response that is protective against a wide range of variants/subtypes of the same pathogen or of closely related pathogens. In additional to mapping the epitopes of affinity matured antibodies, the epitopes recognized by the un-mutated ancestors of these antibodies, once deduced from B-cell repertoire cloning experiments, can be mapped by this technique. This information could aid in the design of immunogens that selectively amplify a desired un-mutated ancestral antibody and then direct its affinity maturation to a broadly and potently neutralizing antibody.

Candidate immunogens that have been modified from a native immunogen (be it in order to prepare a universal vaccine or for other reasons) can be tested for the presence of a native epitope of interest using the methods of the invention. In a particular embodiment, the invention therefore further relates to a method for determining the structural differences between two variants of a heterologous protein, wherein the method comprises the steps of (i) recoating a rotavirus DLP with a first chimeric surface protein comprising a first variant of the heterologous protein to yield a suspension of a first rotavirus particle displaying the first chimeric surface protein, (ii) freezing the suspension, (iii) imaging the first rotavirus particle using cryo-EM to obtain a plurality of micrographs, (iv) analysing the plurality of micrographs to obtain a three-dimensional model of the first chimeric surface protein, (v) repeating steps (i)-(iv) with a second chimeric surface protein comprising a second variant of the heterologous protein, wherein the first and second chimeric surface protein are identical to each other apart from the difference between the first variant and the second variant, and (vi) comparing the three-dimensional model of the first chimeric surface protein to the three dimensional model of the second chimeric surface protein to determine the structural differences between the first variant and the second variant of the heterologous protein. This method can be repeated for further variants of the same heterologous protein to provide a screening assay for the identification of a variant with certain desired structural characteristics.

In some instances, the structures of the native immunogen and of a plurality of modified immunogens each in complex with an antibody recognising an epitope may be determined Comparing the structure of the modified immunogens to the native immunogen will assist in selecting candidate immunogens that best preserve the native epitope for further testing in vivo.

Immunogenic Compositions

In a further aspect, the present invention relates to the use of rotavirus particles comprising the chimeric surface protein of the invention in the preparation of a medicament. In particular, rotavirus particles comprising the chimeric surface protein of the invention may be used in immunogenic compositions suitable for human vaccination. For example, the chimeric surface protein can be designed to display a heterologous protein that elicits a protective immune response when administered to a patient.

The use of chimeric viruses to elicit an immune response to a pathogen-derived antigen is well-known in the art. Traditionally, this approach requires the reengineering of the genome of the host virus that is selected as a vector for the pathogen-derived antigen. Such an approach has a number of limitations. Typically, the virus genome is modified to contain a pathogen-derived gene encoding the antigen. The genome size of the chosen virus therefore may limit the size of the pathogen-derived antigen which can be expressed. Similarly, the insertion of a gene encoding the pathogen-derived antigen may interfere with the propagation of the virus and limit the yields that can be achieved. Therefore preparation of chimeric viruses needs to be optimised for each pathogen-derived antigen.

Creating a chimeric virus with a new surface protein using recombinant genetics to alter the genome of the host virus by inserting a coding region for a pathogen-derived antigen could potentially change the host range of the chimeric virus and therefore have unforeseeable consequences on the pathogenicity of the newly created virus. Therefore additional steps have to be taken to provide a sufficiently attenuated chimeric virus that is not able to replicate in the subject to be vaccinated.

The present invention overcomes the problems associated with the traditional approach because it allows the preparation of any kind of chimeric surface protein that can be used to recoat rotavirus DLPs. The recoated rotavirus particles do not contain any genetic information for the pathogen-derived antigen. Thus after the initial infection of a host cell with the recoated rotavirus particles, no progeny viruses are formed that carry the pathogen-derived antigen.

The use of a two-part adapter system further reduces the number of optimisation steps. Once a modified rotavirus protein fused to a first adapter polypeptide has been prepared, any known pathogen-derived antigen can be fused to a second adapter polypeptide that forms a stable complex with the first adapter polypeptide. This eliminates any need for genetic engineering of the rotavirus. In most cases, expression and purification of the pathogen-derived antigen is not affected by the presence of the second adapter polypeptide in the pathogen-derived antigen, so that no modification of existing expression and purification methods for the antigen is required. Existing protocols to recoat rotavirus DLPs with a chimeric surface protein comprising the modified rotavirus protein linked to the pathogen-derived antigen via the two-part adapter system can be used to prepare rotavirus particles comprising the chimeric surface protein. These rotavirus particles can then be included in immunogenic compositions to elicit an immune response against the pathogen-derived antigen.

The vaccine platform is particularly useful preparing immunogenic compositions in which the rotavirus particles comprise a trimeric chimeric surface protein that contains a heterologous trimeric viral cell entry protein. Trimeric viral cell entry proteins are the immunodominant surface antigens of many viruses. With the exceptions of hepatitis B surface antigen and human papilloma virus L1 protein, both of which form virus-like particles, and influenza HA, which forms rosettes, subunit vaccines based on immunodominant viral surface antigens have typically failed to result in clinically effective vaccines. By displaying these viral surface antigens in their native conformation on rotavirus particles, immunogenic compositions can be prepared that elicit a protective immune response against the virus from which the surface antigen was originally derived.

Specific examples of trimeric viral cell entry protein include influenza HA, HIV gp140, the Ebola virus glycoprotein, rabies virus glycoprotein, the Env protein of caprine arthritis encephalitis virus, the RSV F protein, the gB and optionally its complex with other proteins of human herpes simplex viruses and of HCMV.

Rotavirus Particles

Rotaviruses are particularly useful because various animal strains exist that have a defined host range. For example, some strains are specific for cows and others for monkeys. Most animal strains are antigenically distinct from those strains that typically infect humans and therefore are mostly unable to cause disease in humans. Therefore humans typically do not have any pre-existing immunity to these rotavirus strains that could interfere with an immune response against the chimeric surface protein when these animal strains are used as vectors in immunogenic compositions for human vaccination. In addition, these viruses are naturally attenuated in humans.

In addition, two licensed live, attenuated rotavirus vaccines are currently marketed: Rotarix™ and RotaTeq™. Rotarix™ contains the attenuated human rotavirus strain RIX4414, which passaged 26 times in Primary Green Monkey Kidney cells (AGMK) and is propagated in Vero cells. RotaTeq™ contains a combination of five human rotavirus (HRV)-bovine rotavirus (BRV) reassortant strains, designated as G1, G2, G3, G4, and P1, respectively, which are also propagated in Vero cells. All reassortants are composed of the BRV strain WC3 (G6P7[5]) genome background expressing human VP7 or VP4 proteins.

The previously licensed rhesus rotavirus (RRV)-based vaccine RotaShield™ consists of RRV (G3P5B[3]) and 3 RRV-HRV reassortant rotaviruses. Each reassortant derives 10 genes from RRV and a single HRV gene encoding a VP7 protein for G serotype 1, 2, or 4 specificity (G1P5B[3], G2P5B[3], and G4P5B[3]).

Furthermore, safety of monovalent bovine (NCDV RIT4237 G6P6) and simian (RRV strain MMU18006 G3P5B) rotavirus strains for use as vaccines has been established.

The immunisation, clinical safety and manufacturing experience with these vaccine strains can be directly applied to the rotavirus particles of the invention. For example, any one of the rotaviruses contained in the licensed rotavirus vaccines could be used to prepare DLPs for recoating with the chimeric surface protein of the invention.

Preparation

The modified rotavirus particles included in the immunogenic compositions can be prepared using any of the methods described above. Native rotavirus particles may be propagated and purified. The purified rotavirus particles may then be uncoated to prepare DLPs which can then be recoated with a chimeric surface protein comprising a pathogen-derived antigen.

Typically, a modified rotavirus protein fused to a first adapter polypeptide is added to the DLPs to form rotavirus particles. The addition of further rotavirus proteins that, together with the rotavirus surface protein, form the outer layer of a native rotavirus particle is optional. The rotavirus particles are then incubated with a pathogen-derived antigen fused to a second adapter polypeptide which forms a stable complex with the first adapter polypeptide to provide the chimeric surface protein.

Formulations

The immunogenic composition of the invention may be provided in form of a kit comprising a first container comprising lyophilised rotavirus particles and a second container comprising a solution for extemporaneous resuspension of the lyophilised rotavirus particles. Lyophilised rotavirus particles may comprise one or more lyoprotectant such as sucrose, dextran, sorbitol and amino acids to stabilise the rotavirus particles during lyophilisation.

Alternatively, the immunogenic composition is provided in a single container comprising the rotavirus particles in suspension. Where the immunogenic composition is for injection, it may be provided in a syringe.

Either solution may contain one or more excipient(s).

The solutions are typically water-based. Therefore purified water may form the main excipient. For example, dilution of the rotavirus particles to give the desired final concentration will usually be performed with water for injection (WFI).

The solution typically contains a buffer. Therefore further excipients include buffering agents and pH regulators such as sodium citrate, sodium dihydrogen phosphate monohydrate, and sodium hydroxide. Antacids such as calcium carbonate may be added to prevent inactivation of the virus during passage through the stomach if the immunogenic composition is administered orally. An acidity regulator such as di-sodium adipate may also be included, preferably in place of the antacid.

In some instances, a thickening agent such as xanthan may be present as a further excipient.

A surfactant, in particular a non-ionic surfactant such as polysorbate 80, may also be present.

Other excipients include sucrose, sorbitol, inorganic salts, amino acids and vitamins.

Compositions will generally have an osmolality of between 200 mOsm/kg and 400 mOsm/kg, preferably between 240-360 mOsm/kg, and will more preferably fall within the range of 280-320 mOsm/kg.

The pH of a composition of the invention will generally be between 5.0 and 7.5, and more typically between 5.0 and 6.0 for optimum stability.

Compositions of the invention preferably contain <1 EU (endotoxin unit, a standard measure; 1 EU is equal to 0.2 ng FDA reference standard Endotoxin EC 2 'RSE') per dose, and preferably <0.1 EU per dose.

Compositions of the invention are preferably gluten-free. Furthermore, compositions of the invention are preferably sterile.

Administration

The immunogenic compositions may be used to stimulate a mucosal immune response. Therefore the immunogenic compositions may be administered orally or intratracheally. Other routes of administration such as intramuscular injection may be chosen depending on the pathogen-derived antigen displayed on the surface of the modified rotavirus particle included in the immunogenic composition of the invention.

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x means, for example, x±10% or x+two standard deviations of the value. In certain embodiments, "about" is understood as acceptable variation and tolerances within the specific art. Unless clear from context, all numerical terms herein are understood to be modified by about. The term "antibody" includes antibody fragments such as antigen-binding fragments (Fabs), single-chain variable fragments (scFv), etc. The term "antigen-binding portion" of an antibody (or "antibody portion") includes fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment [63], which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g. references 64 and 65. Such single chain antibodies are also intended to be encompassed within the term "antigen-binding portion" of an antibody.

As use herein, "or" is understood to be inclusive and is interchangeable with "and/or" unless otherwise clearly indicated by context.

As used herein, "a" and "the" are understood to include both singular and plural unless otherwise clearly indicated by context.

Unless specifically stated, a process comprising a step of mixing two or more components does not require any specific order of mixing. Thus components can be mixed in any order. Where there are three components then two components can be combined with each other, and then the combination may be combined with the third component, etc.

Where animal (and particularly bovine) materials are used in the culture of cells for preparation of material for administration to animals, especially humans, they should be obtained from sources that are free from transmissible spongiform encaphalopathies (TSEs), and in particular free from bovine spongiform encephalopathy (BSE). Overall, when products are prepared for administration to animals, and especially humans, it is preferred to culture cells in the total absence of animal-derived materials.

Where a cell substrate is used for reassortment or reverse genetics procedures, it is preferably one that has been approved for use in human vaccine production e.g. as in Ph Eur general chapter 5.2.3 [66].

Identity between polypeptide sequences is preferably determined by the Smith-Waterman homology search algorithm as implemented in the MPSRCH program (Oxford Molecular), using an affine gap search with parameters gap open penalty=12 and gap extension penalty=1.

DESCRIPTION OF THE DRAWINGS

FIG. 2: Schematic overview of the complex formed by a modified trimeric rotavirus VP7 protein and a trimeric heterologous protein. The rotavirus VP7 protein is non-covalently bound to the heterologous protein via a two-part adapter system, where one part of the adapter system (HR2) is linked to the rotavirus VP7 protein and the other part of the adapter system (HR1) is linked to the heterologous protein. HR1 and HR2 form a six-helix bundle resulting in a stable complex for non-covalently attaching the heterologous protein to the rotavirus VP7 protein. The chimeric surface protein can become part of the outer layer of the rotavirus particle by in vitro recoating DLPs.

FIG. 3: Electron micrographs of (A) purified DLPs, (B) DLPs recoated with rotavirus VP7 protein and (C) DLPs recoated with VP7 protein displaying influenza virus HA as the heterologous protein. The particles were negatively stained prior to image acquisition.

FIG. 5: Cross-section through a three-dimensional reconstruction of rotavirus DLP recoated with a modified VP7 protein (A) displaying HA, (B) displaying HA with bound ScFv fragments of antibody CR6261, and (C) displaying HA with bound Fab fragments of antibody CR6261. CR6261 recognizes a highly conserved helical region in the membrane-proximal stem of HA1/HA2. The reconstruction is based on images acquired by performing cryo-EM on recoated DLPs.

MODES FOR CARRYING OUT THE INVENTION

Figure 1:
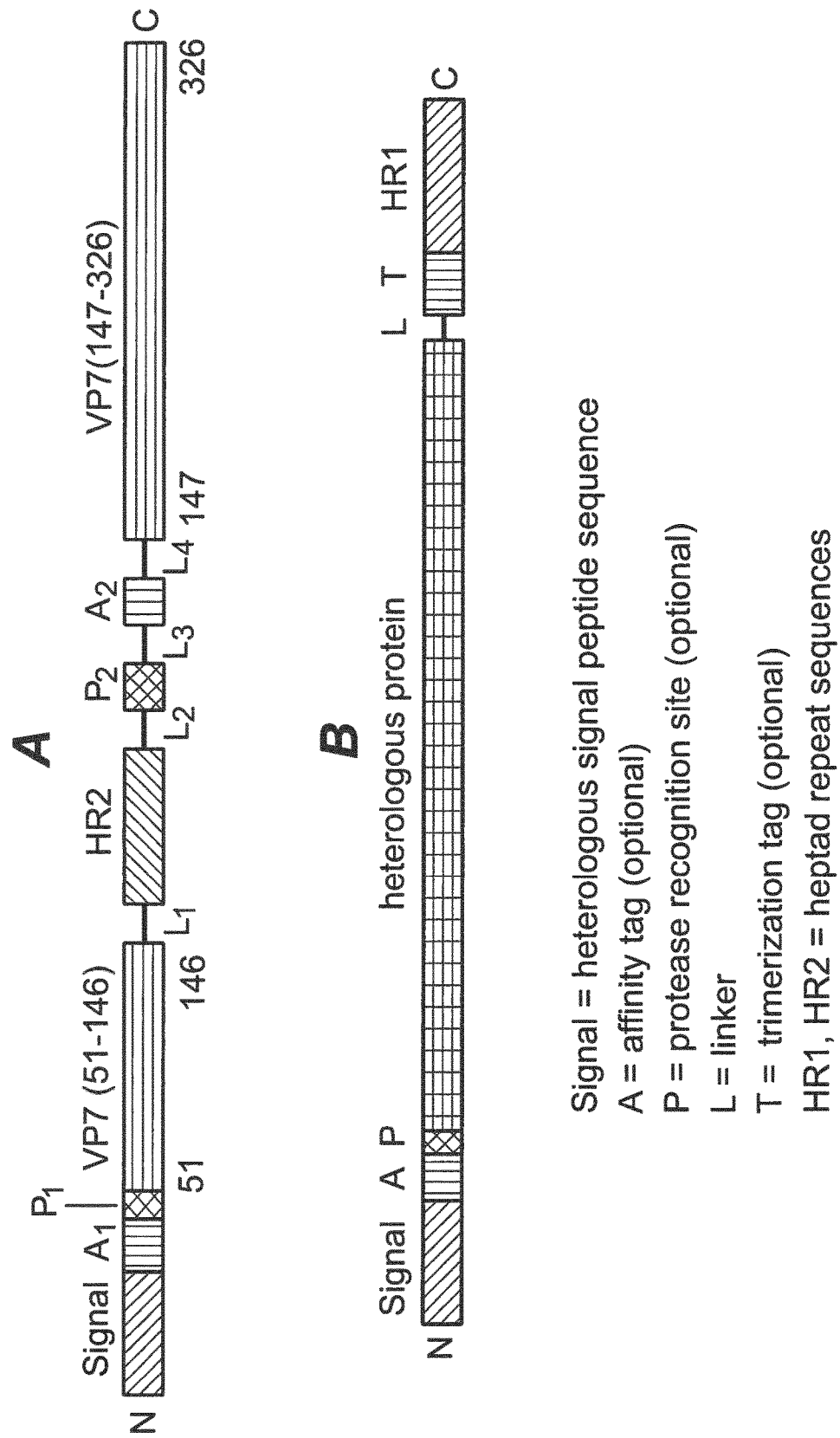
FIG. 1: Schematic overview of modifications made to (A) the rotavirus VP7 protein and (B) the heterologous protein. HR1 and HR2 form part of a two-part adapter system for non-covalently binding the heterologous protein to the rotavirus VP7 protein. The heterologous signal peptide sequences serve the purpose of achieving high expression levels in the chosen expression systems. The affinity tags allow easy purification. Protease recognition site $P_1$ can be used to remove the affinity tag $A_1$ after purification. The second set of affinity and protease recognition sites ($A_2$ and $P_2$) can be replaced by suitable linker sequences and may serve as a spacer sequence that may be needed to display large heterologous protein. The trimerization tag is optional and can be used in aiding in trimer formation of some heterologous proteins which then facilitates binding to the trimeric rotavirus VP7 protein. The trimerization tag, particularly coiled-coil based trimerization tags (e.g. GCN4), can also serve as structural modules to extend the space available for a heterologous protein which is displayed on the surface of a rotavirus particle recoated with a modified rotavirus VP7 protein.
Figure 4A:
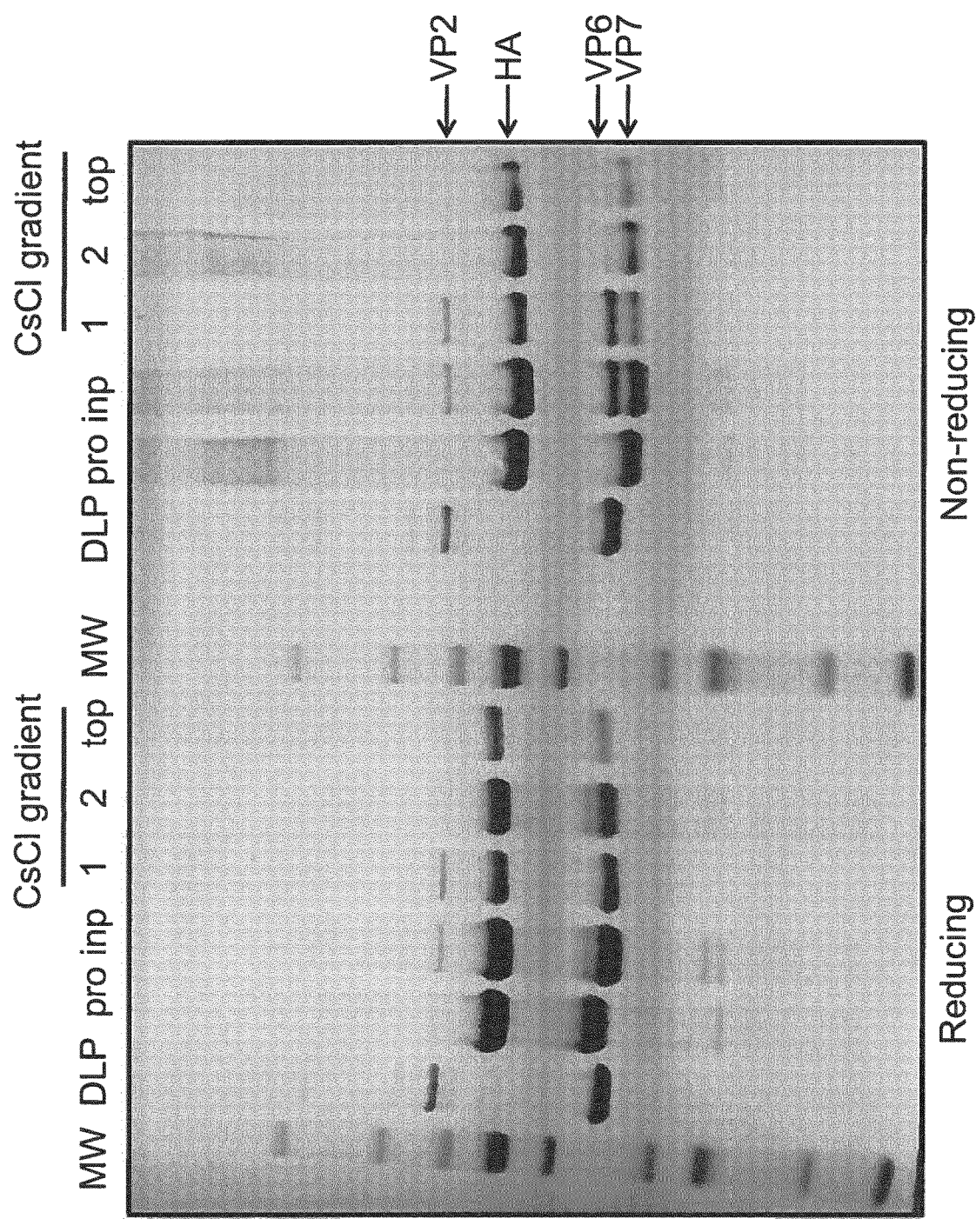
FIG. 4: (A) Coomassie-stained acrylamide gel after SDS-PAGE. Lane 1 shows the molecular weight marker (MW). Lane 2 was loaded with the purified DLPs used in the recoating reaction (DLP). Lane 3 was loaded with the purified VP7-HA protein complex (pro) used for recoating the DLPs. Lane 4 was loaded with the input mixture of DLPs, modified VP7 protein and HA protein for the recoating reaction (inp). Lanes 5-7 was loaded with the bands observed after purification of the recoated particles on a CsCl gradient (bands 1 and 2 and top band). Lanes 8-14 are loaded with the same samples in the same order as lanes 1-7, but no reducing agent was added to the samples prior to SDS-PAGE. (B) Rotavirus DLPs recoated with the VP7-HA protein complex on a CsCl gradient. Bands 1 and 2 and top band correspond to the samples loaded on lanes 5-7 in panel A. The positions where recoated particles and DLPs would typically migrate are indicated by dotted arrows.
Figure 4B:
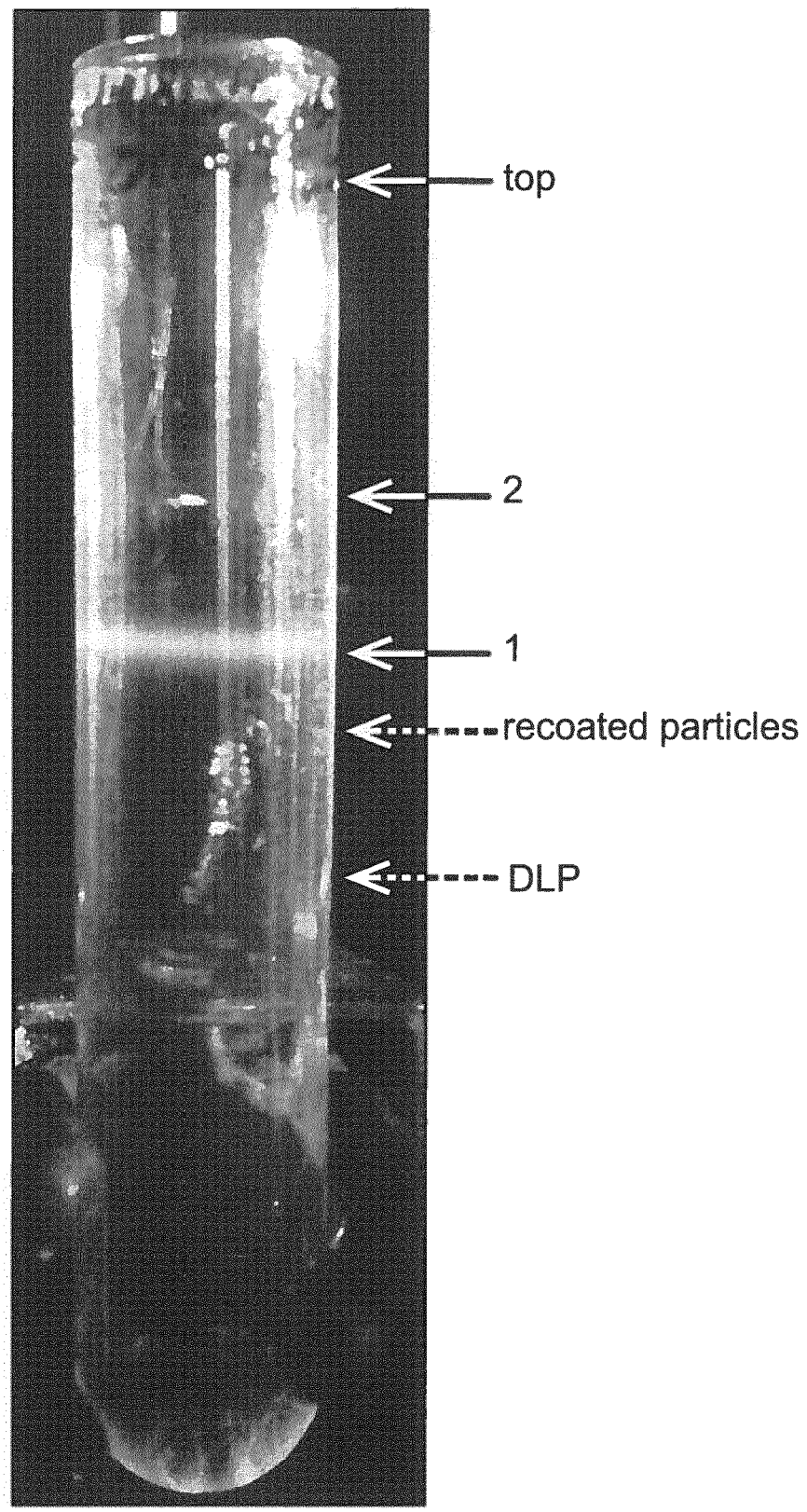

Example 1: Construction of Expression Vector for Modified Recombinant VP7, HA and HIV Gp140 Proteins The wild type VP7 gene of rhesus rotavirus (RRV) G3 strain was cloned into a pFastBacDual vector (Invitrogen™) between the BamH I and Not I restriction sites via standard procedures. A Kozak sequence (GCCACC; SEQ ID NO: 19) was designed at the 5' end before the start codon of the VP7 coding sequence. Modifications of the VP7 coding sequence were carried out by inverted PCR. Primers of appropriate annealing temperatures were designed containing the relevant modifications at the ends of the primers. FIG. 1A shows the various modifications that were added to the rotavirus coding sequence.

The final protein encoded by the modified VP7 coding sequence has the following features: The first 21 amino acids encode the honeybee melittin signal sequence for expression of the modified protein in insect cells. The VP7 protein signal peptide has been removed. Other signal sequences can be used as appropriate, such as the HIV consensus signal sequence or the signal peptide of human tissue plasminogen activator (htPA) for expression in human cells. (b) Amino acid residues 22 to 33 form an optional affinity tag (Strep-tag II plus a linker for more efficient signal peptide cleavage) for protein purification purposes and can be replaced by any other affinity tags, such as His-tag, HA-tag, FLAG-tag, etc. (c) Amino acid residues 34 to 40 form a TEV protease recognition sequence for cleavage of the affinity tag and can be replaced by the recognition sequences of any other proteases, such as PreScission™ protease (i.e. Rhinovirus 3C protease), factor Xa, enterokinase, thrombin, furin, etc. (d) Amino acid residues 41 to 136 are the sequences of rhesus rotavirus VP7 N-terminal portion (VP7 amino acid residues 51 to 146). (e) Amino acid residue 137 is a one-amino acid linker and could be replaced by another appropriate linker sequence. (f) Amino acid residues 138 to 165 are part of the C-heptad repeat of HIV gp41 HXB2 strain and could be replaced by a heptad repeat sequences from another retrovirus, paramyxovirus, etc. as long as replacement sequence is compatible to the heptad repeat sequences used in the modified HA or gp140 protein constructs (see below). (g) Amino acid residues 166 to 187 are a factor Xa protease recognition sequence followed by a protein C-tag flanked by linkers; this modification is optional and could be replaced by other sequences, such as a designed epitope or simply a linker sequence such as GGSGGSGGSGGSGGS (SEQ ID NO: 20) or GGSGGSGGSGGSGGSGG (SEQ ID NO: 21). Presenting an epitope can be useful for packing antibody fragments recognising the epitope to further stabilise the displayed assemblies (including the heterologous protein) for the purpose of structural studies. Like I said, designing for structural studies is way more complex than designing for presenting antigens. (h) Amino acid residues 188 to 367 are the C-terminal portion of rhesus rotavirus VP7 (VP7 amino acid residues 147 to 326). The modified VP7 protein encoded by this modified coding sequence has the amino acid sequence of SEQ ID NO: 22.

Alternative constructs were prepared containing some of the modifications described in the preceding paragraph. For example, some of these constructs include an additional epitope tag which is recognised by anti-HIV antibody 2F5 (e.g. SEQ ID NO: 29 and 31). In other constructs, the C-heptad repeat of the HIV gp41 HXB2 strain was replaced with the C-heptad repeat of Nipah virus (e.g. SEQ ID NO: 32-41).

The length of heptad repeat sequence was varied in some constructs (e.g. SEQ ID NO: 27 and 28). Similarly, the linker connecting the C-heptad repeat sequence and the remainder of the VP7 protein coding sequence was shortened in some of the constructs (see e.g. SEQ ID NO: 24-26) The different variants are summarised in Table 1. The modified VP7 protein sequence of SEQ ID NO: 22 is included as reference sequence. The sequences in Table 1 are shown from N-terminus to C-terminus.

TABLE 1

| Description of construct | Sequence |
| --- | --- |
| signal (honeybee melittin)-linker1 (EDSA)-strep tag II-TEV-VP7 (51-146)-linker 2 (G)-HR2 (HIV, 28 a.a.)-linker 3 (Factor Xa-linker 3a (SGG)-Protein C tag-linker 3b (SGG))-VP7 (147-326) | SEQ ID NO: 22 |
| signal (honeybee melittin)-linker1 (EDSA)-strep tag II-TEV-VP7 (51-146)-linker 2 (G)-HR2 (HIV, 28 a.a.)-linker 3 (Factor Xa-linker 3a (SGG)-Protein C tag-linker 3b (G))-VP7 (147-326) | SEQ ID NO: 23 |
| signal (honeybee melittin)-linker1 (EDSA)-strep tag II-TEV-VP7 (51-146)-linker 2 (G)-HR2 (HIV, 28 a.a.)-linker 3 (linker 3a (SGG)-Protein C tag-linker 3b (SGG))-VP7 (147-326) | SEQ ID NO: 24 |
| signal (honeybee melittin)-linker1 (EDSA)-strep tag II-TEV-VP7 (51-146)-linker 2 (G)-HR2 (HIV, 28 a.a.)-linker 3 (linker 3a (SGG)-Protein C tag-linker 3b (G))-VP7 (147-326) | SEQ ID NO: 25 |
| signal (honeybee melittin)-linker1 (EDSA)-strep tag II-TEV-VP7 (51-146)-linker 2 (G)-HR2 (HIV, 28 a.a.)-linker 3 (linker 3a (G)-Protein C tag-linker 3b (G))-VP7 (147-326) | SEQ ID NO: 26 |
| signal (honeybee melittin)-linker1 (EDSA)-strep tag II-TEV-VP7 (51-146)-linker 2 (G)-HR2 (HIV, 42 a.a.)-linker 3 (linker 3a (SGG)-Protein C tag-linker 3b (SGG))-VP7 (147-326) | SEQ ID NO: 27 |
| signal (honeybee melittin)-linker1 (EDSA)-strep tag II-TEV-VP7 (51-146)-linker 2 (G)-HR2 (HIV, 42 a.a.)-linker 3 (linker 3a (G)-Protein C tag-linker 3b (G))-VP7 (147-326) | SEQ ID NO: 28 |
| signal (honeybee melittin)-linker1 (EDSA)-strep tag II-TEV-VP7 (51-146)-linker 2 (G)-HR2 (HIV, 28 a.a.)-linker 3 (linker 3a (G)-HIV antibody 2F5 epitope-linker 3b (SGG)-Protein C tag-linker 3c (SGG))-VP7 (147-326) | SEQ ID NO: 29 |
| signal (honeybee melittin)-linker1 (EDSA)-strep tag II-TEV-VP7 (51-146)-linker 2 (G)-HR2 (HIV, 28 a.a.)-linker 3 (linker 3a (G)-HIV antibody 2F5 epitope-linker 3b (G)-Protein C tag-linker 3c (G))-VP7 (147-326) | SEQ ID NO: 30 |
| signal (honeybee melittin)-linker1 (EDSA)-strep tag II-TEV-VP7 (51-146)-linker 2 (G)-HR2 (HIV, 28 a.a.)-linker 3 (linker 3a (G)-HIV antibody 2F5 epitope-linker 3b (GS)-Factor Xa-linker 3c (SGG)-Protein C tag-linker 3d (SGG))-VP7 (147-326) | SEQ ID NO: 31 |
| signal (honeybee melittin)-linker1 (EDSA)-strep tag II-TEV-VP7 (51-146)-linker 2 (G)-HR2 (Nipah, 30 a.a.)-linker 3 (linker 3a (K)-Factor Xa-linker 3b (SGG)-Protein C tag-linker 3c (SGG))-VP7 (147-326) | SEQ ID NO: 32 |
| signal (honeybee melittin)-linker1 (EDSA)-strep tag II-TEV-VP7 (51-146)-linker 2 (G)-HR2 (Nipah, 30 a.a.)-linker 3 (linker 3a (K)-Factor Xa-linker 3b (SGG)-Protein C tag-linker 3c (G))-VP7 (147-326) | SEQ ID NO: 33 |
| signal (honeybee melittin)-linker1 (EDSA)-strep tag II-TEV-VP7 (51-146)-linker 2 (G)-HR2 (Nipah, 30 a.a.)-linker 3 (linker 3a (SGG)-Protein C tag-linker 3b (SGG))-VP7 (147-326) | SEQ ID NO: 34 |
| signal (honeybee melittin)-linker1 (EDSA)-strep tag II-TEV-VP7 (51-146)-linker 2 (G)-HR2 (Nipah, 30 a.a.)-linker 3 (linker 3a (SGG)-Protein C tag-linker 3b (G))-VP7 (147-326) | SEQ ID NO: 35 |
| signal (honeybee melittin)-linker1 (EDSA)-strep tag II-TEV-VP7 (51-146)-linker 2 (G)-HR2 (Nipah, 30 a.a.)-linker 3 (linker 3a (G)-Protein C tag-linker 3b (G))-VP7 (147-326) | SEQ ID NO: 36 |
| signal (honeybee melittin)-linker1 (EDSA)-strep tag II-TEV-VP7 (51-146)-linker 2 (G)-HR2 (Nipah, 30 a.a.)-linker 3 (HIV antibody 2F5 epitope (14 a.a.)-linker 3a (SGG)-Protein C tag-linker 3b (SGG))-VP7 (147-326) | SEQ ID NO: 37 |

TABLE 1-continued

| Description of construct | Sequence |
|---|---|
| signal (honeybee melittin)-linker1 (EDSA)-strep tag II-TEV-VP7 (51-146)-linker 2 (G)-HR2 (Nipah, 30 a.a.)-linker 3 (HIV antibody 2F5 epitope (14 a.a.)-linker 3a (G)-Protein C tag-linker 3b (G))-VP7 (147-326) | SEQ ID NO: 38 |
| signal (honeybee melittin)-linker1 (EDSA)-strep tag II-TEV-VP7 (51-146)-linker 2 (G)-HR2 (Nipah, 30 a.a.)-linker 3 (linker 3a (G)-HIV antibody 2F5 epitope (9 a.a.)-linker 3b (SGG)-Protein C tag-linker 3c (SGG))-VP7 (147-326) | SEQ ID NO: 39 |
| signal (honeybee melittin)-linker1 (EDSA)-strep tag II-TEV-VP7 (51-146)-linker 2 (G)-HR2 (Nipah, 30 a.a.)-linker 3 (linker 3a (G)-HIV antibody 2F5 epitope (9 a.a.)-linker 3b (G)-Protein C tag-linker 3c (G))-VP7 (147-326) | SEQ ID NO: 40 |
| signal (honeybee melittin)-linker1 (EDSA)-strep tag II-TEV-VP7 (51-146)-linker 2 (G)-HR2 (Nipah, 30 a.a.)-linker 3 (linker 3a (G)-HIV antibody 2F5 epitope (9 a.a.)-linker 3b (GS)-Factor Xa-linker 3c (SGG)-Protein C tag-linker 3d (SGG))-VP7 (147-326) | SEQ ID NO: 41 |
| signal (htPA)-linker1 (EDSA)-strep tag II-TEV-VP7 (51-146)-linker 2 (G)-HR2 (HIV, 28 a.a.)-linker 3 (Factor Xa-linker 3a (SGG)-Protein C tag-linker 3b (SGG))-VP7 (147-326) | SEQ ID NO: 42 |
| signal (htPA)-linker1 (EDSA)-strep tag II-TEV-VP7 (51-146)-linker 2 (G)-HR2 (HIV, 28 a.a.)-linker 3 (linker 3a (G)-Protein C tag-linker 3b (G))-VP7 (147-326) | SEQ ID NO: 43 |
| signal (htPA)-linker1 (EDSA)-strep tag II-TEV-VP7 (51-146)-linker 2 (G)-HR2 (Nipah, 30 a.a.)-linker 3 (linker 3a (K)-Factor Xa-linker 3b (SGG)-Protein C tag-linker 3c (SGG))-VP7 (147-326) | SEQ ID NO: 44 |
| signal (htPA)-linker1 (EDSA)-strep tag II-TEV-VP7 (51-146)-linker 2 (G)-HR2 (Nipah, 30 a.a.)-linker 3 (linker 3a (G)-Protein C tag-linker 3b (G))-VP7 (147-326) | SEQ ID NO: 45 |

DNAs consisting of both the vector and the modified genes were generated by PCR. The PCR products were gel purified and subjected to T4 polynucleotide kinase treatment to generate phosphorylated ends. Blunt end ligation was then carried out for the resulting DNA by incubating the DNA with appropriate amounts of T4 ligase for 2 hours or overnight at room temperature. The ligation products were then treated with Dpn I for 30 minutes at 37° C. before being used to transform DH5α cells via standard protocols.

Typically three to four colonies were picked and overnight cell cultures were grown to prepare plasmid DNA using the Miniprep Kit (Qiagen™). The plasmids were examined by agarose gel electrophoresis and the correct sequences were confirmed by DNA sequencing. Plasmids of correct sequences were used to transform DH10Bac competent cells via standard procedures. Two to three white colonies were selected for each construct and overnight cell cultures were grown for the extraction of recombinant bacmid DNA by isopropanol/ethanol precipitation (Solution I: 15 mM Tris, pH 8.0, 10 mM EDTA, and 100 µg/mL RNase A; Solution II: 0.2 M NaOH and 1% SDA; and Solution III: 3 M potassium acetate, pH 5.5; all filter-sterilized). The purified bacmids were examined by PCR using the M13 primers and the correct DNAs were used to transfect monolayers of sf9 cells in 6-well plates, each well seeded with 1 million cells. P1 viruses were harvested 5 days post transfection and P2 viruses were produced by infecting sf9 cells (density of 1.5~2 million/mL) with 0.05~0.1% P1 viruses. P2 viruses were harvested 5~7 days post infection and were used for protein expression.

The modified VP7 protein constructs described above can be used to display trimer-forming heterologous proteins with correspondingly modified trimer-forming heterologous protein (see FIG. 1B for a schematic overview of suitable modifications). As shown in FIG. 2, the HR2 heptad repeat sequences of the modified VP7 protein and the HR1 heptad repeat sequences of the correspondingly modified trimer-forming heterologous protein form a stable complex via a six-helix bundle which surfaces as an adaptor for non-covalently mounting the heterologous protein on the rotavirus VP7 protein. Influenza A haemagglutinin (HA) protein and the gp140 fusion protein of HIV-1 were chosen as examples for trimer-forming heterologous proteins.

The HA gene of influenza A virus H1N1 Solomon Islands 2006 was cloned into a pFastBac LIC™ vector (Life Technologies™) by means of ligation independent cloning (LIC) method. The pFastBac LIC™ vector was created by inserting a LIC site in a pFastBac1 vector (Invitrogen). A Kozak sequence (SEQ ID NO: 19) was designed at the 5' end of the start codon before the coding sequence. Modification in the coding sequence of the HA gene were introduced by inverted PCR.

The final protein encoded by the modified HA coding sequence has the following features: (a) The first 38 amino acids encode the Baculovirus gp64 signal peptide for expression of the modified protein in insect cells. The HA protein signal peptide has been removed. Other signal sequences can be used as appropriate, such as the HIV consensus signal sequence or the signal peptide of human tPA for expression in human cells. (b) Amino acid residues 42 to 47 form an optional affinity tag (His-tag plus a linker for more efficient signal peptide cleavage) for protein purification purposes and can be replaced by any other affinity tags, such as strep-tag, HA-tag, FLAG-tag, etc. (c) Amino acid residues 48 to 54 form a TEV protease recognition sequence for cleavage of the affinity tag. A linker sequence is also included. The TEV protease recognition sequence can be replaced by the recognition sequence of any other proteases, such as PreScission™ protease (i e Rhinovirus 3C protease, GE Healthcare™, Life Sciences), factor Xa, enterokinase, thrombin, furin, etc. (d) Amino acid residues 55 to 381 are the sequences of the HA1 portion of the hemagglutinin of influenza A Solomon Islands 2006 strain, which could be modified/mutated as appropriate or be replaced by that of any other influenza strains as shown below. (e) Amino acid residues 382 to 386 are the recognition sequence of enterokinase engineered between HA1 and HA2 for cleavage purposes. This site is optional and could be replaced by recognition sequences of Factor Xa, TEV protease, or others as appropriate. (f) Amino acid residues 387 to 565 are the sequence of HA2 portion of HA. (g) Amino acid residues 566 to 595 are a trimerization tag from bacteriophage T4 fibritin (Foldon), which is optional and can be replaced by any other trimerization tag or linker sequences. (h) Amino acid residues 596 to 629 are part of the N-heptad repeat of HIV gp41 HXB2 strain and could be replaced by other suitable heptad repeat sequences e.g. from any other retrovirus, paramyxovirus, etc. The numbering of the HA amino acid sequences used in the description of the modified HA coding sequence is according to GenBank ID ABU50586.1 (incorporated herein by reference in the version available on the date of the filing of the priority application). The amino acid sequence of this construct is shown in SEQ ID NO: 46.

Alternative constructs were prepared containing some of the modifications described in the preceding paragraph. For example, the trimerization domain was omitted from of the alternative constructs (e.g. SEQ ID NO: 48 and 49). In some constructs, the enterokinase recognition sequence was replaced by the Factor Xa recognition sequence (e.g. SEQ ID NO: 52). This construct also did not include a linker between the HA coding sequence and the C-heptad repeat sequence. In other constructs, both the trimerization domain and the enterokinase recognition sequence were omitted (SEQ ID NO: 51). The N-heptad repeat of Nipah virus was sometimes used in place of the N-heptad repeat of HIV gp41 HXB2 strain (see e.g. SEQ ID NO: 47 and 49). The length of heptad repeat sequence was varied in some constructs (e.g. SEQ ID NO: 54, 56 and 58). In other constructs, the length of the linker connecting the HA coding sequence to the N-heptad repeat sequence was varied (see e.g. SEQ ID NO: 56 and 58). Modified HA genes of H3 Wisconsin 2005 (see SEQ ID NOs: 60 and 61) and H5 Vietnam 2004 (see SEQ ID NOs: 62 and 63) were codon optimized and synthesized by GeneArt™ (Life Technologies™) before they were included in modified constructs. The numbering of the HA amino acid sequences used in the descriptions of these constructs is according to GenBank IDs AAT73274.1 and ACV49644.1 (both incorporated herein by reference in the versions available on the date of the filing of the priority application), respectively. The structure of these modified HA coding sequences is summarised in Table 2. The modified HA protein sequence of SEQ ID NO: 46 is included as reference sequence. The sequences in Table 2 are shown from N-terminus to C-terminus.

TABLE 2

| Description of construct | Sequence |
| --- | --- |
| signal (Baculovirus gp64 signal peptide)-linker 1 (ADP)-6xHis tag-TEV-linker 2 (GYLLE)-HA (18-339, i.e. HA1)-enterokinase (DDDDK)-HA (344-519, i.e. HA2)-linker 3 (RSL)-Foldon (T4 Fibritin C terminal bit)-HR1 (HIV, 34 a.a.) | SEQ ID NO: 46 |
| signal (Baculovirus gp64 signal peptide)-linker 1 (ADP)-6xHis tag-TEV-linker 2 (GYLLE)-HA (18-339, i.e. HA1)-enterokinase (DDDDK)-HA (344-519, i.e. HA2)-linker 3 (RSL)-Foldon (T4 Fibritin C terminal bit)-HR1 (Nipah, 34 a.a.) | SEQ ID NO: 47 |
| signal (Baculovirus gp64 signal peptide)-linker 1 (ADP)-6xHis tag-TEV-linker 2 (GYLLE)-HA (18-339, i.e. HA1)-enterokinase (DDDDK)-HA (344-519, i.e. HA2)-HR1 (HIV, 34 a.a.) | SEQ ID NO: 48 |
| signal (Baculovirus gp64 signal peptide)-linker 1 (ADP)-6xHis tag-TEV-linker 2 (GYLLE)-HA (18-339, i.e. HA1)-enterokinase (DDDDK)-HA (344-519, i.e. HA2)-linker 3 (RS)-HR1 (Nipah, 34 a.a.) | SEQ ID NO: 49 |
| signal (Baculovirus gp64 signal peptide)-linker 1 (ADP)-6xHis tag-TEV-linker 2 (GYLLE)-HA (18-519)-HR1 (HIV, 34 a.a.) | SEQ ID NO: 50 |
| signal (Baculovirus gp64 signal peptide)-linker 1 (ADP)-6xHis tag-TEV-linker 2 (GYLLE)-HA (18-519)-linker 3 (RS)-HR1 (Nipah, 34 a.a.) | SEQ ID NO: 51 |
| signal (Baculovirus gp64 signal peptide)-linker 1 (ADP)-6xHis tag-TEV-linker 2 (GYLLE)-HA (18-339, i.e. HA1)-Factor Xa (IEGR)-HA (344-519, i.e. HA2)-HR1 (HIV, 34 a.a.) | SEQ ID NO: 52 |
| signal (Baculovirus gp64 signal peptide)-linker 1 (ADP)-6xHis tag-TEV-linker 2 (GYLLE)-HA (18-339, i.e. HA1)-Factor Xa (IEGR)-HA (344-519, i.e. HA2)-linker 3 (RS) HR1 (Nipah, 34 a.a.) | SEQ ID NO: 53 |
| signal (Baculovirus gp64 signal peptide)-linker 1 (ADP)-6xHis tag-TEV-linker 2 (GYLLE)-HA (18-339, i.e. HA1)-Enterokinase (DDDDK)-HA (344-511, i.e. HA2)-linker 3 (IGE)-HR1 (HIV, 39 a.a.) | SEQ ID NO: 54 |
| signal (Baculovirus gp64 signal peptide)-linker 1 (ADP)-6xHis tag-TEV-linker 2 (GYLLE)-HA (18-339, i.e. HA1)-Enterokinase (DDDDK)-HA (344-511, i.e. HA2)-linker 3 (IGEARQ)-HR1 (Nipah, 34 a.a.) | SEQ ID NO: 55 |
| signal (Baculovirus gp64 signal peptide)-linker 1 (ADP)-6xHis tag-TEV-linker 2 (GYLLE)-HA (18-339, i.e. HA1)-Enterokinase (DDDDK)-HA (344-519, i.e. HA2)-linker 3 (RSI)-HR1 (HIV, 38 a.a.) | SEQ ID NO: 56 |
| signal (Baculovirus gp64 signal peptide)-linker 1 (ADP)-6xHis tag-TEV-linker 2 (GYLLE)-HA (18-339, i.e. HA1)-Enterokinase (DDDDK)-HA (344-519, i.e. HA2)-linker 3 (RSIRQ)-HR1 (Nipah, 34 a.a.) | SEQ ID NO: 57 |
| signal (Baculovirus gp64 signal peptide)-linker 1 (ADP)-6xHis tag-TEV-linker 2 (GYLLE)-HA (18-339, i.e. HA1)-Enterokinase (DDDDK)-HA (344-519, i.e. HA2)-linker 3 (RSIKKLIGE)-HR1 (HIV, 39 a.a.) | SEQ ID NO: 58 |
| signal (Baculovirus gp64 signal peptide)-linker 1 (ADP)-6xHis tag-TEV-linker 2 (GYLLE)-HA (18-339, i.e. HA1)-Enterokinase (DDDDK)-HA (344-519, i.e. HA2)-linker 3 (RSIKKLIGEARQ)-HR1 (HIV, 34 a.a.) | SEQ ID NO: 59 |
| signal (Baculovirus gp64 signal peptide)-linker 1 (ADP)-6xHis tag-TEV-linker 2 (GYLLE)-HA (17-341, i.e. HA1)-Enterokinase (DDDDK)-HA (347-522, i.e. HA2)-linker 3 (RSL)-HR1 (HIV, 38 a.a.) | SEQ ID NO: 60 |
| signal (Baculovirus gp64 signal peptide)-linker 1 (ADP)-6xHis tag-TEV-linker 2 (GYLLE)-HA (17-341, i.e. HA1)-Enterokinase (DDDDK)-HA (347-522, i.e. HA2)-linker 3 (RSL)-Foldon (T4 fibritin C-terminal bit)-HR1 (HIV, 35 a.a.) | SEQ ID NO: 61 |
| signal (Baculovirus gp64 signal peptide)-HA (17-20)-6xHis tag-TEV-HA (21-345, i.e. HA1)-Enterokinase (DDDDK)-HA (346-521, i.e. HA2)-linker (RSL)-HR1 (HIV, 38 a.a.) | SEQ ID NO: 62 |
| signal (Baculovirus gp64 signal peptide)-HA (17-20)-6xHis tag-TEV-HA (21-345, i.e. HA1)-Enterokinase (DDDDK)-HA (346-521, i.e. HA2)-linker (RSL)-Foldon (T4 fibritin C-terminal bit)-HR1 (HIV, 35 a.a.) | SEQ ID NO: 63 |

Each of the three modified HA genes were subcloned into pFastBacDual™ (Life Technologies™) between the Sal I and Not I sites. Recombinant baculoviruses bearing the modified HA genes were created following similar procedures as those described for VP7.

Modified gp140 genes of HIV-1 clade A 1992 Uganda 037.8 serotype and clade C 1997 were codon optimized and synthesized by GeneArt™ (Life Technologies™). The modified genes were subcloned into pFastBacDual™ (Life Technologies™) between the Sal I and Not I sites.

The final protein encoded by the modified gp140 coding sequence of the HIV-1 clade A strain has the following features: (a) The first 21 amino acids encode the honeybee melittin signal peptide for expression of the modified protein in insect cells. The gp140 signal peptide has been removed. Other signal sequences can be used as appropriate, such as the HIV consensus signal sequence or the signal peptide of human tPA for expression in mammalian/human cells. (b) Amino acid residues 22 to 29 form an optional affinity tag (His-tag plus a linker for more efficient signal peptide cleavage) for protein purification purposes and can be replaced by any other affinity tags, such as strep-tag, HA-tag, FLAG-tag, etc. (c) Amino acid residues 30 to 36 form a TEV protease recognition sequence for cleavage of the affinity tag and can be replaced by the recognition sequences of any other proteases, such as PreScission™ protease (i.e. Rhinovirus 3C protease, GE Healthcare™, Life Sciences), factor Xa, enterokinase, thrombin, furin, etc. (d) Amino acid residues 37 to 685 is the gp140 coding sequence of HIV strain 1992 Uganda 037.8 which could be modified/mutated as appropriate or be replaced by that of any other HIV/SIV strains. (e) Amino acid residues 686 to 694 are a linker and could be replaced by any appropriate other linker sequences. (f) Amino acid residues 695 to 721 are a trimerization tag from bacteriophage T4 fibritin (Foldon), which is optional or can be replaced by any other trimerization tag or linker sequences. (g) Amino acid residues 722 to 755 are part of the N-heptad repeat of HIV gp41 HXB2 strain and could be replaced by other suitable heptad repeat sequences e.g. from any other retrovirus, paramyxovirus, etc. The amino acid sequence of this construct is shown in SEQ ID NO: 64.

Alternative constructs were prepared containing some of the possible modifications indicated in the preceding paragraph. For example, some of these constructs do not include the trimerization tag, and the linker sequence between the gp140 coding region and the N-heptad repeat has been shortened (e.g. SEQ ID NO: 66 and 67). Other constructs are adapted for expression in mammalian cells by replacement of the signal peptide (e.g. SEQ ID NO: 65 and 67). In some constructs, the N-heptad repeat of the HIV gp41 HXB2 strain has been replaced with the N-heptad repeat of Nipah virus (SEQ ID NO: 68-71 and 76-79), in others, the gp140 coding sequence from HIV-1 clade A 1992 Uganda 037.8 serotype has been replaced with the gp140 coding sequence from HIV-1 clade C 1997 (SEQ ID NO: 72-79). The numbering for the clade A and C gp140 is according to GenBank ID AAB05027.1 and AF286227.1 (both incorporated herein by reference in the versions available on the date of the filing of the priority application), respectively.

The different variants are summarised in Table 3. The modified gp140 protein sequence of SEQ ID NO: 64 is also included as reference sequence. The sequences in Table 3 are shown from N-terminus to C-terminus.

TABLE 3

| Description of construct | Sequence |
| --- | --- |
| signal (honeybee melittin signal peptide)-linker1 (ED)-6xHis tag-TEV-HIV clade A gp140 (27-675)-linker2 (linker 2a (SR)-Factor Xa-linker 2b (GSG))-Foldon (T4 Fibritin C-terminal bit)-HR1 (HIV, 34 a.a.) | SEQ ID NO: 64 |
| signal (HIV consensus signal peptide)-linker1 (ED)-6xHis tag-TEV-HIV clade A gp140 (27-675)-linker2 (linker 2a (SR)-Factor Xa-linker 2b (GSG))-Foldon (T4 Fibritin C-terminal bit)-HR1 (HIV, 34 a.a.) | SEQ ID NO: 65 |
| signal (honeybee melittin signal peptide)-linker1 (ED)-6xHis tag-TEV-HIV clade A gp140 (27-675)-linker2 (GSG)-HR1 (HIV, 34 a.a.) | SEQ ID NO: 66 |
| signal (HIV consensus signal peptide)-linker1 (ED)-6xHis tag-TEV-HIV clade A gp140 (27-675)-linker2 (GSG)-HR1 (HIV, 34 a.a.) | SEQ ID NO: 67 |
| signal (honeybee melittin signal peptide)-linker1 (ED)-6xHis tag-TEV-HIV clade A gp140 (27-675)-linker2 (linker 2a (SR)-Factor Xa-linker 2b (GSG))-Foldon (T4 Fibritin C-terminal bit)-HR1 (Nipah, 32 a.a.) | SEQ ID NO: 68 |
| signal (HIV consensus signal peptide)-linker1 (ED)-6xHis tag-TEV-HIV clade A gp140 (27-675)-linker2 (linker 2a (SR)-Factor Xa-linker 2b (GSG))-Foldon (T4 Fibritin C-terminal bit)-HR1 (Nipah, 32 a.a.) | SEQ ID NO: 69 |
| signal (honeybee melittin signal peptide)-linker1 (ED)-6xHis tag-TEV-HIV clade A gp140 (27-675)-linker2 (S)-HR1 (Nipah, 34 a.a.) | SEQ ID NO: 70 |
| signal (HIV consensus signal peptide)-linker1 (ED)-6xHis tag-TEV-HIV clade A gp140 (27-675)-linker2 (S)-HR1 (Nipah, 34 a.a.) | SEQ ID NO: 71 |
| signal (honeybee melittin signal peptide)-linker1 (ED)-6xHis tag-TEV-Linker2 (AENLWV)-HIV clade C gp140 (31-667)-linker3 (S)-Foldon (T4 Fibritin C-terminal bit)-HR1 (HIV, 34 a.a.) | SEQ ID NO: 72 |
| signal (HIV consensus signal peptide)-linker1 (ED)-6xHis tag-TEV-Linker2 (AENLWV)-HIV clade C gp140 (31-667)-linker3 (S)-Foldon (T4 Fibritin C-terminal bit)-HR1 (HIV, 34 a.a.) | SEQ ID NO: 73 |
| signal (honeybee melittin signal peptide)-linker1 (ED)-6xHis tag-TEV-HIV clade C gp140 (31-667)-linker2 (SGI)-HR1 (HIV, 34 a.a.) | SEQ ID NO: 74 |
| signal (HIV consensus signal peptide)-linker1 (ED)-6xHis tag-TEV-HIV clade C gp140 (31-667)-linker2 (SGI)-HR1 (HIV, 34 a.a.) | SEQ ID NO: 75 |
| signal (honeybee melittin signal peptide)-linker1 (ED)-6xHis tag-TEV-Linker2 (AENLWV)-HIV clade C gp140 (31-667)-linker3 (S)-Foldon (T4 Fibritin C-terminal bit)-HR1 (Nipah, 32 a.a.) | SEQ ID NO: 76 |
| signal (HIV consensus signal peptide)-linker1 (ED)-6xHis tag-TEV-Linker2 (AENLWV)-HIV clade C gp140 (31-667)-linker3 (S)-Foldon (T4 Fibritin C-terminal bit)-HR1 (Nipah, 32 a.a.) | SEQ ID NO: 77 |

TABLE 3-continued

| Description of construct | Sequence |
| --- | --- |
| signal (honeybee melittin signal peptide)-linker1 (ED)-6xHis tag-TEV-Linker2 (AENLWV)-HIV clade C gp140 (31-667)-linker3 (S)-HR1 (Nipah, 34 a.a.) | SEQ ID NO: 78 |
| signal (HIV consensus signal peptide)-linker1 (ED)-6xHis tag-TEV-linker2 (AENLWV)-HIV clade C gp140 (31-667)-linker3 (S)-HR1 (Nipah, 34 a.a.) | SEQ ID NO: 79 |

Example 2: Preparation of a Stable VP7-HA Complexes

To produce HA-VP7 complexes, Hi5 cells at the density of $2 \times 10^6$/mL were infected with 0.5% VP7 baculovirus and 1.0% HA baculovirus in the presence of 5.0% heat inactivated FBS (Sigma-Aldrich). The medium was harvested 5 days post infection by spinning down the cells at 4000×g for 45 minutes. The supernatant was diafiltrated against 8 liters of 1×TNC (20 mM Tris, pH 8.0, 100 mM NaCl, and 1.0 mM $CaCl_2$; supplemented with 0.02% sodium azide) using a filter of 10 KDa cutoff in a Cogent M Tangential Flow Filtration System (Millipore). The buffer exchanged samples were supplemented with 1.0 mM PMSF and clarified by centrifugation for 1 hour at 10,000 RPM in a JA10 rotor (Beckman™). The protein complexes were purified from the supernatant by a StrepTactin® column (IBA™), followed by a NiNTA column (Qiagen™), and a Superose 6 column (Amersham™)

The purified HA-VP7 complexes were treated with 0.002% (w/w) enterokinase at 4° C. for 48 hours. The cleavage of HA0 into HA1 and HA2 was examined by SDS-PAGE. Enterokinase was inactivated by adding 1×EDTA-free complete protease inhibitor tablet. The sample was supplemented with a redox buffer (10:1 molar ratio of GSH and GSSG) at a final concentration of 0.2~0.5 mM and treated with TEV protease (1/50~200, w/w) either at room temperature for 4 hours or at 4° C. for overnight. Removal of the tags was also examined by SDS-PAGE.

Example 3: Preparation of a Stable HIV Gp140-VP7 Complexes

The modified VP7 and gp140 genes encoding the proteins of SEQ ID NOs: 22, 26, 32 and 36 and SEQ ID NOs: 64, 66, 68 and 70, respectively were subcloned into pVRC8400 and pVRC-IRES-Puro vectors between Sal I and Not I for expression in mammalian cells. The signal peptide for the VP7 gene were changed to a human tPA signal peptide and the signal peptide for the gp140 gene were changed to the HIV consensus signal peptide sequence. The resulting modified VP7 proteins and modified gp140 proteins have the amino acid sequences of SEQ ID NOs: 42-45 and SEQ ID NOs: 65, 67, 69 and 71, respectively. Co-expression and complex formation were tested for the following combinations of modified VP7 protein and modified gp140 protein: SEQ ID NOs. 42+65, SEQ ID NOs. 42+67, SEQ ID NOs. 43+65, SEQ ID NOs. 43+67, SEQ ID NOs. 44+69, SEQ ID NOs. 44+71, SEQ ID NOs. 45+69, SEQ ID NOs. 45+71.

HIV gp140-VP7 complexes were expressed by co-transfecting 293T cells with a plasmid hosting the gp140-HR1 gene and another hosting the VP7-HR2 gene. Transient transfection was done by following standard protocols using polyethylenimine (PEI, 25 KDa, linear or branched). For higher protein yield, stable cell lines were selected against puromycin. In brief, 70% confluent 293T cells were transfected with a mixture of Lipofectoamine® 2000 (Invitrogen®) and the pVRC-IRES-puro version of the two plasmids (2:1 mass ratio of lipofectoamine to total DNA) following standard procedures. At 20 hours post transfection, the medium was replaced with DMEM (Gibco®) supplemented with 10% Fetal Bovine Serum (Atlas), 1% GlutaMAX™ (Gibco®), 100 unites/mL penicillin/streptomycin (Gibco®), and 2 μg/mL puromycin (Gibco®). The medium was kept fresh by changing it every three to four days until colonies form (visible to the naked eye). Individual colonies were picked and cultured in 24-well plates for small-scale expression tests. Colonies harbouring both genes were selected based on the detection of both proteins on western blots. The colony with the highest yield of the complex was scaled up and saved as stocks in liquid nitrogen. The cells were scaled up in puromycin-containing media and protein expression could be carried out using either adherent or suspension cell cultures in 293 Freestyle medium (Gibco®) supplemented with 5% heat inactivated FBS (Sigma-Aldrich®). The medium was harvested after 5 days by spinning down the cells at 4000×g for 45 minutes. Diafiltration and protein purification were carried out following the same procedures as described for the HA-VP7 complexes.

Example 4: Preparation of Fabs and Fvs

Monoclonal antibody CR6261 recognises a highly conserved helical region in the membrane-proximal stem of the influenza HA protein [67]. Structure factors and coordinates for the CR6261 sHgL Fab fragment were deposited with the Protein Data Bank under accession 4EVN (incorporated herein by reference in the version available on the date of the filing of the priority application) and have been described previously [68].

The coding sequence for the antigen-binding fragment (Fab) and the single chain variable fragment (scFv) of monoclonal antibody CR6261 were cloned into the pVRC-IRES-Puro vector between Sal I and Not I following standard procedures as described above. The human tPA signal peptide was used for efficient secretion in these constructs in mammalian expression systems. The amino acid sequences of the final constructs are shown in SEQ ID NOs: 81-83. An scFv of monoclonal antibody CR6261 for expression in bacterial cells was also prepared (see SEQ ID NO: 80).

Fabs were expressed by transient transfection of 293T cells in roller bottles. For each roller bottle, 125 μg each of the purified plasmid DNA hosting the heavy and light chain genes were mixed in 12.5 mL unsupplemented DMEM (Gibco®) and incubated in the hood for 15 minutes. PEI (500 m, linear or branched) was also diluted in 12.5 mL unsupplemented DMEM and incubated in the hood for 15 minutes before being added drop by drop and mixed well into the DNA mixture. The total of 25 mL mixture was incubated in the hood for an extra 15 minutes to allow a DNA-PEI complex to form before being added to cells at 50~70% confluence in roller bottles. The cells were incubated for over 5 hours with the DNA-PEI complex at 37° C., and the medium was replaced by 250 mL of 293 FreeStyle™ medium (Gibco®) supplemented with 100 units/mL penicillin/streptomycin. Medium was harvested 5 days post transfection, and Fabs were purified using a CaptureSelect® Lc Kappa or Lc Lambda affinity resin, followed by size exclusion chromatography on an S200 column (Amersham™)

ScFvs were expressed either in 293T cells as secreted proteins or in E. coli as inclusion bodies, from which protein was then extracted and refolded. The same transient transfection procedures as described above were followed for mammalian cell expression. For the E. coli expression, protein expression was induced for about 5 hours using 1 mM IPTG at cell density of 0.6~0.8 O.D.600 nm. The cells were harvested, washed with 1×PBS, and lysed by sonication on ice. The inclusion bodies were extracted after removing the soluble fractions of the cells by centrifugation for 15 minutes at 20000×g. Inclusion bodies were dissolved in 100 mM Tris pH 7.5, 8 M urea, and 10 mM β-mercaptoethanol, clarified by centrifugation (20 minutes at 40000× g), and the supernatant was purified on a NiNTA column. The eluted sample, also in the denatured form, was diluted into the refolding buffer (100 mM Tris pH 7.5, 1 M arginine, 500 mM NaCl, 10% glycerol, and 1 mM EDTA) drop by drop at 4° C. to a final protein concentration of lower than 0.1 mg/mL. The refolded sample was dialyzed against 20 mM Tris, pH 7.5, 100 mM NaCl four times, each time 20 volumes. The dialyzed sample was then clarified by centrifugation at 10,000 rpm in a JA10 rotor (Beckman™) and the supernatant was passed through a NiNTA column to concentrate the protein. The eluted fractions were then combined, concentrated, and further purified on an S200 size exclusion column (Amersham™)

Example 5: DLP Preparation

Rhesus rotavirus serotype G3 was amplified by infecting MA-104 cells. Briefly, MA104 cells were grown in M199 medium (Gibco®) supplemented with 10% fetal bovine serum (HyClone™ Laboratories), 10 mM HEPES, pH 7.0, 2 mM L-glutamine, and 100 units/mL penicillin/streptomycin. The cells were maintained and scaled up to a 10-stack cell culture chamber (Corning™) or roller bottles. When the cells became confluent, the medium was replaced by serum-free MA199 supplemented with 1 μg/mL porcine pancreatic trypsin (Sigma-Aldrich®) for rotavirus inoculation and amplification. The medium of infected MA104 cells was harvested about 36~42 hours post infection and stored at −80° C. for future use.

The frozen medium of infected MA104 cells was thawed at 4° C. overnight. Cell debris was cleared by low-speed centrifugation at 3000×g for about 10 minutes. The resulting supernatant was filtered through Whatman® Filter paper to remove residual cell debris before it was further passed through a 0.45 μm ExpressPlus filter unit (Millipore™) under vacuum. The virus particles were then pelleted at 45,000 rpm for 1 h at 4° C. in a 45Ti rotor (Beckman™)

The pellet was resuspended in a total of 10 mL of 1×TNE buffer (20 mM Tris, pH 8.0, 100 mM NaCl, and 1 mM EDTA), briefly sonicated, and extracted twice with Freon 113 (Sigma-Aldrich®). The aqueous phase was recovered and concentrated into about 1 mL in an Amicon® centrifugal filtration device (100 KDa cutoff) at 3000×g for about 10 minutes. The concentrated sample was resuspended by pipetting up and down a few times and layered over a preformed CsCl gradient in 1×TNE (1.26 to 1.45 g/mL density as determined by refractometry). Samples were centrifuged at 55000 rpm in an SW 55Ti rotor (Beckman™) at 4° C. for about 2 hours. The DLP band was collected and dialyzed overnight at 4° C. against 1×TN buffer (20 mM Tris, pH 8.0, 100 mM NaCl) supplemented with 0.02% sodium azide.

The DLPs were negatively stained and visualised using electron microscopy (EM; FIG. 3A).

Example 6: Recoating of DLPs with HA-VP7 Complex

The DLPs obtained in Example 5 and the modified rotavirus VP7 protein prepared in Example 1 were mixed and incubated at 4° C. for at least 1 hour in the presence of 5~10 mM $CaCl_2$. The resulting particles were negatively stained and visualised using EM. A single VP7 layer covering each particle was observed confirming that the modified VP7 protein was able to recoat DLPs (FIG. 3B).

Recoating of DLPs with the HA-VP7 complex obtained in Example 2 was carried out at 4° C. for at least 1 hour by mixing them at a molar ratio of 1:1.5 to 1:2 in the presence of 5~10 mM $CaCl_2$. The recoated rotavirus particles were negatively stained and visualised using EM. In addition to the single VP7 layer covering the DLP, a further layer surrounding the recoated particles was observed suggesting that the HA-VP7 complex correctly assembled on the surface of the DLPs (FIG. 3C).

To confirm that the additional layer was formed by the HA protein, the recoated particles were loaded onto a preformed CsCl gradient in 1×TNC (density 1.25 g/mL to 1.45 g/mL) and centrifuged in a SW60 rotor (Beckman™) at 58,000 rpm for 2 hours. The resulting bands were collected, dialyzed against 1×TNC, and examined by SDS-PAGE. As a control, DLPs, the HA-VP7 complex and the mixture of both as used in the recoating reaction were also loaded on the gel in separate lanes. After separation, separate bands corresponding to the VP2 and VP6 proteins of the DLPs, the VP7 protein and the HA protein were observed at the correct stoichiometry in the sample that corresponded to the recoated particles (FIG. 4). This confirmed that the further layer surrounding the recoated particles was composed of HA protein at full occupancy.

Example 7: Three-Dimensional Image Reconstruction of HA-VP7-Antibody Complex

High-resolution cryo-EM has the potential to replace X-ray crystallography as the method of choice for analysing large molecular complexes, in particular in areas where rapid structural elucidation of a large number of molecular complexes is needed. One such area is influenza vaccine design, where antigenic drift leads to rapid changes in the sequence of the immunodominat surface antigen, the HA protein. Broadly protective monoclonal antibodies have been previously identified and many of these antibodies recognise conserved epitopes that are not subjected to rapid change. To investigate their suitability as protective agents against newly emerging influenza strains, we need to screen these broadly neutralising anti-HA antibodies against different variants of the HA protein.

The feasibility of such an approach using cryo-EM analysis was tested. DLPs were recoated with modified VP7 protein alone or with a HA-VP7 complex as described in Example 6. HA-VP7-antibody recoated particles were obtained by mixing the purified HA-VP7 complexes with the Fabs or scFvs of monoclonal antibody CR6261 prepared in Example 4 at a molar ratio of 1:1.5~2.0. The mixture was incubated at 4° C. for 30 minutes. The complexes were purified by loading the mixture after the end of the incubation period on a Superose 6 column. The purified complexes were then used to recoat DLPs following the same procedures as described in Example 6. Alternatively, the antibody fragments were added directly to particles recoated with HA-VP7 complexes at a molar ratio of 1:1.2~1.5 either before or after the CsCl gradient purification step.

Cryo-grids were prepared with a Vitrobot™ Automated plunger (FEI). Quantifoil Holey carbon grids were glow discharged and left at room temperature overnight before use. For each grid, 4 µL sample at a concentration equivalent to ~5 mg/mL rotavirus DLPs was applied to one side surface of the grid. During plunging, the chamber moisture was maintained close to 100% and the temperature at around 22° C. The grid was then blotted for 4 seconds from both sides with filter paper, immediately followed by plunging into liquid ethane for vitrification. The grids were then stored in liquid nitrogen before being used for data collection.

Data were collected on a Tecnai™ F30 electorn microscrope (FEI) operated at 300 kV. The optical system was aligned using standard procedures (beam shift, beam tilt, eucentric height, pivot points, rotational center, astigmatism, etc.). The image acquisition procedures involved finding the desired imaging area, adjusting defocus (between 0.6 and 3.0 µm), testing grid drift rate (less than 2 Å per second), and the final image exposure. These procedures were semi-automatically achieved using the program SerialEM (Cryo-electron Microscopy Facility, University of Colorado—Boulder). The data were recorded as movies on a K2 Summit™ direct detection camera (Gatan™) using super resolution mode (pixel size: 0.99 Å). The "movie" protocol of reference 24 was used. The dose rate on the sample was ~3 electrons/Å$^2$ per second. Each frame recorded 0.5 second exposure and the final movie consisted of 24 frames with an accumulated dose of ~36 electrons/Å2.

The frames of each movie were aligned using IMOD (Cryo-electron Microscopy Facility, University of Colorado—Boulder) scripts based on image cross correlation. The aligned frames were simply averaged for initial image processing. As the resolution improved later, however, the averaged images from the first 13 frames (or the best series of frames) of each movie, which would correspond to ~20 electron dose, were used. Particle images were picked using e2boxer.py of the EMAN2 image processing suite [69]. Images with obvious defects, aberrations, abnormal focus, contamination, overlap, or large sample drifts were manually excluded after visual inspection. The particle coordinates were used to excise image stacks of individual particles with 1600×1600 pixel dimensions using proc2d of the EMAN2 image processing suite [69]. Defocus values were determined using the program CTFFIND3 [23].

The structure refinement and reconstructions were carried out using the program FREALIGN [40]. The initial orientation search was performed using 4× binned data and a previously calculated map of the VP7 recoated particles (7RP) (see reference 1) as a 3-dimensional reference. The initial alignment parameters of the excised particles, determined by a systematic search (mode 3) at a 1° angular interval, were further refined against the latest reconstructions (mode 1) until there was no further improvement in resolution. During alignment, a radial shell mask between 220 and 400 Å was applied to retain the density corresponding to the rotavirus portion and to exclude density corresponding to the RNA and HA spikes. The images were also low pass filtered (up to 15 Å) to avoid possible overfitting in the alignment process. The alignment parameters were then used to calculate the reconstructions of the entire particle (within the radial shell of 600 Å or between the radii of 220 and 600 Å for the protein contents).

Subsequently, 2× binned and later unbinned images were used to further refine the alignment parameters following similar strategies to those used for the 4× binned data, i.e. an initial systematic search (mode 3) followed by multiple cycles of angular and positional refinement (mode 1) until no further improvement in resolution was observed. During each stage of refinement, the shell mask between 220 and 400 Å was applied and the data were restricted to the most reliable resolution (up to 10 Å for 2× binned data and up to 8 Å for unbinned data). Reconstructions were calculated for the entire particle within the radial shell of 600 Å.

Figure 6:
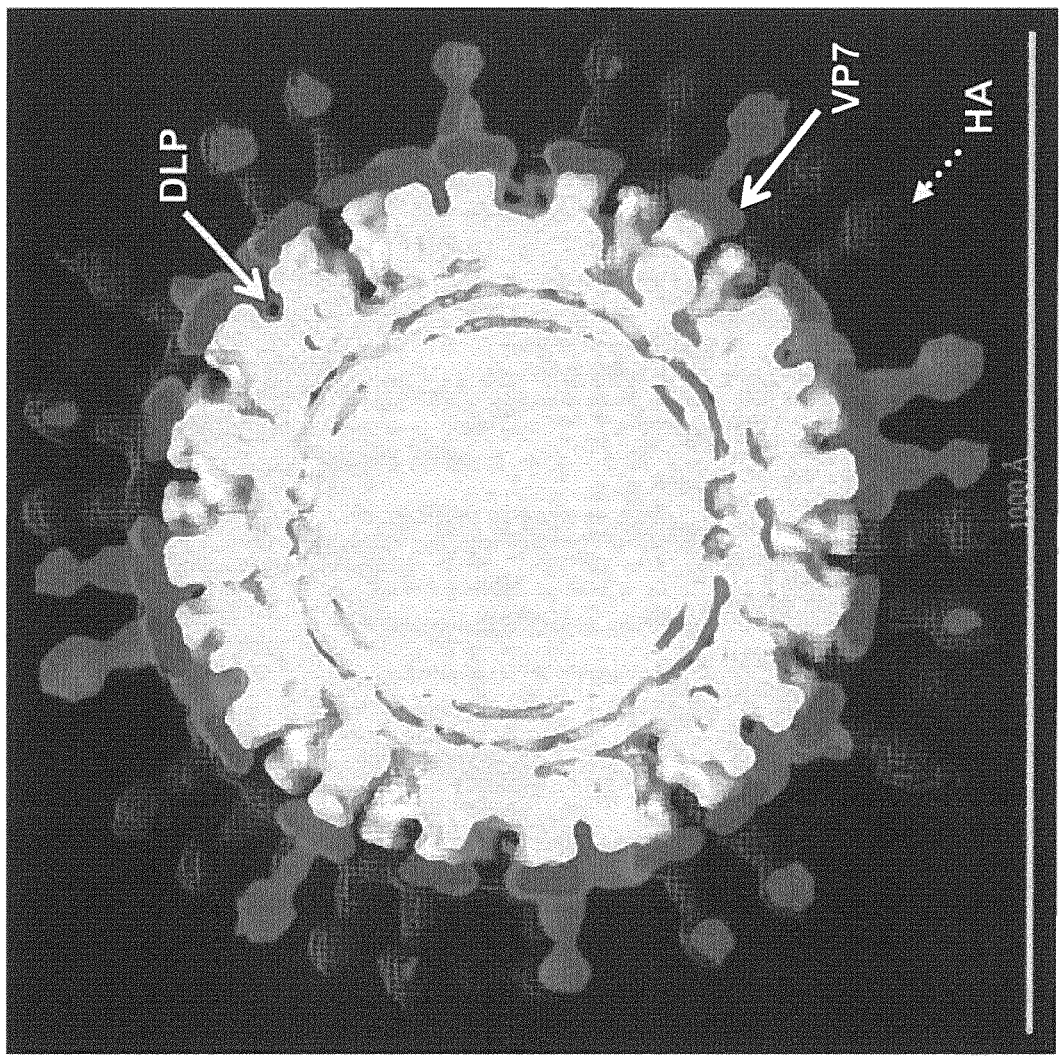
FIG. 6: Superposition of a DLP (white) onto a three-dimensional reconstruction of a DLP recoated with modified rotavirus VP7 protein and influenza virus HA as the modified heterologous protein. The reconstruction is based on images acquired by performing cryo-EM on recoated DLPs.
Figure 7:
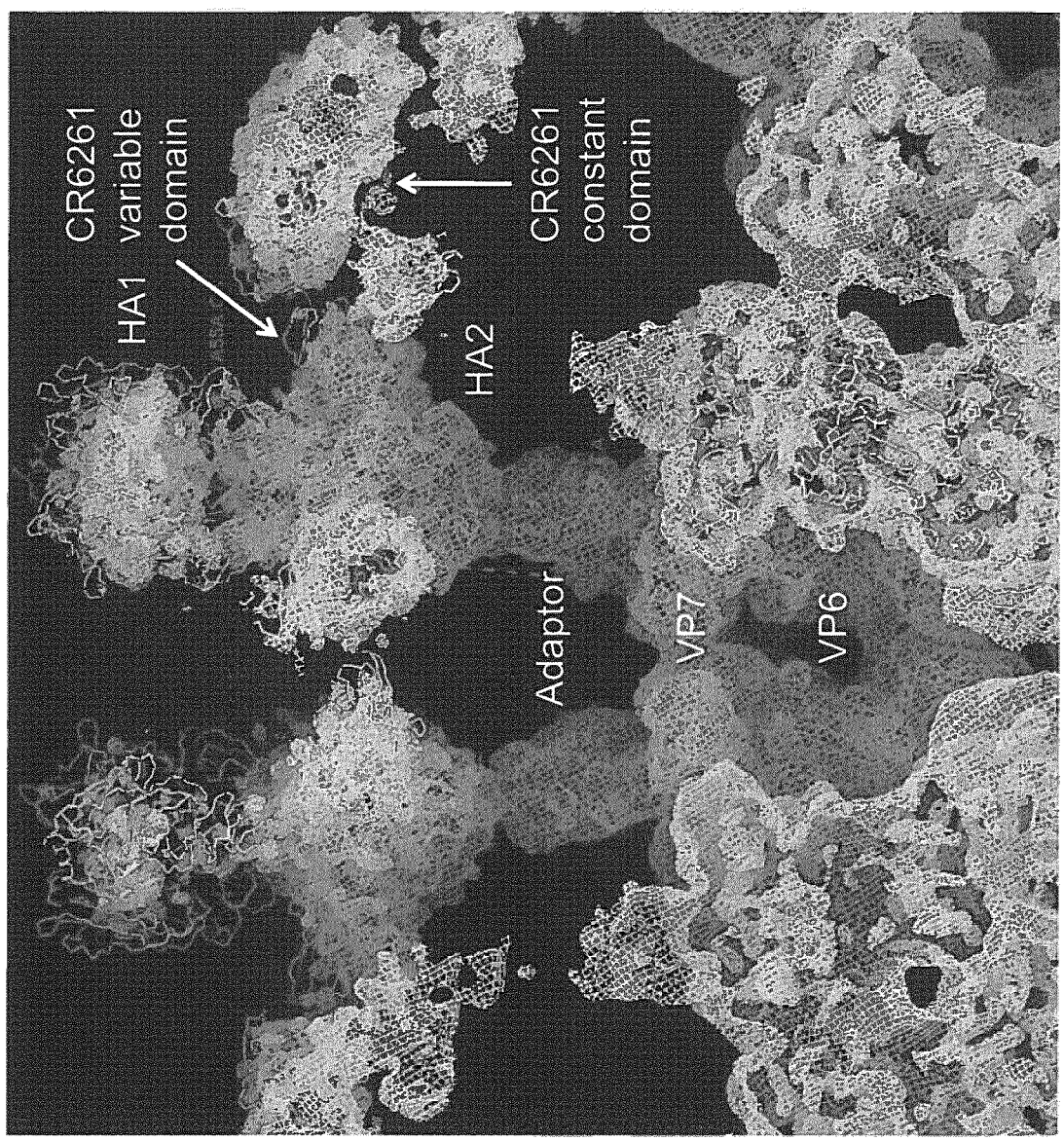
FIG. 7: Detail of three-dimensional reconstruction of a rotavirus particle displaying influenza virus HA bound to Fab fragments of antibody CR6261. The rotavirus particles were prepared by recoating DLPs with a modified VP7 protein containing an adapter sequence (HR2). The HA protein was non-covalently bound to the modified VP7 protein via an C-terminally fused HR1 heptad repeat sequence which forms a six-helix bundle with the HR2 heptad repeat sequences of the VP7 protein. CR6261 binds at the membrane proximal end of each HA subunit (HA1 and HA2). The reconstruction is based on images acquired by performing cryo-EM on recoated DLPs.

FIG. 5A shows a cross-section through a three-dimensional reconstruction of rotavirus DLP recoated with modified VP7 protein only. FIG. 5B shows a cross-section through a three-dimensional reconstruction of rotavirus DLP recoated with an HA-VP7 complex as described in Example 6. FIG. 6 shows a superposition of a DLP onto the three-dimensional reconstruction of the recoated particle shown in FIG. 5B. FIG. 5C shows a cross-section through a three-dimensional reconstruction of rotavirus DLP recoated with modified VP7 protein displaying HA with bound ScFv fragments of antibody CR6261.

To assess the reliability of refinement, different sets of refinement were carried out by masking out different regions of the particle, and the alignment parameters were used to calculate reconstructions for the omitted regions that were not included during refinement. For example, alignment parameters obtained by refining the HA portion (by applying a shell mask between 425 and 600 Å) were used to calculate the reconstruction for the rotavirus portion (by applying a shell mask between 220 and 400 Å). The resulting map contained densities clearly representing VP2, VP6, and VP7, suggesting minimum model bias. The T=13 quasi-equivalent arrangement of the rotavirus VP6 and VP7 layers clearly extended to the adaptor and HA portion of the particle. Local 13-fold averaging was not applied but can be performed to further improve the resolution. Rigid body fitting of the rotavirus VP2, VP6, and VP7, the six-helix bundle, the HA, and the Fabs into the electron density maps was performed using the UCSF chimera [47].

An example of the level of detail that can be achieve by further refining the reconstructions obtained from cryo-EM as described in the preceding paragraph is shown in FIG. 7. A detail of the three-dimensional reconstruction of a rotavirus particle displaying influenza virus HA bound to Fab fragments of antibody CR6261 is shown. Some secondary structures can be visualised in the calculated map. As expected, the variable domain of CR6261 is seen to interact with both HA1 and HA2.

Example 8: Immunisation Studies with HA-VP7 Protein Complexes Mounted on Rotavirus DLPs Female 6-8-week-old BALB/c mice are immunised intramuscularly (IM) three times at three-week intervals with one of three different formulations, each formulated in 100 μl of a calcium-containing buffer. Group 1 receives of formulated HA-VP7 protein complexes mounted on rotavirus DLPs, group 2 receives purified HA, and group 3 receives purified HA mixed with VP7-recoated DLPs. A fourth group of mice is mock-injected with 100 μl buffer. Experiments can include various doses for each of the groups. Equivalent amounts of antigen can be used to compare immune response to equivalent doses of antigen in various formats. Alternatively, equivalent amounts of total protein can be used to compare immune responses to various amounts of total protein.

One or more groups can include an adjuvant. Adjuvants can be particularly useful in stimulating an immune response in the mice in group 2 receiving purified HA antigen.

Each vaccine group contains eight mice, and the "buffer alone" control group contains five mice. Blood is drawn at days −1, 20, 41, 56 and 84 from administration of the first injection.

Mice are monitored after immunisation for body weight change, injection site reactions, and other clinical observations. The antibody responses to the administered antigens are analysed using methods known in the art to analyse antibody specificity (e.g. ELISA assay and competition ELISA assay against HA and rotavirus proteins including VP7 protein) and neutralization activity (e.g. influenza haemagglutination inhibition assay, see e.g. references 70 and 71).

Results demonstrate a substantially higher immune response to the HA-VP7 protein complexes mounted on rotavirus DLPs as compared to the purified HA, including purified HA formulated with adjuvant. Competition ELISA demonstrate that antibody responses to the HA-VP7 protein complexes are predominantly to the HA portion of the complex rather than the VP7 or rotavirus portion of the complex. Results demonstrate substantially higher neutralization antibody titres as a result of immunization with the HA-VP7 protein complexes mounted on rotavirus DLPs as compared to the purified HA, including purified HA formulated with adjuvant. These results demonstrate the increased immunogenicity of flu antigens when mounted on rotavirus VP7-coated DLP as compared to flu antigens not mounted on VP7-coated DLPs.

All animal experiments are performed in accordance with Institutional Animal Care and Use Committee protocols.

Example 9: Immunisation Studies with HA-VP7 Protein Complexes Mounted on Rotavirus DLPs with and without Adjuvant Female BALB/c mice are immunized by two bilateral 50 μl intramuscular injections in the rear quadriceps on days 0, 21, and 42 with 0.3-15 μg of purified antigen H1N1 hemagglutinin (HA) protein complexes as set out in Table 4 below.

The complexes are formulated with PBS or adjuvant 1-2 hours prior to immunization. The formulated subunit vaccines are kept on ice until administration.

Mice are monitored after immunisation for body weight change, injection site reactions, and other clinical observations. Serum samples are obtained from the animals by retro-orbital sinus bleeds on day 20 (3 weeks post first immunization) and day 41 (3 weeks post second immunization) and from bleed-outs of euthanized animals on day 63 (3 weeks post third immunization).

The antibody responses to the administered antigens are analysed using methods known in the art (e.g. ELISA assay, neutralization assay). Results demonstrate a substantially higher immune response to the HA-VP7 protein complexes mounted on rotavirus DLPs as compared to the purified HA, including purified HA formulated with adjuvant or purified HA formulated with, but not mounted on VP7-coated DLPs.

All animal experiments are performed in accordance with Institutional Animal Care and Use Committee protocols.

TABLE 4

| Group | IM Vaccine (dose) | N |
|---|---|---|
| 1 | A/Sol Monobulk (0.3 μg) | 5 |
| 2 | 7RP (0.3 μg) | 5 |
| 3 | 7RP (3 μg) | 5 |
| 4 | 7RP (15 μg) | 5 |
| 5 | HA + 7RP (0.3 μg) | 5 |
| 6 | HA + 7RP (3 μg) | 5 |
| 7 | HA + 7RP (15 μg) | 5 |
| 8 | HA-7RP (0.3 μg) | 5 |
| 9 | HA-7RP (3 μg) | 5 |
| 10 | HA-7RP (15 μg) | 5 |
| 11 | A/Sol HA (0.3 μg) | 5 |
| 12 | A/Sol HA (3 μg) | 5 |
| 13 | A/Sol HA (15 μg) | 5 |

A/Sol monobulk is lipid-oligomerized trimerized, recombinant HA.
7RP is VP7 recoated particles without HA.
HA + 7RP is VP7 recoated particles on which HA cannot be mounted + trimerized recombinant HA.
HA-7RP is VP7 recoated particles mounted with trimerized, recombinant HA.
A/Sol HA is trimerized recombinant HA.

Each of the references, patents, and patent applications cited herein and listed below is hereby incorporated by reference in its entirety as if each were incorporated individually. Each Accession number cited herein is incorporated herein by reference in the version available on the date of the fling of the priority application on which the instant application is based.

It will be understood that the invention has been described by way of example only and modifications may be made whilst remaining within the scope and spirit of the invention.

REFERENCES

[1] Chen et al. (2009) *Proc Natl Acad Sci USA* 106(26): 10644-8
[2] Trask & Dormitzer (2006) *J Virol* 80(22):11293-304
[3] Kobayashi et al. (2007) *Cell Host Microbe* 1(2):147-157
[4] Chandran et al. (1999) *J Virol* 73(5):3941-50
[5] Chandran et al. (2001) *J Virol* 75(11):5335-42
[6] Yan et al. (2011) *J Virol* 85(15):7483-95
[7] Miyazaki et al. (2008) *J Virol* 82(22):11344-53
[8] Zhang et al. (2010) *Cell* 141(3):472-82
[9] Biosafety in Microbiological and Biomedical Laboratories (BMBL) 5th Edition, C D C, 2009
[10] Yang et al. (2000) *J Virol* 74(10):4746-54
[11] Meier et al. (2004) *J Mol Biol* 344(4):1051-69
[12] Wu & Wong (2005) *J Biol Chem* 280(24):23225-31
[13] Beckett et al. (1999) *Protein Sci* 8(4):921-9
[14] Chen et al. (1997) *Cell* 89(2):263-73
[15] Zhu et al. (2003) *Protein Eng* 16(5):373-9
[16] Yu et al. (2002) *J Gen Virol* 83(Pt 3):623-9
[17] Xu et al. (2004) *J Biol Chem* 279(29):30514-22
[18] http://partsregistry.org/Protein_domains/Linker
[19] U.S. Pat. No. 4,769,326
[20] Dormitzer et al. (2001) *J Virol* 75(16):7339-50
[21] Dormitzer et al. (2000) *Virology* 277(2):420-8
[22] Mohd Jaafar et al. (2005) *J Gen Virol* 86(Pt 4):1147-57
[23] Mindell & Grigorieff (2003) *J Struct Biol* 142(3):334-47
[24] Campbell et al. (2012) *Structure* 20(11):1823-8
[25] Settembre et al. (2011) *EMBO J.* 30(2):408-16
[26] Chen & Grigorieff (2007) *J Struct Biol* 157(1):168-73
[27] Wriggers et al. (1999) *J Struct Biol* 125(2-3):185-95
[28] Jiang et al. (2001) *J Mol Biol* 308(5):1033-44
[29] Topf et al. (2005) *J Struct Biol* 149(2):191-203
[30] Tama et al. (2004) *J Struct Biol* 147(3):315-2
[31] Topf et al. (2008) *Structure* 16(2):295-307

[32] Trabuco et al. (2009) *Methods* 49(2):174-80
[33] Schroder et al. (2007) *Structure* 15(12):1630-41
[34] Zhang et al. (2010) *Nature* 463(7279):379-83
[35] Baker et al. (2006) *PLoS Comput Biol* 2(10):e146
[36] DiMaio et al. (2009) *J Mol Biol* 392(1):181-90
[37] Topf et al. (2006) *J Mol Biol* 357(5):1655-68
[38] Zhu et al. (2010) *J Mol Biol* 397(3):835-51
[39] Liang et al. (2002) *J Struct Biol* 137(3):292-304
[40] Grigorieff (2007) *J Struct Biol* 157(1):117-25
[41] Cheng et al. (2010) *J Mol Biol* 397(3):852-63
[42] Jiang et al. (2008) *Nature* 451(7182):1130-4
[43] Ludtke et al. (2008) *Structure* 16(3):441-8
[44] Yu et al. (2008) *Nature* 453(7193):415-9
[45] Ludtke et al. (1999) *J Struct Biol* 128(1):82-97
[46] Baker et al. (2007) *Structure* 15(1):7-19
[47] Pettersen et al. (2004) *J Comput Chem* 25(13):1605-12
[48] Emsley & Cowtan (2004) *Acta Crystallogr D Biol Crystallogr* 60(Pt 12 Pt 1):2126-32
[49] Emsley et al. (2010) *Acta Crystallogr D Biol Crystallogr* 66(Pt 4):486-501
[50] Baker et al. (2011) *J Struct Biol* 174(2):360-73
[51] Zhu et al. (2010) *J Mol Biol* 397(3):835-51
[52] Jones et al. (1991) *Acta Cystallogr A* 47 (Pt 2):110-9
[53] Brünger et al. (1998) *Acta Cystallogr D Biol Crystallogr* 54(Pt 5):905-21
[54] Li & Zhang (2009) *Proteins* 76(3):665-76
[55] Brünger (1992) *Nature* 355(6359):472-5
[56] Laskowski et al. (1993) *J Appl Cryst* 26:283-91
[57] Whittle et al. (2011) *Proc Natl Acad Sci USA* 108(34): 14216-21
[58] Aoki et al. (2009) *Science* 324(5933):1444-7
[59] Krause et al. (2011) *J Virol* 85(20):10905-8
[60] Bommakanti et al. (2010) *Proc Natl Acad Sci USA* 107(31):13701-6
[61] Chakraborty et al. (2006) *Biochem J* 399(3):483-91
[62] Bhattacharyya et al. (2010) *J Biol Chem* 285(35): 27100-10
[63] Ward et al. (1989) *Nature* 341:544-546
[64] Bird et al. (1988) *Science* 242:423-426
[65] Huston et al. (1988) *Proc. Natl. Acad. Sci. USA* 85:5879-5883
[66] Council of Europe (2014) *European pharmacopoeia*
[67] Ekiert et al. (2009) *Science* 324(5924): 246-251
[68] Lingwood et al. (2012) *Nature* 489(7417):566-70
[69] Tang et al. (2007) *J Struct Biol* 157(1):38-46
[70] Salk et al. (1945) *Am J Hyg* 42:57-93
[71] de Jong et al., Haemagglutination-inhibiting antibody to influenza virus. In Brown et al. (eds.) (2003) *Laboratory Correlates of Immunity to Influenza—A Reassessment*. Basel, Switzerland: Karger, 63-73

The invention claimed is:

1. A chimeric protein complex comprising a trimer-forming rotavirus VP7 surface protein linked to a heterologous protein, wherein the rotavirus VP7 surface protein is linked to the heterologous protein non-covalently by a two-part adapter system, wherein the first part of the adapter system comprises a first adapter polypeptide that is fused to the rotavirus VP7 surface protein optionally via a linker sequence, and the second part of the adapter system comprises a second adapter polypeptide that is fused to the heterologous protein optionally via a linker sequence, wherein the first and the second parts of the adapter system form a stable complex with each other, and wherein the chimeric protein complex is capable of recoating and thereby forming a part of an outer layer of double-layered rotavirus particles in vitro.

2. The chimeric protein complex of claim 1, wherein the first adapter polypeptide and the second adapter polypeptide comprise a heptad repeat sequence.

3. A rotavirus particle comprising the chimeric protein complex of claim 1.

4. A formulation comprising a rotavirus particle of claim 3 and a solution, optionally together with an excipient.

5. A nucleic acid composition comprising:
   (a) an open reading frame encoding a modified rotavirus surface protein comprising
       a trimer-forming rotavirus VP7 surface protein,
       a first adapter polypeptide that is fused to the trimer-forming rotavirus VP7 surface protein optionally via a linker sequence; and
   (b) an open reading frame encoding a fusion protein comprising
       a protein that is heterologous to the trimer-forming rotavirus VP7 surface protein,
       a second adapter polypeptide that is fused to the heterologous protein optionally via a linker sequence,
   wherein the first and the second adapter polypeptides form a stable protein complex with each other; and
   (c) optionally a promoter sequence that is operationally linked to the open reading frame of (a) and further optionally a promoter sequence that is operationally linked to the open reading frame of (b).

6. The nucleic acid composition of claim 5, wherein the adapter polypeptide comprises a heptad repeat sequence.

7. A kit comprising:
   (a) a first nucleic acid encoding a modified rotavirus surface protein comprising a trimer-forming rotavirus VP7 surface protein and a first adapter polypeptide, and a second nucleic acid comprising a nucleotide sequence encoding a second adapter polypeptide and a multiple cloning site, and wherein insertion of a coding region for a heterologous protein in the multiple cloning site yields an open reading frame encoding a fusion protein comprising the heterologous protein and the second adapter polypeptide; or
   (b) a first nucleic acid encoding a modified rotavirus surface protein comprising a trimer-forming rotavirus VP7 surface protein and a first adapter polypeptide and a second nucleic acid encoding a fusion protein comprising a heterologous protein and a second adapter polypeptide;
   wherein, in each case (a) and (b), the first adapter polypeptide and the second adapter polypeptide are able to form a stable protein complex,
   optionally wherein the kit further comprises a rotavirus particle, wherein the particle is from the same species of rotavirus as the rotavirus from which the trimer-forming VP7 surface protein originated or from a different rotavirus species.

8. A method for preparing the rotavirus particle of claim 3, wherein the method comprises propagating a rotavirus particle comprising an outer layer in a cell grown in a culture medium, purifying the rotavirus particle from the culture medium, removing the outer layer from the rotavirus particle to obtain a rotavirus double-layered particle (DLP), and recoating the rotavirus DLP with the chimeric protein complex of claim 1 to yield the rotavirus particle of claim 3.

9. A method for preparing the rotavirus particle of claim 3, wherein the method comprises propagating a rotavirus particle comprising an outer layer in a cell grown in a culture medium, purifying the rotavirus particle from the culture medium, removing the outer layer from the rotavirus particle to obtain a rotavirus DLP, and recoating the rotavirus DLP with a first fusion protein comprising a trimer-forming rotavirus VP7 surface protein, a first adapter polypeptide comprising a heptad repeat sequence, and optionally a linker sequence and mixing the recoated rotavirus DLP with a second fusion protein comprising a trimer-forming heterologous protein, a second adapter polypeptide comprising a heptad repeat sequence, and optionally a linker sequence to yield the rotavirus particle of claim 3.

10. A method for preparing the rotavirus particle of claim 3 comprising mixing a rotavirus particle comprising a first fusion protein comprising a trimer-forming rotavirus VP7 surface protein, a first adapter polypeptide comprising a heptad repeat sequence, and optionally a linker sequence with a second fusion protein comprising a trimer-forming heterologous protein, a second adapter polypeptide comprising a heptad repeat sequence, and optionally a linker sequence to yield the rotavirus particle of claim 3.

11. A method for determining a structure of a heterologous protein, wherein the method comprises the steps of (i) recoating a rotavirus double-layered particle (DLP) with the chimeric protein complex of claim 1 to yield a suspension of rotavirus particles displaying the chimeric protein complex, (ii) freezing the suspension, (iii) imaging the rotavirus particles using cryo-EM to obtain a plurality of micrographs, and (iv) analysing the plurality of micrographs to obtain a three-dimensional model of the chimeric protein complex.

12. A method for determining a structure of a heterologous protein in complex with a molecule, wherein the method comprises the steps of (i) recoating a rotavirus double-layered particle (DLP) with the chimeric protein complex of claim 1 to yield a suspension of rotavirus particles displaying the chimeric protein complex, (ii) adding to the suspension a molecule that specifically binds to the heterologous protein, wherein the molecule forms a complex with the chimeric protein complex, (iii) freezing the suspension, (iv) imaging the rotavirus particles using cryo-EM to obtain a plurality of micrographs, and (vi) analysing the plurality of micrographs to obtain a three-dimensional model of the chimeric surface protein comprising all or part of the heterologous protein complexed to the molecule.

13. The method of claim 12, wherein the molecule is a proteinaceous molecule.

14. The method of claim 13, wherein the proteinaceous molecule is (a) an antibody or fragment thereof, wherein the antibody or fragment specifically binds the heterologous protein; or (b) a cell surface receptor, wherein the heterologous protein is a viral cell entry protein and the proteinaceous molecule is bound by the viral cell entry protein.

* * * * *

UNITED STATES PATENT AND TRADEMARK OFFICE
CERTIFICATE OF CORRECTION

PATENT NO. : 10,192,025 B2
APPLICATION NO. : 14/900829
DATED : January 29, 2019
INVENTOR(S) : Philip R. Dormitzer et al.

Page 1 of 1

It is certified that error appears in the above-identified patent and that said Letters Patent is hereby corrected as shown below:

On the Title Page

Item (73) ASSIGNEE:
Replace "Novartis AG" with -- Novartis AG, Basel, Switzerland, Children's Medical Center Corporation, Boston, MA, and Brandeis University, Waltham, MA --

Signed and Sealed this
Eighteenth Day of June, 2019

Andrei Iancu
*Director of the United States Patent and Trademark Office*

UNITED STATES PATENT AND TRADEMARK OFFICE
CERTIFICATE OF CORRECTION

PATENT NO. : 10,192,025 B2
APPLICATION NO. : 14/900829
DATED : January 29, 2019
INVENTOR(S) : Philip R. Dormitzer et al.

Page 1 of 1

It is certified that error appears in the above-identified patent and that said Letters Patent is hereby corrected as shown below:

In the Specification

GOVERNMENT SUPPORT:
Column 1, Line 6:
Replace "This invention was made with U.S. government support under Grant Nos. P01-GM062580 and AI-89618 awarded by the National Institutes of Health." with -- This invention was made with government support under Grant Nos. AI089618, AI053174, CA013202 and GM062580 awarded by the National Institutes of Health. --

This certificate supersedes the Certificate of Correction issued June 18, 2019.

Signed and Sealed this
Fourteenth Day of April, 2020

Andrei Iancu
*Director of the United States Patent and Trademark Office*

SEQUENCE LISTING

```
<160> NUMBER OF SEQ ID NOS: 83

<210> SEQ ID NO 1
<211> LENGTH: 28
<212> TYPE: PRT
<213> ORGANISM: Artificial Sequence
<220> FEATURE:
<223> OTHER INFORMATION: HIV HXB2 strain HR2 sequence

<400> SEQUENCE: 1

Trp Met Glu Trp Asp Arg Glu Ile Asn Asn Tyr Thr Ser Leu Ile His
1               5                   10                  15

Ser Leu Ile Glu Glu Ser Gln Asn Gln Gln Glu Lys
            20                  25

<210> SEQ ID NO 2
<211> LENGTH: 34
<212> TYPE: PRT
<213> ORGANISM: Artificial Sequence
<220> FEATURE:
<223> OTHER INFORMATION: HIV HXB2 HR1 sequence

<400> SEQUENCE: 2

Ser Gly Ile Val Gln Gln Gln Asn Asn Leu Leu Arg Ala Ile Glu Ala
1               5                   10                  15

Gln Gln His Leu Leu Gln Leu Thr Val Trp Gly Ile Lys Gln Leu Gln
            20                  25                  30

Ala Arg

<210> SEQ ID NO 3
<211> LENGTH: 30
<212> TYPE: PRT
<213> ORGANISM: Artificial Sequence
<220> FEATURE:
<223> OTHER INFORMATION: Nipah virus HR2 sequence

<400> SEQUENCE: 3

Asp Ile Ser Ser Gln Ile Ser Ser Met Asn Gln Ser Leu Gln Gln Ser
```

```
1               5                   10                  15
Lys Asp Tyr Ile Lys Glu Ala Gln Arg Leu Leu Asp Thr Val
            20                  25                  30
```

<210> SEQ ID NO 4
<211> LENGTH: 32
<212> TYPE: PRT
<213> ORGANISM: Artificial Sequence
<220> FEATURE:
<223> OTHER INFORMATION: Nipah virus HR1 sequence

<400> SEQUENCE: 4

```
Asn Lys Leu Lys Ser Ser Ile Glu Ser Thr Asn Glu Ala Val Val Lys
1               5                   10                  15

Leu Gln Glu Thr Ala Glu Lys Thr Val Tyr Val Leu Thr Ala Leu Gln
            20                  25                  30
```

<210> SEQ ID NO 5
<211> LENGTH: 5
<212> TYPE: PRT
<213> ORGANISM: Artificial Sequence
<220> FEATURE:
<223> OTHER INFORMATION: Linker

<400> SEQUENCE: 5

```
Gly Gly Ser Gly Gly
1               5
```

<210> SEQ ID NO 6
<211> LENGTH: 8
<212> TYPE: PRT
<213> ORGANISM: Artificial Sequence
<220> FEATURE:
<223> OTHER INFORMATION: Linker

<400> SEQUENCE: 6

```
Gly Ser Gly Ser Gly Ser Gly Thr
1               5
```

<210> SEQ ID NO 7
<211> LENGTH: 5
<212> TYPE: PRT
<213> ORGANISM: Artificial Sequence
<220> FEATURE:
<223> OTHER INFORMATION: Linker

<400> SEQUENCE: 7

```
Glu Ala Ala Ala Arg
1               5
```

<210> SEQ ID NO 8
<211> LENGTH: 12
<212> TYPE: PRT
<213> ORGANISM: Artificial Sequence
<220> FEATURE:
<223> OTHER INFORMATION: Human factor XI recognition site

<400> SEQUENCE: 8

```
Gln Thr Ser Lys Leu Thr Arg Ala Glu Ala Val Phe
1               5                   10
```

<210> SEQ ID NO 9
<211> LENGTH: 12
<212> TYPE: PRT
<213> ORGANISM: Artificial Sequence
<220> FEATURE:

<223> OTHER INFORMATION: Human factor XI recognition site

<400> SEQUENCE: 9

Ser Phe Asn Asp Phe Thr Arg Val Val Gly Gly Glu
1               5                   10

<210> SEQ ID NO 10
<211> LENGTH: 13
<212> TYPE: PRT
<213> ORGANISM: Artificial Sequence
<220> FEATURE:
<223> OTHER INFORMATION: Human kallikrein recognition site

<400> SEQUENCE: 10

Leu Phe Ser Ser Met Thr Arg Val Val Gly Gly Leu Val
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Human facor XII recognition site

<400> SEQUENCE: 11

Lys Ile Lys Pro Arg Ile Val Gly Gly Thr
1               5                   10

<210> SEQ ID NO 12
<211> LENGTH: 8
<212> TYPE: PRT
<213> ORGANISM: Artificial Sequence
<220> FEATURE:
<223> OTHER INFORMATION: FLAG-tag

<400> SEQUENCE: 12

Asp Tyr Lys Asp Asp Asp Asp Lys
1               5

<210> SEQ ID NO 13
<211> LENGTH: 9
<212> TYPE: PRT
<213> ORGANISM: Artificial Sequence
<220> FEATURE:
<223> OTHER INFORMATION: HA-tag

<400> SEQUENCE: 13

Tyr Pro Tyr Asp Val Pro Asp Tyr Ala
1               5

<210> SEQ ID NO 14
<211> LENGTH: 6
<212> TYPE: PRT
<213> ORGANISM: Artificial Sequence
<220> FEATURE:
<223> OTHER INFORMATION: His-tag

<400> SEQUENCE: 14

His His His His His His
1               5

<210> SEQ ID NO 15
<211> LENGTH: 10
<212> TYPE: PRT
<213> ORGANISM: Artificial Sequence
<220> FEATURE:
<223> OTHER INFORMATION: Myc-tag

```
<400> SEQUENCE: 15

Glu Gln Lys Leu Ile Ser Glu Glu Asp Leu
1               5                   10

<210> SEQ ID NO 16
<211> LENGTH: 9
<212> TYPE: PRT
<213> ORGANISM: Artificial Sequence
<220> FEATURE:
<223> OTHER INFORMATION: Strep-tag I

<400> SEQUENCE: 16

Ala Trp Arg His Pro Gln Phe Gly Gly
1               5

<210> SEQ ID NO 17
<211> LENGTH: 9
<212> TYPE: PRT
<213> ORGANISM: Artificial Sequence
<220> FEATURE:
<223> OTHER INFORMATION: Strep-tag II

<400> SEQUENCE: 17

Asn Trp Ser His Pro Gln Phe Glu Lys
1               5

<210> SEQ ID NO 18
<211> LENGTH: 12
<212> TYPE: PRT
<213> ORGANISM: Artificial Sequence
<220> FEATURE:
<223> OTHER INFORMATION: protein C-tag

<400> SEQUENCE: 18

Glu Asp Gln Val Asp Pro Arg Leu Ile Asp Gly Lys
1               5                   10

<210> SEQ ID NO 19
<211> LENGTH: 6
<212> TYPE: DNA
<213> ORGANISM: Artificial Sequence
<220> FEATURE:
<223> OTHER INFORMATION: Kozak sequence

<400> SEQUENCE: 19 gccacc                                                                6

<210> SEQ ID NO 20
<211> LENGTH: 15
<212> TYPE: PRT
<213> ORGANISM: Artificial Sequence
<220> FEATURE:
<223> OTHER INFORMATION: Linker

<400> SEQUENCE: 20

Gly Gly Ser Gly Gly Ser Gly Gly Ser Gly Gly Ser Gly Gly Ser
1               5                   10                  15

<210> SEQ ID NO 21
<211> LENGTH: 17
<212> TYPE: PRT
<213> ORGANISM: Artificial Sequence
<220> FEATURE:
<223> OTHER INFORMATION: Linker

<400> SEQUENCE: 21
```

```
Gly Gly Ser Gly Gly Ser Gly Gly Ser Gly Gly Ser Gly
1               5                   10                  15

Gly
```

<210> SEQ ID NO 22
<211> LENGTH: 367
<212> TYPE: PRT
<213> ORGANISM: Artificial Sequence
<220> FEATURE:
<223> OTHER INFORMATION: Engineered Rhesus Rotavirus VP7-HR2HXB2 fusion
      protein

<400> SEQUENCE: 22

```
Met Lys Phe Leu Val Asn Val Ala Leu Val Phe Met Val Val Tyr Ile
1               5                   10                  15

Ser Tyr Ile Tyr Ala Glu Asp Ser Ala Trp Ser His Pro Gln Phe Glu
            20                  25                  30

Lys Glu Asn Leu Tyr Phe Gln Gly Gln Asn Tyr Gly Ile Asn Leu Pro
        35                  40                  45

Ile Thr Gly Ser Met Asp Thr Ala Tyr Ala Asn Ser Thr Gln Glu Glu
    50                  55                  60

Thr Phe Leu Thr Ser Thr Leu Cys Leu Tyr Tyr Pro Thr Glu Ala Ala
65                  70                  75                  80

Thr Glu Ile Asn Asp Asn Ser Trp Lys Asp Thr Leu Ser Gln Leu Phe
                85                  90                  95

Leu Thr Lys Gly Trp Pro Thr Gly Ser Val Tyr Phe Lys Glu Tyr Thr
            100                 105                 110

Asp Ile Ala Ser Phe Ser Val Asp Pro Gln Leu Tyr Cys Asp Tyr Asn
        115                 120                 125

Val Val Leu Met Lys Tyr Asp Ala Gly Trp Met Glu Trp Asp Arg Glu
    130                 135                 140

Ile Asn Asn Tyr Thr Ser Leu Ile His Ser Leu Ile Glu Glu Ser Gln
145                 150                 155                 160

Asn Gln Gln Glu Lys Ile Glu Gly Arg Ser Gly Gly Glu Asp Gln Val
                165                 170                 175

Asp Pro Arg Leu Ile Asp Gly Lys Ser Gly Gly Thr Leu Gln Leu Asp
            180                 185                 190

Met Ser Glu Leu Ala Asp Leu Ile Leu Asn Glu Trp Leu Cys Asn Pro
        195                 200                 205

Met Asp Ile Thr Leu Tyr Tyr Tyr Gln Gln Thr Asp Glu Ala Asn Lys
    210                 215                 220

Trp Ile Ser Met Gly Ser Ser Cys Thr Ile Lys Val Cys Pro Leu Asn
225                 230                 235                 240

Thr Gln Thr Leu Gly Ile Gly Cys Leu Thr Thr Asp Thr Ala Thr Phe
                245                 250                 255

Glu Glu Val Ala Thr Ala Glu Lys Leu Val Ile Thr Asp Val Val Asp
            260                 265                 270

Gly Val Asn His Lys Leu Asp Val Thr Thr Ala Thr Cys Thr Ile Arg
        275                 280                 285

Asn Cys Lys Lys Leu Gly Pro Arg Glu Asn Val Ala Val Ile Gln Val
    290                 295                 300

Gly Gly Ser Asp Val Leu Asp Ile Thr Ala Asp Pro Thr Thr Ala Pro
305                 310                 315                 320

Gln Thr Glu Arg Met Met Arg Ile Asn Trp Lys Lys Trp Trp Gln Val
                325                 330                 335
```

```
Phe Tyr Thr Val Val Asp Tyr Val Asn Gln Ile Ile Gln Ala Met Ser
                340                 345                 350

Lys Arg Ser Arg Ser Leu Asn Ser Ala Ala Phe Tyr Tyr Arg Ile
                355                 360                 365

<210> SEQ ID NO 23
<211> LENGTH: 365
<212> TYPE: PRT
<213> ORGANISM: Artificial Sequence
<220> FEATURE:
<223> OTHER INFORMATION: Engineered Rhesus Rotavirus VP7-HR2HXB2 fusion
      protein

<400> SEQUENCE: 23

Met Lys Phe Leu Val Asn Val Ala Leu Val Phe Met Val Val Tyr Ile
1               5                   10                  15

Ser Tyr Ile Tyr Ala Glu Asp Ser Ala Trp Ser His Pro Gln Phe Glu
                20                  25                  30

Lys Glu Asn Leu Tyr Phe Gln Gly Gln Asn Tyr Gly Ile Asn Leu Pro
                35                  40                  45

Ile Thr Gly Ser Met Asp Thr Ala Tyr Ala Asn Ser Thr Gln Glu Glu
        50                  55                  60

Thr Phe Leu Thr Ser Thr Leu Cys Leu Tyr Tyr Pro Thr Glu Ala Ala
65              70                  75                  80

Thr Glu Ile Asn Asp Asn Ser Trp Lys Asp Thr Leu Ser Gln Leu Phe
                85                  90                  95

Leu Thr Lys Gly Trp Pro Thr Gly Ser Val Tyr Phe Lys Glu Tyr Thr
                100                 105                 110

Asp Ile Ala Ser Phe Ser Val Asp Pro Gln Leu Tyr Cys Asp Tyr Asn
            115                 120                 125

Val Val Leu Met Lys Tyr Asp Ala Gly Trp Met Glu Trp Asp Arg Glu
130                 135                 140

Ile Asn Asn Tyr Thr Ser Leu Ile His Ser Leu Ile Glu Glu Ser Gln
145                 150                 155                 160

Asn Gln Gln Glu Lys Ile Glu Gly Arg Ser Gly Gly Glu Asp Gln Val
                165                 170                 175

Asp Pro Arg Leu Ile Asp Gly Lys Gly Thr Leu Gln Leu Asp Met Ser
            180                 185                 190

Glu Leu Ala Asp Leu Ile Leu Asn Glu Trp Leu Cys Asn Pro Met Asp
                195                 200                 205

Ile Thr Leu Tyr Tyr Gln Gln Thr Asp Glu Ala Asn Lys Trp Ile
            210                 215                 220

Ser Met Gly Ser Ser Cys Thr Ile Lys Val Cys Pro Leu Asn Thr Gln
225                 230                 235                 240

Thr Leu Gly Ile Gly Cys Leu Thr Thr Asp Thr Ala Thr Phe Glu Glu
                245                 250                 255

Val Ala Thr Ala Glu Lys Leu Val Ile Thr Asp Val Val Asp Gly Val
                260                 265                 270

Asn His Lys Leu Asp Val Thr Thr Ala Thr Cys Thr Ile Arg Asn Cys
            275                 280                 285

Lys Lys Leu Gly Pro Arg Glu Asn Val Ala Val Ile Gln Val Gly Gly
        290                 295                 300

Ser Asp Val Leu Asp Ile Thr Ala Asp Pro Thr Thr Ala Pro Gln Thr
305                 310                 315                 320

Glu Arg Met Met Arg Ile Asn Trp Lys Lys Trp Trp Gln Val Phe Tyr
```

```
            325                 330                 335
Thr Val Asp Tyr Val Asn Gln Ile Ile Gln Ala Met Ser Lys Arg
            340                 345                 350
Ser Arg Ser Leu Asn Ser Ala Ala Phe Tyr Tyr Arg Ile
            355                 360             365

<210> SEQ ID NO 24
<211> LENGTH: 363
<212> TYPE: PRT
<213> ORGANISM: Artificial Sequence
<220> FEATURE:
<223> OTHER INFORMATION: Engineered Rhesus Rotavirus VP7-HR2HXB2 fusion
      protein

<400> SEQUENCE: 24

Met Lys Phe Leu Val Asn Val Ala Leu Val Phe Met Val Val Tyr Ile
1               5                   10                  15

Ser Tyr Ile Tyr Ala Glu Asp Ser Ala Trp Ser His Pro Gln Phe Glu
            20                  25                  30

Lys Glu Asn Leu Tyr Phe Gln Gly Gln Asn Tyr Gly Ile Asn Leu Pro
        35                  40                  45

Ile Thr Gly Ser Met Asp Thr Ala Tyr Ala Asn Ser Thr Gln Glu Glu
    50                  55                  60

Thr Phe Leu Thr Ser Thr Leu Cys Leu Tyr Tyr Pro Thr Glu Ala Ala
65                  70                  75                  80

Thr Glu Ile Asn Asp Asn Ser Trp Lys Asp Thr Leu Ser Gln Leu Phe
                85                  90                  95

Leu Thr Lys Gly Trp Pro Thr Gly Ser Val Tyr Phe Lys Glu Tyr Thr
            100                 105                 110

Asp Ile Ala Ser Phe Ser Val Asp Pro Gln Leu Tyr Cys Asp Tyr Asn
        115                 120                 125

Val Val Leu Met Lys Tyr Asp Ala Gly Trp Met Glu Trp Asp Arg Glu
    130                 135                 140

Ile Asn Asn Tyr Thr Ser Leu Ile His Ser Leu Ile Glu Glu Ser Gln
145                 150                 155                 160

Asn Gln Gln Glu Lys Ser Gly Gly Glu Asp Gln Val Asp Pro Arg Leu
                165                 170                 175

Ile Asp Gly Lys Ser Gly Gly Thr Leu Gln Leu Asp Met Ser Glu Leu
            180                 185                 190

Ala Asp Leu Ile Leu Asn Glu Trp Leu Cys Asn Pro Met Asp Ile Thr
        195                 200                 205

Leu Tyr Tyr Tyr Gln Gln Thr Asp Glu Ala Asn Lys Trp Ile Ser Met
    210                 215                 220

Gly Ser Ser Cys Thr Ile Lys Val Cys Pro Leu Asn Thr Gln Thr Leu
225                 230                 235                 240

Gly Ile Gly Cys Leu Thr Thr Asp Thr Ala Thr Phe Glu Glu Val Ala
                245                 250                 255

Thr Ala Glu Lys Leu Val Ile Thr Asp Val Val Asp Gly Val Asn His
            260                 265                 270

Lys Leu Asp Val Thr Thr Ala Thr Cys Thr Ile Arg Asn Cys Lys Lys
        275                 280                 285

Leu Gly Pro Arg Glu Asn Val Ala Val Ile Gln Val Gly Gly Ser Asp
    290                 295                 300

Val Leu Asp Ile Thr Ala Asp Pro Thr Thr Ala Pro Gln Thr Glu Arg
305                 310                 315                 320
```

```
Met Met Arg Ile Asn Trp Lys Lys Trp Trp Gln Val Phe Tyr Thr Val
            325                 330                 335

Val Asp Tyr Val Asn Gln Ile Ile Gln Ala Met Ser Lys Arg Ser Arg
        340                 345                 350

Ser Leu Asn Ser Ala Ala Phe Tyr Tyr Arg Ile
        355                 360

<210> SEQ ID NO 25
<211> LENGTH: 361
<212> TYPE: PRT
<213> ORGANISM: Artificial Sequence
<220> FEATURE:
<223> OTHER INFORMATION: Engineered Rhesus Rotavirus VP7-HR2HXB2 fusion
      protein

<400> SEQUENCE: 25

Met Lys Phe Leu Val Asn Val Ala Leu Val Phe Met Val Val Tyr Ile
1               5                   10                  15

Ser Tyr Ile Tyr Ala Glu Asp Ser Ala Trp Ser His Pro Gln Phe Glu
            20                  25                  30

Lys Glu Asn Leu Tyr Phe Gln Gly Gln Asn Tyr Gly Ile Asn Leu Pro
        35                  40                  45

Ile Thr Gly Ser Met Asp Thr Ala Tyr Ala Asn Ser Thr Gln Glu Glu
    50                  55                  60

Thr Phe Leu Thr Ser Thr Leu Cys Leu Tyr Tyr Pro Thr Glu Ala Ala
65                  70                  75                  80

Thr Glu Ile Asn Asp Asn Ser Trp Lys Asp Thr Leu Ser Gln Leu Phe
                85                  90                  95

Leu Thr Lys Gly Trp Pro Thr Gly Ser Val Tyr Phe Lys Glu Tyr Thr
            100                 105                 110

Asp Ile Ala Ser Phe Ser Val Asp Pro Gln Leu Tyr Cys Asp Tyr Asn
        115                 120                 125

Val Val Leu Met Lys Tyr Asp Ala Gly Trp Met Glu Trp Asp Arg Glu
    130                 135                 140

Ile Asn Asn Tyr Thr Ser Leu Ile His Ser Leu Ile Glu Glu Ser Gln
145                 150                 155                 160

Asn Gln Gln Glu Lys Ser Gly Gly Glu Asp Gln Val Asp Pro Arg Leu
                165                 170                 175

Ile Asp Gly Lys Gly Thr Leu Gln Leu Asp Met Ser Glu Leu Ala Asp
            180                 185                 190

Leu Ile Leu Asn Glu Trp Leu Cys Asn Pro Met Asp Ile Thr Leu Tyr
        195                 200                 205

Tyr Tyr Gln Gln Thr Asp Glu Ala Asn Lys Trp Ile Ser Met Gly Ser
    210                 215                 220

Ser Cys Thr Ile Lys Val Cys Pro Leu Asn Thr Gln Thr Leu Gly Ile
225                 230                 235                 240

Gly Cys Leu Thr Thr Asp Thr Ala Thr Phe Glu Glu Val Ala Thr Ala
                245                 250                 255

Glu Lys Leu Val Ile Thr Asp Val Val Asp Gly Val Asn His Lys Leu
            260                 265                 270

Asp Val Thr Thr Ala Thr Cys Thr Ile Arg Asn Cys Lys Lys Leu Gly
        275                 280                 285

Pro Arg Glu Asn Val Ala Val Ile Gln Val Gly Gly Ser Asp Val Leu
    290                 295                 300

Asp Ile Thr Ala Asp Pro Thr Thr Ala Pro Gln Thr Glu Arg Met Met
305                 310                 315                 320
```

Arg Ile Asn Trp Lys Lys Trp Gln Val Phe Tyr Thr Val Val Asp
            325                 330                 335

Tyr Val Asn Gln Ile Ile Gln Ala Met Ser Lys Arg Ser Arg Ser Leu
            340                 345                 350

Asn Ser Ala Ala Phe Tyr Tyr Arg Ile
            355                 360

<210> SEQ ID NO 26
<211> LENGTH: 359
<212> TYPE: PRT
<213> ORGANISM: Artificial Sequence
<220> FEATURE:
<223> OTHER INFORMATION: Engineered Rhesus Rotavirus VP7-HR2HXB2 fusion
      protein

<400> SEQUENCE: 26

Met Lys Phe Leu Val Asn Val Ala Leu Val Phe Met Val Val Tyr Ile
1               5                   10                  15

Ser Tyr Ile Tyr Ala Glu Asp Ser Ala Trp Ser His Pro Gln Phe Glu
            20                  25                  30

Lys Glu Asn Leu Tyr Phe Gln Gly Gln Asn Tyr Gly Ile Asn Leu Pro
            35                  40                  45

Ile Thr Gly Ser Met Asp Thr Ala Tyr Ala Asn Ser Thr Gln Glu Glu
        50                  55                  60

Thr Phe Leu Thr Ser Thr Leu Cys Leu Tyr Tyr Pro Thr Glu Ala Ala
65              70                  75                  80

Thr Glu Ile Asn Asp Asn Ser Trp Lys Asp Thr Leu Ser Gln Leu Phe
                85                  90                  95

Leu Thr Lys Gly Trp Pro Thr Gly Ser Val Tyr Phe Lys Glu Tyr Thr
            100                 105                 110

Asp Ile Ala Ser Phe Ser Val Asp Pro Gln Leu Tyr Cys Asp Tyr Asn
        115                 120                 125

Val Val Leu Met Lys Tyr Asp Ala Gly Trp Met Glu Trp Asp Arg Glu
130             135                 140

Ile Asn Asn Tyr Thr Ser Leu Ile His Ser Leu Ile Glu Glu Ser Gln
145             150                 155                 160

Asn Gln Gln Glu Lys Gly Glu Asp Gln Val Asp Pro Arg Leu Ile Asp
            165                 170                 175

Gly Lys Gly Thr Leu Gln Leu Asp Met Ser Glu Leu Ala Asp Leu Ile
        180                 185                 190

Leu Asn Glu Trp Leu Cys Asn Pro Met Asp Ile Thr Leu Tyr Tyr Tyr
            195                 200                 205

Gln Gln Thr Asp Glu Ala Asn Lys Trp Ile Ser Met Gly Ser Ser Cys
        210                 215                 220

Thr Ile Lys Val Cys Pro Leu Asn Thr Gln Thr Leu Gly Ile Gly Cys
225             230                 235                 240

Leu Thr Thr Asp Thr Ala Thr Phe Glu Glu Val Ala Thr Ala Glu Lys
            245                 250                 255

Leu Val Ile Thr Asp Val Val Asp Gly Val Asn His Lys Leu Asp Val
            260                 265                 270

Thr Thr Ala Thr Cys Thr Ile Arg Asn Cys Lys Lys Leu Gly Pro Arg
        275                 280                 285

Glu Asn Val Ala Val Ile Gln Val Gly Gly Ser Asp Val Leu Asp Ile
290                 295                 300

Thr Ala Asp Pro Thr Thr Ala Pro Gln Thr Glu Arg Met Met Arg Ile

```
                    305                 310                 315                 320
Asn Trp Lys Lys Trp Trp Gln Val Phe Tyr Thr Val Asp Tyr Val
                325                 330                 335

Asn Gln Ile Ile Gln Ala Met Ser Lys Arg Ser Arg Ser Leu Asn Ser
            340                 345                 350

Ala Ala Phe Tyr Tyr Arg Ile
        355

<210> SEQ ID NO 27
<211> LENGTH: 377
<212> TYPE: PRT
<213> ORGANISM: Artificial Sequence
<220> FEATURE:
<223> OTHER INFORMATION: Engineered Rhesus Rotavirus VP7-HR2HXB2 fusion
      protein

<400> SEQUENCE: 27

Met Lys Phe Leu Val Asn Val Ala Leu Val Phe Met Val Val Tyr Ile
1               5                   10                  15

Ser Tyr Ile Tyr Ala Glu Asp Ser Ala Trp Ser His Pro Gln Phe Glu
            20                  25                  30

Lys Glu Asn Leu Tyr Phe Gln Gly Gln Asn Tyr Gly Ile Asn Leu Pro
        35                  40                  45

Ile Thr Gly Ser Met Asp Thr Ala Tyr Ala Asn Ser Thr Gln Glu Glu
50                  55                  60

Thr Phe Leu Thr Ser Thr Leu Cys Leu Tyr Tyr Pro Thr Glu Ala Ala
65                  70                  75                  80

Thr Glu Ile Asn Asp Asn Ser Trp Lys Asp Thr Leu Ser Gln Leu Phe
                85                  90                  95

Leu Thr Lys Gly Trp Pro Thr Gly Ser Val Tyr Phe Lys Glu Tyr Thr
            100                 105                 110

Asp Ile Ala Ser Phe Ser Val Asp Pro Gln Leu Tyr Cys Asp Tyr Asn
        115                 120                 125

Val Val Leu Met Lys Tyr Asp Ala Gly Trp Met Glu Trp Asp Arg Glu
130                 135                 140

Ile Asn Asn Tyr Thr Ser Leu Ile His Ser Leu Ile Glu Glu Ser Gln
145                 150                 155                 160

Asn Gln Gln Glu Lys Asn Glu Gln Glu Leu Leu Glu Leu Asp Lys Trp
                165                 170                 175

Ala Ser Leu Ser Gly Gly Glu Asp Gln Val Asp Pro Arg Leu Ile Asp
            180                 185                 190

Gly Lys Ser Gly Gly Thr Leu Gln Leu Asp Met Ser Glu Leu Ala Asp
        195                 200                 205

Leu Ile Leu Asn Glu Trp Leu Cys Asn Pro Met Asp Ile Thr Leu Tyr
210                 215                 220

Tyr Tyr Gln Gln Thr Asp Glu Ala Asn Lys Trp Ile Ser Met Gly Ser
225                 230                 235                 240

Ser Cys Thr Ile Lys Val Cys Pro Leu Asn Thr Gln Thr Leu Gly Ile
                245                 250                 255

Gly Cys Leu Thr Thr Asp Thr Ala Thr Phe Glu Glu Val Ala Thr Ala
            260                 265                 270

Glu Lys Leu Val Ile Thr Asp Val Val Asp Gly Val Asn His Lys Leu
        275                 280                 285

Asp Val Thr Thr Ala Thr Cys Thr Ile Arg Asn Cys Lys Lys Leu Gly
    290                 295                 300
```

```
Pro Arg Glu Asn Val Ala Val Ile Gln Val Gly Gly Ser Asp Val Leu
305                 310                 315                 320

Asp Ile Thr Ala Asp Pro Thr Thr Ala Pro Gln Thr Glu Arg Met Met
            325                 330                 335

Arg Ile Asn Trp Lys Lys Trp Trp Gln Val Phe Tyr Thr Val Val Asp
                340                 345                 350

Tyr Val Asn Gln Ile Ile Gln Ala Met Ser Lys Arg Ser Arg Ser Leu
            355                 360                 365

Asn Ser Ala Ala Phe Tyr Tyr Arg Ile
        370                 375

<210> SEQ ID NO 28
<211> LENGTH: 373
<212> TYPE: PRT
<213> ORGANISM: Artificial Sequence
<220> FEATURE:
<223> OTHER INFORMATION: Engineered Rhesus Rotavirus VP7-HR2HXB2 fusion
      protein

<400> SEQUENCE: 28

Met Lys Phe Leu Val Asn Val Ala Leu Val Phe Met Val Val Tyr Ile
1               5                   10                  15

Ser Tyr Ile Tyr Ala Glu Asp Ser Ala Trp Ser His Pro Gln Phe Glu
            20                  25                  30

Lys Glu Asn Leu Tyr Phe Gln Gly Gln Asn Tyr Gly Ile Asn Leu Pro
        35                  40                  45

Ile Thr Gly Ser Met Asp Thr Ala Tyr Ala Asn Ser Thr Gln Glu Glu
    50                  55                  60

Thr Phe Leu Thr Ser Thr Leu Cys Leu Tyr Tyr Pro Thr Glu Ala Ala
65                  70                  75                  80

Thr Glu Ile Asn Asp Asn Ser Trp Lys Asp Thr Leu Ser Gln Leu Phe
                85                  90                  95

Leu Thr Lys Gly Trp Pro Thr Gly Ser Val Tyr Phe Lys Glu Tyr Thr
            100                 105                 110

Asp Ile Ala Ser Phe Ser Val Asp Pro Gln Leu Tyr Cys Asp Tyr Asn
        115                 120                 125

Val Val Leu Met Lys Tyr Asp Ala Gly Trp Met Glu Trp Asp Arg Glu
    130                 135                 140

Ile Asn Asn Tyr Thr Ser Leu Ile His Ser Leu Ile Glu Glu Ser Gln
145                 150                 155                 160

Asn Gln Gln Glu Lys Asn Glu Gln Glu Leu Leu Glu Leu Asp Lys Trp
                165                 170                 175

Ala Ser Leu Gly Glu Asp Gln Val Asp Pro Arg Leu Ile Asp Gly Lys
            180                 185                 190

Gly Thr Leu Gln Leu Asp Met Ser Glu Leu Ala Asp Leu Ile Leu Asn
        195                 200                 205

Glu Trp Leu Cys Asn Pro Met Asp Ile Thr Leu Tyr Tyr Tyr Gln Gln
    210                 215                 220

Thr Asp Glu Ala Asn Lys Trp Ile Ser Met Gly Ser Ser Cys Thr Ile
225                 230                 235                 240

Lys Val Cys Pro Leu Asn Thr Gln Thr Leu Gly Ile Gly Cys Leu Thr
                245                 250                 255

Thr Asp Thr Ala Thr Phe Glu Glu Val Ala Thr Ala Glu Lys Leu Val
            260                 265                 270

Ile Thr Asp Val Val Asp Gly Val Asn His Lys Leu Asp Val Thr Thr
        275                 280                 285
```

```
Ala Thr Cys Thr Ile Arg Asn Cys Lys Lys Leu Gly Pro Arg Glu Asn
    290                 295                 300

Val Ala Val Ile Gln Val Gly Gly Ser Asp Val Leu Asp Ile Thr Ala
305                 310                 315                 320

Asp Pro Thr Thr Ala Pro Gln Thr Glu Arg Met Met Arg Ile Asn Trp
                325                 330                 335

Lys Lys Trp Trp Gln Val Phe Tyr Thr Val Val Asp Tyr Val Asn Gln
            340                 345                 350

Ile Ile Gln Ala Met Ser Lys Arg Ser Arg Ser Leu Asn Ser Ala Ala
        355                 360                 365

Phe Tyr Tyr Arg Ile
    370

<210> SEQ ID NO 29
<211> LENGTH: 373
<212> TYPE: PRT
<213> ORGANISM: Artificial Sequence
<220> FEATURE:
<223> OTHER INFORMATION: Engineered Rhesus Rotavirus VP7-HR2HXB2 fusion
      protein

<400> SEQUENCE: 29

Met Lys Phe Leu Val Asn Val Ala Leu Val Phe Met Val Val Tyr Ile
1               5                   10                  15

Ser Tyr Ile Tyr Ala Glu Asp Ser Ala Trp Ser His Pro Gln Phe Glu
            20                  25                  30

Lys Glu Asn Leu Tyr Phe Gln Gly Gln Asn Tyr Gly Ile Asn Leu Pro
        35                  40                  45

Ile Thr Gly Ser Met Asp Thr Ala Tyr Ala Asn Ser Thr Gln Glu Glu
    50                  55                  60

Thr Phe Leu Thr Ser Thr Leu Cys Leu Tyr Tyr Pro Thr Glu Ala Ala
65                  70                  75                  80

Thr Glu Ile Asn Asp Asn Ser Trp Lys Asp Thr Leu Ser Gln Leu Phe
                85                  90                  95

Leu Thr Lys Gly Trp Pro Thr Gly Ser Val Tyr Phe Lys Glu Tyr Thr
            100                 105                 110

Asp Ile Ala Ser Phe Ser Val Asp Pro Gln Leu Tyr Cys Asp Tyr Asn
        115                 120                 125

Val Val Leu Met Lys Tyr Asp Ala Gly Trp Met Glu Trp Asp Arg Glu
    130                 135                 140

Ile Asn Asn Tyr Thr Ser Leu Ile His Ser Leu Ile Glu Glu Ser Gln
145                 150                 155                 160

Asn Gln Gln Glu Lys Gly Leu Glu Leu Asp Lys Trp Ala Ser Leu Ser
                165                 170                 175

Gly Gly Glu Asp Gln Val Asp Pro Arg Leu Ile Asp Gly Lys Ser Gly
            180                 185                 190

Gly Thr Leu Gln Leu Asp Met Ser Glu Leu Ala Asp Leu Ile Leu Asn
        195                 200                 205

Glu Trp Leu Cys Asn Pro Met Asp Ile Thr Leu Tyr Tyr Tyr Gln Gln
    210                 215                 220

Thr Asp Glu Ala Asn Lys Trp Ile Ser Met Gly Ser Ser Cys Thr Ile
225                 230                 235                 240

Lys Val Cys Pro Leu Asn Thr Gln Thr Leu Gly Ile Gly Cys Leu Thr
                245                 250                 255

Thr Asp Thr Ala Thr Phe Glu Glu Val Ala Thr Ala Glu Lys Leu Val
```

```
            260                 265                 270
Ile Thr Asp Val Val Asp Gly Val Asn His Lys Leu Asp Val Thr Thr
            275                 280                 285
Ala Thr Cys Thr Ile Arg Asn Cys Lys Lys Leu Gly Pro Arg Glu Asn
            290                 295                 300
Val Ala Val Ile Gln Val Gly Gly Ser Asp Val Leu Asp Ile Thr Ala
305                 310                 315                 320
Asp Pro Thr Thr Ala Pro Gln Thr Glu Arg Met Met Arg Ile Asn Trp
            325                 330                 335
Lys Lys Trp Trp Gln Val Phe Tyr Thr Val Val Asp Tyr Val Asn Gln
            340                 345                 350
Ile Ile Gln Ala Met Ser Lys Arg Ser Arg Ser Leu Asn Ser Ala Ala
            355                 360                 365
Phe Tyr Tyr Arg Ile
            370

<210> SEQ ID NO 30
<211> LENGTH: 369
<212> TYPE: PRT
<213> ORGANISM: Artificial Sequence
<220> FEATURE:
<223> OTHER INFORMATION: Engineered Rhesus Rotavirus VP7-HR2HXB2 fusion
      protein

<400> SEQUENCE: 30

Met Lys Phe Leu Val Asn Val Ala Leu Val Phe Met Val Val Tyr Ile
1               5                   10                  15
Ser Tyr Ile Tyr Ala Glu Asp Ser Ala Trp Ser His Pro Gln Phe Glu
            20                  25                  30
Lys Glu Asn Leu Tyr Phe Gln Gly Gln Asn Tyr Gly Ile Asn Leu Pro
            35                  40                  45
Ile Thr Gly Ser Met Asp Thr Ala Tyr Ala Asn Ser Thr Gln Glu Glu
50                  55                  60
Thr Phe Leu Thr Ser Thr Leu Cys Leu Tyr Tyr Pro Thr Glu Ala Ala
65                  70                  75                  80
Thr Glu Ile Asn Asp Asn Ser Trp Lys Asp Thr Leu Ser Gln Leu Phe
            85                  90                  95
Leu Thr Lys Gly Trp Pro Thr Gly Ser Val Tyr Phe Lys Glu Tyr Thr
            100                 105                 110
Asp Ile Ala Ser Phe Ser Val Asp Pro Gln Leu Tyr Cys Asp Tyr Asn
            115                 120                 125
Val Val Leu Met Lys Tyr Asp Ala Gly Trp Met Glu Trp Asp Arg Glu
130                 135                 140
Ile Asn Asn Tyr Thr Ser Leu Ile His Ser Leu Ile Glu Glu Ser Gln
145                 150                 155                 160
Asn Gln Gln Glu Lys Gly Leu Glu Leu Asp Lys Trp Ala Ser Leu Gly
            165                 170                 175
Glu Asp Gln Val Asp Pro Arg Leu Ile Asp Gly Lys Gly Thr Leu Gln
            180                 185                 190
Leu Asp Met Ser Glu Leu Ala Asp Leu Ile Leu Asn Glu Trp Leu Cys
            195                 200                 205
Asn Pro Met Asp Ile Thr Leu Tyr Tyr Gln Gln Thr Asp Glu Ala
            210                 215                 220
Asn Lys Trp Ile Ser Met Gly Ser Ser Cys Thr Ile Lys Val Cys Pro
225                 230                 235                 240
```

```
Leu Asn Thr Gln Thr Leu Gly Ile Gly Cys Leu Thr Thr Asp Thr Ala
                245                 250                 255

Thr Phe Glu Glu Val Ala Thr Ala Glu Lys Leu Val Ile Thr Asp Val
            260                 265                 270

Val Asp Gly Val Asn His Lys Leu Asp Val Thr Thr Ala Thr Cys Thr
        275                 280                 285

Ile Arg Asn Cys Lys Lys Leu Gly Pro Arg Glu Asn Val Ala Val Ile
    290                 295                 300

Gln Val Gly Gly Ser Asp Val Leu Asp Ile Thr Ala Asp Pro Thr Thr
305                 310                 315                 320

Ala Pro Gln Thr Glu Arg Met Met Arg Ile Asn Trp Lys Lys Trp Trp
                325                 330                 335

Gln Val Phe Tyr Thr Val Val Asp Tyr Val Asn Gln Ile Ile Gln Ala
            340                 345                 350

Met Ser Lys Arg Ser Arg Ser Leu Asn Ser Ala Ala Phe Tyr Tyr Arg
        355                 360                 365

Ile
```

<210> SEQ ID NO 31
<211> LENGTH: 379
<212> TYPE: PRT
<213> ORGANISM: Artificial Sequence
<220> FEATURE:
<223> OTHER INFORMATION: Engineered Rhesus Rotavirus VP7-HR2HXB2 fusion
      protein

<400> SEQUENCE: 31

```
Met Lys Phe Leu Val Asn Val Ala Leu Val Phe Met Val Val Tyr Ile
1               5                   10                  15

Ser Tyr Ile Tyr Ala Glu Asp Ser Ala Trp Ser His Pro Gln Phe Glu
            20                  25                  30

Lys Glu Asn Leu Tyr Phe Gln Gly Gln Asn Tyr Gly Ile Asn Leu Pro
        35                  40                  45

Ile Thr Gly Ser Met Asp Thr Ala Tyr Ala Asn Ser Thr Gln Glu Glu
    50                  55                  60

Thr Phe Leu Thr Ser Thr Leu Cys Leu Tyr Tyr Pro Thr Glu Ala Ala
65                  70                  75                  80

Thr Glu Ile Asn Asp Asn Ser Trp Lys Asp Thr Leu Ser Gln Leu Phe
                85                  90                  95

Leu Thr Lys Gly Trp Pro Thr Gly Ser Val Tyr Phe Lys Glu Tyr Thr
            100                 105                 110

Asp Ile Ala Ser Phe Ser Val Asp Pro Gln Leu Tyr Cys Asp Tyr Asn
        115                 120                 125

Val Val Leu Met Lys Tyr Asp Ala Gly Trp Met Glu Trp Asp Arg Glu
    130                 135                 140

Ile Asn Asn Tyr Thr Ser Leu Ile His Ser Leu Ile Glu Glu Ser Gln
145                 150                 155                 160

Asn Gln Gln Glu Lys Gly Leu Glu Leu Asp Lys Trp Ala Ser Leu Gly
                165                 170                 175

Ser Ile Glu Gly Arg Ser Gly Gly Glu Asp Gln Val Asp Pro Arg Leu
            180                 185                 190

Ile Asp Gly Lys Ser Gly Gly Thr Leu Gln Leu Asp Met Ser Glu Leu
        195                 200                 205

Ala Asp Leu Ile Leu Asn Glu Trp Leu Cys Asn Pro Met Asp Ile Thr
    210                 215                 220
```

```
Leu Tyr Tyr Tyr Gln Gln Thr Asp Glu Ala Asn Lys Trp Ile Ser Met
225                 230                 235                 240

Gly Ser Ser Cys Thr Ile Lys Val Cys Pro Leu Asn Thr Gln Thr Leu
            245                 250                 255

Gly Ile Gly Cys Leu Thr Thr Asp Thr Ala Thr Phe Glu Glu Val Ala
            260                 265                 270

Thr Ala Glu Lys Leu Val Ile Thr Asp Val Val Asp Gly Val Asn His
        275                 280                 285

Lys Leu Asp Val Thr Thr Ala Thr Cys Thr Ile Arg Asn Cys Lys Lys
    290                 295                 300

Leu Gly Pro Arg Glu Asn Val Ala Val Ile Gln Val Gly Gly Ser Asp
305                 310                 315                 320

Val Leu Asp Ile Thr Ala Asp Pro Thr Thr Ala Pro Gln Thr Glu Arg
                325                 330                 335

Met Met Arg Ile Asn Trp Lys Lys Trp Trp Gln Val Phe Tyr Thr Val
            340                 345                 350

Val Asp Tyr Val Asn Gln Ile Ile Gln Ala Met Ser Lys Arg Ser Arg
            355                 360                 365

Ser Leu Asn Ser Ala Ala Phe Tyr Tyr Arg Ile
    370                 375

<210> SEQ ID NO 32
<211> LENGTH: 370
<212> TYPE: PRT
<213> ORGANISM: Artificial Sequence
<220> FEATURE:
<223> OTHER INFORMATION: Engineered Rhesus Rotavirus VP7-HR2Nipah fusion
      protein

<400> SEQUENCE: 32

Met Lys Phe Leu Val Asn Val Ala Leu Val Phe Met Val Val Tyr Ile
1               5                   10                  15

Ser Tyr Ile Tyr Ala Glu Asp Ser Ala Trp Ser His Pro Gln Phe Glu
            20                  25                  30

Lys Glu Asn Leu Tyr Phe Gln Gly Gln Asn Tyr Gly Ile Asn Leu Pro
        35                  40                  45

Ile Thr Gly Ser Met Asp Thr Ala Tyr Ala Asn Ser Thr Gln Glu Glu
    50                  55                  60

Thr Phe Leu Thr Ser Thr Leu Cys Leu Tyr Tyr Pro Thr Glu Ala Ala
65                  70                  75                  80

Thr Glu Ile Asn Asp Asn Ser Trp Lys Asp Thr Leu Ser Gln Leu Phe
                85                  90                  95

Leu Thr Lys Gly Trp Pro Thr Gly Ser Val Tyr Phe Lys Glu Tyr Thr
            100                 105                 110

Asp Ile Ala Ser Phe Ser Val Asp Pro Gln Leu Tyr Cys Asp Tyr Asn
        115                 120                 125

Val Val Leu Met Lys Tyr Asp Ala Gly Asp Ile Ser Ser Gln Ile Ser
    130                 135                 140

Ser Met Asn Gln Ser Leu Gln Gln Ser Lys Asp Tyr Ile Lys Glu Ala
145                 150                 155                 160

Gln Arg Leu Leu Asp Thr Val Lys Ile Glu Gly Arg Ser Gly Gly Glu
                165                 170                 175

Asp Gln Val Asp Pro Arg Leu Ile Asp Gly Lys Ser Gly Gly Thr Leu
            180                 185                 190

Gln Leu Asp Met Ser Glu Leu Ala Asp Leu Ile Leu Asn Glu Trp Leu
        195                 200                 205
```

```
Cys Asn Pro Met Asp Ile Thr Leu Tyr Tyr Tyr Gln Gln Thr Asp Glu
    210                 215                 220

Ala Asn Lys Trp Ile Ser Met Gly Ser Ser Cys Thr Ile Lys Val Cys
225                 230                 235                 240

Pro Leu Asn Thr Gln Thr Leu Gly Ile Gly Cys Leu Thr Thr Asp Thr
                245                 250                 255

Ala Thr Phe Glu Glu Val Ala Thr Ala Glu Lys Leu Val Ile Thr Asp
                260                 265                 270

Val Val Asp Gly Val Asn His Lys Leu Asp Val Thr Thr Ala Thr Cys
            275                 280                 285

Thr Ile Arg Asn Cys Lys Lys Leu Gly Pro Arg Glu Asn Val Ala Val
    290                 295                 300

Ile Gln Val Gly Gly Ser Asp Val Leu Asp Ile Thr Ala Asp Pro Thr
305                 310                 315                 320

Thr Ala Pro Gln Thr Glu Arg Met Met Arg Ile Asn Trp Lys Lys Trp
                325                 330                 335

Trp Gln Val Phe Tyr Thr Val Val Asp Tyr Val Asn Gln Ile Ile Gln
                340                 345                 350

Ala Met Ser Lys Arg Ser Arg Ser Leu Asn Ser Ala Ala Phe Tyr Tyr
            355                 360                 365

Arg Ile
    370

<210> SEQ ID NO 33
<211> LENGTH: 368
<212> TYPE: PRT
<213> ORGANISM: Artificial Sequence
<220> FEATURE:
<223> OTHER INFORMATION: Engineered Rhesus Rotavirus VP7-HR2Nipah fusion
      protein

<400> SEQUENCE: 33

Met Lys Phe Leu Val Asn Val Ala Leu Val Phe Met Val Val Tyr Ile
1               5                   10                  15

Ser Tyr Ile Tyr Ala Glu Asp Ser Ala Trp Ser His Pro Gln Phe Glu
            20                  25                  30

Lys Glu Asn Leu Tyr Phe Gln Gly Gln Asn Tyr Gly Ile Asn Leu Pro
        35                  40                  45

Ile Thr Gly Ser Met Asp Thr Ala Tyr Ala Asn Ser Thr Gln Glu Glu
    50                  55                  60

Thr Phe Leu Thr Ser Thr Leu Cys Leu Tyr Tyr Pro Thr Glu Ala Ala
65                  70                  75                  80

Thr Glu Ile Asn Asp Asn Ser Trp Lys Asp Thr Leu Ser Gln Leu Phe
                85                  90                  95

Leu Thr Lys Gly Trp Pro Thr Gly Ser Val Tyr Phe Lys Glu Tyr Thr
            100                 105                 110

Asp Ile Ala Ser Phe Ser Val Asp Pro Gln Leu Tyr Cys Asp Tyr Asn
        115                 120                 125

Val Val Leu Met Lys Tyr Asp Ala Gly Asp Ile Ser Ser Gln Ile Ser
    130                 135                 140

Ser Met Asn Gln Ser Leu Gln Gln Ser Lys Asp Tyr Ile Lys Glu Ala
145                 150                 155                 160

Gln Arg Leu Leu Asp Thr Val Lys Ile Glu Gly Arg Ser Gly Gly Glu
                165                 170                 175

Asp Gln Val Asp Pro Arg Leu Ile Asp Gly Lys Gly Thr Leu Gln Leu
```

```
                180                185                190
Asp Met Ser Glu Leu Ala Asp Leu Ile Leu Asn Glu Trp Leu Cys Asn
            195                200                205
Pro Met Asp Ile Thr Leu Tyr Tyr Tyr Gln Gln Thr Asp Glu Ala Asn
        210                215                220
Lys Trp Ile Ser Met Gly Ser Ser Cys Thr Ile Lys Val Cys Pro Leu
225                230                235                240
Asn Thr Gln Thr Leu Gly Ile Gly Cys Leu Thr Thr Asp Thr Ala Thr
                245                250                255
Phe Glu Glu Val Ala Thr Ala Glu Lys Leu Val Ile Thr Asp Val Val
            260                265                270
Asp Gly Val Asn His Lys Leu Asp Val Thr Thr Ala Thr Cys Thr Ile
        275                280                285
Arg Asn Cys Lys Lys Leu Gly Pro Arg Glu Asn Val Ala Val Ile Gln
290                295                300
Val Gly Gly Ser Asp Val Leu Asp Ile Thr Ala Asp Pro Thr Thr Ala
305                310                315                320
Pro Gln Thr Glu Arg Met Met Arg Ile Asn Trp Lys Lys Trp Trp Gln
                325                330                335
Val Phe Tyr Thr Val Val Asp Tyr Val Asn Gln Ile Ile Gln Ala Met
            340                345                350
Ser Lys Arg Ser Arg Ser Leu Asn Ser Ala Ala Phe Tyr Tyr Arg Ile
        355                360                365

<210> SEQ ID NO 34
<211> LENGTH: 365
<212> TYPE: PRT
<213> ORGANISM: Artificial Sequence
<220> FEATURE:
<223> OTHER INFORMATION: Engineered Rhesus Rotavirus VP7-HR2Nipah fusion
      protein

<400> SEQUENCE: 34

Met Lys Phe Leu Val Asn Val Ala Leu Val Phe Met Val Val Tyr Ile
1               5                  10                 15
Ser Tyr Ile Tyr Ala Glu Asp Ser Ala Trp Ser His Pro Gln Phe Glu
            20                 25                 30
Lys Glu Asn Leu Tyr Phe Gln Gly Gln Asn Tyr Gly Ile Asn Leu Pro
        35                 40                 45
Ile Thr Gly Ser Met Asp Thr Ala Tyr Ala Asn Ser Thr Gln Glu Glu
    50                 55                 60
Thr Phe Leu Thr Ser Thr Leu Cys Leu Tyr Tyr Pro Thr Glu Ala Ala
65                 70                 75                  80
Thr Glu Ile Asn Asp Asn Ser Trp Lys Asp Thr Leu Ser Gln Leu Phe
                85                 90                 95
Leu Thr Lys Gly Trp Pro Thr Gly Ser Val Tyr Phe Lys Glu Tyr Thr
            100                105                110
Asp Ile Ala Ser Phe Ser Val Asp Pro Gln Leu Tyr Cys Asp Tyr Asn
        115                120                125
Val Val Leu Met Lys Tyr Asp Ala Gly Asp Ile Ser Ser Gln Ile Ser
    130                135                140
Ser Met Asn Gln Ser Leu Gln Gln Ser Lys Asp Tyr Ile Lys Glu Ala
145                150                155                160
Gln Arg Leu Leu Asp Thr Val Ser Gly Gly Glu Asp Gln Val Asp Pro
                165                170                175
```

```
Arg Leu Ile Asp Gly Lys Ser Gly Gly Thr Leu Gln Leu Asp Met Ser
            180                 185                 190

Glu Leu Ala Asp Leu Ile Leu Asn Glu Trp Leu Cys Asn Pro Met Asp
        195                 200                 205

Ile Thr Leu Tyr Tyr Gln Gln Thr Asp Glu Ala Asn Lys Trp Ile
    210                 215                 220

Ser Met Gly Ser Ser Cys Thr Ile Lys Val Cys Pro Leu Asn Thr Gln
225                 230                 235                 240

Thr Leu Gly Ile Gly Cys Leu Thr Thr Asp Thr Ala Thr Phe Glu Glu
                245                 250                 255

Val Ala Thr Ala Glu Lys Leu Val Ile Thr Asp Val Val Asp Gly Val
        260                 265                 270

Asn His Lys Leu Asp Val Thr Thr Ala Thr Cys Thr Ile Arg Asn Cys
            275                 280                 285

Lys Lys Leu Gly Pro Arg Glu Asn Val Ala Val Ile Gln Val Gly Gly
        290                 295                 300

Ser Asp Val Leu Asp Ile Thr Ala Asp Pro Thr Thr Ala Pro Gln Thr
305                 310                 315                 320

Glu Arg Met Met Arg Ile Asn Trp Lys Lys Trp Trp Gln Val Phe Tyr
                325                 330                 335

Thr Val Val Asp Tyr Val Asn Gln Ile Ile Gln Ala Met Ser Lys Arg
            340                 345                 350

Ser Arg Ser Leu Asn Ser Ala Ala Phe Tyr Tyr Arg Ile
        355                 360                 365

<210> SEQ ID NO 35
<211> LENGTH: 363
<212> TYPE: PRT
<213> ORGANISM: Artificial Sequence
<220> FEATURE:
<223> OTHER INFORMATION: Engineered Rhesus Rotavirus VP7-HR2Nipah fusion
      protein

<400> SEQUENCE: 35

Met Lys Phe Leu Val Asn Val Ala Leu Val Phe Met Val Val Tyr Ile
1               5                   10                  15

Ser Tyr Ile Tyr Ala Glu Asp Ser Ala Trp Ser His Pro Gln Phe Glu
            20                  25                  30

Lys Glu Asn Leu Tyr Phe Gln Gly Gln Asn Tyr Gly Ile Asn Leu Pro
        35                  40                  45

Ile Thr Gly Ser Met Asp Thr Ala Tyr Ala Asn Ser Thr Gln Glu Glu
    50                  55                  60

Thr Phe Leu Thr Ser Thr Leu Cys Leu Tyr Tyr Pro Thr Glu Ala Ala
65                  70                  75                  80

Thr Glu Ile Asn Asp Asn Ser Trp Lys Asp Thr Leu Ser Gln Leu Phe
                85                  90                  95

Leu Thr Lys Gly Trp Pro Thr Gly Ser Val Tyr Phe Lys Glu Tyr Thr
            100                 105                 110

Asp Ile Ala Ser Phe Ser Val Asp Pro Gln Leu Tyr Cys Asp Tyr Asn
        115                 120                 125

Val Val Leu Met Lys Tyr Asp Ala Gly Asp Ile Ser Ser Gln Ile Ser
    130                 135                 140

Ser Met Asn Gln Ser Leu Gln Gln Ser Lys Asp Tyr Ile Lys Glu Ala
145                 150                 155                 160

Gln Arg Leu Leu Asp Thr Val Ser Gly Gly Glu Asp Gln Val Asp Pro
                165                 170                 175
```

```
Arg Leu Ile Asp Gly Lys Gly Thr Leu Gln Leu Asp Met Ser Glu Leu
            180                 185                 190

Ala Asp Leu Ile Leu Asn Glu Trp Leu Cys Asn Pro Met Asp Ile Thr
            195                 200                 205

Leu Tyr Tyr Tyr Gln Gln Thr Asp Glu Ala Asn Lys Trp Ile Ser Met
        210                 215                 220

Gly Ser Ser Cys Thr Ile Lys Val Cys Pro Leu Asn Thr Gln Thr Leu
225                 230                 235                 240

Gly Ile Gly Cys Leu Thr Thr Asp Thr Ala Thr Phe Glu Glu Val Ala
                245                 250                 255

Thr Ala Glu Lys Leu Val Ile Thr Asp Val Val Asp Gly Val Asn His
                260                 265                 270

Lys Leu Asp Val Thr Thr Ala Thr Cys Thr Ile Arg Asn Cys Lys Lys
            275                 280                 285

Leu Gly Pro Arg Glu Asn Val Ala Val Ile Gln Val Gly Gly Ser Asp
        290                 295                 300

Val Leu Asp Ile Thr Ala Asp Pro Thr Thr Ala Pro Gln Thr Glu Arg
305                 310                 315                 320

Met Met Arg Ile Asn Trp Lys Lys Trp Trp Gln Val Phe Tyr Thr Val
                325                 330                 335

Val Asp Tyr Val Asn Gln Ile Ile Gln Ala Met Ser Lys Arg Ser Arg
                340                 345                 350

Ser Leu Asn Ser Ala Ala Phe Tyr Tyr Arg Ile
            355                 360

<210> SEQ ID NO 36
<211> LENGTH: 361
<212> TYPE: PRT
<213> ORGANISM: Artificial Sequence
<220> FEATURE:
<223> OTHER INFORMATION: Engineered Rhesus Rotavirus VP7-HR2Nipah fusion
      protein

<400> SEQUENCE: 36

Met Lys Phe Leu Val Asn Val Ala Leu Val Phe Met Val Val Tyr Ile
1               5                   10                  15

Ser Tyr Ile Tyr Ala Glu Asp Ser Ala Trp Ser His Pro Gln Phe Glu
            20                  25                  30

Lys Glu Asn Leu Tyr Phe Gln Gly Gln Asn Tyr Gly Ile Asn Leu Pro
        35                  40                  45

Ile Thr Gly Ser Met Asp Thr Ala Tyr Ala Asn Ser Thr Gln Glu Glu
50                  55                  60

Thr Phe Leu Thr Ser Thr Leu Cys Leu Tyr Tyr Pro Thr Glu Ala Ala
65                  70                  75                  80

Thr Glu Ile Asn Asp Asn Ser Trp Lys Asp Thr Leu Ser Gln Leu Phe
                85                  90                  95

Leu Thr Lys Gly Trp Pro Thr Gly Ser Val Tyr Phe Lys Glu Tyr Thr
            100                 105                 110

Asp Ile Ala Ser Phe Ser Val Asp Pro Gln Leu Tyr Cys Asp Tyr Asn
        115                 120                 125

Val Val Leu Met Lys Tyr Asp Ala Gly Asp Ile Ser Gln Ile Ser
130                 135                 140

Ser Met Asn Gln Ser Leu Gln Gln Ser Lys Asp Tyr Ile Lys Glu Ala
145                 150                 155                 160

Gln Arg Leu Leu Asp Thr Val Gly Glu Asp Gln Val Asp Pro Arg Leu
```

```
                      165                 170                 175
Ile Asp Gly Lys Gly Thr Leu Gln Leu Asp Met Ser Glu Leu Ala Asp
            180                 185                 190

Leu Ile Leu Asn Glu Trp Leu Cys Asn Pro Met Asp Ile Thr Leu Tyr
        195                 200                 205

Tyr Tyr Gln Gln Thr Asp Glu Ala Asn Lys Trp Ile Ser Met Gly Ser
    210                 215                 220

Ser Cys Thr Ile Lys Val Cys Pro Leu Asn Thr Gln Thr Leu Gly Ile
225                 230                 235                 240

Gly Cys Leu Thr Thr Asp Thr Ala Thr Phe Glu Glu Val Ala Thr Ala
                245                 250                 255

Glu Lys Leu Val Ile Thr Asp Val Val Asp Gly Val Asn His Lys Leu
            260                 265                 270

Asp Val Thr Thr Ala Thr Cys Thr Ile Arg Asn Cys Lys Lys Leu Gly
        275                 280                 285

Pro Arg Glu Asn Val Ala Val Ile Gln Val Gly Gly Ser Asp Val Leu
    290                 295                 300

Asp Ile Thr Ala Asp Pro Thr Thr Ala Pro Gln Thr Glu Arg Met Met
305                 310                 315                 320

Arg Ile Asn Trp Lys Lys Trp Trp Gln Val Phe Tyr Thr Val Val Asp
                325                 330                 335

Tyr Val Asn Gln Ile Ile Gln Ala Met Ser Lys Arg Ser Arg Ser Leu
            340                 345                 350

Asn Ser Ala Ala Phe Tyr Tyr Arg Ile
        355                 360

<210> SEQ ID NO 37
<211> LENGTH: 379
<212> TYPE: PRT
<213> ORGANISM: Artificial Sequence
<220> FEATURE:
<223> OTHER INFORMATION: Engineered Rhesus Rotavirus VP7-HR2Nipah fusion
      protein

<400> SEQUENCE: 37

Met Lys Phe Leu Val Asn Val Ala Leu Val Phe Met Val Val Tyr Ile
1               5                   10                  15

Ser Tyr Ile Tyr Ala Glu Asp Ser Ala Trp Ser His Pro Gln Phe Glu
            20                  25                  30

Lys Glu Asn Leu Tyr Phe Gln Gly Gln Asn Tyr Gly Ile Asn Leu Pro
        35                  40                  45

Ile Thr Gly Ser Met Asp Thr Ala Tyr Ala Asn Ser Thr Gln Glu Glu
    50                  55                  60

Thr Phe Leu Thr Ser Thr Leu Cys Leu Tyr Tyr Pro Thr Glu Ala Ala
65                  70                  75                  80

Thr Glu Ile Asn Asp Asn Ser Trp Lys Asp Thr Leu Ser Gln Leu Phe
                85                  90                  95

Leu Thr Lys Gly Trp Pro Thr Gly Ser Val Tyr Phe Lys Glu Tyr Thr
            100                 105                 110

Asp Ile Ala Ser Phe Ser Val Asp Pro Gln Leu Tyr Cys Asp Tyr Asn
        115                 120                 125

Val Val Leu Met Lys Tyr Asp Ala Gly Asp Ile Ser Ser Gln Ile Ser
    130                 135                 140

Ser Met Asn Gln Ser Leu Gln Gln Ser Lys Asp Tyr Ile Lys Glu Ala
145                 150                 155                 160
```

Gln Arg Leu Leu Asp Thr Val Asn Glu Gln Glu Leu Glu Leu Asp
            165                 170                 175

Lys Trp Ala Ser Leu Ser Gly Gly Glu Asp Gln Val Asp Pro Arg Leu
        180                 185                 190

Ile Asp Gly Lys Ser Gly Gly Thr Leu Gln Leu Asp Met Ser Glu Leu
            195                 200                 205

Ala Asp Leu Ile Leu Asn Glu Trp Leu Cys Asn Pro Met Asp Ile Thr
        210                 215                 220

Leu Tyr Tyr Tyr Gln Gln Thr Asp Glu Ala Asn Lys Trp Ile Ser Met
225                 230                 235                 240

Gly Ser Ser Cys Thr Ile Lys Val Cys Pro Leu Asn Thr Gln Thr Leu
                245                 250                 255

Gly Ile Gly Cys Leu Thr Thr Asp Thr Ala Thr Phe Glu Glu Val Ala
            260                 265                 270

Thr Ala Glu Lys Leu Val Ile Thr Asp Val Val Asp Gly Val Asn His
        275                 280                 285

Lys Leu Asp Val Thr Thr Ala Thr Cys Thr Ile Arg Asn Cys Lys Lys
    290                 295                 300

Leu Gly Pro Arg Glu Asn Val Ala Val Ile Gln Val Gly Gly Ser Asp
305                 310                 315                 320

Val Leu Asp Ile Thr Ala Asp Pro Thr Thr Ala Pro Gln Thr Glu Arg
                325                 330                 335

Met Met Arg Ile Asn Trp Lys Lys Trp Trp Gln Val Phe Tyr Thr Val
            340                 345                 350

Val Asp Tyr Val Asn Gln Ile Ile Gln Ala Met Ser Lys Arg Ser Arg
        355                 360                 365

Ser Leu Asn Ser Ala Ala Phe Tyr Tyr Arg Ile
    370                 375

<210> SEQ ID NO 38
<211> LENGTH: 376
<212> TYPE: PRT
<213> ORGANISM: Artificial Sequence
<220> FEATURE:
<223> OTHER INFORMATION: Engineered Rhesus Rotavirus VP7-HR2Nipah fusion
      protein

<400> SEQUENCE: 38

Met Lys Phe Leu Val Asn Val Ala Leu Val Phe Met Val Tyr Ile
1               5                   10                  15

Ser Tyr Ile Tyr Ala Glu Asp Ser Ala Trp Ser His Pro Gln Phe Glu
            20                  25                  30

Lys Glu Asn Leu Tyr Phe Gln Gly Gln Asn Tyr Gly Ile Asn Leu Pro
        35                  40                  45

Ile Thr Gly Ser Met Asp Thr Ala Tyr Ala Asn Ser Thr Gln Glu Glu
    50                  55                  60

Thr Phe Leu Thr Ser Thr Leu Cys Leu Tyr Tyr Pro Thr Glu Ala Ala
65                  70                  75                  80

Thr Glu Ile Asn Asp Asn Ser Trp Lys Asp Thr Leu Ser Gln Leu Phe
                85                  90                  95

Leu Thr Lys Gly Trp Pro Thr Gly Ser Val Tyr Phe Lys Glu Tyr Thr
            100                 105                 110

Asp Ile Ala Ser Phe Ser Val Asp Pro Gln Leu Tyr Cys Asp Tyr Asn
        115                 120                 125

Val Val Leu Met Lys Tyr Asp Ala Gly Asp Ile Ser Ser Gln Ile Ser
    130                 135                 140

Ser Met Asn Gln Ser Leu Gln Gln Ser Lys Asp Tyr Ile Lys Glu Ala
145                 150                 155                 160

Gln Arg Leu Leu Asp Thr Val Lys Asn Glu Gln Glu Leu Leu Glu Leu
            165                 170                 175

Asp Lys Trp Ala Ser Leu Gly Glu Asp Gln Val Asp Pro Arg Leu Ile
        180                 185                 190

Asp Gly Lys Gly Thr Leu Gln Leu Asp Met Ser Glu Leu Ala Asp Leu
            195                 200                 205

Ile Leu Asn Glu Trp Leu Cys Asn Pro Met Asp Ile Thr Leu Tyr Tyr
    210                 215                 220

Tyr Gln Gln Thr Asp Glu Ala Asn Lys Trp Ile Ser Met Gly Ser Ser
225                 230                 235                 240

Cys Thr Ile Lys Val Cys Pro Leu Asn Thr Gln Thr Leu Gly Ile Gly
            245                 250                 255

Cys Leu Thr Thr Asp Thr Ala Thr Phe Glu Glu Val Ala Thr Ala Glu
        260                 265                 270

Lys Leu Val Ile Thr Asp Val Val Asp Gly Val Asn His Lys Leu Asp
            275                 280                 285

Val Thr Thr Ala Thr Cys Thr Ile Arg Asn Cys Lys Lys Leu Gly Pro
    290                 295                 300

Arg Glu Asn Val Ala Val Ile Gln Val Gly Gly Ser Asp Val Leu Asp
305                 310                 315                 320

Ile Thr Ala Asp Pro Thr Thr Ala Pro Gln Thr Glu Arg Met Met Arg
            325                 330                 335

Ile Asn Trp Lys Lys Trp Trp Gln Val Phe Tyr Thr Val Val Asp Tyr
        340                 345                 350

Val Asn Gln Ile Ile Gln Ala Met Ser Lys Arg Ser Arg Ser Leu Asn
            355                 360                 365

Ser Ala Ala Phe Tyr Tyr Arg Ile
        370                 375

<210> SEQ ID NO 39
<211> LENGTH: 375
<212> TYPE: PRT
<213> ORGANISM: Artificial Sequence
<220> FEATURE:
<223> OTHER INFORMATION: Engineered Rhesus Rotavirus VP7-HR2Nipah fusion
      protein

<400> SEQUENCE: 39

Met Lys Phe Leu Val Asn Val Ala Leu Val Phe Met Val Val Tyr Ile
1               5                   10                  15

Ser Tyr Ile Tyr Ala Glu Asp Ser Ala Trp Ser His Pro Gln Phe Glu
            20                  25                  30

Lys Glu Asn Leu Tyr Phe Gln Gly Gln Asn Tyr Gly Ile Asn Leu Pro
        35                  40                  45

Ile Thr Gly Ser Met Asp Thr Ala Tyr Ala Asn Ser Thr Gln Glu Glu
    50                  55                  60

Thr Phe Leu Thr Ser Thr Leu Cys Leu Tyr Tyr Pro Thr Glu Ala Ala
65                  70                  75                  80

Thr Glu Ile Asn Asp Asn Ser Trp Lys Asp Thr Leu Ser Gln Leu Phe
            85                  90                  95

Leu Thr Lys Gly Trp Pro Thr Gly Ser Val Tyr Phe Lys Glu Tyr Thr
        100                 105                 110

Asp Ile Ala Ser Phe Ser Val Asp Pro Gln Leu Tyr Cys Asp Tyr Asn

```
            115                 120                 125
Val Val Leu Met Lys Tyr Asp Ala Gly Asp Ile Ser Ser Gln Ile Ser
            130                 135                 140

Ser Met Asn Gln Ser Leu Gln Gln Ser Lys Asp Tyr Ile Lys Glu Ala
145                 150                 155                 160

Gln Arg Leu Leu Asp Thr Val Gly Leu Glu Leu Asp Lys Trp Ala Ser
                165                 170                 175

Leu Ser Gly Gly Glu Asp Gln Val Asp Pro Arg Leu Ile Asp Gly Lys
            180                 185                 190

Ser Gly Gly Thr Leu Gln Leu Asp Met Ser Glu Leu Ala Asp Leu Ile
            195                 200                 205

Leu Asn Glu Trp Leu Cys Asn Pro Met Asp Ile Thr Leu Tyr Tyr Tyr
            210                 215                 220

Gln Gln Thr Asp Glu Ala Asn Lys Trp Ile Ser Met Gly Ser Ser Cys
225                 230                 235                 240

Thr Ile Lys Val Cys Pro Leu Asn Thr Gln Thr Leu Gly Ile Gly Cys
                245                 250                 255

Leu Thr Thr Asp Thr Ala Thr Phe Glu Glu Val Ala Thr Ala Glu Lys
            260                 265                 270

Leu Val Ile Thr Asp Val Val Asp Gly Val Asn His Lys Leu Asp Val
            275                 280                 285

Thr Thr Ala Thr Cys Thr Ile Arg Asn Cys Lys Lys Leu Gly Pro Arg
290                 295                 300

Glu Asn Val Ala Val Ile Gln Val Gly Gly Ser Asp Val Leu Asp Ile
305                 310                 315                 320

Thr Ala Asp Pro Thr Thr Ala Pro Gln Thr Glu Arg Met Met Arg Ile
                325                 330                 335

Asn Trp Lys Lys Trp Trp Gln Val Phe Tyr Thr Val Val Asp Tyr Val
            340                 345                 350

Asn Gln Ile Ile Gln Ala Met Ser Lys Arg Ser Arg Ser Leu Asn Ser
            355                 360                 365

Ala Ala Phe Tyr Tyr Arg Ile
            370                 375

<210> SEQ ID NO 40
<211> LENGTH: 371
<212> TYPE: PRT
<213> ORGANISM: Artificial Sequence
<220> FEATURE:
<223> OTHER INFORMATION: Engineered Rhesus Rotavirus VP7-HR2Nipah fusion
      protein

<400> SEQUENCE: 40

Met Lys Phe Leu Val Asn Val Ala Leu Val Phe Met Val Val Tyr Ile
1               5                   10                  15

Ser Tyr Ile Tyr Ala Glu Asp Ser Ala Trp Ser His Pro Gln Phe Glu
            20                  25                  30

Lys Glu Asn Leu Tyr Phe Gln Gly Gln Asn Tyr Gly Ile Asn Leu Pro
        35                  40                  45

Ile Thr Gly Ser Met Asp Thr Ala Tyr Ala Asn Ser Thr Gln Glu Glu
    50                  55                  60

Thr Phe Leu Thr Ser Thr Leu Cys Leu Tyr Tyr Pro Thr Glu Ala Ala
65                  70                  75                  80

Thr Glu Ile Asn Asp Asn Ser Trp Lys Asp Thr Leu Ser Gln Leu Phe
                85                  90                  95
```

```
Leu Thr Lys Gly Trp Pro Thr Gly Ser Val Tyr Phe Lys Glu Tyr Thr
            100                 105                 110

Asp Ile Ala Ser Phe Ser Val Asp Pro Gln Leu Tyr Cys Asp Tyr Asn
            115                 120                 125

Val Val Leu Met Lys Tyr Asp Ala Gly Asp Ile Ser Ser Gln Ile Ser
        130                 135                 140

Ser Met Asn Gln Ser Leu Gln Gln Ser Lys Asp Tyr Ile Lys Glu Ala
145                 150                 155                 160

Gln Arg Leu Leu Asp Thr Val Gly Leu Glu Leu Asp Lys Trp Ala Ser
                165                 170                 175

Leu Gly Glu Asp Gln Val Asp Pro Arg Leu Ile Asp Gly Lys Gly Thr
            180                 185                 190

Leu Gln Leu Asp Met Ser Glu Leu Ala Asp Leu Ile Leu Asn Glu Trp
        195                 200                 205

Leu Cys Asn Pro Met Asp Ile Thr Leu Tyr Tyr Tyr Gln Gln Thr Asp
210                 215                 220

Glu Ala Asn Lys Trp Ile Ser Met Gly Ser Ser Cys Thr Ile Lys Val
225                 230                 235                 240

Cys Pro Leu Asn Thr Gln Thr Leu Gly Ile Gly Cys Leu Thr Thr Asp
                245                 250                 255

Thr Ala Thr Phe Glu Glu Val Ala Thr Ala Glu Lys Leu Val Ile Thr
            260                 265                 270

Asp Val Val Asp Gly Val Asn His Lys Leu Asp Val Thr Thr Ala Thr
        275                 280                 285

Cys Thr Ile Arg Asn Cys Lys Lys Leu Gly Pro Arg Glu Asn Val Ala
290                 295                 300

Val Ile Gln Val Gly Gly Ser Asp Val Leu Asp Ile Thr Ala Asp Pro
305                 310                 315                 320

Thr Thr Ala Pro Gln Thr Glu Arg Met Met Arg Ile Asn Trp Lys Lys
                325                 330                 335

Trp Trp Gln Val Phe Tyr Thr Val Asp Tyr Val Asn Gln Ile Ile
            340                 345                 350

Gln Ala Met Ser Lys Arg Ser Arg Ser Leu Asn Ser Ala Ala Phe Tyr
        355                 360                 365

Tyr Arg Ile
370

<210> SEQ ID NO 41
<211> LENGTH: 381
<212> TYPE: PRT
<213> ORGANISM: Artificial Sequence
<220> FEATURE:
<223> OTHER INFORMATION: Engineered Rhesus Rotavirus VP7-HR2Nipah fusion
      protein

<400> SEQUENCE: 41

Met Lys Phe Leu Val Asn Val Ala Leu Val Phe Met Val Val Tyr Ile
1               5                   10                  15

Ser Tyr Ile Tyr Ala Glu Asp Ser Ala Trp Ser His Pro Gln Phe Glu
            20                  25                  30

Lys Glu Asn Leu Tyr Phe Gln Gly Gln Asn Tyr Gly Ile Asn Leu Pro
        35                  40                  45

Ile Thr Gly Ser Met Asp Thr Ala Tyr Ala Asn Ser Thr Gln Glu Glu
    50                  55                  60

Thr Phe Leu Thr Ser Thr Leu Cys Leu Tyr Tyr Pro Thr Glu Ala Ala
65                  70                  75                  80
```

```
Thr Glu Ile Asn Asp Asn Ser Trp Lys Asp Thr Leu Ser Gln Leu Phe
                    85                  90                  95

Leu Thr Lys Gly Trp Pro Thr Gly Ser Val Tyr Phe Lys Glu Tyr Thr
            100                 105                 110

Asp Ile Ala Ser Phe Ser Val Asp Pro Gln Leu Tyr Cys Asp Tyr Asn
        115                 120                 125

Val Val Leu Met Lys Tyr Asp Ala Gly Asp Ile Ser Ser Gln Ile Ser
130                 135                 140

Ser Met Asn Gln Ser Leu Gln Gln Ser Lys Asp Tyr Ile Lys Glu Ala
145                 150                 155                 160

Gln Arg Leu Leu Asp Thr Val Gly Leu Glu Leu Asp Lys Trp Ala Ser
                165                 170                 175

Leu Gly Ser Ile Glu Gly Arg Ser Gly Gly Glu Asp Gln Val Asp Pro
            180                 185                 190

Arg Leu Ile Asp Gly Lys Ser Gly Gly Thr Leu Gln Leu Asp Met Ser
        195                 200                 205

Glu Leu Ala Asp Leu Ile Leu Asn Glu Trp Leu Cys Asn Pro Met Asp
210                 215                 220

Ile Thr Leu Tyr Tyr Gln Gln Thr Asp Glu Ala Asn Lys Trp Ile
225                 230                 235                 240

Ser Met Gly Ser Ser Cys Thr Ile Lys Val Cys Pro Leu Asn Thr Gln
                245                 250                 255

Thr Leu Gly Ile Gly Cys Leu Thr Thr Asp Thr Ala Thr Phe Glu Glu
            260                 265                 270

Val Ala Thr Ala Glu Lys Leu Val Ile Thr Asp Val Val Asp Gly Val
        275                 280                 285

Asn His Lys Leu Asp Val Thr Thr Ala Thr Cys Thr Ile Arg Asn Cys
290                 295                 300

Lys Lys Leu Gly Pro Arg Glu Asn Val Ala Val Ile Gln Val Gly Gly
305                 310                 315                 320

Ser Asp Val Leu Asp Ile Thr Ala Asp Pro Thr Thr Ala Pro Gln Thr
                325                 330                 335

Glu Arg Met Met Arg Ile Asn Trp Lys Lys Trp Trp Gln Val Phe Tyr
            340                 345                 350

Thr Val Val Asp Tyr Val Asn Gln Ile Ile Gln Ala Met Ser Lys Arg
        355                 360                 365

Ser Arg Ser Leu Asn Ser Ala Ala Phe Tyr Tyr Arg Ile
370                 375                 380

<210> SEQ ID NO 42
<211> LENGTH: 369
<212> TYPE: PRT
<213> ORGANISM: Artificial Sequence
<220> FEATURE:
<223> OTHER INFORMATION: Engineered Rhesus Rotavirus VP7-HR2HXB2 fusion
      protein

<400> SEQUENCE: 42

Met Asp Ala Met Lys Arg Gly Leu Cys Cys Val Leu Leu Cys Gly
1               5                   10                  15

Ala Val Phe Val Ser Pro Ser Glu Asp Ser Ala Trp Ser His Pro Gln
            20                  25                  30

Phe Glu Lys Glu Asn Leu Tyr Phe Gln Gly Gln Asn Tyr Gly Ile Asn
        35                  40                  45

Leu Pro Ile Thr Gly Ser Met Asp Thr Ala Tyr Ala Asn Ser Thr Gln
```

```
            50                  55                  60
Glu Glu Thr Phe Leu Thr Ser Thr Leu Cys Leu Tyr Tyr Pro Thr Glu
 65                  70                  75                  80

Ala Ala Thr Glu Ile Asn Asp Asn Ser Trp Lys Asp Thr Leu Ser Gln
                     85                  90                  95

Leu Phe Leu Thr Lys Gly Trp Pro Thr Gly Ser Val Tyr Phe Lys Glu
                    100                 105                 110

Tyr Thr Asp Ile Ala Ser Phe Ser Val Asp Pro Gln Leu Tyr Cys Asp
                115                 120                 125

Tyr Asn Val Val Leu Met Lys Tyr Asp Ala Gly Trp Met Glu Trp Asp
            130                 135                 140

Arg Glu Ile Asn Asn Tyr Thr Ser Leu Ile His Ser Leu Ile Glu Glu
145                 150                 155                 160

Ser Gln Asn Gln Gln Glu Lys Ile Glu Gly Arg Ser Gly Gly Glu Asp
                    165                 170                 175

Gln Val Asp Pro Arg Leu Ile Asp Gly Lys Ser Gly Gly Thr Leu Gln
                180                 185                 190

Leu Asp Met Ser Glu Leu Ala Asp Leu Ile Leu Asn Glu Trp Leu Cys
            195                 200                 205

Asn Pro Met Asp Ile Thr Leu Tyr Tyr Gln Gln Thr Asp Glu Ala
210                 215                 220

Asn Lys Trp Ile Ser Met Gly Ser Ser Cys Thr Ile Lys Val Cys Pro
225                 230                 235                 240

Leu Asn Thr Gln Thr Leu Gly Ile Gly Cys Leu Thr Thr Asp Thr Ala
                    245                 250                 255

Thr Phe Glu Glu Val Ala Thr Ala Glu Lys Leu Val Ile Thr Asp Val
                260                 265                 270

Val Asp Gly Val Asn His Lys Leu Asp Val Thr Thr Ala Thr Cys Thr
            275                 280                 285

Ile Arg Asn Cys Lys Lys Leu Gly Pro Arg Glu Asn Val Ala Val Ile
290                 295                 300

Gln Val Gly Gly Ser Asp Val Leu Asp Ile Thr Ala Asp Pro Thr Thr
305                 310                 315                 320

Ala Pro Gln Thr Glu Arg Met Met Arg Ile Asn Trp Lys Lys Trp Trp
                    325                 330                 335

Gln Val Phe Tyr Thr Val Val Asp Tyr Val Asn Gln Ile Ile Gln Ala
                340                 345                 350

Met Ser Lys Arg Ser Arg Ser Leu Asn Ser Ala Ala Phe Tyr Tyr Arg
            355                 360                 365

Ile
```

<210> SEQ ID NO 43
<211> LENGTH: 361
<212> TYPE: PRT
<213> ORGANISM: Artificial Sequence
<220> FEATURE:
<223> OTHER INFORMATION: Engineered Rhesus Rotavirus VP7-HR2HXB2 fusion
      protein

<400> SEQUENCE: 43

```
Met Asp Ala Met Lys Arg Gly Leu Cys Cys Val Leu Leu Leu Cys Gly
  1               5                  10                  15

Ala Val Phe Val Ser Pro Ser Glu Asp Ser Ala Trp Ser His Pro Gln
                 20                  25                  30

Phe Glu Lys Glu Asn Leu Tyr Phe Gln Gly Gln Asn Tyr Gly Ile Asn
```

```
                35                  40                  45
Leu Pro Ile Thr Gly Ser Met Asp Thr Ala Tyr Ala Asn Ser Thr Gln
 50                  55                  60

Glu Glu Thr Phe Leu Thr Ser Thr Leu Cys Leu Tyr Tyr Pro Thr Glu
 65                  70                  75                  80

Ala Ala Thr Glu Ile Asn Asp Asn Ser Trp Lys Asp Thr Leu Ser Gln
                 85                  90                  95

Leu Phe Leu Thr Lys Gly Trp Pro Thr Gly Ser Val Tyr Phe Lys Glu
                100                 105                 110

Tyr Thr Asp Ile Ala Ser Phe Ser Val Asp Pro Gln Leu Tyr Cys Asp
            115                 120                 125

Tyr Asn Val Val Leu Met Lys Tyr Asp Ala Gly Trp Met Glu Trp Asp
        130                 135                 140

Arg Glu Ile Asn Asn Tyr Thr Ser Leu Ile His Ser Leu Ile Glu Glu
145                 150                 155                 160

Ser Gln Asn Gln Gln Glu Lys Gly Glu Asp Gln Val Asp Pro Arg Leu
                165                 170                 175

Ile Asp Gly Lys Gly Thr Leu Gln Leu Asp Met Ser Glu Leu Ala Asp
            180                 185                 190

Leu Ile Leu Asn Glu Trp Leu Cys Asn Pro Met Asp Ile Thr Leu Tyr
        195                 200                 205

Tyr Tyr Gln Gln Thr Asp Glu Ala Asn Lys Trp Ile Ser Met Gly Ser
    210                 215                 220

Ser Cys Thr Ile Lys Val Cys Pro Leu Asn Thr Gln Thr Leu Gly Ile
225                 230                 235                 240

Gly Cys Leu Thr Thr Asp Thr Ala Thr Phe Glu Glu Val Ala Thr Ala
                245                 250                 255

Glu Lys Leu Val Ile Thr Asp Val Val Asp Gly Val Asn His Lys Leu
                260                 265                 270

Asp Val Thr Thr Ala Thr Cys Thr Ile Arg Asn Cys Lys Lys Leu Gly
            275                 280                 285

Pro Arg Glu Asn Val Ala Val Ile Gln Val Gly Gly Ser Asp Val Leu
        290                 295                 300

Asp Ile Thr Ala Asp Pro Thr Thr Ala Pro Gln Thr Glu Arg Met Met
305                 310                 315                 320

Arg Ile Asn Trp Lys Lys Trp Trp Gln Val Phe Tyr Thr Val Val Asp
                325                 330                 335

Tyr Val Asn Gln Ile Ile Gln Ala Met Ser Lys Arg Ser Arg Ser Leu
            340                 345                 350

Asn Ser Ala Ala Phe Tyr Tyr Arg Ile
        355                 360
```

<210> SEQ ID NO 44
<211> LENGTH: 372
<212> TYPE: PRT
<213> ORGANISM: Artificial Sequence
<220> FEATURE:
<223> OTHER INFORMATION: Engineered Rhesus Rotavirus VP7-HR2Nipah fusion protein

<400> SEQUENCE: 44

```
Met Asp Ala Met Lys Arg Gly Leu Cys Cys Val Leu Leu Leu Cys Gly
 1               5                  10                  15

Ala Val Phe Val Ser Pro Ser Glu Asp Ser Ala Trp Ser His Pro Gln
                20                  25                  30
```

```
Phe Glu Lys Glu Asn Leu Tyr Phe Gln Gly Gln Asn Tyr Gly Ile Asn
         35                  40                  45
Leu Pro Ile Thr Gly Ser Met Asp Thr Ala Tyr Ala Asn Ser Thr Gln
 50                  55                  60
Glu Glu Thr Phe Leu Thr Ser Thr Leu Cys Leu Tyr Tyr Pro Thr Glu
 65                  70                  75                  80
Ala Ala Thr Glu Ile Asn Asp Asn Ser Trp Lys Asp Thr Leu Ser Gln
                 85                  90                  95
Leu Phe Leu Thr Lys Gly Trp Pro Thr Gly Ser Val Tyr Phe Lys Glu
            100                 105                 110
Tyr Thr Asp Ile Ala Ser Phe Ser Val Asp Pro Gln Leu Tyr Cys Asp
            115                 120                 125
Tyr Asn Val Val Leu Met Lys Tyr Asp Ala Gly Asp Ile Ser Ser Gln
130                 135                 140
Ile Ser Ser Met Asn Gln Ser Leu Gln Gln Ser Lys Asp Tyr Ile Lys
145                 150                 155                 160
Glu Ala Gln Arg Leu Leu Asp Thr Val Lys Ile Glu Gly Arg Ser Gly
                165                 170                 175
Gly Glu Asp Gln Val Asp Pro Arg Leu Ile Asp Gly Lys Ser Gly Gly
            180                 185                 190
Thr Leu Gln Leu Asp Met Ser Glu Leu Ala Asp Leu Ile Leu Asn Glu
            195                 200                 205
Trp Leu Cys Asn Pro Met Asp Ile Thr Leu Tyr Tyr Gln Gln Thr
210                 215                 220
Asp Glu Ala Asn Lys Trp Ile Ser Met Gly Ser Ser Cys Thr Ile Lys
225                 230                 235                 240
Val Cys Pro Leu Asn Thr Gln Thr Leu Gly Ile Gly Cys Leu Thr Thr
                245                 250                 255
Asp Thr Ala Thr Phe Glu Glu Val Ala Thr Ala Glu Lys Leu Val Ile
            260                 265                 270
Thr Asp Val Val Asp Gly Val Asn His Lys Leu Asp Val Thr Thr Ala
            275                 280                 285
Thr Cys Thr Ile Arg Asn Cys Lys Lys Leu Gly Pro Arg Glu Asn Val
290                 295                 300
Ala Val Ile Gln Val Gly Gly Ser Asp Val Leu Asp Ile Thr Ala Asp
305                 310                 315                 320
Pro Thr Thr Ala Pro Gln Thr Glu Arg Met Met Arg Ile Asn Trp Lys
                325                 330                 335
Lys Trp Trp Gln Val Phe Tyr Thr Val Val Asp Tyr Val Asn Gln Ile
            340                 345                 350
Ile Gln Ala Met Ser Lys Arg Ser Arg Ser Leu Asn Ser Ala Ala Phe
            355                 360                 365
Tyr Tyr Arg Ile
370

<210> SEQ ID NO 45
<211> LENGTH: 363
<212> TYPE: PRT
<213> ORGANISM: Artificial Sequence
<220> FEATURE:
<223> OTHER INFORMATION: Engineered Rhesus Rotavirus VP7-HR2Nipah fusion
      protein

<400> SEQUENCE: 45

Met Asp Ala Met Lys Arg Gly Leu Cys Cys Val Leu Leu Leu Cys Gly
 1               5                  10                  15
```

Ala Val Phe Val Ser Pro Ser Glu Asp Ser Ala Trp Ser His Pro Gln
            20                  25                  30

Phe Glu Lys Glu Asn Leu Tyr Phe Gln Gly Gln Asn Tyr Gly Ile Asn
        35                  40                  45

Leu Pro Ile Thr Gly Ser Met Asp Thr Ala Tyr Ala Asn Ser Thr Gln
 50                  55                  60

Glu Glu Thr Phe Leu Thr Ser Thr Leu Cys Leu Tyr Tyr Pro Thr Glu
 65                  70                  75                  80

Ala Ala Thr Glu Ile Asn Asp Asn Ser Trp Lys Asp Thr Leu Ser Gln
                85                  90                  95

Leu Phe Leu Thr Lys Gly Trp Pro Thr Gly Ser Val Tyr Phe Lys Glu
            100                 105                 110

Tyr Thr Asp Ile Ala Ser Phe Ser Val Asp Pro Gln Leu Tyr Cys Asp
        115                 120                 125

Tyr Asn Val Val Leu Met Lys Tyr Asp Ala Gly Asp Ile Ser Ser Gln
130                 135                 140

Ile Ser Ser Met Asn Gln Ser Leu Gln Gln Ser Lys Asp Tyr Ile Lys
145                 150                 155                 160

Glu Ala Gln Arg Leu Leu Asp Thr Val Gly Glu Asp Gln Val Asp Pro
                165                 170                 175

Arg Leu Ile Asp Gly Lys Gly Thr Leu Gln Leu Asp Met Ser Glu Leu
            180                 185                 190

Ala Asp Leu Ile Leu Asn Glu Trp Leu Cys Asn Pro Met Asp Ile Thr
        195                 200                 205

Leu Tyr Tyr Tyr Gln Gln Thr Asp Glu Ala Asn Lys Trp Ile Ser Met
210                 215                 220

Gly Ser Ser Cys Thr Ile Lys Val Cys Pro Leu Asn Thr Gln Thr Leu
225                 230                 235                 240

Gly Ile Gly Cys Leu Thr Thr Asp Thr Ala Thr Phe Glu Glu Val Ala
                245                 250                 255

Thr Ala Glu Lys Leu Val Ile Thr Asp Val Val Asp Gly Val Asn His
            260                 265                 270

Lys Leu Asp Val Thr Thr Ala Thr Cys Thr Ile Arg Asn Cys Lys Lys
        275                 280                 285

Leu Gly Pro Arg Glu Asn Val Ala Val Ile Gln Val Gly Gly Ser Asp
290                 295                 300

Val Leu Asp Ile Thr Ala Asp Pro Thr Thr Ala Pro Gln Thr Glu Arg
305                 310                 315                 320

Met Met Arg Ile Asn Trp Lys Lys Trp Trp Gln Val Phe Tyr Thr Val
                325                 330                 335

Val Asp Tyr Val Asn Gln Ile Ile Gln Ala Met Ser Lys Arg Ser Arg
            340                 345                 350

Ser Leu Asn Ser Ala Ala Phe Tyr Tyr Arg Ile
        355                 360

<210> SEQ ID NO 46
<211> LENGTH: 629
<212> TYPE: PRT
<213> ORGANISM: Artificial Sequence
<220> FEATURE:
<223> OTHER INFORMATION: Engineered influenza virus hemagglutinin (H1
      Solomon Islands 2006) ectodomain-HR1HXB2 fusion protein

<400> SEQUENCE: 46

Met Leu Leu Val Asn Gln Ser His Gln Gly Phe Asn Lys Glu His Thr

-continued

```
1               5                   10                  15
Ser Lys Met Val Ser Ala Ile Val Leu Tyr Val Leu Ala Ala Ala
                20                  25                  30
Ala His Ser Ala Phe Ala Ala Asp Pro His His His His His Glu
                35                  40                  45
Asn Leu Tyr Phe Gln Gly Gly Tyr Leu Leu Glu Asp Thr Ile Cys Ile
50                      55                  60
Gly Tyr His Ala Asn Asn Ser Thr Asp Thr Val Asp Thr Val Leu Glu
65                      70                  75                  80
Lys Asn Val Thr Val Thr His Ser Val Asn Leu Leu Glu Asp Ser His
                85                  90                  95
Asn Gly Lys Leu Cys Leu Leu Lys Gly Ile Ala Pro Leu Gln Leu Gly
                100                 105                 110
Asn Cys Ser Val Ala Gly Trp Ile Leu Gly Asn Pro Glu Cys Glu Leu
                115                 120                 125
Leu Ile Ser Arg Glu Ser Trp Ser Tyr Ile Val Glu Lys Pro Asn Pro
                130                 135                 140
Glu Asn Gly Thr Cys Tyr Pro Gly His Phe Ala Asp Tyr Glu Glu Leu
145                     150                 155                 160
Arg Glu Gln Leu Ser Ser Val Ser Ser Phe Glu Arg Phe Glu Ile Phe
                165                 170                 175
Pro Lys Glu Ser Ser Trp Pro Asn His Thr Thr Thr Gly Val Ser Ala
                180                 185                 190
Ser Cys Ser His Asn Gly Glu Ser Ser Phe Tyr Lys Asn Leu Leu Trp
                195                 200                 205
Leu Thr Gly Lys Asn Gly Leu Tyr Pro Asn Leu Ser Lys Ser Tyr Ala
210                     215                 220
Asn Asn Lys Glu Lys Glu Val Leu Val Leu Trp Gly Val His His Pro
225                     230                 235                 240
Pro Asn Ile Gly Asp Gln Arg Ala Leu Tyr His Thr Glu Asn Ala Tyr
                245                 250                 255
Val Ser Val Val Ser Ser His Tyr Ser Arg Lys Phe Thr Pro Glu Ile
                260                 265                 270
Ala Lys Arg Pro Lys Val Arg Asp Arg Glu Gly Arg Ile Asn Tyr Tyr
                275                 280                 285
Trp Thr Leu Leu Glu Pro Gly Asp Thr Ile Ile Phe Glu Ala Asn Gly
                290                 295                 300
Asn Leu Ile Ala Pro Arg Tyr Ala Phe Ala Leu Ser Arg Gly Phe Gly
305                     310                 315                 320
Ser Gly Ile Ile Asn Ser Asn Ala Pro Met Asp Glu Cys Asp Ala Lys
                325                 330                 335
Cys Gln Thr Pro Gln Gly Ala Ile Asn Ser Ser Leu Pro Phe Gln Asn
                340                 345                 350
Val His Pro Val Thr Ile Gly Glu Cys Pro Lys Tyr Val Arg Ser Ala
                355                 360                 365
Lys Leu Arg Met Val Thr Gly Leu Arg Asn Ile Pro Ser Asp Asp Asp
                370                 375                 380
Asp Lys Gly Leu Phe Gly Ala Ile Ala Gly Phe Ile Glu Gly Gly Trp
385                     390                 395                 400
Thr Gly Met Val Asp Gly Trp Tyr Gly Tyr His His Gln Asn Glu Gln
                405                 410                 415
Gly Ser Gly Tyr Ala Ala Asp Gln Lys Ser Thr Gln Asn Ala Ile Asn
                420                 425                 430
```

-continued

```
Gly Ile Thr Asn Lys Val Asn Ser Val Ile Glu Lys Met Asn Thr Gln
            435                 440                 445

Phe Thr Ala Val Gly Lys Glu Phe Asn Lys Leu Glu Arg Arg Met Glu
450                 455                 460

Asn Leu Asn Lys Lys Val Asp Asp Gly Phe Ile Asp Ile Trp Thr Tyr
465                 470                 475                 480

Asn Ala Glu Leu Leu Val Leu Leu Glu Asn Glu Arg Thr Leu Asp Phe
                485                 490                 495

His Asp Ser Asn Val Lys Asn Leu Tyr Glu Lys Val Lys Ser Gln Leu
            500                 505                 510

Lys Asn Asn Ala Lys Glu Ile Gly Asn Gly Cys Phe Glu Phe Tyr His
            515                 520                 525

Lys Cys Asn Asp Glu Cys Met Glu Ser Val Lys Asn Gly Thr Tyr Asp
530                 535                 540

Tyr Pro Lys Tyr Ser Glu Glu Ser Lys Leu Asn Arg Glu Lys Ile Asp
545                 550                 555                 560

Gly Val Arg Ser Leu Gln Glu Ala Gly Tyr Ile Pro Glu Ala Pro Arg
                565                 570                 575

Asp Gly Gln Ala Tyr Val Arg Lys Asp Gly Glu Trp Val Leu Leu Ser
            580                 585                 590

Thr Phe Leu Ser Gly Ile Val Gln Gln Asn Asn Leu Leu Arg Ala
            595                 600                 605

Ile Glu Ala Gln Gln His Leu Leu Gln Leu Thr Val Trp Gly Ile Lys
610                 615                 620

Gln Leu Gln Ala Arg
625

<210> SEQ ID NO 47
<211> LENGTH: 627
<212> TYPE: PRT
<213> ORGANISM: Artificial Sequence
<220> FEATURE:
<223> OTHER INFORMATION: Engineered influenza virus hemagglutinin (H1
      Solomon Islands 2006) ectodomain-HR1Nipah fusion protein

<400> SEQUENCE: 47

Met Leu Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
                20                  25                  30

Ala His Ser Ala Phe Ala Ala Asp Pro His His His His His His Glu
            35                  40                  45

Asn Leu Tyr Phe Gln Gly Gly Tyr Leu Leu Glu Asp Thr Ile Cys Ile
        50                  55                  60

Gly Tyr His Ala Asn Asn Ser Thr Asp Thr Val Asp Thr Val Leu Glu
65                  70                  75                  80

Lys Asn Val Thr Val Thr His Ser Val Asn Leu Leu Glu Asp Ser His
                85                  90                  95

Asn Gly Lys Leu Cys Leu Leu Lys Gly Ile Ala Pro Leu Gln Leu Gly
            100                 105                 110

Asn Cys Ser Val Ala Gly Trp Ile Leu Gly Asn Pro Glu Cys Glu Leu
        115                 120                 125

Leu Ile Ser Arg Glu Ser Trp Ser Tyr Ile Val Glu Lys Pro Asn Pro
    130                 135                 140

Glu Asn Gly Thr Cys Tyr Pro Gly His Phe Ala Asp Tyr Glu Glu Leu
```

```
            145                 150                 155                 160
        Arg Glu Gln Leu Ser Ser Val Ser Ser Phe Glu Arg Phe Glu Ile Phe
                            165                 170                 175
        Pro Lys Glu Ser Ser Trp Pro Asn His Thr Thr Gly Val Ser Ala
                            180                 185                 190
        Ser Cys Ser His Asn Gly Glu Ser Phe Tyr Lys Asn Leu Leu Trp
                            195                 200                 205
        Leu Thr Gly Lys Asn Gly Leu Tyr Pro Asn Leu Ser Lys Ser Tyr Ala
                210                 215                 220
        Asn Asn Lys Glu Lys Glu Val Leu Val Leu Trp Gly Val His His Pro
        225                 230                 235                 240
        Pro Asn Ile Gly Asp Gln Arg Ala Leu Tyr His Thr Glu Asn Ala Tyr
                            245                 250                 255
        Val Ser Val Val Ser Ser His Tyr Ser Arg Lys Phe Thr Pro Glu Ile
                            260                 265                 270
        Ala Lys Arg Pro Lys Val Arg Asp Arg Glu Gly Arg Ile Asn Tyr Tyr
                            275                 280                 285
        Trp Thr Leu Leu Glu Pro Gly Asp Thr Ile Ile Phe Glu Ala Asn Gly
                290                 295                 300
        Asn Leu Ile Ala Pro Arg Tyr Ala Phe Ala Leu Ser Arg Gly Phe Gly
        305                 310                 315                 320
        Ser Gly Ile Ile Asn Ser Asn Ala Pro Met Asp Glu Cys Asp Ala Lys
                            325                 330                 335
        Cys Gln Thr Pro Gln Gly Ala Ile Asn Ser Ser Leu Pro Phe Gln Asn
                            340                 345                 350
        Val His Pro Val Thr Ile Gly Glu Cys Pro Lys Tyr Val Arg Ser Ala
                            355                 360                 365
        Lys Leu Arg Met Val Thr Gly Leu Arg Asn Ile Pro Ser Asp Asp Asp
                            370                 375                 380
        Asp Lys Gly Leu Phe Gly Ala Ile Ala Gly Phe Ile Glu Gly Gly Trp
        385                 390                 395                 400
        Thr Gly Met Val Asp Gly Trp Tyr Gly Tyr His His Gln Asn Glu Gln
                            405                 410                 415
        Gly Ser Gly Tyr Ala Ala Asp Gln Lys Ser Thr Gln Asn Ala Ile Asn
                            420                 425                 430
        Gly Ile Thr Asn Lys Val Asn Ser Val Ile Glu Lys Met Asn Thr Gln
                            435                 440                 445
        Phe Thr Ala Val Gly Lys Glu Phe Asn Lys Leu Glu Arg Arg Met Glu
                            450                 455                 460
        Asn Leu Asn Lys Lys Val Asp Asp Gly Phe Ile Asp Ile Trp Thr Tyr
        465                 470                 475                 480
        Asn Ala Glu Leu Leu Val Leu Leu Glu Asn Glu Arg Thr Leu Asp Phe
                            485                 490                 495
        His Asp Ser Asn Val Lys Asn Leu Tyr Glu Lys Val Lys Ser Gln Leu
                            500                 505                 510
        Lys Asn Asn Ala Lys Glu Ile Gly Asn Gly Cys Phe Glu Phe Tyr His
                            515                 520                 525
        Lys Cys Asn Asp Glu Cys Met Glu Ser Val Lys Asn Gly Thr Tyr Asp
                            530                 535                 540
        Tyr Pro Lys Tyr Ser Glu Glu Ser Lys Leu Asn Arg Glu Lys Ile Asp
        545                 550                 555                 560
        Gly Val Arg Ser Leu Gln Glu Ala Gly Tyr Ile Pro Glu Ala Pro Arg
                            565                 570                 575
```

Asp Gly Gln Ala Tyr Val Arg Lys Asp Gly Glu Trp Val Leu Leu Ser
            580                 585                 590

Thr Asn Ile Asn Lys Leu Lys Ser Ser Ile Glu Ser Thr Asn Glu Ala
            595                 600                 605

Val Val Lys Leu Gln Glu Thr Ala Glu Lys Thr Val Tyr Val Leu Thr
            610                 615                 620

Ala Leu Gln
625

<210> SEQ ID NO 48
<211> LENGTH: 596
<212> TYPE: PRT
<213> ORGANISM: Artificial Sequence
<220> FEATURE:
<223> OTHER INFORMATION: Engineered influenza virus hemagglutinin (H1
      Solomon Islands 2006) ectodomain-HR1HXB2 fusion protein

<400> SEQUENCE: 48

Met Leu Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
            20                  25                  30

Ala His Ser Ala Phe Ala Ala Asp Pro His His His His His His Glu
        35                  40                  45

Asn Leu Tyr Phe Gln Gly Gly Tyr Leu Leu Glu Asp Thr Ile Cys Ile
    50                  55                  60

Gly Tyr His Ala Asn Asn Ser Thr Asp Thr Val Asp Thr Val Leu Glu
65                  70                  75                  80

Lys Asn Val Thr Val Thr His Ser Val Asn Leu Leu Glu Asp Ser His
                85                  90                  95

Asn Gly Lys Leu Cys Leu Leu Lys Gly Ile Ala Pro Leu Gln Leu Gly
            100                 105                 110

Asn Cys Ser Val Ala Gly Trp Ile Leu Gly Asn Pro Glu Cys Glu Leu
        115                 120                 125

Leu Ile Ser Arg Glu Ser Trp Ser Tyr Ile Val Glu Lys Pro Asn Pro
    130                 135                 140

Glu Asn Gly Thr Cys Tyr Pro Gly His Phe Ala Asp Tyr Glu Glu Leu
145                 150                 155                 160

Arg Glu Gln Leu Ser Ser Val Ser Ser Phe Glu Arg Phe Glu Ile Phe
                165                 170                 175

Pro Lys Glu Ser Ser Trp Pro Asn His Thr Thr Thr Gly Val Ser Ala
            180                 185                 190

Ser Cys Ser His Asn Gly Glu Ser Ser Phe Tyr Lys Asn Leu Leu Trp
        195                 200                 205

Leu Thr Gly Lys Asn Gly Leu Tyr Pro Asn Leu Ser Lys Ser Tyr Ala
    210                 215                 220

Asn Asn Lys Glu Lys Glu Val Leu Val Leu Trp Gly Val His His Pro
225                 230                 235                 240

Pro Asn Ile Gly Asp Gln Arg Ala Leu Tyr His Thr Glu Asn Ala Tyr
                245                 250                 255

Val Ser Val Val Ser Ser His Tyr Ser Arg Lys Phe Thr Pro Glu Ile
            260                 265                 270

Ala Lys Arg Pro Lys Val Arg Asp Arg Glu Gly Arg Ile Asn Tyr Tyr
        275                 280                 285

Trp Thr Leu Leu Glu Pro Gly Asp Thr Ile Ile Phe Glu Ala Asn Gly

```
                290                 295                 300
Asn Leu Ile Ala Pro Arg Tyr Ala Phe Ala Leu Ser Arg Gly Phe Gly
305                 310                 315                 320

Ser Gly Ile Ile Asn Ser Asn Ala Pro Met Asp Glu Cys Asp Ala Lys
                325                 330                 335

Cys Gln Thr Pro Gln Gly Ala Ile Asn Ser Ser Leu Pro Phe Gln Asn
            340                 345                 350

Val His Pro Val Thr Ile Gly Glu Cys Pro Lys Tyr Val Arg Ser Ala
        355                 360                 365

Lys Leu Arg Met Val Thr Gly Leu Arg Asn Ile Pro Ser Asp Asp Asp
    370                 375                 380

Asp Lys Gly Leu Phe Gly Ala Ile Ala Gly Phe Ile Glu Gly Gly Trp
385                 390                 395                 400

Thr Gly Met Val Asp Gly Trp Tyr Gly Tyr His His Gln Asn Glu Gln
                405                 410                 415

Gly Ser Gly Tyr Ala Ala Asp Gln Lys Ser Thr Gln Asn Ala Ile Asn
            420                 425                 430

Gly Ile Thr Asn Lys Val Asn Ser Val Ile Glu Lys Met Asn Thr Gln
        435                 440                 445

Phe Thr Ala Val Gly Lys Glu Phe Asn Lys Leu Glu Arg Arg Met Glu
    450                 455                 460

Asn Leu Asn Lys Lys Val Asp Asp Gly Phe Ile Asp Ile Trp Thr Tyr
465                 470                 475                 480

Asn Ala Glu Leu Leu Val Leu Leu Glu Asn Glu Arg Thr Leu Asp Phe
                485                 490                 495

His Asp Ser Asn Val Lys Asn Leu Tyr Glu Lys Val Lys Ser Gln Leu
            500                 505                 510

Lys Asn Asn Ala Lys Glu Ile Gly Asn Gly Cys Phe Glu Phe Tyr His
        515                 520                 525

Lys Cys Asn Asp Glu Cys Met Glu Ser Val Lys Asn Gly Thr Tyr Asp
    530                 535                 540

Tyr Pro Lys Tyr Ser Glu Glu Ser Lys Leu Asn Arg Glu Lys Ile Asp
545                 550                 555                 560

Gly Val Ser Gly Ile Val Gln Gln Gln Asn Asn Leu Leu Arg Ala Ile
                565                 570                 575

Glu Ala Gln Gln His Leu Leu Gln Leu Thr Val Trp Gly Ile Lys Gln
            580                 585                 590

Leu Gln Ala Arg
        595

<210> SEQ ID NO 49
<211> LENGTH: 598
<212> TYPE: PRT
<213> ORGANISM: Artificial Sequence
<220> FEATURE:
<223> OTHER INFORMATION: Engineered influenza virus hemagglutinin (H1
      Solomon Islands 2006) ectodomain-HR1HXB2 fusion protein

<400> SEQUENCE: 49

Met Leu Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
            20                  25                  30

Ala His Ser Ala Phe Ala Ala Asp Pro His His His His His His Glu
        35                  40                  45
```

-continued

```
Asn Leu Tyr Phe Gln Gly Gly Tyr Leu Leu Glu Asp Thr Ile Cys Ile
 50                  55                  60
Gly Tyr His Ala Asn Asn Ser Thr Asp Thr Val Asp Thr Val Leu Glu
 65                      70                  75                  80
Lys Asn Val Thr Val Thr His Ser Val Asn Leu Leu Glu Asp Ser His
                     85                  90                  95
Asn Gly Lys Leu Cys Leu Leu Lys Gly Ile Ala Pro Leu Gln Leu Gly
             100                 105                 110
Asn Cys Ser Val Ala Gly Trp Ile Leu Gly Asn Pro Glu Cys Glu Leu
             115                 120                 125
Leu Ile Ser Arg Glu Ser Trp Ser Tyr Ile Val Glu Lys Pro Asn Pro
 130                 135                 140
Glu Asn Gly Thr Cys Tyr Pro Gly His Phe Ala Asp Tyr Glu Glu Leu
 145                 150                 155                 160
Arg Glu Gln Leu Ser Ser Val Ser Ser Phe Glu Arg Phe Glu Ile Phe
                 165                 170                 175
Pro Lys Glu Ser Ser Trp Pro Asn His Thr Thr Thr Gly Val Ser Ala
             180                 185                 190
Ser Cys Ser His Asn Gly Glu Ser Ser Phe Tyr Lys Asn Leu Leu Trp
             195                 200                 205
Leu Thr Gly Lys Asn Gly Leu Tyr Pro Asn Leu Ser Lys Ser Tyr Ala
 210                 215                 220
Asn Asn Lys Glu Lys Glu Val Leu Val Leu Trp Gly Val His His Pro
 225                 230                 235                 240
Pro Asn Ile Gly Asp Gln Arg Ala Leu Tyr His Thr Glu Asn Ala Tyr
                 245                 250                 255
Val Ser Val Val Ser Ser His Tyr Ser Arg Lys Phe Thr Pro Glu Ile
             260                 265                 270
Ala Lys Arg Pro Lys Val Arg Asp Arg Glu Gly Arg Ile Asn Tyr Tyr
             275                 280                 285
Trp Thr Leu Leu Glu Pro Gly Asp Thr Ile Ile Phe Glu Ala Asn Gly
 290                 295                 300
Asn Leu Ile Ala Pro Arg Tyr Ala Phe Ala Leu Ser Arg Gly Phe Gly
 305                 310                 315                 320
Ser Gly Ile Ile Asn Ser Asn Ala Pro Met Asp Glu Cys Asp Ala Lys
                 325                 330                 335
Cys Gln Thr Pro Gln Gly Ala Ile Asn Ser Ser Leu Pro Phe Gln Asn
             340                 345                 350
Val His Pro Val Thr Ile Gly Glu Cys Pro Lys Tyr Val Arg Ser Ala
             355                 360                 365
Lys Leu Arg Met Val Thr Gly Leu Arg Asn Ile Pro Ser Asp Asp Asp
 370                 375                 380
Asp Lys Gly Leu Phe Gly Ala Ile Ala Gly Phe Ile Glu Gly Gly Trp
 385                 390                 395                 400
Thr Gly Met Val Asp Gly Trp Tyr Gly Tyr His His Gln Asn Glu Gln
                 405                 410                 415
Gly Ser Gly Tyr Ala Ala Asp Gln Lys Ser Thr Gln Asn Ala Ile Asn
             420                 425                 430
Gly Ile Thr Asn Lys Val Asn Ser Val Ile Glu Lys Met Asn Thr Gln
             435                 440                 445
Phe Thr Ala Val Gly Lys Glu Phe Asn Lys Leu Glu Arg Arg Met Glu
 450                 455                 460
Asn Leu Asn Lys Lys Val Asp Asp Gly Phe Ile Asp Ile Trp Thr Tyr
```

```
            465                 470                 475                 480
Asn Ala Glu Leu Leu Val Leu Leu Gly Asn Glu Arg Thr Leu Asp Phe
                485                 490                 495
His Asp Ser Asn Val Lys Asn Leu Tyr Glu Lys Val Lys Ser Gln Leu
                500                 505                 510
Lys Asn Asn Ala Lys Glu Ile Gly Asn Gly Cys Phe Glu Phe Tyr His
                515                 520                 525
Lys Cys Asn Asp Glu Cys Met Glu Ser Val Lys Asn Gly Thr Tyr Asp
            530                 535                 540
Tyr Pro Lys Tyr Ser Glu Glu Ser Lys Leu Asn Arg Glu Lys Ile Asp
545                 550                 555                 560
Gly Val Arg Ser Asn Ile Asn Lys Leu Lys Ser Ser Ile Glu Ser Thr
                565                 570                 575
Asn Glu Ala Val Val Lys Leu Gln Glu Thr Ala Glu Lys Thr Val Tyr
                580                 585                 590
Val Leu Thr Ala Leu Gln
            595

<210> SEQ ID NO 50
<211> LENGTH: 595
<212> TYPE: PRT
<213> ORGANISM: Artificial Sequence
<220> FEATURE:
<223> OTHER INFORMATION: Engineered influenza virus hemagglutinin (H1
      Solomon Islands 2006) ectodomain-HR1HXB2 fusion protein

<400> SEQUENCE: 50

Met Leu Leu Val Asn Gln Ser His Gln Gly Phe Asn Lys Glu His Thr
1               5                   10                  15
Ser Lys Met Val Ser Ala Ile Val Leu Tyr Val Leu Leu Ala Ala Ala
                20                  25                  30
Ala His Ser Ala Phe Ala Ala Asp Pro His His His His His His Glu
            35                  40                  45
Asn Leu Tyr Phe Gln Gly Gly Tyr Leu Leu Glu Asp Thr Ile Cys Ile
        50                  55                  60
Gly Tyr His Ala Asn Asn Ser Thr Asp Thr Val Asp Thr Val Leu Glu
65                  70                  75                  80
Lys Asn Val Thr Val Thr His Ser Val Asn Leu Leu Glu Asp Ser His
                85                  90                  95
Asn Gly Lys Leu Cys Leu Leu Lys Gly Ile Ala Pro Leu Gln Leu Gly
            100                 105                 110
Asn Cys Ser Val Ala Gly Trp Ile Leu Gly Asn Pro Glu Cys Glu Leu
        115                 120                 125
Leu Ile Ser Arg Glu Ser Trp Ser Tyr Ile Val Glu Lys Pro Asn Pro
    130                 135                 140
Glu Asn Gly Thr Cys Tyr Pro Gly His Phe Ala Asp Tyr Glu Glu Leu
145                 150                 155                 160
Arg Glu Gln Leu Ser Ser Val Ser Ser Phe Glu Arg Phe Glu Ile Phe
                165                 170                 175
Pro Lys Glu Ser Ser Trp Pro Asn His Thr Thr Thr Gly Val Ser Ala
            180                 185                 190
Ser Cys Ser His Asn Gly Glu Ser Ser Phe Tyr Lys Asn Leu Leu Trp
        195                 200                 205
Leu Thr Gly Lys Asn Gly Leu Tyr Pro Asn Leu Ser Lys Ser Tyr Ala
    210                 215                 220
```

Asn Asn Lys Glu Lys Glu Val Leu Val Leu Trp Gly Val His His Pro
225                 230                 235                 240

Pro Asn Ile Gly Asp Gln Arg Ala Leu Tyr His Thr Glu Asn Ala Tyr
            245                 250                 255

Val Ser Val Val Ser Ser His Tyr Ser Arg Lys Phe Thr Pro Glu Ile
                260                 265                 270

Ala Lys Arg Pro Lys Val Arg Asp Gln Gly Arg Ile Asn Tyr Tyr
        275                 280                 285

Trp Thr Leu Leu Glu Pro Gly Asp Thr Ile Ile Phe Glu Ala Asn Gly
        290                 295                 300

Asn Leu Ile Ala Pro Arg Tyr Ala Phe Ala Leu Ser Arg Gly Phe Gly
305                 310                 315                 320

Ser Gly Ile Ile Asn Ser Asn Ala Pro Met Asp Glu Cys Asp Ala Lys
                325                 330                 335

Cys Gln Thr Pro Gln Gly Ala Ile Asn Ser Ser Leu Pro Phe Gln Asn
                340                 345                 350

Val His Pro Val Thr Ile Gly Glu Cys Pro Lys Tyr Val Arg Ser Ala
            355                 360                 365

Lys Leu Arg Met Val Thr Gly Leu Arg Asn Ile Pro Ser Ile Gln Ser
370                 375                 380

Arg Gly Leu Phe Gly Ala Ile Ala Gly Phe Ile Glu Gly Gly Trp Thr
385                 390                 395                 400

Gly Met Val Asp Gly Trp Tyr Gly Tyr His His Gln Asn Glu Gln Gly
                405                 410                 415

Ser Gly Tyr Ala Ala Asp Gln Lys Ser Thr Gln Asn Ala Ile Asn Gly
            420                 425                 430

Ile Thr Asn Lys Val Asn Ser Val Ile Glu Lys Met Asn Thr Gln Phe
        435                 440                 445

Thr Ala Val Gly Lys Glu Phe Asn Lys Leu Glu Arg Arg Met Glu Asn
    450                 455                 460

Leu Asn Lys Lys Val Asp Asp Gly Phe Ile Asp Ile Trp Thr Tyr Asn
465                 470                 475                 480

Ala Glu Leu Leu Val Leu Leu Glu Asn Glu Arg Thr Leu Asp Phe His
                485                 490                 495

Asp Ser Asn Val Lys Asn Leu Tyr Glu Lys Val Lys Ser Gln Leu Lys
            500                 505                 510

Asn Asn Ala Lys Glu Ile Gly Asn Gly Cys Phe Glu Phe Tyr His Lys
        515                 520                 525

Cys Asn Asp Glu Cys Met Glu Ser Val Lys Asn Gly Thr Tyr Asp Tyr
530                 535                 540

Pro Lys Tyr Ser Glu Glu Ser Lys Leu Asn Arg Glu Lys Ile Asp Gly
545                 550                 555                 560

Val Ser Gly Ile Val Gln Gln Asn Asn Leu Leu Arg Ala Ile Glu
                565                 570                 575

Ala Gln Gln His Leu Leu Gln Leu Thr Val Trp Gly Ile Lys Gln Leu
            580                 585                 590

Gln Ala Arg
        595

<210> SEQ ID NO 51
<211> LENGTH: 597
<212> TYPE: PRT
<213> ORGANISM: Artificial Sequence
<220> FEATURE:
<223> OTHER INFORMATION: Engineered influenza virus hemagglutinin (H1

Solomon Islands 2006) ectodomain-HR1Nipah fusion protein

<400> SEQUENCE: 51

```
Met Leu Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
            20                  25                  30

Ala His Ser Ala Phe Ala Ala Asp Pro His His His His His His Glu
        35                  40                  45

Asn Leu Tyr Phe Gln Gly Gly Tyr Leu Leu Glu Asp Thr Ile Cys Ile
    50                  55                  60

Gly Tyr His Ala Asn Asn Ser Thr Asp Thr Val Asp Thr Val Leu Glu
65                  70                  75                  80

Lys Asn Val Thr Val Thr His Ser Val Asn Leu Leu Glu Asp Ser His
                85                  90                  95

Asn Gly Lys Leu Cys Leu Leu Lys Gly Ile Ala Pro Leu Gln Leu Gly
            100                 105                 110

Asn Cys Ser Val Ala Gly Trp Ile Leu Gly Asn Pro Glu Cys Glu Leu
        115                 120                 125

Leu Ile Ser Arg Glu Ser Trp Ser Tyr Ile Val Glu Lys Pro Asn Pro
    130                 135                 140

Glu Asn Gly Thr Cys Tyr Pro Gly His Phe Ala Asp Tyr Glu Glu Leu
145                 150                 155                 160

Arg Glu Gln Leu Ser Ser Val Ser Ser Phe Glu Arg Phe Glu Ile Phe
                165                 170                 175

Pro Lys Glu Ser Ser Trp Pro Asn His Thr Thr Thr Gly Val Ser Ala
            180                 185                 190

Ser Cys Ser His Asn Gly Glu Ser Ser Phe Tyr Lys Asn Leu Leu Trp
        195                 200                 205

Leu Thr Gly Lys Asn Gly Leu Tyr Pro Asn Leu Ser Lys Ser Tyr Ala
    210                 215                 220

Asn Asn Lys Glu Lys Glu Val Leu Val Leu Trp Gly Val His His Pro
225                 230                 235                 240

Pro Asn Ile Gly Asp Gln Arg Ala Leu Tyr His Thr Glu Asn Ala Tyr
                245                 250                 255

Val Ser Val Val Ser Ser His Tyr Ser Arg Lys Phe Thr Pro Glu Ile
            260                 265                 270

Ala Lys Arg Pro Lys Val Arg Asp Arg Glu Gly Arg Ile Asn Tyr Tyr
        275                 280                 285

Trp Thr Leu Leu Glu Pro Gly Asp Thr Ile Ile Phe Glu Ala Asn Gly
    290                 295                 300

Asn Leu Ile Ala Pro Arg Tyr Ala Phe Ala Leu Ser Arg Gly Phe Gly
305                 310                 315                 320

Ser Gly Ile Ile Asn Ser Asn Ala Pro Met Asp Glu Cys Asp Ala Lys
                325                 330                 335

Cys Gln Thr Pro Gln Gly Ala Ile Asn Ser Ser Leu Pro Phe Gln Asn
            340                 345                 350

Val His Pro Val Thr Ile Gly Glu Cys Pro Lys Tyr Val Arg Ser Ala
        355                 360                 365

Lys Leu Arg Met Val Thr Gly Leu Arg Asn Ile Pro Ser Ile Gln Ser
    370                 375                 380

Arg Gly Leu Phe Gly Ala Ile Ala Gly Phe Ile Glu Gly Gly Trp Thr
385                 390                 395                 400
```

Gly Met Val Asp Gly Trp Tyr Gly Tyr His His Gln Asn Glu Gln Gly
            405                 410                 415

Ser Gly Tyr Ala Ala Asp Gln Lys Ser Thr Gln Asn Ala Ile Asn Gly
        420                 425                 430

Ile Thr Asn Lys Val Asn Ser Val Ile Glu Lys Met Asn Thr Gln Phe
    435                 440                 445

Thr Ala Val Gly Lys Glu Phe Asn Lys Leu Glu Arg Arg Met Glu Asn
450                 455                 460

Leu Asn Lys Lys Val Asp Asp Gly Phe Ile Asp Ile Trp Thr Tyr Asn
465                 470                 475                 480

Ala Glu Leu Leu Val Leu Leu Glu Asn Glu Arg Thr Leu Asp Phe His
                485                 490                 495

Asp Ser Asn Val Lys Asn Leu Tyr Glu Lys Val Lys Ser Gln Leu Lys
            500                 505                 510

Asn Asn Ala Lys Glu Ile Gly Asn Gly Cys Phe Glu Phe Tyr His Lys
        515                 520                 525

Cys Asn Asp Glu Cys Met Glu Ser Val Lys Asn Gly Thr Tyr Asp Tyr
    530                 535                 540

Pro Lys Tyr Ser Glu Glu Ser Lys Leu Asn Arg Glu Lys Ile Asp Gly
545                 550                 555                 560

Val Arg Ser Asn Ile Asn Lys Leu Lys Ser Ser Ile Glu Ser Thr Asn
                565                 570                 575

Glu Ala Val Val Lys Leu Gln Glu Thr Ala Glu Lys Thr Val Tyr Val
            580                 585                 590

Leu Thr Ala Leu Gln
        595

<210> SEQ ID NO 52
<211> LENGTH: 595
<212> TYPE: PRT
<213> ORGANISM: Artificial Sequence
<220> FEATURE:
<223> OTHER INFORMATION: Engineered influenza virus hemagglutinin (H1
      Solomon Islands 2006) ectodomain-HR1HXB2 fusion protein

<400> SEQUENCE: 52

Met Leu Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
            20                  25                  30

Ala His Ser Ala Phe Ala Ala Asp Pro His His His His His His Glu
        35                  40                  45

Asn Leu Tyr Phe Gln Gly Gly Tyr Leu Leu Glu Asp Thr Ile Cys Ile
    50                  55                  60

Gly Tyr His Ala Asn Asn Ser Thr Asp Thr Val Asp Thr Val Leu Glu
65                  70                  75                  80

Lys Asn Val Thr Val Thr His Ser Val Asn Leu Leu Glu Asp Ser His
                85                  90                  95

Asn Gly Lys Leu Cys Leu Leu Lys Gly Ile Ala Pro Leu Gln Leu Gly
            100                 105                 110

Asn Cys Ser Val Ala Gly Trp Ile Leu Gly Asn Pro Glu Cys Glu Leu
        115                 120                 125

Leu Ile Ser Arg Glu Ser Trp Ser Tyr Ile Val Glu Lys Pro Asn Pro
    130                 135                 140

Glu Asn Gly Thr Cys Tyr Pro Gly His Phe Ala Asp Tyr Glu Glu Leu
145                 150                 155                 160

-continued

Arg Glu Gln Leu Ser Ser Val Ser Ser Phe Glu Arg Phe Glu Ile Phe
                165                 170                 175

Pro Lys Glu Ser Ser Trp Pro Asn His Thr Thr Thr Gly Val Ser Ala
            180                 185                 190

Ser Cys Ser His Asn Gly Glu Ser Ser Phe Tyr Lys Asn Leu Leu Trp
        195                 200                 205

Leu Thr Gly Lys Asn Gly Leu Tyr Pro Asn Leu Ser Lys Ser Tyr Ala
    210                 215                 220

Asn Asn Lys Glu Lys Glu Val Leu Val Leu Trp Gly Val His His Pro
225                 230                 235                 240

Pro Asn Ile Gly Asp Gln Arg Ala Leu Tyr His Thr Glu Asn Ala Tyr
                245                 250                 255

Val Ser Val Val Ser Ser His Tyr Ser Arg Lys Phe Thr Pro Glu Ile
            260                 265                 270

Ala Lys Arg Pro Lys Val Arg Asp Arg Glu Gly Arg Ile Asn Tyr Tyr
        275                 280                 285

Trp Thr Leu Leu Glu Pro Gly Asp Thr Ile Ile Phe Glu Ala Asn Gly
    290                 295                 300

Asn Leu Ile Ala Pro Arg Tyr Ala Phe Ala Leu Ser Arg Gly Phe Gly
305                 310                 315                 320

Ser Gly Ile Ile Asn Ser Asn Ala Pro Met Asp Glu Cys Asp Ala Lys
                325                 330                 335

Cys Gln Thr Pro Gln Gly Ala Ile Asn Ser Ser Leu Pro Phe Gln Asn
            340                 345                 350

Val His Pro Val Thr Ile Gly Glu Cys Pro Lys Tyr Val Arg Ser Ala
        355                 360                 365

Lys Leu Arg Met Val Thr Gly Leu Arg Asn Ile Pro Ser Ile Glu Gly
    370                 375                 380

Arg Gly Leu Phe Gly Ala Ile Ala Gly Phe Ile Glu Gly Gly Trp Thr
385                 390                 395                 400

Gly Met Val Asp Gly Trp Tyr Gly Tyr His His Gln Asn Glu Gln Gly
                405                 410                 415

Ser Gly Tyr Ala Ala Asp Gln Lys Ser Thr Gln Asn Ala Ile Asn Gly
            420                 425                 430

Ile Thr Asn Lys Val Asn Ser Val Ile Glu Lys Met Asn Thr Gln Phe
        435                 440                 445

Thr Ala Val Gly Lys Glu Phe Asn Lys Leu Glu Arg Arg Met Glu Asn
    450                 455                 460

Leu Asn Lys Lys Val Asp Asp Gly Phe Ile Asp Ile Trp Thr Tyr Asn
465                 470                 475                 480

Ala Glu Leu Leu Val Leu Leu Glu Asn Glu Arg Thr Leu Asp Phe His
                485                 490                 495

Asp Ser Asn Val Lys Asn Leu Tyr Glu Lys Val Lys Ser Gln Leu Lys
            500                 505                 510

Asn Asn Ala Lys Glu Ile Gly Asn Gly Cys Phe Glu Phe Tyr His Lys
        515                 520                 525

Cys Asn Asp Glu Cys Met Glu Ser Val Lys Asn Gly Thr Tyr Asp Tyr
    530                 535                 540

Pro Lys Tyr Ser Glu Glu Ser Lys Leu Asn Arg Glu Lys Ile Asp Gly
545                 550                 555                 560

Val Ser Gly Ile Val Gln Gln Gln Asn Asn Leu Leu Arg Ala Ile Glu
                565                 570                 575

```
Ala Gln Gln His Leu Leu Gln Leu Thr Val Trp Gly Ile Lys Gln Leu
            580                 585                 590

Gln Ala Arg
    595
```

<210> SEQ ID NO 53
<211> LENGTH: 597
<212> TYPE: PRT
<213> ORGANISM: Artificial Sequence
<220> FEATURE:
<223> OTHER INFORMATION: Engineered influenza virus hemagglutinin (H1
      Solomon Islands 2006) ectodomain-HR1Nipah fusion protein

<400> SEQUENCE: 53

```
Met Leu Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
            20                  25                  30

Ala His Ser Ala Phe Ala Ala Asp Pro His His His His His His Glu
        35                  40                  45

Asn Leu Tyr Phe Gln Gly Gly Tyr Leu Leu Glu Asp Thr Ile Cys Ile
    50                  55                  60

Gly Tyr His Ala Asn Asn Ser Thr Asp Thr Val Asp Thr Val Leu Glu
65                  70                  75                  80

Lys Asn Val Thr Val Thr His Ser Val Asn Leu Leu Glu Asp Ser His
                85                  90                  95

Asn Gly Lys Leu Cys Leu Leu Lys Gly Ile Ala Pro Leu Gln Leu Gly
            100                 105                 110

Asn Cys Ser Val Ala Gly Trp Ile Leu Gly Asn Pro Glu Cys Glu Leu
        115                 120                 125

Leu Ile Ser Arg Glu Ser Trp Ser Tyr Ile Val Glu Lys Pro Asn Pro
    130                 135                 140

Glu Asn Gly Thr Cys Tyr Pro Gly His Phe Ala Asp Tyr Glu Glu Leu
145                 150                 155                 160

Arg Glu Gln Leu Ser Ser Val Ser Ser Phe Glu Arg Phe Glu Ile Phe
                165                 170                 175

Pro Lys Glu Ser Ser Trp Pro Asn His Thr Thr Thr Gly Val Ser Ala
            180                 185                 190

Ser Cys Ser His Asn Gly Glu Ser Ser Phe Tyr Lys Asn Leu Leu Trp
        195                 200                 205

Leu Thr Gly Lys Asn Gly Leu Tyr Pro Asn Leu Ser Lys Ser Tyr Ala
    210                 215                 220

Asn Asn Lys Glu Lys Glu Val Leu Val Leu Trp Gly Val His His Pro
225                 230                 235                 240

Pro Asn Ile Gly Asp Gln Arg Ala Leu Tyr His Thr Glu Asn Ala Tyr
                245                 250                 255

Val Ser Val Val Ser Ser His Tyr Ser Arg Lys Phe Thr Pro Glu Ile
            260                 265                 270

Ala Lys Arg Pro Lys Val Arg Asp Arg Glu Gly Arg Ile Asn Tyr Tyr
        275                 280                 285

Trp Thr Leu Leu Glu Pro Gly Asp Thr Ile Ile Phe Glu Ala Asn Gly
    290                 295                 300

Asn Leu Ile Ala Pro Arg Tyr Ala Phe Ala Leu Ser Arg Gly Phe Gly
305                 310                 315                 320

Ser Gly Ile Ile Asn Ser Asn Ala Pro Met Asp Glu Cys Asp Ala Lys
                325                 330                 335
```

```
Cys Gln Thr Pro Gln Gly Ala Ile Asn Ser Ser Leu Pro Phe Gln Asn
            340                 345                 350

Val His Pro Val Thr Ile Gly Glu Cys Pro Lys Tyr Val Arg Ser Ala
        355                 360                 365

Lys Leu Arg Met Val Thr Gly Leu Arg Asn Ile Pro Ser Ile Glu Gly
    370                 375                 380

Arg Gly Leu Phe Gly Ala Ile Ala Gly Phe Ile Glu Gly Gly Trp Thr
385                 390                 395                 400

Gly Met Val Asp Gly Trp Tyr Gly Tyr His His Gln Asn Glu Gln Gly
                405                 410                 415

Ser Gly Tyr Ala Ala Asp Gln Lys Ser Thr Gln Asn Ala Ile Asn Gly
            420                 425                 430

Ile Thr Asn Lys Val Asn Ser Val Ile Glu Lys Met Asn Thr Gln Phe
        435                 440                 445

Thr Ala Val Gly Lys Glu Phe Asn Lys Leu Glu Arg Arg Met Glu Asn
    450                 455                 460

Leu Asn Lys Lys Val Asp Asp Gly Phe Ile Asp Ile Trp Thr Tyr Asn
465                 470                 475                 480

Ala Glu Leu Leu Val Leu Leu Glu Asn Glu Arg Thr Leu Asp Phe His
                485                 490                 495

Asp Ser Asn Val Lys Asn Leu Tyr Glu Lys Val Lys Ser Gln Leu Lys
            500                 505                 510

Asn Asn Ala Lys Glu Ile Gly Asn Gly Cys Phe Glu Phe Tyr His Lys
        515                 520                 525

Cys Asn Asp Glu Cys Met Glu Ser Val Lys Asn Gly Thr Tyr Asp Tyr
    530                 535                 540

Pro Lys Tyr Ser Glu Glu Ser Lys Leu Asn Arg Glu Lys Ile Asp Gly
545                 550                 555                 560

Val Arg Ser Asn Ile Asn Lys Leu Lys Ser Ser Ile Glu Ser Thr Asn
                565                 570                 575

Glu Ala Val Val Lys Leu Gln Glu Thr Ala Glu Lys Thr Val Tyr Val
            580                 585                 590

Leu Thr Ala Leu Gln
        595

<210> SEQ ID NO 54
<211> LENGTH: 596
<212> TYPE: PRT
<213> ORGANISM: Artificial Sequence
<220> FEATURE:
<223> OTHER INFORMATION: Engineered influenza virus hemagglutinin (H1
      Solomon Islands 2006) ectodomain-HR1HXB2 fusion protein

<400> SEQUENCE: 54

Met Leu Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
            20                  25                  30

Ala His Ser Ala Phe Ala Ala Asp Pro His His His His His His Glu
        35                  40                  45

Asn Leu Tyr Phe Gln Gly Gly Tyr Leu Leu Glu Asp Thr Ile Cys Ile
    50                  55                  60

Gly Tyr His Ala Asn Asn Ser Thr Asp Thr Val Asp Thr Val Leu Glu
65                  70                  75                  80

Lys Asn Val Thr Val Thr His Ser Val Asn Leu Leu Glu Asp Ser His
```

85                  90                  95
Asn Gly Lys Leu Cys Leu Leu Lys Gly Ile Ala Pro Leu Gln Leu Gly
                100                 105                 110

Asn Cys Ser Val Ala Gly Trp Ile Leu Gly Asn Pro Glu Cys Glu Leu
                115                 120                 125

Leu Ile Ser Arg Glu Ser Trp Ser Tyr Ile Val Glu Lys Pro Asn Pro
            130                 135                 140

Glu Asn Gly Thr Cys Tyr Pro Gly His Phe Ala Asp Tyr Glu Glu Leu
145                 150                 155                 160

Arg Glu Gln Leu Ser Ser Val Ser Ser Phe Glu Arg Phe Glu Ile Phe
                165                 170                 175

Pro Lys Glu Ser Ser Trp Pro Asn His Thr Thr Thr Gly Val Ser Ala
                180                 185                 190

Ser Cys Ser His Asn Gly Glu Ser Ser Phe Tyr Lys Asn Leu Leu Trp
                195                 200                 205

Leu Thr Gly Lys Asn Gly Leu Tyr Pro Asn Leu Ser Lys Ser Tyr Ala
            210                 215                 220

Asn Asn Lys Glu Lys Glu Val Leu Val Leu Trp Gly Val His His Pro
225                 230                 235                 240

Pro Asn Ile Gly Asp Gln Arg Ala Leu Tyr His Thr Glu Asn Ala Tyr
                245                 250                 255

Val Ser Val Val Ser Ser His Tyr Ser Arg Lys Phe Thr Pro Glu Ile
                260                 265                 270

Ala Lys Arg Pro Lys Val Arg Asp Arg Glu Gly Arg Ile Asn Tyr Tyr
            275                 280                 285

Trp Thr Leu Leu Glu Pro Gly Asp Thr Ile Ile Phe Glu Ala Asn Gly
            290                 295                 300

Asn Leu Ile Ala Pro Arg Tyr Ala Phe Ala Leu Ser Arg Gly Phe Gly
305                 310                 315                 320

Ser Gly Ile Ile Asn Ser Asn Ala Pro Met Asp Glu Cys Asp Ala Lys
                325                 330                 335

Cys Gln Thr Pro Gln Gly Ala Ile Asn Ser Ser Leu Pro Phe Gln Asn
                340                 345                 350

Val His Pro Val Thr Ile Gly Glu Cys Pro Lys Tyr Val Arg Ser Ala
            355                 360                 365

Lys Leu Arg Met Val Thr Gly Leu Arg Asn Ile Pro Ser Asp Asp Asp
            370                 375                 380

Asp Lys Gly Leu Phe Gly Ala Ile Ala Gly Phe Ile Glu Gly Gly Trp
385                 390                 395                 400

Thr Gly Met Val Asp Gly Trp Tyr Gly Tyr His His Gln Asn Glu Gln
                405                 410                 415

Gly Ser Gly Tyr Ala Ala Asp Gln Lys Ser Thr Gln Asn Ala Ile Asn
                420                 425                 430

Gly Ile Thr Asn Lys Val Asn Ser Val Ile Glu Lys Met Asn Thr Gln
            435                 440                 445

Phe Thr Ala Val Gly Lys Glu Phe Asn Lys Leu Glu Arg Arg Met Glu
        450                 455                 460

Asn Leu Asn Lys Lys Val Asp Asp Gly Phe Ile Asp Ile Trp Thr Tyr
465                 470                 475                 480

Asn Ala Glu Leu Leu Val Leu Leu Glu Asn Glu Arg Thr Leu Asp Phe
                485                 490                 495

His Asp Ser Asn Val Lys Asn Leu Tyr Glu Lys Val Lys Ser Gln Leu
            500                 505                 510

-continued

```
Lys Asn Asn Ala Lys Glu Ile Gly Asn Gly Cys Phe Glu Phe Tyr His
            515                 520                 525

Lys Cys Asn Asp Glu Cys Met Glu Ser Val Lys Asn Gly Thr Tyr Asp
        530                 535                 540

Tyr Pro Lys Tyr Ser Glu Glu Ser Lys Leu Ile Gly Glu Ala Arg Gln
545                 550                 555                 560

Leu Leu Ser Gly Ile Val Gln Gln Asn Asn Leu Leu Arg Ala Ile
                565                 570                 575

Glu Ala Gln Gln His Leu Leu Gln Leu Thr Val Trp Gly Ile Lys Gln
                580                 585                 590

Leu Gln Ala Arg
        595

<210> SEQ ID NO 55
<211> LENGTH: 594
<212> TYPE: PRT
<213> ORGANISM: Artificial Sequence
<220> FEATURE:
<223> OTHER INFORMATION: Engineered influenza virus hemagglutinin (H1
      Solomon Islands 2006) ectodomain-HR1Nipah fusion protein

<400> SEQUENCE: 55

Met Leu Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
            20                  25                  30

Ala His Ser Ala Phe Ala Ala Asp Pro His His His His His His Glu
        35                  40                  45

Asn Leu Tyr Phe Gln Gly Gly Tyr Leu Leu Glu Asp Thr Ile Cys Ile
    50                  55                  60

Gly Tyr His Ala Asn Asn Ser Thr Asp Thr Val Asp Thr Val Leu Glu
65                  70                  75                  80

Lys Asn Val Thr Val Thr His Ser Val Asn Leu Leu Glu Asp Ser His
                85                  90                  95

Asn Gly Lys Leu Cys Leu Leu Lys Gly Ile Ala Pro Leu Gln Leu Gly
            100                 105                 110

Asn Cys Ser Val Ala Gly Trp Ile Leu Gly Asn Pro Glu Cys Glu Leu
        115                 120                 125

Leu Ile Ser Arg Glu Ser Trp Ser Tyr Ile Val Glu Lys Pro Asn Pro
    130                 135                 140

Glu Asn Gly Thr Cys Tyr Pro Gly His Phe Ala Asp Tyr Glu Glu Leu
145                 150                 155                 160

Arg Glu Gln Leu Ser Ser Val Ser Ser Phe Glu Arg Phe Glu Ile Phe
                165                 170                 175

Pro Lys Glu Ser Ser Trp Pro Asn His Thr Thr Thr Gly Val Ser Ala
            180                 185                 190

Ser Cys Ser His Asn Gly Glu Ser Ser Phe Tyr Lys Asn Leu Leu Trp
        195                 200                 205

Leu Thr Gly Lys Asn Gly Leu Tyr Pro Asn Leu Ser Lys Ser Tyr Ala
    210                 215                 220

Asn Asn Lys Glu Lys Glu Val Leu Val Leu Trp Gly Val His His Pro
225                 230                 235                 240

Pro Asn Ile Gly Asp Gln Arg Ala Leu Tyr His Thr Glu Asn Ala Tyr
                245                 250                 255

Val Ser Val Val Ser Ser His Tyr Ser Arg Lys Phe Thr Pro Glu Ile
```

```
                    260                 265                 270
Ala Lys Arg Pro Lys Val Arg Asp Arg Glu Gly Arg Ile Asn Tyr Tyr
            275                 280                 285

Trp Thr Leu Leu Glu Pro Gly Asp Thr Ile Ile Phe Glu Ala Asn Gly
        290                 295                 300

Asn Leu Ile Ala Pro Arg Tyr Ala Phe Ala Leu Ser Arg Gly Phe Gly
305                 310                 315                 320

Ser Gly Ile Ile Asn Ser Asn Ala Pro Met Asp Glu Cys Asp Ala Lys
                325                 330                 335

Cys Gln Thr Pro Gln Gly Ala Ile Asn Ser Ser Leu Pro Phe Gln Asn
            340                 345                 350

Val His Pro Val Thr Ile Gly Glu Cys Pro Lys Tyr Val Arg Ser Ala
        355                 360                 365

Lys Leu Arg Met Val Thr Gly Leu Arg Asn Ile Pro Ser Asp Asp
370                 375                 380

Asp Lys Gly Leu Phe Gly Ala Ile Ala Gly Phe Ile Glu Gly Gly Trp
385                 390                 395                 400

Thr Gly Met Val Asp Gly Trp Tyr Gly Tyr His His Gln Asn Glu Gln
                405                 410                 415

Gly Ser Gly Tyr Ala Ala Asp Gln Lys Ser Thr Gln Asn Ala Ile Asn
            420                 425                 430

Gly Ile Thr Asn Lys Val Asn Ser Val Ile Glu Lys Met Asn Thr Gln
        435                 440                 445

Phe Thr Ala Val Gly Lys Glu Phe Asn Lys Leu Glu Arg Arg Met Glu
    450                 455                 460

Asn Leu Asn Lys Lys Val Asp Asp Gly Phe Ile Asp Ile Trp Thr Tyr
465                 470                 475                 480

Asn Ala Glu Leu Leu Val Leu Leu Glu Asn Glu Arg Thr Leu Asp Phe
                485                 490                 495

His Asp Ser Asn Val Lys Asn Leu Tyr Glu Lys Val Lys Ser Gln Leu
            500                 505                 510

Lys Asn Asn Ala Lys Glu Ile Gly Asn Gly Cys Phe Glu Phe Tyr His
        515                 520                 525

Lys Cys Asn Asp Glu Cys Met Glu Ser Val Lys Asn Gly Thr Tyr Asp
    530                 535                 540

Tyr Pro Lys Tyr Ser Glu Glu Ser Lys Leu Ile Gly Glu Ala Arg Gln
545                 550                 555                 560

Asn Ile Asn Lys Leu Lys Ser Ser Ile Glu Ser Thr Asn Glu Ala Val
                565                 570                 575

Val Lys Leu Gln Glu Thr Ala Glu Lys Thr Val Tyr Val Leu Thr Ala
            580                 585                 590

Leu Gln

<210> SEQ ID NO 56
<211> LENGTH: 603
<212> TYPE: PRT
<213> ORGANISM: Artificial Sequence
<220> FEATURE:
<223> OTHER INFORMATION: Engineered influenza virus hemagglutinin (H1
      Solomon Islands 2006) ectodomain-HR1HXB2 fusion protein

<400> SEQUENCE: 56

Met Leu Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
```

```
                  20                  25                  30
Ala His Ser Ala Phe Ala Ala Asp Pro His His His His His Glu
            35                  40                  45

Asn Leu Tyr Phe Gln Gly Gly Tyr Leu Leu Glu Asp Thr Ile Cys Ile
 50                  55                  60

Gly Tyr His Ala Asn Asn Ser Thr Asp Thr Val Asp Thr Val Leu Glu
 65                  70                  75                  80

Lys Asn Val Thr Val Thr His Ser Val Asn Leu Leu Glu Asp Ser His
                85                  90                  95

Asn Gly Lys Leu Cys Leu Leu Lys Gly Ile Ala Pro Leu Gln Leu Gly
            100                 105                 110

Asn Cys Ser Val Ala Gly Trp Ile Leu Gly Asn Pro Glu Cys Glu Leu
            115                 120                 125

Leu Ile Ser Arg Glu Ser Trp Ser Tyr Ile Val Glu Lys Pro Asn Pro
            130                 135                 140

Glu Asn Gly Thr Cys Tyr Pro Gly His Phe Ala Asp Tyr Glu Glu Leu
145                 150                 155                 160

Arg Glu Gln Leu Ser Ser Val Ser Ser Phe Glu Arg Phe Glu Ile Phe
                165                 170                 175

Pro Lys Glu Ser Ser Trp Pro Asn His Thr Thr Thr Gly Val Ser Ala
            180                 185                 190

Ser Cys Ser His Asn Gly Glu Ser Ser Phe Tyr Lys Asn Leu Leu Trp
            195                 200                 205

Leu Thr Gly Lys Asn Gly Leu Tyr Pro Asn Leu Ser Lys Ser Tyr Ala
            210                 215                 220

Asn Asn Lys Glu Lys Glu Val Leu Val Leu Trp Gly Val His His Pro
225                 230                 235                 240

Pro Asn Ile Gly Asp Gln Arg Ala Leu Tyr His Thr Glu Asn Ala Tyr
                245                 250                 255

Val Ser Val Val Ser Ser His Tyr Ser Arg Lys Phe Thr Pro Glu Ile
            260                 265                 270

Ala Lys Arg Pro Lys Val Arg Asp Arg Glu Gly Arg Ile Asn Tyr Tyr
            275                 280                 285

Trp Thr Leu Leu Glu Pro Gly Asp Thr Ile Ile Phe Glu Ala Asn Gly
            290                 295                 300

Asn Leu Ile Ala Pro Arg Tyr Ala Phe Ala Leu Ser Arg Gly Phe Gly
305                 310                 315                 320

Ser Gly Ile Ile Asn Ser Asn Ala Pro Met Asp Glu Cys Asp Ala Lys
                325                 330                 335

Cys Gln Thr Pro Gln Gly Ala Ile Asn Ser Ser Leu Pro Phe Gln Asn
            340                 345                 350

Val His Pro Val Thr Ile Gly Glu Cys Pro Lys Tyr Val Arg Ser Ala
            355                 360                 365

Lys Leu Arg Met Val Thr Gly Leu Arg Asn Ile Pro Ser Asp Asp Asp
            370                 375                 380

Asp Lys Gly Leu Phe Gly Ala Ile Ala Gly Phe Ile Glu Gly Gly Trp
385                 390                 395                 400

Thr Gly Met Val Asp Gly Trp Tyr Gly Tyr His His Gln Asn Glu Gln
                405                 410                 415

Gly Ser Gly Tyr Ala Ala Asp Gln Lys Ser Thr Gln Asn Ala Ile Asn
            420                 425                 430

Gly Ile Thr Asn Lys Val Asn Ser Val Ile Glu Lys Met Asn Thr Gln
            435                 440                 445
```

```
Phe Thr Ala Val Gly Lys Glu Phe Asn Lys Leu Glu Arg Arg Met Glu
        450                 455                 460

Asn Leu Asn Lys Lys Val Asp Asp Gly Phe Ile Asp Ile Trp Thr Tyr
465                 470                 475                 480

Asn Ala Glu Leu Leu Val Leu Leu Glu Asn Glu Arg Thr Leu Asp Phe
                485                 490                 495

His Asp Ser Asn Val Lys Asn Leu Tyr Glu Lys Val Lys Ser Gln Leu
            500                 505                 510

Lys Asn Asn Ala Lys Glu Ile Gly Asn Gly Cys Phe Glu Phe Tyr His
        515                 520                 525

Lys Cys Asn Asp Glu Cys Met Glu Ser Val Lys Asn Gly Thr Tyr Asp
    530                 535                 540

Tyr Pro Lys Tyr Ser Glu Glu Ser Lys Leu Asn Arg Glu Lys Ile Asp
545                 550                 555                 560

Gly Val Arg Ser Ile Arg Gln Leu Leu Ser Gly Ile Val Gln Gln Gln
                565                 570                 575

Asn Asn Leu Leu Arg Ala Ile Glu Ala Gln Gln His Leu Leu Gln Leu
            580                 585                 590

Thr Val Trp Gly Ile Lys Gln Leu Gln Ala Arg
        595                 600

<210> SEQ ID NO 57
<211> LENGTH: 601
<212> TYPE: PRT
<213> ORGANISM: Artificial Sequence
<220> FEATURE:
<223> OTHER INFORMATION: Engineered influenza virus hemagglutinin (H1
      Solomon Islands 2006) ectodomain-HR1Nipah fusion protein

<400> SEQUENCE: 57

Met Leu Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
            20                  25                  30

Ala His Ser Ala Phe Ala Ala Asp Pro His His His His His His Glu
        35                  40                  45

Asn Leu Tyr Phe Gln Gly Gly Tyr Leu Leu Glu Asp Thr Ile Cys Ile
50                  55                  60

Gly Tyr His Ala Asn Asn Ser Thr Asp Thr Val Asp Thr Val Leu Glu
65                  70                  75                  80

Lys Asn Val Thr Val Thr His Ser Val Asn Leu Leu Glu Asp Ser His
                85                  90                  95

Asn Gly Lys Leu Cys Leu Leu Lys Gly Ile Ala Pro Leu Gln Leu Gly
            100                 105                 110

Asn Cys Ser Val Ala Gly Trp Ile Leu Gly Asn Pro Glu Cys Glu Leu
        115                 120                 125

Leu Ile Ser Arg Glu Ser Trp Ser Tyr Ile Val Glu Lys Pro Asn Pro
    130                 135                 140

Glu Asn Gly Thr Cys Tyr Pro Gly His Phe Ala Asp Tyr Glu Glu Leu
145                 150                 155                 160

Arg Glu Gln Leu Ser Ser Val Ser Ser Phe Glu Arg Phe Glu Ile Phe
                165                 170                 175

Pro Lys Glu Ser Ser Trp Pro Asn His Thr Thr Thr Gly Val Ser Ala
            180                 185                 190

Ser Cys Ser His Asn Gly Glu Ser Ser Phe Tyr Lys Asn Leu Leu Trp
```

```
            195                 200                 205
Leu Thr Gly Lys Asn Gly Leu Tyr Pro Asn Leu Ser Lys Ser Tyr Ala
    210                 215                 220
Asn Asn Lys Glu Lys Glu Val Leu Val Leu Trp Gly Val His His Pro
225                 230                 235                 240
Pro Asn Ile Gly Asp Gln Arg Ala Leu Tyr His Thr Glu Asn Ala Tyr
                245                 250                 255
Val Ser Val Val Ser Ser His Tyr Ser Arg Lys Phe Thr Pro Glu Ile
                260                 265                 270
Ala Lys Arg Pro Lys Val Arg Asp Arg Glu Gly Arg Ile Asn Tyr Tyr
            275                 280                 285
Trp Thr Leu Leu Glu Pro Gly Asp Thr Ile Ile Phe Glu Ala Asn Gly
            290                 295                 300
Asn Leu Ile Ala Pro Arg Tyr Ala Phe Ala Leu Ser Arg Gly Phe Gly
305                 310                 315                 320
Ser Gly Ile Ile Asn Ser Asn Ala Pro Met Asp Glu Cys Asp Ala Lys
                325                 330                 335
Cys Gln Thr Pro Gln Gly Ala Ile Asn Ser Ser Leu Pro Phe Gln Asn
                340                 345                 350
Val His Pro Val Thr Ile Gly Glu Cys Pro Lys Tyr Val Arg Ser Ala
            355                 360                 365
Lys Leu Arg Met Val Thr Gly Leu Arg Asn Ile Pro Ser Asp Asp Asp
        370                 375                 380
Asp Lys Gly Leu Phe Gly Ala Ile Ala Gly Phe Ile Glu Gly Gly Trp
385                 390                 395                 400
Thr Gly Met Val Asp Gly Trp Tyr Gly Tyr His His Gln Asn Glu Gln
                405                 410                 415
Gly Ser Gly Tyr Ala Ala Asp Gln Lys Ser Thr Gln Asn Ala Ile Asn
            420                 425                 430
Gly Ile Thr Asn Lys Val Asn Ser Val Ile Glu Lys Met Asn Thr Gln
        435                 440                 445
Phe Thr Ala Val Gly Lys Glu Phe Asn Lys Leu Glu Arg Arg Met Glu
    450                 455                 460
Asn Leu Asn Lys Lys Val Asp Asp Gly Phe Ile Asp Ile Trp Thr Tyr
465                 470                 475                 480
Asn Ala Glu Leu Leu Val Leu Leu Glu Asn Glu Arg Thr Leu Asp Phe
                485                 490                 495
His Asp Ser Asn Val Lys Asn Leu Tyr Glu Lys Val Lys Ser Gln Leu
            500                 505                 510
Lys Asn Asn Ala Lys Glu Ile Gly Asn Gly Cys Phe Glu Phe Tyr His
        515                 520                 525
Lys Cys Asn Asp Glu Cys Met Glu Ser Val Lys Asn Gly Thr Tyr Asp
    530                 535                 540
Tyr Pro Lys Tyr Ser Glu Glu Ser Lys Leu Asn Arg Glu Lys Ile Asp
545                 550                 555                 560
Gly Val Arg Ser Ile Arg Gln Asn Ile Asn Lys Leu Lys Ser Ser Ile
                565                 570                 575
Glu Ser Thr Asn Glu Ala Val Val Lys Leu Gln Glu Thr Ala Glu Lys
            580                 585                 590
Thr Val Tyr Val Leu Thr Ala Leu Gln
        595                 600

<210> SEQ ID NO 58
```

<211> LENGTH: 610
<212> TYPE: PRT
<213> ORGANISM: Artificial Sequence
<220> FEATURE:
<223> OTHER INFORMATION: Engineered influenza virus hemagglutinin (H1 Solomon Islands 2006) ectodomain-HR1HXB2 fusion protein

<400> SEQUENCE: 58

```
Met Leu Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
            20                  25                  30

Ala His Ser Ala Phe Ala Ala Asp Pro His His His His His His Glu
        35                  40                  45

Asn Leu Tyr Phe Gln Gly Gly Tyr Leu Leu Glu Asp Thr Ile Cys Ile
    50                  55                  60

Gly Tyr His Ala Asn Asn Ser Thr Asp Thr Val Asp Thr Val Leu Glu
65                  70                  75                  80

Lys Asn Val Thr Val Thr His Ser Val Asn Leu Leu Glu Asp Ser His
                85                  90                  95

Asn Gly Lys Leu Cys Leu Leu Lys Gly Ile Ala Pro Leu Gln Leu Gly
            100                 105                 110

Asn Cys Ser Val Ala Gly Trp Ile Leu Gly Asn Pro Glu Cys Glu Leu
        115                 120                 125

Leu Ile Ser Arg Glu Ser Trp Ser Tyr Ile Val Glu Lys Pro Asn Pro
    130                 135                 140

Glu Asn Gly Thr Cys Tyr Pro Gly His Phe Ala Asp Tyr Glu Glu Leu
145                 150                 155                 160

Arg Glu Gln Leu Ser Ser Val Ser Ser Phe Glu Arg Phe Glu Ile Phe
                165                 170                 175

Pro Lys Glu Ser Ser Trp Pro Asn His Thr Thr Thr Gly Val Ser Ala
            180                 185                 190

Ser Cys Ser His Asn Gly Glu Ser Ser Phe Tyr Lys Asn Leu Leu Trp
        195                 200                 205

Leu Thr Gly Lys Asn Gly Leu Tyr Pro Asn Leu Ser Lys Ser Tyr Ala
    210                 215                 220

Asn Asn Lys Glu Lys Glu Val Leu Val Leu Trp Gly Val His His Pro
225                 230                 235                 240

Pro Asn Ile Gly Asp Gln Arg Ala Leu Tyr His Thr Glu Asn Ala Tyr
                245                 250                 255

Val Ser Val Val Ser Ser His Tyr Ser Arg Lys Phe Thr Pro Glu Ile
            260                 265                 270

Ala Lys Arg Pro Lys Val Arg Asp Arg Glu Gly Arg Ile Asn Tyr Tyr
        275                 280                 285

Trp Thr Leu Leu Glu Pro Gly Asp Thr Ile Ile Phe Glu Ala Asn Gly
    290                 295                 300

Asn Leu Ile Ala Pro Arg Tyr Ala Phe Ala Leu Ser Arg Gly Phe Gly
305                 310                 315                 320

Ser Gly Ile Ile Asn Ser Asn Ala Pro Met Asp Glu Cys Asp Ala Lys
                325                 330                 335

Cys Gln Thr Pro Gln Gly Ala Ile Asn Ser Ser Leu Pro Phe Gln Asn
            340                 345                 350

Val His Pro Val Thr Ile Gly Glu Cys Pro Lys Tyr Val Arg Ser Ala
        355                 360                 365

Lys Leu Arg Met Val Thr Gly Leu Arg Asn Ile Pro Ser Asp Asp Asp
```

```
                    370                 375                 380
Asp Lys Gly Leu Phe Gly Ala Ile Ala Gly Phe Ile Glu Gly Trp
385                 390                 395                 400

Thr Gly Met Val Asp Gly Trp Tyr Gly Tyr His His Gln Asn Glu Gln
                    405                 410                 415

Gly Ser Gly Tyr Ala Ala Asp Gln Lys Ser Thr Gln Asn Ala Ile Asn
                    420                 425                 430

Gly Ile Thr Asn Lys Val Asn Ser Val Ile Glu Lys Met Asn Thr Gln
                    435                 440                 445

Phe Thr Ala Val Gly Lys Glu Phe Asn Lys Leu Glu Arg Arg Met Glu
                    450                 455                 460

Asn Leu Asn Lys Lys Val Asp Asp Gly Phe Ile Asp Ile Trp Thr Tyr
465                 470                 475                 480

Asn Ala Glu Leu Leu Val Leu Leu Glu Asn Glu Arg Thr Leu Asp Phe
                    485                 490                 495

His Asp Ser Asn Val Lys Asn Leu Tyr Glu Lys Val Lys Ser Gln Leu
                    500                 505                 510

Lys Asn Asn Ala Lys Glu Ile Gly Asn Gly Cys Phe Glu Phe Tyr His
                    515                 520                 525

Lys Cys Asn Asp Glu Cys Met Glu Ser Val Lys Asn Gly Thr Tyr Asp
                    530                 535                 540

Tyr Pro Lys Tyr Ser Glu Glu Ser Lys Leu Asn Arg Glu Lys Ile Asp
545                 550                 555                 560

Gly Val Arg Ser Ile Lys Lys Leu Ile Gly Glu Ala Arg Gln Leu Leu
                    565                 570                 575

Ser Gly Ile Val Gln Gln Gln Asn Asn Leu Leu Arg Ala Ile Glu Ala
                    580                 585                 590

Gln Gln His Leu Leu Gln Leu Thr Val Trp Gly Ile Lys Gln Leu Gln
                    595                 600                 605

Ala Arg
    610

<210> SEQ ID NO 59
<211> LENGTH: 608
<212> TYPE: PRT
<213> ORGANISM: Artificial Sequence
<220> FEATURE:
<223> OTHER INFORMATION: Engineered influenza virus hemagglutinin (H1
      Solomon Islands 2006) ectodomain-HR1Nipah fusion protein

<400> SEQUENCE: 59

Met Leu Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
                    20                  25                  30

Ala His Ser Ala Phe Ala Ala Asp Pro His His His His His His Glu
                    35                  40                  45

Asn Leu Tyr Phe Gln Gly Gly Tyr Leu Leu Glu Asp Thr Ile Cys Ile
                    50                  55                  60

Gly Tyr His Ala Asn Asn Ser Thr Asp Thr Val Asp Thr Val Leu Glu
65                  70                  75                  80

Lys Asn Val Thr Val Thr His Ser Val Asn Leu Leu Glu Asp Ser His
                    85                  90                  95

Asn Gly Lys Leu Cys Leu Leu Lys Gly Ile Ala Pro Leu Gln Leu Gly
                    100                 105                 110
```

-continued

Asn Cys Ser Val Ala Gly Trp Ile Leu Gly Asn Pro Glu Cys Glu Leu
            115                 120                 125

Leu Ile Ser Arg Glu Ser Trp Ser Tyr Ile Val Glu Lys Pro Asn Pro
        130                 135                 140

Glu Asn Gly Thr Cys Tyr Pro Gly His Phe Ala Asp Tyr Glu Glu Leu
145                 150                 155                 160

Arg Glu Gln Leu Ser Ser Val Ser Ser Phe Glu Arg Phe Glu Ile Phe
                165                 170                 175

Pro Lys Glu Ser Ser Trp Pro Asn His Thr Thr Thr Gly Val Ser Ala
            180                 185                 190

Ser Cys Ser His Asn Gly Glu Ser Ser Phe Tyr Lys Asn Leu Leu Trp
        195                 200                 205

Leu Thr Gly Lys Asn Gly Leu Tyr Pro Asn Leu Ser Lys Ser Tyr Ala
    210                 215                 220

Asn Asn Lys Glu Lys Glu Val Leu Val Leu Trp Gly Val His His Pro
225                 230                 235                 240

Pro Asn Ile Gly Asp Gln Arg Ala Leu Tyr His Thr Glu Asn Ala Tyr
                245                 250                 255

Val Ser Val Val Ser Ser His Tyr Ser Arg Lys Phe Thr Pro Glu Ile
            260                 265                 270

Ala Lys Arg Pro Lys Val Arg Asp Arg Glu Gly Arg Ile Asn Tyr Tyr
        275                 280                 285

Trp Thr Leu Leu Glu Pro Gly Asp Thr Ile Ile Phe Glu Ala Asn Gly
    290                 295                 300

Asn Leu Ile Ala Pro Arg Tyr Ala Phe Ala Leu Ser Arg Gly Phe Gly
305                 310                 315                 320

Ser Gly Ile Ile Asn Ser Asn Ala Pro Met Asp Glu Cys Asp Ala Lys
                325                 330                 335

Cys Gln Thr Pro Gln Gly Ala Ile Asn Ser Ser Leu Pro Phe Gln Asn
            340                 345                 350

Val His Pro Val Thr Ile Gly Glu Cys Pro Lys Tyr Val Arg Ser Ala
        355                 360                 365

Lys Leu Arg Met Val Thr Gly Leu Arg Asn Ile Pro Ser Asp Asp Asp
    370                 375                 380

Asp Lys Gly Leu Phe Gly Ala Ile Ala Gly Phe Ile Glu Gly Gly Trp
385                 390                 395                 400

Thr Gly Met Val Asp Gly Trp Tyr Gly Tyr His His Gln Asn Glu Gln
                405                 410                 415

Gly Ser Gly Tyr Ala Ala Asp Gln Lys Ser Thr Gln Asn Ala Ile Asn
            420                 425                 430

Gly Ile Thr Asn Lys Val Asn Ser Val Ile Glu Lys Met Asn Thr Gln
        435                 440                 445

Phe Thr Ala Val Gly Lys Glu Phe Asn Lys Leu Glu Arg Arg Met Glu
    450                 455                 460

Asn Leu Asn Lys Lys Val Asp Asp Gly Phe Ile Asp Ile Trp Thr Tyr
465                 470                 475                 480

Asn Ala Glu Leu Leu Val Leu Leu Glu Asn Glu Arg Thr Leu Asp Phe
                485                 490                 495

His Asp Ser Asn Val Lys Asn Leu Tyr Glu Lys Val Lys Ser Gln Leu
            500                 505                 510

Lys Asn Asn Ala Lys Glu Ile Gly Asn Gly Cys Phe Glu Phe Tyr His
        515                 520                 525

Lys Cys Asn Asp Glu Cys Met Glu Ser Val Lys Asn Gly Thr Tyr Asp

```
            530                 535                 540
Tyr Pro Lys Tyr Ser Glu Glu Ser Lys Leu Asn Arg Glu Lys Ile Asp
545                 550                 555                 560

Gly Val Arg Ser Ile Lys Lys Leu Ile Gly Glu Ala Arg Gln Asn Ile
                565                 570                 575

Asn Lys Leu Lys Ser Ser Ile Glu Ser Thr Asn Glu Ala Val Val Lys
                580                 585                 590

Leu Gln Glu Thr Ala Glu Lys Thr Val Tyr Val Leu Thr Ala Leu Gln
                595                 600                 605

<210> SEQ ID NO 60
<211> LENGTH: 606
<212> TYPE: PRT
<213> ORGANISM: Artificial Sequence
<220> FEATURE:
<223> OTHER INFORMATION: Engineered influenza virus hemagglutinin (H5
      Vietnam 2004) ectodomain-HR1HXB2 fusion protein

<400> SEQUENCE: 60

Met Leu Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
                20                  25                  30

Ala His Ser Ala Phe Ala Ala Asp Pro His His His His His His Glu
                35                  40                  45

Asn Leu Tyr Phe Gln Gly Gly Tyr Leu Leu Glu Asp Gln Ile Cys Ile
            50                  55                  60

Gly Tyr His Ala Asn Asn Ser Thr Glu Gln Val Asp Thr Ile Met Glu
65                  70                  75                  80

Lys Asn Val Thr Val Thr His Ala Gln Asp Ile Leu Glu Lys His
                85                  90                  95

Asn Gly Lys Leu Cys Asp Leu Asp Gly Val Lys Pro Leu Ile Leu Arg
            100                 105                 110

Asp Cys Ser Val Ala Gly Trp Leu Leu Gly Asn Pro Met Cys Asp Glu
            115                 120                 125

Phe Ile Asn Val Pro Glu Trp Ser Tyr Ile Val Glu Lys Ala Asn Pro
        130                 135                 140

Val Asn Asp Leu Cys Tyr Pro Gly Asp Phe Asn Asp Tyr Glu Glu Leu
145                 150                 155                 160

Lys His Leu Leu Ser Arg Ile Asn His Phe Glu Lys Ile Gln Ile Ile
                165                 170                 175

Pro Lys Ser Ser Trp Ser Ser His Glu Ala Ser Leu Gly Val Ser Ser
            180                 185                 190

Ala Cys Pro Tyr Gln Gly Lys Ser Ser Phe Phe Arg Asn Val Val Trp
            195                 200                 205

Leu Ile Lys Lys Asn Ser Thr Tyr Pro Thr Ile Lys Arg Ser Tyr Asn
210                 215                 220

Asn Thr Asn Gln Glu Asp Leu Leu Val Leu Trp Gly Ile His His Pro
225                 230                 235                 240

Asn Asp Ala Ala Glu Gln Thr Lys Leu Tyr Gln Asn Pro Thr Thr Tyr
                245                 250                 255

Ile Ser Val Gly Thr Ser Thr Leu Asn Gln Arg Leu Val Pro Arg Ile
            260                 265                 270

Ala Thr Arg Ser Lys Val Asn Gly Gln Ser Gly Arg Met Glu Phe Phe
            275                 280                 285
```

```
Trp Thr Ile Leu Lys Pro Asn Asp Ala Ile Asn Phe Glu Ser Asn Gly
    290                 295                 300

Asn Phe Ile Ala Pro Glu Tyr Ala Tyr Lys Ile Val Lys Lys Gly Asp
305                 310                 315                 320

Ser Thr Ile Met Lys Ser Glu Leu Glu Tyr Gly Asn Cys Asn Thr Lys
                325                 330                 335

Cys Gln Thr Pro Met Gly Ala Ile Asn Ser Ser Met Pro Phe His Asn
            340                 345                 350

Ile His Pro Leu Thr Ile Gly Glu Cys Pro Lys Tyr Val Lys Ser Asn
        355                 360                 365

Arg Leu Val Leu Ala Thr Gly Leu Arg Asn Ser Pro Gln Arg Glu Arg
370                 375                 380

Asp Asp Asp Asp Lys Gly Leu Phe Gly Ala Ile Ala Gly Phe Ile Glu
385                 390                 395                 400

Gly Gly Trp Gln Gly Met Val Asp Gly Trp Tyr Gly Tyr His His Ser
                405                 410                 415

Asn Glu Gln Gly Ser Gly Tyr Ala Ala Asp Lys Glu Ser Thr Gln Lys
            420                 425                 430

Ala Ile Asp Gly Val Thr Asn Lys Val Asn Ser Ile Ile Asp Lys Met
        435                 440                 445

Asn Thr Gln Phe Glu Ala Val Gly Arg Glu Phe Asn Asn Leu Glu Arg
450                 455                 460

Arg Ile Glu Asn Leu Asn Lys Lys Met Glu Asp Gly Phe Leu Asp Val
465                 470                 475                 480

Trp Thr Tyr Asn Ala Glu Leu Leu Val Leu Met Glu Asn Glu Arg Thr
                485                 490                 495

Leu Asp Phe His Asp Ser Asn Val Lys Asn Leu Tyr Asp Lys Val Arg
            500                 505                 510

Leu Gln Leu Arg Asp Asn Ala Lys Glu Leu Gly Asn Gly Cys Phe Glu
        515                 520                 525

Phe Tyr His Lys Cys Asp Asn Glu Cys Met Glu Ser Val Arg Asn Gly
530                 535                 540

Thr Tyr Asp Tyr Pro Gln Tyr Ser Glu Glu Ala Arg Leu Lys Arg Glu
545                 550                 555                 560

Glu Ile Ser Gly Val Arg Ser Leu Arg Gln Leu Leu Ser Gly Ile Val
                565                 570                 575

Gln Gln Gln Asn Asn Leu Leu Arg Ala Ile Glu Ala Gln Gln His Leu
            580                 585                 590

Leu Gln Leu Thr Val Trp Gly Ile Lys Gln Leu Gln Ala Arg
        595                 600                 605

<210> SEQ ID NO 61
<211> LENGTH: 632
<212> TYPE: PRT
<213> ORGANISM: Artificial Sequence
<220> FEATURE:
<223> OTHER INFORMATION: Engineered influenza virus hemagglutinin (H5
      Vietnam 2004) ectodomain-HR1HXB2 fusion protein

<400> SEQUENCE: 61

Met Leu Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
            20                  25                  30

Ala His Ser Ala Phe Ala Ala Asp Pro His His His His His His Glu
        35                  40                  45
```

```
Asn Leu Tyr Phe Gln Gly Gly Tyr Leu Leu Glu Asp Gln Ile Cys Ile
        50                  55                  60

Gly Tyr His Ala Asn Asn Ser Thr Glu Gln Val Asp Thr Ile Met Glu
 65                  70                  75                  80

Lys Asn Val Thr Val Thr His Ala Gln Asp Ile Leu Glu Lys Lys His
                     85                  90                  95

Asn Gly Lys Leu Cys Asp Leu Asp Gly Val Lys Pro Leu Ile Leu Arg
                100                 105                 110

Asp Cys Ser Val Ala Gly Trp Leu Leu Gly Asn Pro Met Cys Asp Glu
            115                 120                 125

Phe Ile Asn Val Pro Glu Trp Ser Tyr Ile Val Glu Lys Ala Asn Pro
            130                 135                 140

Val Asn Asp Leu Cys Tyr Pro Gly Asp Phe Asn Asp Tyr Glu Glu Leu
145                 150                 155                 160

Lys His Leu Leu Ser Arg Ile Asn His Phe Glu Lys Ile Gln Ile Ile
                165                 170                 175

Pro Lys Ser Ser Trp Ser Ser His Glu Ala Ser Leu Gly Val Ser Ser
                180                 185                 190

Ala Cys Pro Tyr Gln Gly Lys Ser Ser Phe Phe Arg Asn Val Val Trp
            195                 200                 205

Leu Ile Lys Lys Asn Ser Thr Tyr Pro Thr Ile Lys Arg Ser Tyr Asn
210                 215                 220

Asn Thr Asn Gln Glu Asp Leu Leu Val Leu Trp Gly Ile His His Pro
225                 230                 235                 240

Asn Asp Ala Ala Glu Gln Thr Lys Leu Tyr Gln Asn Pro Thr Thr Tyr
                245                 250                 255

Ile Ser Val Gly Thr Ser Thr Leu Asn Gln Arg Leu Val Pro Arg Ile
            260                 265                 270

Ala Thr Arg Ser Lys Val Asn Gly Gln Ser Gly Arg Met Glu Phe Phe
            275                 280                 285

Trp Thr Ile Leu Lys Pro Asn Asp Ala Ile Asn Phe Glu Ser Asn Gly
        290                 295                 300

Asn Phe Ile Ala Pro Glu Tyr Ala Tyr Lys Ile Val Lys Lys Gly Asp
305                 310                 315                 320

Ser Thr Ile Met Lys Ser Glu Leu Glu Tyr Gly Asn Cys Asn Thr Lys
                325                 330                 335

Cys Gln Thr Pro Met Gly Ala Ile Asn Ser Ser Met Pro Phe His Asn
            340                 345                 350

Ile His Pro Leu Thr Ile Gly Glu Cys Pro Lys Tyr Val Lys Ser Asn
        355                 360                 365

Arg Leu Val Leu Ala Thr Gly Leu Arg Asn Ser Pro Gln Arg Glu Arg
        370                 375                 380

Asp Asp Asp Asp Lys Gly Leu Phe Gly Ala Ile Ala Gly Phe Ile Glu
385                 390                 395                 400

Gly Gly Trp Gln Gly Met Val Asp Gly Trp Tyr Gly Tyr His His Ser
                405                 410                 415

Asn Glu Gln Gly Ser Gly Tyr Ala Ala Asp Lys Glu Ser Thr Gln Lys
            420                 425                 430

Ala Ile Asp Gly Val Thr Asn Lys Val Asn Ser Ile Ile Asp Lys Met
            435                 440                 445

Asn Thr Gln Phe Glu Ala Val Gly Arg Glu Phe Asn Asn Leu Glu Arg
        450                 455                 460
```

```
Arg Ile Glu Asn Leu Asn Lys Lys Met Glu Asp Gly Phe Leu Asp Val
465                 470                 475                 480

Trp Thr Tyr Asn Ala Glu Leu Leu Val Leu Met Glu Asn Glu Arg Thr
            485                 490                 495

Leu Asp Phe His Asp Ser Asn Val Lys Asn Leu Tyr Asp Lys Val Arg
                500                 505                 510

Leu Gln Leu Arg Asp Asn Ala Lys Glu Leu Gly Asn Gly Cys Phe Glu
            515                 520                 525

Phe Tyr His Lys Cys Asp Asn Glu Cys Met Glu Ser Val Arg Asn Gly
        530                 535                 540

Thr Tyr Asp Tyr Pro Gln Tyr Ser Glu Glu Ala Arg Leu Lys Arg Glu
545                 550                 555                 560

Glu Ile Ser Gly Val Arg Ser Leu Gln Glu Ala Gly Tyr Ile Pro Glu
                565                 570                 575

Ala Pro Arg Asp Gly Gln Ala Tyr Val Arg Lys Asp Gly Glu Trp Val
            580                 585                 590

Leu Leu Ser Thr Phe Leu Ser Gly Ile Val Gln Gln Asn Asn Leu
        595                 600                 605

Leu Arg Ala Ile Glu Ala Gln Gln His Leu Leu Gln Leu Thr Val Trp
610                 615                 620

Gly Ile Lys Gln Leu Gln Ala Arg
625                 630

<210> SEQ ID NO 62
<211> LENGTH: 602
<212> TYPE: PRT
<213> ORGANISM: Artificial Sequence
<220> FEATURE:
<223> OTHER INFORMATION: Engineered influenza virus hemagglutinin (H3
      Wisconsin 2005) ectodomain-HR1HXB2 fusion protein

<400> SEQUENCE: 62

Met Leu Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
                20                  25                  30

Ala His Ser Ala Phe Ala Gln Lys Leu Pro His His His His His His
            35                  40                  45

Glu Asn Leu Tyr Phe Gln Gly Gly Asn Asp Asn Ser Thr Ala Thr Leu
        50                  55                  60

Cys Leu Gly His His Ala Val Pro Asn Gly Thr Ile Val Lys Thr Ile
65                  70                  75                  80

Thr Asn Asp Gln Ile Glu Val Thr Asn Ala Thr Glu Leu Val Gln Ser
                85                  90                  95

Ser Ser Thr Gly Gly Ile Cys Asp Ser Pro His Gln Ile Leu Asp Gly
                100                 105                 110

Glu Asn Cys Thr Leu Ile Asp Ala Leu Leu Gly Asp Pro Gln Cys Asp
            115                 120                 125

Gly Phe Gln Asn Lys Lys Trp Asp Leu Phe Val Glu Arg Ser Lys Ala
        130                 135                 140

Tyr Ser Asn Cys Tyr Pro Tyr Asp Val Pro Asp Tyr Ala Ser Leu Arg
145                 150                 155                 160

Ser Leu Val Ala Ser Ser Gly Thr Leu Glu Phe Asn Asp Glu Ser Phe
                165                 170                 175

Asn Trp Thr Gly Val Thr Gln Asn Gly Thr Ser Ser Ser Cys Lys Arg
            180                 185                 190
```

```
Arg Ser Asn Asn Ser Phe Phe Ser Arg Leu Asn Trp Leu Thr Gln Leu
        195                 200                 205

Lys Phe Lys Tyr Pro Ala Leu Asn Val Thr Met Pro Asn Asn Glu Lys
    210                 215                 220

Phe Asp Lys Leu Tyr Ile Trp Gly Val His His Pro Val Thr Asp Asn
225                 230                 235                 240

Asp Gln Ile Phe Leu Tyr Ala Gln Ala Ser Gly Arg Ile Thr Val Ser
                245                 250                 255

Thr Lys Arg Ser Gln Gln Thr Val Ile Pro Asn Ile Gly Ser Arg Pro
            260                 265                 270

Arg Ile Arg Asn Ile Pro Ser Arg Ile Ser Ile Tyr Trp Thr Ile Val
        275                 280                 285

Lys Pro Gly Asp Ile Leu Leu Ile Asn Ser Thr Gly Asn Leu Ile Ala
    290                 295                 300

Pro Arg Gly Tyr Phe Lys Ile Arg Ser Gly Lys Ser Ser Ile Met Arg
305                 310                 315                 320

Ser Asp Ala Pro Ile Gly Lys Cys Asn Ser Glu Cys Ile Thr Pro Asn
                325                 330                 335

Gly Ser Ile Pro Asn Asp Lys Pro Phe Gln Asn Val Asn Arg Ile Thr
            340                 345                 350

Tyr Gly Ala Cys Pro Arg Tyr Val Lys Gln Asn Thr Leu Lys Leu Ala
        355                 360                 365

Thr Gly Met Arg Asn Val Pro Glu Lys Gln Thr Arg Asp Asp Asp Asp
    370                 375                 380

Lys Gly Ile Phe Gly Ala Ile Ala Gly Phe Ile Glu Asn Gly Trp Glu
385                 390                 395                 400

Gly Met Val Asp Gly Trp Tyr Gly Phe Arg His Gln Asn Ser Glu Gly
                405                 410                 415

Ile Gly Gln Ala Ala Asp Leu Lys Ser Thr Gln Ala Ala Ile Asn Gln
            420                 425                 430

Ile Asn Gly Lys Leu Asn Arg Leu Ile Gly Lys Thr Asn Glu Lys Phe
        435                 440                 445

His Gln Ile Glu Lys Glu Phe Ser Glu Val Glu Gly Arg Ile Gln Asp
    450                 455                 460

Leu Glu Lys Tyr Val Glu Asp Thr Lys Ile Asp Leu Trp Ser Tyr Asn
465                 470                 475                 480

Ala Glu Leu Leu Val Ala Leu Glu Asn Gln His Thr Ile Asp Leu Thr
                485                 490                 495

Asp Ser Glu Met Asn Lys Leu Phe Glu Arg Thr Lys Lys Gln Leu Arg
            500                 505                 510

Glu Asn Ala Glu Asp Met Gly Asn Gly Cys Phe Lys Ile Tyr His Lys
        515                 520                 525

Cys Asp Asn Ala Cys Ile Gly Ser Ile Arg Asn Gly Thr Tyr Asp His
    530                 535                 540

Asp Val Tyr Arg Asp Glu Ala Leu Asn Asn Arg Phe Gln Ile Lys Gly
545                 550                 555                 560

Val Arg Ser Leu Arg Gln Leu Leu Ser Gly Ile Val Gln Gln Gln Asn
                565                 570                 575

Asn Leu Leu Arg Ala Ile Glu Ala Gln Gln His Leu Leu Gln Leu Thr
            580                 585                 590

Val Trp Gly Ile Lys Gln Leu Gln Ala Arg
        595                 600
```

-continued

```
<210> SEQ ID NO 63
<211> LENGTH: 628
<212> TYPE: PRT
<213> ORGANISM: Artificial Sequence
<220> FEATURE:
<223> OTHER INFORMATION: Engineered influenza virus hemagglutinin (H3
      Wisconsin 2005) ectodomain-HR1HXB2 fusion protein

<400> SEQUENCE: 63
```

Met Leu Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
            20                  25                  30

Ala His Ser Ala Phe Ala Gln Lys Leu Pro His His His His His His
        35                  40                  45

Glu Asn Leu Tyr Phe Gln Gly Gly Asn Asp Asn Ser Thr Ala Thr Leu
    50                  55                  60

Cys Leu Gly His His Ala Val Pro Asn Gly Thr Ile Val Lys Thr Ile
65                  70                  75                  80

Thr Asn Asp Gln Ile Glu Val Thr Asn Ala Thr Glu Leu Val Gln Ser
                85                  90                  95

Ser Ser Thr Gly Gly Ile Cys Asp Ser Pro His Gln Ile Leu Asp Gly
            100                 105                 110

Glu Asn Cys Thr Leu Ile Asp Ala Leu Leu Gly Asp Pro Gln Cys Asp
        115                 120                 125

Gly Phe Gln Asn Lys Lys Trp Asp Leu Phe Val Glu Arg Ser Lys Ala
    130                 135                 140

Tyr Ser Asn Cys Tyr Pro Tyr Asp Val Pro Asp Tyr Ala Ser Leu Arg
145                 150                 155                 160

Ser Leu Val Ala Ser Ser Gly Thr Leu Glu Phe Asn Asp Glu Ser Phe
                165                 170                 175

Asn Trp Thr Gly Val Thr Gln Asn Gly Thr Ser Ser Ser Cys Lys Arg
            180                 185                 190

Arg Ser Asn Asn Ser Phe Phe Ser Arg Leu Asn Trp Leu Thr Gln Leu
        195                 200                 205

Lys Phe Lys Tyr Pro Ala Leu Asn Val Thr Met Pro Asn Asn Glu Lys
    210                 215                 220

Phe Asp Lys Leu Tyr Ile Trp Gly Val His His Pro Val Thr Asp Asn
225                 230                 235                 240

Asp Gln Ile Phe Leu Tyr Ala Gln Ala Ser Gly Arg Ile Thr Val Ser
                245                 250                 255

Thr Lys Arg Ser Gln Gln Thr Val Ile Pro Asn Ile Gly Ser Arg Pro
            260                 265                 270

Arg Ile Arg Asn Ile Pro Ser Arg Ile Ser Ile Tyr Trp Thr Ile Val
        275                 280                 285

Lys Pro Gly Asp Ile Leu Leu Ile Asn Ser Thr Gly Asn Leu Ile Ala
    290                 295                 300

Pro Arg Gly Tyr Phe Lys Ile Arg Ser Gly Lys Ser Ser Ile Met Arg
305                 310                 315                 320

Ser Asp Ala Pro Ile Gly Lys Cys Asn Ser Glu Cys Ile Thr Pro Asn
                325                 330                 335

Gly Ser Ile Pro Asn Asp Lys Pro Phe Gln Asn Val Asn Arg Ile Thr
            340                 345                 350

Tyr Gly Ala Cys Pro Arg Tyr Val Lys Gln Asn Thr Leu Lys Leu Ala
        355                 360                 365

```
Thr Gly Met Arg Asn Val Pro Glu Lys Gln Thr Arg Asp Asp Asp Asp
    370                 375                 380
Lys Gly Ile Phe Gly Ala Ile Ala Gly Phe Ile Glu Asn Gly Trp Glu
385                 390                 395                 400
Gly Met Val Asp Gly Trp Tyr Gly Phe Arg His Gln Asn Ser Glu Gly
                405                 410                 415
Ile Gly Gln Ala Ala Asp Leu Lys Ser Thr Gln Ala Ala Ile Asn Gln
            420                 425                 430
Ile Asn Gly Lys Leu Asn Arg Leu Ile Gly Lys Thr Asn Glu Lys Phe
        435                 440                 445

His Gln Ile Glu Lys Glu Phe Ser Glu Val Glu Gly Arg Ile Gln Asp
    450                 455                 460
Leu Glu Lys Tyr Val Glu Asp Thr Lys Ile Asp Leu Trp Ser Tyr Asn
465                 470                 475                 480
Ala Glu Leu Leu Val Ala Leu Glu Asn Gln His Thr Ile Asp Leu Thr
                485                 490                 495
Asp Ser Glu Met Asn Lys Leu Phe Glu Arg Thr Lys Lys Gln Leu Arg
            500                 505                 510
Glu Asn Ala Glu Asp Met Gly Asn Gly Cys Phe Lys Ile Tyr His Lys
        515                 520                 525
Cys Asp Asn Ala Cys Ile Gly Ser Ile Arg Asn Gly Thr Tyr Asp His
    530                 535                 540
Asp Val Tyr Arg Asp Glu Ala Leu Asn Asn Arg Phe Gln Ile Lys Gly
545                 550                 555                 560
Val Arg Ser Leu Gln Glu Ala Gly Tyr Ile Pro Glu Ala Pro Arg Asp
                565                 570                 575
Gly Gln Ala Tyr Val Arg Lys Asp Gly Glu Trp Val Leu Leu Ser Thr
            580                 585                 590

Phe Leu Ser Gly Ile Val Gln Gln Gln Asn Asn Leu Leu Arg Ala Ile
        595                 600                 605
Glu Ala Gln Gln His Leu Leu Gln Leu Thr Val Trp Gly Ile Lys Gln
    610                 615                 620
Leu Gln Ala Arg
625
```

<210> SEQ ID NO 64
<211> LENGTH: 755
<212> TYPE: PRT
<213> ORGANISM: Artificial Sequence
<220> FEATURE:
<223> OTHER INFORMATION: Engineered HIV-1 (1992 Uganda, serotype 037.8, clade A) envelope glycoprotein ectodomain (gp140)-HR1HXB2 fusion protein

<400> SEQUENCE: 64

```
Met Lys Phe Leu Val Asn Val Ala Leu Val Phe Met Val Val Tyr Ile
1               5                   10                  15

Ser Tyr Ile Tyr Ala Glu Asp His His His His His His Glu Asn Leu
            20                  25                  30

Tyr Phe Gln Gly Ala Glu Asn Leu Trp Val Thr Val Tyr Tyr Gly Val
        35                  40                  45

Pro Val Trp Lys Asp Ala Glu Thr Thr Leu Phe Cys Ala Ser Asp Ala
    50                  55                  60

Lys Ala Tyr Asp Thr Glu Val His Asn Val Trp Ala Thr His Ala Cys
65                  70                  75                  80
```

-continued

```
Val Pro Thr Asp Pro Asn Pro Gln Glu Ile Tyr Met Glu Asn Val Thr
                 85                  90                  95
Glu Glu Phe Asn Met Trp Lys Asn Asn Met Val Glu Gln Met His Thr
            100                 105                 110
Asp Ile Ile Ser Leu Trp Asp Gln Ser Leu Lys Pro Cys Val Gln Leu
        115                 120                 125
Thr Pro Leu Cys Val Thr Leu Asp Cys Ser Tyr Asn Ile Thr Asn Asn
    130                 135                 140
Ile Thr Asn Ser Ile Thr Asn Ser Ser Val Asn Met Arg Glu Glu Ile
145                 150                 155                 160
Lys Asn Cys Ser Phe Asn Met Thr Thr Glu Leu Arg Asp Lys Asn Arg
                165                 170                 175
Lys Val Tyr Ser Leu Phe Tyr Lys Leu Asp Val Val Gln Ile Asn Asn
            180                 185                 190
Gly Asn Asn Ser Ser Asn Leu Tyr Arg Leu Ile Asn Cys Asn Thr Ser
        195                 200                 205
Ala Leu Thr Gln Ala Cys Pro Lys Val Thr Phe Glu Pro Ile Pro Ile
    210                 215                 220
Arg Tyr Cys Ala Pro Ala Gly Tyr Ala Ile Leu Lys Cys Asn Asp Lys
225                 230                 235                 240
Glu Phe Asn Gly Thr Gly Leu Cys Lys Asn Val Ser Thr Val Gln Cys
                245                 250                 255
Thr His Gly Ile Arg Pro Val Val Ser Thr Gln Leu Leu Leu Asn Gly
            260                 265                 270
Ser Leu Ala Glu Gly Lys Val Met Ile Arg Ser Glu Asn Ile Thr Asn
        275                 280                 285
Asn Val Lys Asn Ile Ile Val Gln Leu Asn Glu Thr Val Thr Ile Asn
    290                 295                 300
Cys Thr Arg Pro Asn Asn Asn Thr Arg Lys Ser Val Arg Ile Gly Pro
305                 310                 315                 320
Gly Gln Thr Phe Tyr Ala Thr Gly Asp Ile Ile Gly Asp Ile Arg Gln
                325                 330                 335
Ala His Cys Asn Val Ser Gly Ser Gln Trp Asn Arg Ala Leu His Gln
            340                 345                 350
Val Val Gly Gln Leu Arg Glu Tyr Trp Asn Thr Thr Ile Ile Phe Lys
        355                 360                 365
Asn Ser Ser Gly Gly Asp Leu Glu Ile Thr Thr His Ser Phe Asn Cys
    370                 375                 380
Gly Gly Glu Phe Phe Tyr Cys Asn Thr Ser Gly Leu Phe Asn Ser Asn
385                 390                 395                 400
Trp Thr His Asn Asp Thr Ala Ser Met Lys Pro Asn Asp Thr Ile Thr
                405                 410                 415
Leu Pro Cys Arg Ile Lys Gln Ile Ile Asn Met Trp Gln Arg Val Gly
            420                 425                 430
Gln Ala Ile Tyr Ala Pro Pro Ile Gln Gly Val Ile Arg Cys Glu Ser
        435                 440                 445
Asn Ile Thr Gly Leu Ile Leu Thr Arg Asp Gly Gly Asn Ile Asn
    450                 455                 460
Glu Ser Gln Ile Phe Arg Pro Gly Gly Gly Asp Met Arg Asp Asn Trp
465                 470                 475                 480
Arg Ser Glu Leu Tyr Lys Tyr Lys Val Val Arg Ile Glu Pro Leu Gly
                485                 490                 495
Val Ala Pro Thr Lys Ala Lys Arg Arg Val Val Glu Arg Glu Lys Arg
```

```
            500                 505                 510

Ala Val Val Glu Leu Gly Ala Val Phe Ile Gly Phe Leu Gly Thr Ala
        515                 520                 525

Gly Ser Thr Met Gly Ala Ala Ser Ile Thr Leu Thr Val Gln Val Arg
    530                 535                 540

Lys Leu Leu Ser Gly Ile Val Gln Gln Gln Ser Asn Leu Leu Arg Ala
545                 550                 555                 560

Ile Glu Ala Gln Gln His Leu Leu Lys Leu Thr Val Trp Gly Ile Lys
                565                 570                 575

Gln Leu Gln Ala Arg Val Leu Ala Val Glu Arg Tyr Leu Arg Asp Gln
            580                 585                 590

Gln Leu Leu Gly Ile Trp Gly Cys Ser Gly Lys Leu Ile Cys Thr Thr
        595                 600                 605

Asn Val Pro Trp Asn Ser Ser Trp Ser Asn Lys Ser Glu Arg Glu Ile
    610                 615                 620

Trp Glu Asn Met Thr Trp Leu Gln Trp Asp Lys Glu Ile Ser Asn Tyr
625                 630                 635                 640

Thr His Ile Ile Tyr Glu Leu Ile Glu Glu Ser Gln Lys Gln Gln Glu
                645                 650                 655

Lys Asn Glu Gln Glu Leu Leu Glu Leu Asp Lys Trp Ala Asn Leu Trp
            660                 665                 670

Asn Trp Phe Asp Ile Ser Asn Trp Leu Trp Tyr Ile Lys Ser Arg Ile
        675                 680                 685

Glu Gly Arg Gly Ser Gly Gly Tyr Ile Pro Glu Ala Pro Arg Asp Gly
    690                 695                 700

Gln Ala Tyr Val Arg Lys Asp Gly Glu Trp Val Leu Leu Ser Thr Phe
705                 710                 715                 720

Leu Ser Gly Ile Val Gln Gln Gln Asn Asn Leu Leu Arg Ala Ile Glu
                725                 730                 735

Ala Gln Gln His Leu Leu Gln Leu Thr Val Trp Gly Ile Lys Gln Leu
            740                 745                 750

Gln Ala Arg
        755

<210> SEQ ID NO 65
<211> LENGTH: 763
<212> TYPE: PRT
<213> ORGANISM: Artificial Sequence
<220> FEATURE:
<223> OTHER INFORMATION: Engineered HIV-1 (1992 Uganda, serotype 037.8,
      clade A) envelope glycoprotein ectodomain (gp140)-HR1HXB2 fusion
      protein

<400> SEQUENCE: 65

Met Arg Val Arg Gly Ile Gln Arg Asn Cys Gln His Leu Trp Arg Trp
1               5                   10                  15

Gly Thr Leu Ile Leu Gly Met Leu Met Ile Cys Ser Ala Glu Asp His
            20                  25                  30

His His His His His Glu Asn Leu Tyr Phe Gln Gly Ala Glu Asn Leu
        35                  40                  45

Trp Val Thr Val Tyr Tyr Gly Val Pro Val Trp Lys Asp Ala Glu Thr
    50                  55                  60

Thr Leu Phe Cys Ala Ser Asp Ala Lys Ala Tyr Asp Thr Glu Val His
65                  70                  75                  80

Asn Val Trp Ala Thr His Ala Cys Val Pro Thr Asp Pro Asn Pro Gln
                85                  90                  95
```

```
Glu Ile Tyr Met Glu Asn Val Thr Glu Glu Phe Asn Met Trp Lys Asn
            100                 105                 110

Asn Met Val Glu Gln Met His Thr Asp Ile Ile Ser Leu Trp Asp Gln
            115                 120                 125

Ser Leu Lys Pro Cys Val Gln Leu Thr Pro Leu Cys Val Thr Leu Asp
            130                 135                 140

Cys Ser Tyr Asn Ile Thr Asn Asn Ile Thr Asn Ser Ile Thr Asn Ser
145                 150                 155                 160

Ser Val Asn Met Arg Glu Ile Lys Asn Cys Ser Phe Asn Met Thr
                165                 170                 175

Thr Glu Leu Arg Asp Lys Asn Arg Lys Val Tyr Ser Leu Phe Tyr Lys
                180                 185                 190

Leu Asp Val Val Gln Ile Asn Asn Gly Asn Asn Ser Ser Asn Leu Tyr
            195                 200                 205

Arg Leu Ile Asn Cys Asn Thr Ser Ala Leu Thr Gln Ala Cys Pro Lys
            210                 215                 220

Val Thr Phe Glu Pro Ile Pro Ile Arg Tyr Cys Ala Pro Ala Gly Tyr
225                 230                 235                 240

Ala Ile Leu Lys Cys Asn Asp Lys Glu Phe Asn Gly Thr Gly Leu Cys
                245                 250                 255

Lys Asn Val Ser Thr Val Gln Cys Thr His Gly Ile Arg Pro Val Val
                260                 265                 270

Ser Thr Gln Leu Leu Leu Asn Gly Ser Leu Ala Glu Gly Lys Val Met
                275                 280                 285

Ile Arg Ser Glu Asn Ile Thr Asn Asn Val Lys Asn Ile Ile Val Gln
            290                 295                 300

Leu Asn Glu Thr Val Thr Ile Asn Cys Thr Arg Pro Asn Asn Asn Thr
305                 310                 315                 320

Arg Lys Ser Val Arg Ile Gly Pro Gly Gln Thr Phe Tyr Ala Thr Gly
                325                 330                 335

Asp Ile Ile Gly Asp Ile Arg Gln Ala His Cys Asn Val Ser Gly Ser
                340                 345                 350

Gln Trp Asn Arg Ala Leu His Gln Val Val Gly Gln Leu Arg Glu Tyr
                355                 360                 365

Trp Asn Thr Thr Ile Ile Phe Lys Asn Ser Ser Gly Gly Asp Leu Glu
            370                 375                 380

Ile Thr Thr His Ser Phe Asn Cys Gly Gly Glu Phe Phe Tyr Cys Asn
385                 390                 395                 400

Thr Ser Gly Leu Phe Asn Ser Asn Trp Thr His Asn Asp Thr Ala Ser
                405                 410                 415

Met Lys Pro Asn Asp Thr Ile Thr Leu Pro Cys Arg Ile Lys Gln Ile
                420                 425                 430

Ile Asn Met Trp Gln Arg Val Gly Gln Ala Ile Tyr Ala Pro Pro Ile
            435                 440                 445

Gln Gly Val Ile Arg Cys Glu Ser Asn Ile Thr Gly Leu Ile Leu Thr
            450                 455                 460

Arg Asp Gly Gly Gly Asn Ile Asn Glu Ser Gln Ile Phe Arg Pro Gly
465                 470                 475                 480

Gly Gly Asp Met Arg Asp Asn Trp Arg Ser Glu Leu Tyr Lys Tyr Lys
                485                 490                 495

Val Val Arg Ile Glu Pro Leu Gly Val Ala Pro Thr Lys Ala Lys Arg
            500                 505                 510
```

```
Arg Val Val Glu Arg Glu Lys Arg Ala Val Val Glu Leu Gly Ala Val
            515                 520                 525

Phe Ile Gly Phe Leu Gly Thr Ala Gly Ser Thr Met Gly Ala Ala Ser
530                 535                 540

Ile Thr Leu Thr Val Gln Val Arg Lys Leu Leu Ser Gly Ile Val Gln
545                 550                 555                 560

Gln Gln Ser Asn Leu Leu Arg Ala Ile Glu Ala Gln Gln His Leu Leu
                565                 570                 575

Lys Leu Thr Val Trp Gly Ile Lys Gln Leu Gln Ala Arg Val Leu Ala
            580                 585                 590

Val Glu Arg Tyr Leu Arg Asp Gln Gln Leu Leu Gly Ile Trp Gly Cys
        595                 600                 605

Ser Gly Lys Leu Ile Cys Thr Thr Asn Val Pro Trp Asn Ser Ser Trp
    610                 615                 620

Ser Asn Lys Ser Glu Arg Glu Ile Trp Glu Asn Met Thr Trp Leu Gln
625                 630                 635                 640

Trp Asp Lys Glu Ile Ser Asn Tyr Thr His Ile Ile Tyr Glu Leu Ile
                645                 650                 655

Glu Glu Ser Gln Lys Gln Gln Glu Lys Asn Glu Gln Glu Leu Leu Glu
            660                 665                 670

Leu Asp Lys Trp Ala Asn Leu Trp Asn Trp Phe Asp Ile Ser Asn Trp
        675                 680                 685

Leu Trp Tyr Ile Lys Ser Arg Ile Glu Gly Arg Gly Ser Gly Gly Tyr
    690                 695                 700

Ile Pro Glu Ala Pro Arg Asp Gly Gln Ala Tyr Val Arg Lys Asp Gly
705                 710                 715                 720

Glu Trp Val Leu Leu Ser Thr Phe Leu Ser Gly Ile Val Gln Gln Gln
                725                 730                 735

Asn Asn Leu Leu Arg Ala Ile Glu Ala Gln Gln His Leu Leu Gln Leu
            740                 745                 750

Thr Val Trp Gly Ile Lys Gln Leu Gln Ala Arg
        755                 760

<210> SEQ ID NO 66
<211> LENGTH: 722
<212> TYPE: PRT
<213> ORGANISM: Artificial Sequence
<220> FEATURE:
<223> OTHER INFORMATION: Engineered HIV-1 (1992 Uganda, serotype 037.8,
      clade A) envelope glycoprotein ectodomain (gp140)-HR1HXB2 fusion
      protein

<400> SEQUENCE: 66

Met Lys Phe Leu Val Asn Val Ala Leu Val Phe Met Val Val Tyr Ile
1               5                   10                  15

Ser Tyr Ile Tyr Ala Glu Asp His His His His His Glu Asn Leu
            20                  25                  30

Tyr Phe Gln Gly Ala Glu Asn Leu Trp Val Thr Val Tyr Tyr Gly Val
        35                  40                  45

Pro Val Trp Lys Asp Ala Glu Thr Thr Leu Phe Cys Ala Ser Asp Ala
50                  55                  60

Lys Ala Tyr Asp Thr Glu Val His Asn Val Trp Ala Thr His Ala Cys
65                  70                  75                  80

Val Pro Thr Asp Pro Asn Pro Gln Glu Ile Tyr Met Glu Asn Val Thr
                85                  90                  95

Glu Glu Phe Asn Met Trp Lys Asn Asn Met Val Glu Gln Met His Thr
```

-continued

```
                100                 105                 110
Asp Ile Ile Ser Leu Trp Asp Gln Ser Leu Lys Pro Cys Val Gln Leu
            115                 120                 125
Thr Pro Leu Cys Val Thr Leu Asp Cys Ser Tyr Asn Ile Thr Asn Asn
        130                 135                 140
Ile Thr Asn Ser Ile Thr Asn Ser Ser Val Asn Met Arg Glu Glu Ile
145                 150                 155                 160
Lys Asn Cys Ser Phe Asn Met Thr Thr Glu Leu Arg Asp Lys Asn Arg
                165                 170                 175
Lys Val Tyr Ser Leu Phe Tyr Lys Leu Asp Val Val Gln Ile Asn Asn
            180                 185                 190
Gly Asn Asn Ser Ser Asn Leu Tyr Arg Leu Ile Asn Cys Asn Thr Ser
        195                 200                 205
Ala Leu Thr Gln Ala Cys Pro Lys Val Thr Phe Glu Pro Ile Pro Ile
    210                 215                 220
Arg Tyr Cys Ala Pro Ala Gly Tyr Ala Ile Leu Lys Cys Asn Asp Lys
225                 230                 235                 240
Glu Phe Asn Gly Thr Gly Leu Cys Lys Asn Val Ser Thr Val Gln Cys
                245                 250                 255
Thr His Gly Ile Arg Pro Val Val Ser Thr Gln Leu Leu Asn Gly
            260                 265                 270
Ser Leu Ala Glu Gly Lys Val Met Ile Arg Ser Glu Asn Ile Thr Asn
        275                 280                 285
Asn Val Lys Asn Ile Ile Val Gln Leu Asn Glu Thr Val Thr Ile Asn
    290                 295                 300
Cys Thr Arg Pro Asn Asn Asn Thr Arg Lys Ser Val Arg Ile Gly Pro
305                 310                 315                 320
Gly Gln Thr Phe Tyr Ala Thr Gly Asp Ile Ile Gly Asp Ile Arg Gln
                325                 330                 335
Ala His Cys Asn Val Ser Gly Ser Gln Trp Asn Arg Ala Leu His Gln
            340                 345                 350
Val Val Gly Gln Leu Arg Glu Tyr Trp Asn Thr Thr Ile Ile Phe Lys
        355                 360                 365
Asn Ser Ser Gly Gly Asp Leu Glu Ile Thr Thr His Ser Phe Asn Cys
    370                 375                 380
Gly Gly Glu Phe Phe Tyr Cys Asn Thr Ser Gly Leu Phe Asn Ser Asn
385                 390                 395                 400
Trp Thr His Asn Asp Thr Ala Ser Met Lys Pro Asn Asp Thr Ile Thr
                405                 410                 415
Leu Pro Cys Arg Ile Lys Gln Ile Ile Asn Met Trp Gln Arg Val Gly
            420                 425                 430
Gln Ala Ile Tyr Ala Pro Pro Ile Gln Gly Val Ile Arg Cys Glu Ser
        435                 440                 445
Asn Ile Thr Gly Leu Ile Leu Thr Arg Asp Gly Gly Asn Ile Asn
    450                 455                 460
Glu Ser Gln Ile Phe Arg Pro Gly Gly Gly Asp Met Arg Asp Asn Trp
465                 470                 475                 480
Arg Ser Glu Leu Tyr Lys Tyr Lys Val Val Arg Ile Glu Pro Leu Gly
                485                 490                 495
Val Ala Pro Thr Lys Ala Lys Arg Arg Val Val Glu Arg Glu Lys Arg
            500                 505                 510
Ala Val Val Glu Leu Gly Ala Val Phe Ile Gly Phe Leu Gly Thr Ala
        515                 520                 525
```

```
Gly Ser Thr Met Gly Ala Ala Ser Ile Thr Leu Thr Val Gln Val Arg
    530                 535                 540

Lys Leu Leu Ser Gly Ile Val Gln Gln Gln Ser Asn Leu Leu Arg Ala
545                 550                 555                 560

Ile Glu Ala Gln Gln His Leu Leu Lys Leu Thr Val Trp Gly Ile Lys
                565                 570                 575

Gln Leu Gln Ala Arg Val Leu Ala Val Glu Arg Tyr Leu Arg Asp Gln
            580                 585                 590

Gln Leu Leu Gly Ile Trp Gly Cys Ser Gly Lys Leu Ile Cys Thr Thr
        595                 600                 605

Asn Val Pro Trp Asn Ser Ser Trp Ser Asn Lys Ser Glu Arg Glu Ile
    610                 615                 620

Trp Glu Asn Met Thr Trp Leu Gln Trp Asp Lys Glu Ile Ser Asn Tyr
625                 630                 635                 640

Thr His Ile Ile Tyr Glu Leu Ile Glu Glu Ser Gln Lys Gln Gln Glu
                645                 650                 655

Lys Asn Glu Gln Glu Leu Leu Glu Leu Asp Lys Trp Ala Asn Leu Trp
            660                 665                 670

Asn Trp Phe Asp Ile Ser Asn Trp Leu Trp Tyr Ile Lys Gly Ser Gly
        675                 680                 685

Ser Gly Ile Val Gln Gln Gln Asn Asn Leu Leu Arg Ala Ile Glu Ala
    690                 695                 700

Gln Gln His Leu Leu Gln Leu Thr Val Trp Gly Ile Lys Gln Leu Gln
705                 710                 715                 720

Ala Arg

<210> SEQ ID NO 67
<211> LENGTH: 730
<212> TYPE: PRT
<213> ORGANISM: Artificial Sequence
<220> FEATURE:
<223> OTHER INFORMATION: Engineered HIV-1 (1992 Uganda, serotype 037.8,
      clade A) envelope glycoprotein ectodomain (gp140)-HR1HXB2 fusion
      protein

<400> SEQUENCE: 67

Met Arg Val Arg Gly Ile Gln Arg Asn Cys Gln His Leu Trp Arg Trp
1               5                   10                  15

Gly Thr Leu Ile Leu Gly Met Leu Met Ile Cys Ser Ala Glu Asp His
            20                  25                  30

His His His His His Glu Asn Leu Tyr Phe Gln Gly Ala Glu Asn Leu
        35                  40                  45

Trp Val Thr Val Tyr Tyr Gly Val Pro Val Trp Lys Asp Ala Glu Thr
    50                  55                  60

Thr Leu Phe Cys Ala Ser Asp Ala Lys Ala Tyr Asp Thr Glu Val His
65                  70                  75                  80

Asn Val Trp Ala Thr His Ala Cys Val Pro Thr Asp Pro Asn Pro Gln
                85                  90                  95

Glu Ile Tyr Met Glu Asn Val Thr Glu Glu Phe Asn Met Trp Lys Asn
            100                 105                 110

Asn Met Val Glu Gln Met His Thr Asp Ile Ile Ser Leu Trp Asp Gln
        115                 120                 125

Ser Leu Lys Pro Cys Val Gln Leu Thr Pro Leu Cys Val Thr Leu Asp
    130                 135                 140

Cys Ser Tyr Asn Ile Thr Asn Asn Ile Thr Asn Ser Ile Thr Asn Ser
```

-continued

```
            145                 150                 155                 160
        Ser Val Asn Met Arg Glu Glu Ile Lys Asn Cys Ser Phe Asn Met Thr
                        165                 170                 175

Thr Glu Leu Arg Asp Lys Asn Arg Lys Val Tyr Ser Leu Phe Tyr Lys
                        180                 185                 190

Leu Asp Val Val Gln Ile Asn Gly Asn Asn Ser Ser Asn Leu Tyr
                        195                 200                 205

Arg Leu Ile Asn Cys Asn Thr Ser Ala Leu Thr Gln Ala Cys Pro Lys
        210                 215                 220

Val Thr Phe Glu Pro Ile Pro Ile Arg Tyr Cys Ala Pro Ala Gly Tyr
        225                 230                 235                 240

Ala Ile Leu Lys Cys Asn Asp Lys Glu Phe Asn Gly Thr Gly Leu Cys
                        245                 250                 255

Lys Asn Val Ser Thr Val Gln Cys Thr His Gly Ile Arg Pro Val Val
                        260                 265                 270

Ser Thr Gln Leu Leu Leu Asn Gly Ser Leu Ala Glu Gly Lys Val Met
                        275                 280                 285

Ile Arg Ser Glu Asn Ile Thr Asn Asn Val Lys Asn Ile Ile Val Gln
                        290                 295                 300

Leu Asn Glu Thr Val Thr Ile Asn Cys Thr Arg Pro Asn Asn Asn Thr
        305                 310                 315                 320

Arg Lys Ser Val Arg Ile Gly Pro Gly Gln Thr Phe Tyr Ala Thr Gly
                        325                 330                 335

Asp Ile Ile Gly Asp Ile Arg Gln Ala His Cys Asn Val Ser Gly Ser
                        340                 345                 350

Gln Trp Asn Arg Ala Leu His Gln Val Val Gly Gln Leu Arg Glu Tyr
                        355                 360                 365

Trp Asn Thr Thr Ile Ile Phe Lys Asn Ser Ser Gly Gly Asp Leu Glu
                        370                 375                 380

Ile Thr Thr His Ser Phe Asn Cys Gly Gly Glu Phe Phe Tyr Cys Asn
        385                 390                 395                 400

Thr Ser Gly Leu Phe Asn Ser Asn Trp Thr His Asn Asp Thr Ala Ser
                        405                 410                 415

Met Lys Pro Asn Asp Thr Ile Thr Leu Pro Cys Arg Ile Lys Gln Ile
                        420                 425                 430

Ile Asn Met Trp Gln Arg Val Gly Gln Ala Ile Tyr Ala Pro Pro Ile
                        435                 440                 445

Gln Gly Val Ile Arg Cys Glu Ser Asn Ile Thr Gly Leu Ile Leu Thr
                        450                 455                 460

Arg Asp Gly Gly Gly Asn Ile Asn Glu Ser Gln Ile Phe Arg Pro Gly
        465                 470                 475                 480

Gly Gly Asp Met Arg Asp Asn Trp Arg Ser Glu Leu Tyr Lys Tyr Lys
                        485                 490                 495

Val Val Arg Ile Glu Pro Leu Gly Val Ala Pro Thr Lys Ala Lys Arg
                        500                 505                 510

Arg Val Val Glu Arg Glu Lys Arg Ala Val Val Glu Leu Gly Ala Val
                        515                 520                 525

Phe Ile Gly Phe Leu Gly Thr Ala Gly Ser Thr Met Gly Ala Ala Ser
                        530                 535                 540

Ile Thr Leu Thr Val Gln Val Arg Lys Leu Leu Ser Gly Ile Val Gln
        545                 550                 555                 560

Gln Gln Ser Asn Leu Leu Arg Ala Ile Glu Ala Gln Gln His Leu Leu
                        565                 570                 575
```

-continued

```
Lys Leu Thr Val Trp Gly Ile Lys Gln Leu Gln Ala Arg Val Leu Ala
                580                 585                 590

Val Glu Arg Tyr Leu Arg Asp Gln Gln Leu Leu Gly Ile Trp Gly Cys
            595                 600                 605

Ser Gly Lys Leu Ile Cys Thr Thr Asn Val Pro Trp Asn Ser Ser Trp
610                 615                 620

Ser Asn Lys Ser Glu Arg Glu Ile Trp Glu Asn Met Thr Trp Leu Gln
625                 630                 635                 640

Trp Asp Lys Glu Ile Ser Asn Tyr Thr His Ile Ile Tyr Glu Leu Ile
                645                 650                 655

Glu Glu Ser Gln Lys Gln Gln Glu Lys Asn Glu Gln Glu Leu Leu Glu
            660                 665                 670

Leu Asp Lys Trp Ala Asn Leu Trp Asn Trp Phe Asp Ile Ser Asn Trp
        675                 680                 685

Leu Trp Tyr Ile Lys Gly Ser Gly Ser Gly Ile Val Gln Gln Gln Asn
    690                 695                 700

Asn Leu Leu Arg Ala Ile Glu Ala Gln Gln His Leu Leu Gln Leu Thr
705                 710                 715                 720

Val Trp Gly Ile Lys Gln Leu Gln Ala Arg
                725                 730

<210> SEQ ID NO 68
<211> LENGTH: 753
<212> TYPE: PRT
<213> ORGANISM: Artificial Sequence
<220> FEATURE:
<223> OTHER INFORMATION: Engineered HIV-1 (1992 Uganda, serotype 037.8,
      clade A) envelope glycoprotein ectodomain (gp140)-HR1Nipah fusion
      protein

<400> SEQUENCE: 68

Met Lys Phe Leu Val Asn Val Ala Leu Val Phe Met Val Val Tyr Ile
1               5                   10                  15

Ser Tyr Ile Tyr Ala Glu Asp His His His His His His Glu Asn Leu
            20                  25                  30

Tyr Phe Gln Gly Ala Glu Asn Leu Trp Val Thr Val Tyr Tyr Gly Val
        35                  40                  45

Pro Val Trp Lys Asp Ala Glu Thr Thr Leu Phe Cys Ala Ser Asp Ala
    50                  55                  60

Lys Ala Tyr Asp Thr Glu Val His Asn Val Trp Ala Thr His Ala Cys
65                  70                  75                  80

Val Pro Thr Asp Pro Asn Pro Gln Glu Ile Tyr Met Glu Asn Val Thr
                85                  90                  95

Glu Glu Phe Asn Met Trp Lys Asn Asn Met Val Glu Gln Met His Thr
            100                 105                 110

Asp Ile Ile Ser Leu Trp Asp Gln Ser Leu Lys Pro Cys Val Gln Leu
        115                 120                 125

Thr Pro Leu Cys Val Thr Leu Asp Cys Ser Tyr Asn Ile Thr Asn Asn
    130                 135                 140

Ile Thr Asn Ser Ile Thr Asn Ser Ser Val Asn Met Arg Glu Glu Ile
145                 150                 155                 160

Lys Asn Cys Ser Phe Asn Met Thr Thr Glu Leu Arg Asp Lys Asn Arg
                165                 170                 175

Lys Val Tyr Ser Leu Phe Tyr Lys Leu Asp Val Val Gln Ile Asn Asn
            180                 185                 190
```

Gly Asn Asn Ser Ser Asn Leu Tyr Arg Leu Ile Asn Cys Asn Thr Ser
            195                 200                 205

Ala Leu Thr Gln Ala Cys Pro Lys Val Thr Phe Glu Pro Ile Pro Ile
210                 215                 220

Arg Tyr Cys Ala Pro Ala Gly Tyr Ala Ile Leu Lys Cys Asn Asp Lys
225                 230                 235                 240

Glu Phe Asn Gly Thr Gly Leu Cys Lys Asn Val Ser Thr Val Gln Cys
                245                 250                 255

Thr His Gly Ile Arg Pro Val Val Ser Thr Gln Leu Leu Leu Asn Gly
            260                 265                 270

Ser Leu Ala Glu Gly Lys Val Met Ile Arg Ser Glu Asn Ile Thr Asn
        275                 280                 285

Asn Val Lys Asn Ile Ile Val Gln Leu Asn Glu Thr Val Thr Ile Asn
290                 295                 300

Cys Thr Arg Pro Asn Asn Asn Thr Arg Lys Ser Val Arg Ile Gly Pro
305                 310                 315                 320

Gly Gln Thr Phe Tyr Ala Thr Gly Asp Ile Ile Gly Asp Ile Arg Gln
                325                 330                 335

Ala His Cys Asn Val Ser Gly Ser Gln Trp Asn Arg Ala Leu His Gln
            340                 345                 350

Val Val Gly Gln Leu Arg Glu Tyr Trp Asn Thr Thr Ile Ile Phe Lys
        355                 360                 365

Asn Ser Ser Gly Gly Asp Leu Glu Ile Thr Thr His Ser Phe Asn Cys
    370                 375                 380

Gly Gly Glu Phe Phe Tyr Cys Asn Thr Ser Gly Leu Phe Asn Ser Asn
385                 390                 395                 400

Trp Thr His Asn Asp Thr Ala Ser Met Lys Pro Asn Asp Thr Ile Thr
                405                 410                 415

Leu Pro Cys Arg Ile Lys Gln Ile Ile Asn Met Trp Gln Arg Val Gly
            420                 425                 430

Gln Ala Ile Tyr Ala Pro Pro Ile Gln Gly Val Ile Arg Cys Glu Ser
        435                 440                 445

Asn Ile Thr Gly Leu Ile Leu Thr Arg Asp Gly Gly Gly Asn Ile Asn
450                 455                 460

Glu Ser Gln Ile Phe Arg Pro Gly Gly Gly Asp Met Arg Asp Asn Trp
465                 470                 475                 480

Arg Ser Glu Leu Tyr Lys Tyr Lys Val Val Arg Ile Glu Pro Leu Gly
                485                 490                 495

Val Ala Pro Thr Lys Ala Lys Arg Arg Val Val Glu Arg Glu Lys Arg
            500                 505                 510

Ala Val Val Glu Leu Gly Ala Val Phe Ile Gly Phe Leu Gly Thr Ala
        515                 520                 525

Gly Ser Thr Met Gly Ala Ala Ser Ile Thr Leu Thr Val Gln Val Arg
    530                 535                 540

Lys Leu Leu Ser Gly Ile Val Gln Gln Gln Ser Asn Leu Leu Arg Ala
545                 550                 555                 560

Ile Glu Ala Gln Gln His Leu Leu Lys Leu Thr Val Trp Gly Ile Lys
                565                 570                 575

Gln Leu Gln Ala Arg Val Leu Ala Val Glu Arg Tyr Leu Arg Asp Gln
            580                 585                 590

Gln Leu Leu Gly Ile Trp Gly Cys Ser Gly Lys Leu Ile Cys Thr Thr
        595                 600                 605

Asn Val Pro Trp Asn Ser Ser Trp Ser Asn Lys Ser Glu Arg Glu Ile

```
                610              615                  620
Trp Glu Asn Met Thr Trp Leu Gln Trp Asp Lys Glu Ile Ser Asn Tyr
625                 630                 635                 640

Thr His Ile Ile Tyr Glu Leu Ile Glu Glu Ser Gln Lys Gln Gln Glu
                645                 650                 655

Lys Asn Glu Gln Glu Leu Leu Glu Leu Asp Lys Trp Ala Asn Leu Trp
                660                 665                 670

Asn Trp Phe Asp Ile Ser Asn Trp Leu Trp Tyr Ile Lys Ser Arg Ile
            675                 680                 685

Glu Gly Arg Gly Ser Gly Gly Tyr Ile Pro Glu Ala Pro Arg Asp Gly
690                 695                 700

Gln Ala Tyr Val Arg Lys Asp Gly Glu Trp Val Leu Leu Ser Thr Phe
705                 710                 715                 720

Leu Asn Lys Leu Lys Ser Ser Ile Glu Ser Thr Asn Glu Ala Val Val
                725                 730                 735

Lys Leu Gln Glu Thr Ala Glu Lys Thr Val Tyr Val Leu Thr Ala Leu
                740                 745                 750

Gln

<210> SEQ ID NO 69
<211> LENGTH: 761
<212> TYPE: PRT
<213> ORGANISM: Artificial Sequence
<220> FEATURE:
<223> OTHER INFORMATION: Engineered HIV-1 (1992 Uganda, serotype 037.8,
      clade A) envelope glycoprotein ectodomain (gp140)-HR1Nipah fusion
      protein

<400> SEQUENCE: 69

Met Arg Val Arg Gly Ile Gln Arg Asn Cys Gln His Leu Trp Arg Trp
1               5                   10                  15

Gly Thr Leu Ile Leu Gly Met Leu Met Ile Cys Ser Ala Glu Asp His
                20                  25                  30

His His His His Glu Asn Leu Tyr Phe Gln Gly Ala Glu Asn Leu
            35                  40                  45

Trp Val Thr Val Tyr Tyr Gly Val Pro Val Trp Lys Asp Ala Glu Thr
50                  55                  60

Thr Leu Phe Cys Ala Ser Asp Ala Lys Ala Tyr Asp Thr Glu Val His
65                  70                  75                  80

Asn Val Trp Ala Thr His Ala Cys Val Pro Thr Asp Pro Asn Pro Gln
                85                  90                  95

Glu Ile Tyr Met Glu Asn Val Thr Glu Glu Phe Asn Met Trp Lys Asn
            100                 105                 110

Asn Met Val Glu Gln Met His Thr Asp Ile Ile Ser Leu Trp Asp Gln
        115                 120                 125

Ser Leu Lys Pro Cys Val Gln Leu Thr Pro Leu Cys Val Thr Leu Asp
130                 135                 140

Cys Ser Tyr Asn Ile Thr Asn Asn Ile Thr Asn Ser Ile Thr Asn Ser
145                 150                 155                 160

Ser Val Asn Met Arg Glu Glu Ile Lys Asn Cys Ser Phe Asn Met Thr
                165                 170                 175

Thr Glu Leu Arg Asp Lys Asn Arg Lys Val Tyr Ser Leu Phe Tyr Lys
            180                 185                 190

Leu Asp Val Val Gln Ile Asn Asn Gly Asn Asn Ser Ser Asn Leu Tyr
        195                 200                 205
```

-continued

```
Arg Leu Ile Asn Cys Asn Thr Ser Ala Leu Thr Gln Ala Cys Pro Lys
210                 215                 220

Val Thr Phe Glu Pro Ile Pro Ile Arg Tyr Cys Ala Pro Ala Gly Tyr
225                 230                 235                 240

Ala Ile Leu Lys Cys Asn Asp Lys Glu Phe Asn Gly Thr Gly Leu Cys
            245                 250                 255

Lys Asn Val Ser Thr Val Gln Cys Thr His Gly Ile Arg Pro Val Val
            260                 265                 270

Ser Thr Gln Leu Leu Asn Gly Ser Leu Ala Glu Gly Lys Val Met
        275                 280                 285

Ile Arg Ser Glu Asn Ile Thr Asn Asn Val Lys Asn Ile Ile Val Gln
290                 295                 300

Leu Asn Glu Thr Val Thr Ile Asn Cys Thr Arg Pro Asn Asn Asn Thr
305                 310                 315                 320

Arg Lys Ser Val Arg Ile Gly Pro Gly Gln Thr Phe Tyr Ala Thr Gly
            325                 330                 335

Asp Ile Ile Gly Asp Ile Arg Gln Ala His Cys Asn Val Ser Gly Ser
            340                 345                 350

Gln Trp Asn Arg Ala Leu His Gln Val Val Gly Gln Leu Arg Glu Tyr
        355                 360                 365

Trp Asn Thr Thr Ile Ile Phe Lys Asn Ser Ser Gly Gly Asp Leu Glu
370                 375                 380

Ile Thr Thr His Ser Phe Asn Cys Gly Gly Glu Phe Phe Tyr Cys Asn
385                 390                 395                 400

Thr Ser Gly Leu Phe Asn Ser Asn Trp Thr His Asn Asp Thr Ala Ser
            405                 410                 415

Met Lys Pro Asn Asp Thr Ile Thr Leu Pro Cys Arg Ile Lys Gln Ile
            420                 425                 430

Ile Asn Met Trp Gln Arg Val Gly Gln Ala Ile Tyr Ala Pro Pro Ile
        435                 440                 445

Gln Gly Val Ile Arg Cys Glu Ser Asn Ile Thr Gly Leu Ile Leu Thr
450                 455                 460

Arg Asp Gly Gly Asn Ile Asn Glu Ser Gln Ile Phe Arg Pro Gly
465                 470                 475                 480

Gly Gly Asp Met Arg Asp Asn Trp Arg Ser Glu Leu Tyr Lys Tyr Lys
            485                 490                 495

Val Val Arg Ile Glu Pro Leu Gly Val Ala Pro Thr Lys Ala Lys Arg
            500                 505                 510

Arg Val Val Glu Arg Glu Lys Arg Ala Val Val Glu Leu Gly Ala Val
        515                 520                 525

Phe Ile Gly Phe Leu Gly Thr Ala Gly Ser Thr Met Gly Ala Ala Ser
530                 535                 540

Ile Thr Leu Thr Val Gln Val Arg Lys Leu Leu Ser Gly Ile Val Gln
545                 550                 555                 560

Gln Gln Ser Asn Leu Leu Arg Ala Ile Glu Ala Gln Gln His Leu Leu
            565                 570                 575

Lys Leu Thr Val Trp Gly Ile Lys Gln Leu Gln Ala Arg Val Leu Ala
            580                 585                 590

Val Glu Arg Tyr Leu Arg Asp Gln Gln Leu Leu Gly Ile Trp Gly Cys
        595                 600                 605

Ser Gly Lys Leu Ile Cys Thr Thr Asn Val Pro Trp Asn Ser Ser Trp
610                 615                 620

Ser Asn Lys Ser Glu Arg Glu Ile Trp Glu Asn Met Thr Trp Leu Gln
```

```
                625                 630                 635                 640

Trp Asp Lys Glu Ile Ser Asn Tyr Thr His Ile Ile Tyr Glu Leu Ile
                    645                 650                 655

Glu Glu Ser Gln Lys Gln Gln Glu Lys Asn Glu Gln Glu Leu Leu Glu
                    660                 665                 670

Leu Asp Lys Trp Ala Asn Leu Trp Asn Trp Phe Asp Ile Ser Asn Trp
                    675                 680                 685

Leu Trp Tyr Ile Lys Ser Arg Ile Glu Gly Arg Gly Ser Gly Gly Tyr
                690                 695                 700

Ile Pro Glu Ala Pro Arg Asp Gly Gln Ala Tyr Val Arg Lys Asp Gly
705                 710                 715                 720

Glu Trp Val Leu Leu Ser Thr Phe Leu Asn Lys Leu Lys Ser Ser Ile
                    725                 730                 735

Glu Ser Thr Asn Glu Ala Val Val Lys Leu Gln Glu Thr Ala Glu Lys
                    740                 745                 750

Thr Val Tyr Val Leu Thr Ala Leu Gln
                    755                 760

<210> SEQ ID NO 70
<211> LENGTH: 720
<212> TYPE: PRT
<213> ORGANISM: Artificial Sequence
<220> FEATURE:
<223> OTHER INFORMATION: Engineered HIV-1 (1992 Uganda, serotype 037.8,
      clade A) envelope glycoprotein ectodomain (gp140)-HR1Nipah fusion
      protein

<400> SEQUENCE: 70

Met Lys Phe Leu Val Asn Val Ala Leu Val Phe Met Val Val Tyr Ile
1               5                   10                  15

Ser Tyr Ile Tyr Ala Glu Asp His His His His His Glu Asn Leu
                20                  25                  30

Tyr Phe Gln Gly Ala Glu Asn Leu Trp Val Thr Val Tyr Tyr Gly Val
            35                  40                  45

Pro Val Trp Lys Asp Ala Glu Thr Thr Leu Phe Cys Ala Ser Asp Ala
        50                  55                  60

Lys Ala Tyr Asp Thr Glu Val His Asn Val Trp Ala Thr His Ala Cys
65                  70                  75                  80

Val Pro Thr Asp Pro Asn Pro Gln Glu Ile Tyr Met Glu Asn Val Thr
                85                  90                  95

Glu Glu Phe Asn Met Trp Lys Asn Asn Met Val Glu Gln Met His Thr
            100                 105                 110

Asp Ile Ile Ser Leu Trp Asp Gln Ser Leu Lys Pro Cys Val Gln Leu
        115                 120                 125

Thr Pro Leu Cys Val Thr Leu Asp Cys Ser Tyr Asn Ile Thr Asn Asn
    130                 135                 140

Ile Thr Asn Ser Ile Thr Asn Ser Ser Val Asn Met Arg Glu Glu Ile
145                 150                 155                 160

Lys Asn Cys Ser Phe Asn Met Thr Thr Glu Leu Arg Asp Lys Asn Arg
                165                 170                 175

Lys Val Tyr Ser Leu Phe Tyr Lys Leu Asp Val Val Gln Ile Asn Asn
            180                 185                 190

Gly Asn Asn Ser Ser Asn Leu Tyr Arg Leu Ile Asn Cys Asn Thr Ser
        195                 200                 205

Ala Leu Thr Gln Ala Cys Pro Lys Val Thr Phe Glu Pro Ile Pro Ile
    210                 215                 220
```

-continued

Arg Tyr Cys Ala Pro Ala Gly Tyr Ala Ile Leu Lys Cys Asn Asp Lys
225                 230                 235                 240

Glu Phe Asn Gly Thr Gly Leu Cys Lys Asn Val Ser Thr Val Gln Cys
            245                 250                 255

Thr His Gly Ile Arg Pro Val Val Ser Thr Gln Leu Leu Leu Asn Gly
            260                 265                 270

Ser Leu Ala Glu Gly Lys Val Met Ile Arg Ser Glu Asn Ile Thr Asn
        275                 280                 285

Asn Val Lys Asn Ile Ile Val Gln Leu Asn Glu Thr Val Thr Ile Asn
    290                 295                 300

Cys Thr Arg Pro Asn Asn Asn Thr Arg Lys Ser Val Arg Ile Gly Pro
305                 310                 315                 320

Gly Gln Thr Phe Tyr Ala Thr Gly Asp Ile Ile Gly Asp Ile Arg Gln
                325                 330                 335

Ala His Cys Asn Val Ser Gly Ser Gln Trp Asn Arg Ala Leu His Gln
            340                 345                 350

Val Val Gly Gln Leu Arg Glu Tyr Trp Asn Thr Thr Ile Ile Phe Lys
        355                 360                 365

Asn Ser Ser Gly Gly Asp Leu Glu Ile Thr Thr His Ser Phe Asn Cys
    370                 375                 380

Gly Gly Glu Phe Phe Tyr Cys Asn Thr Ser Gly Leu Phe Asn Ser Asn
385                 390                 395                 400

Trp Thr His Asn Asp Thr Ala Ser Met Lys Pro Asn Asp Thr Ile Thr
                405                 410                 415

Leu Pro Cys Arg Ile Lys Gln Ile Ile Asn Met Trp Gln Arg Val Gly
            420                 425                 430

Gln Ala Ile Tyr Ala Pro Pro Ile Gln Gly Val Ile Arg Cys Glu Ser
        435                 440                 445

Asn Ile Thr Gly Leu Ile Leu Thr Arg Asp Gly Gly Asn Ile Asn
    450                 455                 460

Glu Ser Gln Ile Phe Arg Pro Gly Gly Gly Asp Met Arg Asp Asn Trp
465                 470                 475                 480

Arg Ser Glu Leu Tyr Lys Tyr Lys Val Val Arg Ile Glu Pro Leu Gly
                485                 490                 495

Val Ala Pro Thr Lys Ala Lys Arg Arg Val Val Glu Arg Glu Lys Arg
            500                 505                 510

Ala Val Val Glu Leu Gly Ala Val Phe Ile Gly Phe Leu Gly Thr Ala
        515                 520                 525

Gly Ser Thr Met Gly Ala Ala Ser Ile Thr Leu Thr Val Gln Val Arg
    530                 535                 540

Lys Leu Leu Ser Gly Ile Val Gln Gln Ser Asn Leu Leu Arg Ala
545                 550                 555                 560

Ile Glu Ala Gln Gln His Leu Leu Lys Leu Thr Val Trp Gly Ile Lys
                565                 570                 575

Gln Leu Gln Ala Arg Val Leu Ala Val Glu Arg Tyr Leu Arg Asp Gln
            580                 585                 590

Gln Leu Leu Gly Ile Trp Gly Cys Ser Gly Lys Leu Ile Cys Thr Thr
        595                 600                 605

Asn Val Pro Trp Asn Ser Ser Trp Ser Asn Lys Ser Glu Arg Glu Ile
    610                 615                 620

Trp Glu Asn Met Thr Trp Leu Gln Trp Asp Lys Glu Ile Ser Asn Tyr
625                 630                 635                 640

```
Thr His Ile Ile Tyr Glu Leu Ile Glu Glu Ser Gln Lys Gln Gln Glu
            645                 650                 655

Lys Asn Glu Gln Glu Leu Leu Glu Leu Asp Lys Trp Ala Asn Leu Trp
            660                 665                 670

Asn Trp Phe Asp Ile Ser Asn Trp Leu Trp Tyr Ile Lys Ser Asn Ile
            675                 680                 685

Asn Lys Leu Lys Ser Ser Ile Glu Ser Thr Asn Glu Ala Val Val Lys
            690                 695                 700

Leu Gln Glu Thr Ala Glu Lys Thr Val Tyr Val Leu Thr Ala Leu Gln
705                 710                 715                 720

<210> SEQ ID NO 71
<211> LENGTH: 728
<212> TYPE: PRT
<213> ORGANISM: Artificial Sequence
<220> FEATURE:
<223> OTHER INFORMATION: Engineered HIV-1 (1992 Uganda, serotype 037.8,
      clade A) envelope glycoprotein ectodomain (gp140)-HR1Nipah fusion
      protein

<400> SEQUENCE: 71

Met Arg Val Arg Gly Ile Gln Arg Asn Cys Gln His Leu Trp Arg Trp
1               5                   10                  15

Gly Thr Leu Ile Leu Gly Met Leu Met Ile Cys Ser Ala Glu Asp His
            20                  25                  30

His His His His His Glu Asn Leu Tyr Phe Gln Gly Ala Glu Asn Leu
            35                  40                  45

Trp Val Thr Val Tyr Tyr Gly Val Pro Val Trp Lys Asp Ala Glu Thr
        50                  55                  60

Thr Leu Phe Cys Ala Ser Asp Ala Lys Ala Tyr Asp Thr Glu Val His
65                  70                  75                  80

Asn Val Trp Ala Thr His Ala Cys Val Pro Thr Asp Pro Asn Pro Gln
                85                  90                  95

Glu Ile Tyr Met Glu Asn Val Thr Glu Glu Phe Asn Met Trp Lys Asn
            100                 105                 110

Asn Met Val Glu Gln Met His Thr Asp Ile Ile Ser Leu Trp Asp Gln
            115                 120                 125

Ser Leu Lys Pro Cys Val Gln Leu Thr Pro Leu Cys Val Thr Leu Asp
        130                 135                 140

Cys Ser Tyr Asn Ile Thr Asn Asn Ile Thr Asn Ser Ile Thr Asn Ser
145                 150                 155                 160

Ser Val Asn Met Arg Glu Glu Ile Lys Asn Cys Ser Phe Asn Met Thr
                165                 170                 175

Thr Glu Leu Arg Asp Lys Asn Arg Lys Val Tyr Ser Leu Phe Tyr Lys
            180                 185                 190

Leu Asp Val Val Gln Ile Asn Asn Gly Asn Asn Ser Ser Asn Leu Tyr
        195                 200                 205

Arg Leu Ile Asn Cys Asn Thr Ser Ala Leu Thr Gln Ala Cys Pro Lys
210                 215                 220

Val Thr Phe Glu Pro Ile Pro Ile Arg Tyr Cys Ala Pro Ala Gly Tyr
225                 230                 235                 240

Ala Ile Leu Lys Cys Asn Asp Lys Glu Phe Asn Gly Thr Gly Leu Cys
                245                 250                 255

Lys Asn Val Ser Thr Val Gln Cys Thr His Gly Ile Arg Pro Val Val
            260                 265                 270

Ser Thr Gln Leu Leu Leu Asn Gly Ser Leu Ala Glu Gly Lys Val Met
```

```
                275                 280                 285
Ile Arg Ser Glu Asn Ile Thr Asn Asn Val Lys Asn Ile Ile Val Gln
    290                 295                 300
Leu Asn Glu Thr Val Thr Ile Asn Cys Thr Arg Pro Asn Asn Asn Thr
305                 310                 315                 320
Arg Lys Ser Val Arg Ile Gly Pro Gly Gln Thr Phe Tyr Ala Thr Gly
                325                 330                 335
Asp Ile Ile Gly Asp Ile Arg Gln Ala His Cys Asn Val Ser Gly Ser
                340                 345                 350
Gln Trp Asn Arg Ala Leu His Gln Val Val Gly Gln Leu Arg Glu Tyr
                355                 360                 365
Trp Asn Thr Thr Ile Ile Phe Lys Asn Ser Ser Gly Asp Leu Glu
    370                 375                 380
Ile Thr Thr His Ser Phe Asn Cys Gly Gly Glu Phe Phe Tyr Cys Asn
385                 390                 395                 400
Thr Ser Gly Leu Phe Asn Ser Asn Trp Thr His Asn Asp Thr Ala Ser
                405                 410                 415
Met Lys Pro Asn Asp Thr Ile Thr Leu Pro Cys Arg Ile Lys Gln Ile
                420                 425                 430
Ile Asn Met Trp Gln Arg Val Gly Gln Ala Ile Tyr Ala Pro Pro Ile
                435                 440                 445
Gln Gly Val Ile Arg Cys Glu Ser Asn Ile Thr Gly Leu Ile Leu Thr
                450                 455                 460
Arg Asp Gly Gly Gly Asn Ile Asn Glu Ser Gln Ile Phe Arg Pro Gly
465                 470                 475                 480
Gly Gly Asp Met Arg Asp Asn Trp Arg Ser Glu Leu Tyr Lys Tyr Lys
                485                 490                 495
Val Val Arg Ile Glu Pro Leu Gly Val Ala Pro Thr Lys Ala Lys Arg
                500                 505                 510
Arg Val Val Glu Arg Glu Lys Arg Ala Val Val Glu Leu Gly Ala Val
                515                 520                 525
Phe Ile Gly Phe Leu Gly Thr Ala Gly Ser Thr Met Gly Ala Ala Ser
                530                 535                 540
Ile Thr Leu Thr Val Gln Val Arg Lys Leu Leu Ser Gly Ile Val Gln
545                 550                 555                 560
Gln Gln Ser Asn Leu Leu Arg Ala Ile Glu Ala Gln Gln His Leu Leu
                565                 570                 575
Lys Leu Thr Val Trp Gly Ile Lys Gln Leu Gln Ala Arg Val Leu Ala
                580                 585                 590
Val Glu Arg Tyr Leu Arg Asp Gln Gln Leu Leu Gly Ile Trp Gly Cys
                595                 600                 605
Ser Gly Lys Leu Ile Cys Thr Thr Asn Val Pro Trp Asn Ser Ser Trp
                610                 615                 620
Ser Asn Lys Ser Glu Arg Glu Ile Trp Glu Asn Met Thr Trp Leu Gln
625                 630                 635                 640
Trp Asp Lys Glu Ile Ser Asn Tyr Thr His Ile Ile Tyr Glu Leu Ile
                645                 650                 655
Glu Glu Ser Gln Lys Gln Gln Glu Lys Asn Glu Gln Glu Leu Leu Glu
                660                 665                 670
Leu Asp Lys Trp Ala Asn Leu Trp Asn Trp Phe Asp Ile Ser Asn Trp
                675                 680                 685
Leu Trp Tyr Ile Lys Ser Asn Ile Asn Lys Leu Lys Ser Ser Ile Glu
                690                 695                 700
```

```
Ser Thr Asn Glu Ala Val Val Lys Leu Gln Glu Thr Ala Glu Lys Thr
705                 710                 715                 720

Val Tyr Val Leu Thr Ala Leu Gln
                725

<210> SEQ ID NO 72
<211> LENGTH: 741
<212> TYPE: PRT
<213> ORGANISM: Artificial Sequence
<220> FEATURE:
<223> OTHER INFORMATION: Engineered HIV-1 clade C 1997 envelope
      glycoprotein ectodomain (gp140)-HR1HXB2 fusion protein

<400> SEQUENCE: 72

Met Lys Phe Leu Val Asn Val Ala Leu Val Phe Met Val Val Tyr Ile
1               5                   10                  15

Ser Tyr Ile Tyr Ala Glu Asp His His His His His His Glu Asn Leu
                20                  25                  30

Tyr Phe Gln Gly Ala Glu Asn Leu Trp Val Gly Asn Met Trp Val Thr
            35                  40                  45

Val Tyr Tyr Gly Val Pro Val Trp Thr Asp Ala Lys Thr Thr Leu Phe
    50                  55                  60

Cys Ala Ser Asp Thr Lys Ala Tyr Asp Arg Glu Val His Asn Val Trp
65                  70                  75                  80

Ala Thr His Ala Cys Val Pro Thr Asp Pro Asn Pro Gln Glu Ile Val
                85                  90                  95

Leu Glu Asn Val Thr Glu Asn Phe Asn Met Trp Lys Asn Asp Met Val
            100                 105                 110

Asp Gln Met His Glu Asp Ile Ile Ser Leu Trp Asp Gln Ser Leu Lys
        115                 120                 125

Pro Cys Val Lys Leu Thr Pro Leu Cys Val Thr Leu His Cys Thr Asn
130                 135                 140

Ala Thr Phe Lys Asn Asn Val Thr Asn Asp Met Asn Lys Glu Ile Arg
145                 150                 155                 160

Asn Cys Ser Phe Asn Thr Thr Thr Glu Ile Arg Asp Lys Lys Gln Gln
                165                 170                 175

Gly Tyr Ala Leu Phe Tyr Arg Pro Asp Ile Val Leu Leu Lys Glu Asn
            180                 185                 190

Arg Asn Asn Ser Asn Asn Ser Glu Tyr Ile Leu Ile Asn Cys Asn Ala
        195                 200                 205

Ser Thr Ile Thr Gln Ala Cys Pro Lys Val Asn Phe Asp Pro Ile Pro
    210                 215                 220

Ile His Tyr Cys Ala Pro Ala Gly Tyr Ala Ile Leu Lys Cys Asn Asn
225                 230                 235                 240

Lys Thr Phe Ser Gly Lys Gly Pro Cys Asn Asn Val Ser Thr Val Gln
                245                 250                 255

Cys Thr His Gly Ile Lys Pro Val Val Ser Thr Gln Leu Leu Leu Asn
            260                 265                 270

Gly Ser Leu Ala Glu Lys Glu Ile Ile Ile Arg Ser Glu Asn Leu Thr
        275                 280                 285

Asp Asn Val Lys Thr Ile Ile Val His Leu Asn Lys Ser Val Glu Ile
    290                 295                 300

Val Cys Thr Arg Pro Asn Asn Asn Thr Arg Lys Ser Met Arg Ile Gly
305                 310                 315                 320

Pro Gly Gln Thr Phe Tyr Ala Thr Gly Asp Ile Ile Gly Asp Ile Arg
```

```
                    325                 330                 335
Gln Ala Tyr Cys Asn Ile Ser Gly Ser Lys Trp Asn Glu Thr Leu Lys
                340                 345                 350
Arg Val Lys Glu Lys Leu Gln Glu Asn Tyr Asn Asn Asn Lys Thr Ile
                355                 360                 365
Lys Phe Ala Pro Ser Ser Gly Asp Leu Glu Ile Thr Thr His Ser
            370                 375                 380
Phe Asn Cys Arg Gly Glu Phe Phe Tyr Cys Asn Thr Thr Arg Leu Phe
385                 390                 395                 400
Asn Asn Asn Ala Thr Glu Asp Glu Thr Ile Thr Leu Pro Cys Arg Ile
                405                 410                 415
Lys Gln Ile Ile Asn Met Trp Gln Gly Val Gly Arg Ala Met Tyr Ala
                420                 425                 430
Pro Pro Ile Ala Gly Asn Ile Thr Cys Lys Ser Asn Ile Thr Gly Leu
                435                 440                 445
Leu Leu Val Arg Asp Gly Gly Glu Asp Asn Lys Thr Glu Glu Ile Phe
            450                 455                 460
Arg Pro Gly Gly Gly Asn Met Lys Asp Asn Trp Arg Ser Glu Leu Tyr
465                 470                 475                 480
Lys Tyr Lys Val Ile Glu Leu Lys Pro Leu Gly Ile Ala Pro Thr Gly
                485                 490                 495
Ala Lys Arg Arg Val Val Glu Arg Glu Lys Arg Ala Val Gly Ile Gly
                500                 505                 510
Ala Val Phe Leu Gly Phe Leu Gly Ala Ala Gly Ser Thr Met Gly Ala
            515                 520                 525
Ala Ser Leu Thr Leu Thr Val Gln Ala Arg Gln Leu Leu Ser Ser Ile
            530                 535                 540
Val Gln Gln Gln Ser Asn Leu Leu Arg Ala Ile Glu Ala Gln Gln His
545                 550                 555                 560
Met Leu Gln Leu Thr Val Trp Gly Ile Lys Gln Leu Gln Thr Arg Val
                565                 570                 575
Leu Ala Ile Glu Arg Tyr Leu Lys Asp Gln Gln Leu Leu Gly Ile Trp
            580                 585                 590
Gly Cys Ser Gly Lys Leu Ile Cys Thr Thr Asn Val Pro Trp Asn Ser
            595                 600                 605
Ser Trp Ser Asn Lys Ser Gln Thr Asp Ile Trp Asn Asn Met Thr Trp
            610                 615                 620
Met Glu Trp Asp Arg Glu Ile Ser Asn Tyr Thr Asp Thr Ile Tyr Arg
625                 630                 635                 640
Leu Leu Glu Asp Ser Gln Thr Gln Gln Glu Lys Asn Glu Lys Asp Leu
                645                 650                 655
Leu Ala Leu Asp Ser Trp Lys Asn Leu Trp Ser Trp Phe Asp Ile Ser
            660                 665                 670
Asn Trp Leu Trp Tyr Ile Lys Ser Gly Tyr Ile Pro Glu Ala Pro Arg
            675                 680                 685
Asp Gly Gln Ala Tyr Val Arg Lys Asp Gly Glu Trp Val Leu Leu Ser
            690                 695                 700
Thr Phe Leu Ser Gly Ile Val Gln Gln Gln Asn Asn Leu Leu Arg Ala
705                 710                 715                 720
Ile Glu Ala Gln Gln His Leu Leu Gln Leu Thr Val Trp Gly Ile Lys
                725                 730                 735
Gln Leu Gln Ala Arg
            740
```

<210> SEQ ID NO 73
<211> LENGTH: 749
<212> TYPE: PRT
<213> ORGANISM: Artificial Sequence
<220> FEATURE:
<223> OTHER INFORMATION: Engineered HIV-1 clade C 1997 envelope
glycoprotein ectodomain (gp140)-HR1HXB2 fusion protein

<400> SEQUENCE: 73

```
Met Arg Val Arg Gly Ile Gln Arg Asn Cys Gln His Leu Trp Arg Trp
1               5                   10                  15

Gly Thr Leu Ile Leu Gly Met Leu Met Ile Cys Ser Ala Glu Asp His
            20                  25                  30

His His His His His Glu Asn Leu Tyr Phe Gln Gly Ala Glu Asn Leu
        35                  40                  45

Trp Val Gly Asn Met Trp Val Thr Val Tyr Tyr Gly Val Pro Val Trp
    50                  55                  60

Thr Asp Ala Lys Thr Thr Leu Phe Cys Ala Ser Asp Thr Lys Ala Tyr
65                  70                  75                  80

Asp Arg Glu Val His Asn Val Trp Ala Thr His Ala Cys Val Pro Thr
                85                  90                  95

Asp Pro Asn Pro Gln Glu Ile Val Leu Glu Asn Val Thr Glu Asn Phe
            100                 105                 110

Asn Met Trp Lys Asn Asp Met Val Asp Gln Met His Glu Asp Ile Ile
        115                 120                 125

Ser Leu Trp Asp Gln Ser Leu Lys Pro Cys Val Lys Leu Thr Pro Leu
    130                 135                 140

Cys Val Thr Leu His Cys Thr Asn Ala Thr Phe Lys Asn Asn Val Thr
145                 150                 155                 160

Asn Asp Met Asn Lys Glu Ile Arg Asn Cys Ser Phe Asn Thr Thr Thr
                165                 170                 175

Glu Ile Arg Asp Lys Lys Gln Gln Gly Tyr Ala Leu Phe Tyr Arg Pro
            180                 185                 190

Asp Ile Val Leu Leu Lys Glu Asn Arg Asn Asn Ser Asn Asn Ser Glu
        195                 200                 205

Tyr Ile Leu Ile Asn Cys Asn Ala Ser Thr Ile Thr Gln Ala Cys Pro
    210                 215                 220

Lys Val Asn Phe Asp Pro Ile Pro Ile His Tyr Cys Ala Pro Ala Gly
225                 230                 235                 240

Tyr Ala Ile Leu Lys Cys Asn Asn Lys Thr Phe Ser Gly Lys Gly Pro
                245                 250                 255

Cys Asn Asn Val Ser Thr Val Gln Cys Thr His Gly Ile Lys Pro Val
            260                 265                 270

Val Ser Thr Gln Leu Leu Leu Asn Gly Ser Leu Ala Glu Lys Glu Ile
        275                 280                 285

Ile Ile Arg Ser Glu Asn Leu Thr Asp Asn Val Lys Thr Ile Ile Val
    290                 295                 300

His Leu Asn Lys Ser Val Glu Ile Val Cys Thr Arg Pro Asn Asn Asn
305                 310                 315                 320

Thr Arg Lys Ser Met Arg Ile Gly Pro Gly Gln Thr Phe Tyr Ala Thr
                325                 330                 335

Gly Asp Ile Ile Gly Asp Ile Arg Gln Ala Tyr Cys Asn Ile Ser Gly
            340                 345                 350

Ser Lys Trp Asn Glu Thr Leu Lys Arg Val Lys Glu Lys Leu Gln Glu
```

```
            355                 360                 365
Asn Tyr Asn Asn Asn Lys Thr Ile Lys Phe Ala Pro Ser Ser Gly Gly
        370                 375                 380

Asp Leu Glu Ile Thr Thr His Ser Phe Asn Cys Arg Gly Glu Phe Phe
385                 390                 395                 400

Tyr Cys Asn Thr Thr Arg Leu Phe Asn Asn Asn Ala Thr Glu Asp Glu
                405                 410                 415

Thr Ile Thr Leu Pro Cys Arg Ile Lys Gln Ile Ile Asn Met Trp Gln
            420                 425                 430

Gly Val Gly Arg Ala Met Tyr Ala Pro Pro Ile Ala Gly Asn Ile Thr
        435                 440                 445

Cys Lys Ser Asn Ile Thr Gly Leu Leu Leu Val Arg Asp Gly Gly Glu
    450                 455                 460

Asp Asn Lys Thr Glu Glu Ile Phe Arg Pro Gly Gly Gly Asn Met Lys
465                 470                 475                 480

Asp Asn Trp Arg Ser Glu Leu Tyr Lys Tyr Lys Val Ile Glu Leu Lys
                485                 490                 495

Pro Leu Gly Ile Ala Pro Thr Gly Ala Lys Arg Arg Val Val Glu Arg
            500                 505                 510

Glu Lys Arg Ala Val Gly Ile Gly Ala Val Phe Leu Gly Phe Leu Gly
        515                 520                 525

Ala Ala Gly Ser Thr Met Gly Ala Ala Ser Leu Thr Leu Thr Val Gln
    530                 535                 540

Ala Arg Gln Leu Leu Ser Ser Ile Val Gln Gln Gln Ser Asn Leu Leu
545                 550                 555                 560

Arg Ala Ile Glu Ala Gln Gln His Met Leu Gln Leu Thr Val Trp Gly
                565                 570                 575

Ile Lys Gln Leu Gln Thr Arg Val Leu Ala Ile Glu Arg Tyr Leu Lys
            580                 585                 590

Asp Gln Gln Leu Leu Gly Ile Trp Gly Cys Ser Gly Lys Leu Ile Cys
        595                 600                 605

Thr Thr Asn Val Pro Trp Asn Ser Ser Trp Ser Asn Lys Ser Gln Thr
    610                 615                 620

Asp Ile Trp Asn Asn Met Thr Trp Met Glu Trp Asp Arg Glu Ile Ser
625                 630                 635                 640

Asn Tyr Thr Asp Thr Ile Tyr Arg Leu Leu Glu Asp Ser Gln Thr Gln
                645                 650                 655

Gln Glu Lys Asn Glu Lys Asp Leu Leu Ala Leu Asp Ser Trp Lys Asn
            660                 665                 670

Leu Trp Ser Trp Phe Asp Ile Ser Asn Trp Leu Trp Tyr Ile Lys Ser
        675                 680                 685

Gly Tyr Ile Pro Glu Ala Pro Arg Asp Gly Gln Ala Tyr Val Arg Lys
    690                 695                 700

Asp Gly Glu Trp Val Leu Leu Ser Thr Phe Leu Ser Gly Ile Val Gln
705                 710                 715                 720

Gln Gln Asn Asn Leu Leu Arg Ala Ile Glu Ala Gln Gln His Leu Leu
                725                 730                 735

Gln Leu Thr Val Trp Gly Ile Lys Gln Leu Gln Ala Arg
            740                 745

<210> SEQ ID NO 74
<211> LENGTH: 716
<212> TYPE: PRT
<213> ORGANISM: Artificial Sequence
```

<220> FEATURE:
<223> OTHER INFORMATION: Engineered HIV-1 clade C 1997 envelope
    glycoprotein ectodomain (gp140)-HR1HXB2 fusion protein

<400> SEQUENCE: 74

Met Lys Phe Leu Val Asn Val Ala Leu Val Phe Met Val Val Tyr Ile
1               5                   10                  15

Ser Tyr Ile Tyr Ala Glu Asp His His His His His Glu Asn Leu
            20                  25                  30

Tyr Phe Gln Gly Ala Glu Asn Leu Trp Val Gly Asn Met Trp Val Thr
            35                  40                  45

Val Tyr Tyr Gly Val Pro Val Trp Thr Asp Ala Lys Thr Thr Leu Phe
        50                  55                  60

Cys Ala Ser Asp Thr Lys Ala Tyr Asp Arg Glu Val His Asn Val Trp
65                  70                  75                  80

Ala Thr His Ala Cys Val Pro Thr Asp Pro Asn Pro Gln Glu Ile Val
                85                  90                  95

Leu Glu Asn Val Thr Glu Asn Phe Asn Met Trp Lys Asn Asp Met Val
            100                 105                 110

Asp Gln Met His Glu Asp Ile Ile Ser Leu Trp Asp Gln Ser Leu Lys
        115                 120                 125

Pro Cys Val Lys Leu Thr Pro Leu Cys Val Thr Leu His Cys Thr Asn
130                 135                 140

Ala Thr Phe Lys Asn Asn Val Thr Asn Asp Met Asn Lys Glu Ile Arg
145                 150                 155                 160

Asn Cys Ser Phe Asn Thr Thr Thr Glu Ile Arg Asp Lys Lys Gln Gln
                165                 170                 175

Gly Tyr Ala Leu Phe Tyr Arg Pro Asp Ile Val Leu Leu Lys Glu Asn
            180                 185                 190

Arg Asn Asn Ser Asn Asn Ser Glu Tyr Ile Leu Ile Asn Cys Asn Ala
        195                 200                 205

Ser Thr Ile Thr Gln Ala Cys Pro Lys Val Asn Phe Asp Pro Ile Pro
    210                 215                 220

Ile His Tyr Cys Ala Pro Ala Gly Tyr Ala Ile Leu Lys Cys Asn Asn
225                 230                 235                 240

Lys Thr Phe Ser Gly Lys Gly Pro Cys Asn Asn Val Ser Thr Val Gln
                245                 250                 255

Cys Thr His Gly Ile Lys Pro Val Val Ser Thr Gln Leu Leu Leu Asn
            260                 265                 270

Gly Ser Leu Ala Glu Lys Glu Ile Ile Ile Arg Ser Glu Asn Leu Thr
        275                 280                 285

Asp Asn Val Lys Thr Ile Ile Val His Leu Asn Lys Ser Val Glu Ile
    290                 295                 300

Val Cys Thr Arg Pro Asn Asn Asn Thr Arg Lys Ser Met Arg Ile Gly
305                 310                 315                 320

Pro Gly Gln Thr Phe Tyr Ala Thr Gly Asp Ile Ile Gly Asp Ile Arg
                325                 330                 335

Gln Ala Tyr Cys Asn Ile Ser Gly Ser Lys Trp Asn Glu Thr Leu Lys
            340                 345                 350

Arg Val Lys Glu Lys Leu Gln Glu Asn Tyr Asn Asn Lys Thr Ile
        355                 360                 365

Lys Phe Ala Pro Ser Ser Gly Gly Asp Leu Glu Ile Thr Thr His Ser
    370                 375                 380

Phe Asn Cys Arg Gly Glu Phe Phe Tyr Cys Asn Thr Thr Arg Leu Phe 385                 390                 395                 400
Asn Asn Asn Ala Thr Glu Asp Glu Thr Ile Thr Leu Pro Cys Arg Ile
                405                 410                 415

Lys Gln Ile Ile Asn Met Trp Gln Gly Val Gly Arg Ala Met Tyr Ala
                420                 425                 430

Pro Pro Ile Ala Gly Asn Ile Thr Cys Lys Ser Asn Ile Thr Gly Leu
                435                 440                 445

Leu Leu Val Arg Asp Gly Gly Glu Asp Asn Lys Thr Glu Glu Ile Phe
450                 455                 460

Arg Pro Gly Gly Gly Asn Met Lys Asp Asn Trp Arg Ser Glu Leu Tyr
465                 470                 475                 480

Lys Tyr Lys Val Ile Glu Leu Lys Pro Leu Gly Ile Ala Pro Thr Gly
                485                 490                 495

Ala Lys Arg Arg Val Val Glu Arg Glu Lys Arg Ala Val Gly Ile Gly
                500                 505                 510

Ala Val Phe Leu Gly Phe Leu Gly Ala Ala Gly Ser Thr Met Gly Ala
                515                 520                 525

Ala Ser Leu Thr Leu Thr Val Gln Ala Arg Gln Leu Leu Ser Ser Ile
530                 535                 540

Val Gln Gln Gln Ser Asn Leu Leu Arg Ala Ile Glu Ala Gln Gln His
545                 550                 555                 560

Met Leu Gln Leu Thr Val Trp Gly Ile Lys Gln Leu Gln Thr Arg Val
                565                 570                 575

Leu Ala Ile Glu Arg Tyr Leu Lys Asp Gln Gln Leu Leu Gly Ile Trp
                580                 585                 590

Gly Cys Ser Gly Lys Leu Ile Cys Thr Thr Asn Val Pro Trp Asn Ser
                595                 600                 605

Ser Trp Ser Asn Lys Ser Gln Thr Asp Ile Trp Asn Asn Met Thr Trp
                610                 615                 620

Met Glu Trp Asp Arg Glu Ile Ser Asn Tyr Thr Asp Thr Ile Tyr Arg
625                 630                 635                 640

Leu Leu Glu Asp Ser Gln Thr Gln Gln Glu Lys Asn Glu Lys Asp Leu
                645                 650                 655

Leu Ala Leu Asp Ser Trp Lys Asn Leu Trp Ser Trp Phe Asp Ile Ser
                660                 665                 670

Asn Trp Leu Trp Tyr Ile Lys Ser Gly Ile Ser Gly Ile Val Gln Gln
                675                 680                 685

Gln Asn Asn Leu Leu Arg Ala Ile Glu Ala Gln Gln His Leu Leu Gln
                690                 695                 700

Leu Thr Val Trp Gly Ile Lys Gln Leu Gln Ala Arg
705                 710                 715

<210> SEQ ID NO 75
<211> LENGTH: 724
<212> TYPE: PRT
<213> ORGANISM: Artificial Sequence
<220> FEATURE:
<223> OTHER INFORMATION: Engineered HIV-1 clade C 1997 envelope
      glycoprotein ectodomain (gp140)-HR1HXB2 fusion protein

<400> SEQUENCE: 75

Met Arg Val Arg Gly Ile Gln Arg Asn Cys Gln His Leu Trp Arg Trp
1               5                   10                  15

Gly Thr Leu Ile Leu Gly Met Leu Met Ile Cys Ser Ala Glu Asp His
                20                  25                  30

```
His His His His His Glu Asn Leu Tyr Phe Gln Gly Ala Glu Asn Leu
             35                  40                  45

Trp Val Gly Asn Met Trp Val Thr Val Tyr Tyr Gly Val Pro Val Trp
 50                  55                  60

Thr Asp Ala Lys Thr Thr Leu Phe Cys Ala Ser Asp Thr Lys Ala Tyr
 65                  70                  75                  80

Asp Arg Glu Val His Asn Val Trp Ala Thr His Ala Cys Val Pro Thr
                 85                  90                  95

Asp Pro Asn Pro Gln Glu Ile Val Leu Glu Asn Val Thr Glu Asn Phe
                100                 105                 110

Asn Met Trp Lys Asn Asp Met Val Asp Gln Met His Glu Asp Ile Ile
            115                 120                 125

Ser Leu Trp Asp Gln Ser Leu Lys Pro Cys Val Lys Leu Thr Pro Leu
    130                 135                 140

Cys Val Thr Leu His Cys Thr Asn Ala Thr Phe Lys Asn Asn Val Thr
145                 150                 155                 160

Asn Asp Met Asn Lys Glu Ile Arg Asn Cys Ser Phe Asn Thr Thr Thr
                165                 170                 175

Glu Ile Arg Asp Lys Lys Gln Gln Gly Tyr Ala Leu Phe Tyr Arg Pro
            180                 185                 190

Asp Ile Val Leu Leu Lys Glu Asn Arg Asn Asn Ser Asn Asn Ser Glu
    195                 200                 205

Tyr Ile Leu Ile Asn Cys Asn Ala Ser Thr Ile Thr Gln Ala Cys Pro
210                 215                 220

Lys Val Asn Phe Asp Pro Ile Pro Ile His Tyr Cys Ala Pro Ala Gly
225                 230                 235                 240

Tyr Ala Ile Leu Lys Cys Asn Asn Lys Thr Phe Ser Gly Lys Gly Pro
            245                 250                 255

Cys Asn Asn Val Ser Thr Val Gln Cys Thr His Gly Ile Lys Pro Val
    260                 265                 270

Val Ser Thr Gln Leu Leu Leu Asn Gly Ser Leu Ala Glu Lys Glu Ile
275                 280                 285

Ile Ile Arg Ser Glu Asn Leu Thr Asp Asn Val Lys Thr Ile Ile Val
290                 295                 300

His Leu Asn Lys Ser Val Glu Ile Val Cys Thr Arg Pro Asn Asn Asn
305                 310                 315                 320

Thr Arg Lys Ser Met Arg Ile Gly Pro Gly Gln Thr Phe Tyr Ala Thr
                325                 330                 335

Gly Asp Ile Ile Gly Asp Ile Arg Gln Ala Tyr Cys Asn Ile Ser Gly
            340                 345                 350

Ser Lys Trp Asn Glu Thr Leu Lys Arg Val Lys Glu Lys Leu Gln Glu
    355                 360                 365

Asn Tyr Asn Asn Asn Lys Thr Ile Lys Phe Ala Pro Ser Ser Gly Gly
370                 375                 380

Asp Leu Glu Ile Thr Thr His Ser Phe Asn Cys Arg Gly Glu Phe Phe
385                 390                 395                 400

Tyr Cys Asn Thr Thr Arg Leu Phe Asn Asn Ala Thr Glu Asp Glu
                405                 410                 415

Thr Ile Thr Leu Pro Cys Arg Ile Lys Gln Ile Ile Asn Met Trp Gln
            420                 425                 430

Gly Val Gly Arg Ala Met Tyr Ala Pro Pro Ile Ala Gly Asn Ile Thr
    435                 440                 445

Cys Lys Ser Asn Ile Thr Gly Leu Leu Leu Val Arg Asp Gly Gly Glu
```

-continued

```
                450             455             460
Asp Asn Lys Thr Glu Glu Ile Phe Arg Pro Gly Gly Gly Asn Met Lys
465                 470                 475                 480

Asp Asn Trp Arg Ser Glu Leu Tyr Lys Tyr Lys Val Ile Glu Leu Lys
                485                 490                 495

Pro Leu Gly Ile Ala Pro Thr Gly Ala Lys Arg Arg Val Val Glu Arg
                500                 505                 510

Glu Lys Arg Ala Val Gly Ile Gly Ala Val Phe Leu Gly Phe Leu Gly
                515                 520                 525

Ala Ala Gly Ser Thr Met Gly Ala Ala Ser Leu Thr Leu Thr Val Gln
                530                 535                 540

Ala Arg Gln Leu Leu Ser Ser Ile Val Gln Gln Ser Asn Leu Leu
545                 550                 555                 560

Arg Ala Ile Glu Ala Gln Gln His Met Leu Gln Leu Thr Val Trp Gly
                565                 570                 575

Ile Lys Gln Leu Gln Thr Arg Val Leu Ala Ile Glu Arg Tyr Leu Lys
                580                 585                 590

Asp Gln Gln Leu Leu Gly Ile Trp Gly Cys Ser Gly Lys Leu Ile Cys
                595                 600                 605

Thr Thr Asn Val Pro Trp Asn Ser Ser Trp Ser Asn Lys Ser Gln Thr
                610                 615                 620

Asp Ile Trp Asn Asn Met Thr Trp Met Glu Trp Asp Arg Glu Ile Ser
625                 630                 635                 640

Asn Tyr Thr Asp Thr Ile Tyr Arg Leu Leu Glu Asp Ser Gln Thr Gln
                645                 650                 655

Gln Glu Lys Asn Glu Lys Asp Leu Leu Ala Leu Asp Ser Trp Lys Asn
                660                 665                 670

Leu Trp Ser Trp Phe Asp Ile Ser Asn Trp Leu Trp Tyr Ile Lys Ser
                675                 680                 685

Gly Ile Ser Gly Ile Val Gln Gln Asn Asn Leu Leu Arg Ala Ile
                690                 695                 700

Glu Ala Gln Gln His Leu Leu Gln Leu Thr Val Trp Gly Ile Lys Gln
705                 710                 715                 720

Leu Gln Ala Arg
```

<210> SEQ ID NO 76
<211> LENGTH: 739
<212> TYPE: PRT
<213> ORGANISM: Artificial Sequence
<220> FEATURE:
<223> OTHER INFORMATION: Engineered HIV-1 clade C 1997 envelope glycoprotein ectodomain (gp140)-HR1Nipah fusion protein

<400> SEQUENCE: 76

```
Met Lys Phe Leu Val Asn Val Ala Leu Val Phe Met Val Val Tyr Ile
1               5                   10                  15

Ser Tyr Ile Tyr Ala Glu Asp His His His His His His Glu Asn Leu
                20                  25                  30

Tyr Phe Gln Gly Ala Glu Asn Leu Trp Val Gly Asn Met Trp Val Thr
                35                  40                  45

Val Tyr Tyr Gly Val Pro Val Trp Thr Asp Ala Lys Thr Thr Leu Phe
                50                  55                  60

Cys Ala Ser Asp Thr Lys Ala Tyr Asp Arg Glu Val His Asn Val Trp
65                  70                  75                  80

Ala Thr His Ala Cys Val Pro Thr Asp Pro Asn Pro Gln Glu Ile Val
```

```
                85                  90                  95
Leu Glu Asn Val Thr Glu Asn Phe Asn Met Trp Lys Asn Asp Met Val
                100                 105                 110

Asp Gln Met His Glu Asp Ile Ile Ser Leu Trp Asp Gln Ser Leu Lys
                115                 120                 125

Pro Cys Val Lys Leu Thr Pro Leu Cys Val Thr Leu His Cys Thr Asn
            130                 135                 140

Ala Thr Phe Lys Asn Asn Val Thr Asn Asp Met Asn Lys Glu Ile Arg
145                 150                 155                 160

Asn Cys Ser Phe Asn Thr Thr Thr Glu Ile Arg Asp Lys Lys Gln Gln
                165                 170                 175

Gly Tyr Ala Leu Phe Tyr Arg Pro Asp Ile Val Leu Leu Lys Glu Asn
                180                 185                 190

Arg Asn Asn Ser Asn Asn Ser Glu Tyr Ile Leu Ile Asn Cys Asn Ala
                195                 200                 205

Ser Thr Ile Thr Gln Ala Cys Pro Lys Val Asn Phe Asp Pro Ile Pro
    210                 215                 220

Ile His Tyr Cys Ala Pro Ala Gly Tyr Ala Ile Leu Lys Cys Asn Asn
225                 230                 235                 240

Lys Thr Phe Ser Gly Lys Gly Pro Cys Asn Asn Val Ser Thr Val Gln
                245                 250                 255

Cys Thr His Gly Ile Lys Pro Val Val Ser Thr Gln Leu Leu Leu Asn
            260                 265                 270

Gly Ser Leu Ala Glu Lys Glu Ile Ile Ile Arg Ser Glu Asn Leu Thr
            275                 280                 285

Asp Asn Val Lys Thr Ile Ile Val His Leu Asn Lys Ser Val Glu Ile
    290                 295                 300

Val Cys Thr Arg Pro Asn Asn Asn Thr Arg Lys Ser Met Arg Ile Gly
305                 310                 315                 320

Pro Gly Gln Thr Phe Tyr Ala Thr Gly Asp Ile Ile Gly Asp Ile Arg
                325                 330                 335

Gln Ala Tyr Cys Asn Ile Ser Gly Ser Lys Trp Asn Glu Thr Leu Lys
                340                 345                 350

Arg Val Lys Glu Lys Leu Gln Glu Asn Tyr Asn Asn Asn Lys Thr Ile
                355                 360                 365

Lys Phe Ala Pro Ser Ser Gly Gly Asp Leu Glu Ile Thr Thr His Ser
            370                 375                 380

Phe Asn Cys Arg Gly Glu Phe Phe Tyr Cys Asn Thr Thr Arg Leu Phe
385                 390                 395                 400

Asn Asn Asn Ala Thr Glu Asp Glu Thr Ile Thr Leu Pro Cys Arg Ile
                405                 410                 415

Lys Gln Ile Ile Asn Met Trp Gln Gly Val Gly Arg Ala Met Tyr Ala
                420                 425                 430

Pro Pro Ile Ala Gly Asn Ile Thr Cys Lys Ser Asn Ile Thr Gly Leu
            435                 440                 445

Leu Leu Val Arg Asp Gly Gly Glu Asp Asn Lys Thr Glu Glu Ile Phe
    450                 455                 460

Arg Pro Gly Gly Gly Asn Met Lys Asp Asn Trp Arg Ser Glu Leu Tyr
465                 470                 475                 480

Lys Tyr Lys Val Ile Glu Leu Lys Pro Leu Gly Ile Ala Pro Thr Gly
                485                 490                 495

Ala Lys Arg Arg Val Val Glu Arg Glu Lys Arg Ala Val Gly Ile Gly
            500                 505                 510
```

```
Ala Val Phe Leu Gly Phe Leu Ala Ala Gly Ser Thr Met Gly Ala
            515                 520                 525

Ala Ser Leu Thr Leu Thr Val Gln Ala Arg Gln Leu Leu Ser Ser Ile
        530                 535                 540

Val Gln Gln Ser Asn Leu Leu Arg Ala Ile Glu Ala Gln Gln His
545                 550                 555                 560

Met Leu Gln Leu Thr Val Trp Gly Ile Lys Gln Leu Gln Thr Arg Val
                565                 570                 575

Leu Ala Ile Glu Arg Tyr Leu Lys Asp Gln Gln Leu Leu Gly Ile Trp
                580                 585                 590

Gly Cys Ser Gly Lys Leu Ile Cys Thr Thr Asn Val Pro Trp Asn Ser
            595                 600                 605

Ser Trp Ser Asn Lys Ser Gln Thr Asp Ile Trp Asn Asn Met Thr Trp
        610                 615                 620

Met Glu Trp Asp Arg Glu Ile Ser Asn Tyr Thr Asp Thr Ile Tyr Arg
625                 630                 635                 640

Leu Leu Glu Asp Ser Gln Thr Gln Gln Glu Lys Asn Glu Lys Asp Leu
                645                 650                 655

Leu Ala Leu Asp Ser Trp Lys Asn Leu Trp Ser Trp Phe Asp Ile Ser
            660                 665                 670

Asn Trp Leu Trp Tyr Ile Lys Ser Gly Tyr Ile Pro Glu Ala Pro Arg
        675                 680                 685

Asp Gly Gln Ala Tyr Val Arg Lys Asp Gly Glu Trp Val Leu Leu Ser
690                 695                 700

Thr Phe Leu Asn Lys Leu Lys Ser Ser Ile Glu Ser Thr Asn Glu Ala
705                 710                 715                 720

Val Val Lys Leu Gln Glu Thr Ala Glu Lys Thr Val Tyr Val Leu Thr
                725                 730                 735

Ala Leu Gln

<210> SEQ ID NO 77
<211> LENGTH: 747
<212> TYPE: PRT
<213> ORGANISM: Artificial Sequence
<220> FEATURE:
<223> OTHER INFORMATION: Engineered HIV-1 clade C 1997 envelope
      glycoprotein ectodomain (gp140)-HR1Nipah fusion protein

<400> SEQUENCE: 77

Met Arg Val Arg Gly Ile Gln Arg Asn Cys Gln His Leu Trp Arg Trp
1               5                   10                  15

Gly Thr Leu Ile Leu Gly Met Leu Met Ile Cys Ser Ala Glu Asp His
                20                  25                  30

His His His His Glu Asn Leu Tyr Phe Gln Gly Ala Glu Asn Leu
            35                  40                  45

Trp Val Gly Asn Met Trp Val Thr Val Tyr Tyr Gly Val Pro Val Trp
        50                  55                  60

Thr Asp Ala Lys Thr Thr Leu Phe Cys Ala Ser Asp Thr Lys Ala Tyr
65                  70                  75                  80

Asp Arg Glu Val His Asn Val Trp Ala Thr His Ala Cys Val Pro Thr
                85                  90                  95

Asp Pro Asn Pro Gln Glu Ile Val Leu Glu Asn Val Thr Glu Asn Phe
            100                 105                 110

Asn Met Trp Lys Asn Asp Met Val Asp Gln Met His Glu Asp Ile Ile
        115                 120                 125
```

Ser Leu Trp Asp Gln Ser Leu Lys Pro Cys Val Lys Leu Thr Pro Leu
    130                 135                 140

Cys Val Thr Leu His Cys Thr Asn Ala Thr Phe Lys Asn Asn Val Thr
145                 150                 155                 160

Asn Asp Met Asn Lys Glu Ile Arg Asn Cys Ser Phe Asn Thr Thr Thr
                165                 170                 175

Glu Ile Arg Asp Lys Lys Gln Gln Gly Tyr Ala Leu Phe Tyr Arg Pro
            180                 185                 190

Asp Ile Val Leu Leu Lys Glu Asn Arg Asn Asn Ser Asn Asn Ser Glu
        195                 200                 205

Tyr Ile Leu Ile Asn Cys Asn Ala Ser Thr Ile Thr Gln Ala Cys Pro
210                 215                 220

Lys Val Asn Phe Asp Pro Ile Pro Ile His Tyr Cys Ala Pro Ala Gly
225                 230                 235                 240

Tyr Ala Ile Leu Lys Cys Asn Asn Lys Thr Phe Ser Gly Lys Gly Pro
                245                 250                 255

Cys Asn Asn Val Ser Thr Val Gln Cys Thr His Gly Ile Lys Pro Val
            260                 265                 270

Val Ser Thr Gln Leu Leu Leu Asn Gly Ser Leu Ala Glu Lys Glu Ile
        275                 280                 285

Ile Ile Arg Ser Glu Asn Leu Thr Asp Asn Val Lys Thr Ile Ile Val
290                 295                 300

His Leu Asn Lys Ser Val Glu Ile Val Cys Thr Arg Pro Asn Asn Asn
305                 310                 315                 320

Thr Arg Lys Ser Met Arg Ile Gly Pro Gly Gln Thr Phe Tyr Ala Thr
                325                 330                 335

Gly Asp Ile Ile Gly Asp Ile Arg Gln Ala Tyr Cys Asn Ile Ser Gly
            340                 345                 350

Ser Lys Trp Asn Glu Thr Leu Lys Arg Val Lys Glu Lys Leu Gln Glu
        355                 360                 365

Asn Tyr Asn Asn Lys Thr Ile Lys Phe Ala Pro Ser Ser Gly Gly
370                 375                 380

Asp Leu Glu Ile Thr Thr His Ser Phe Asn Cys Arg Gly Glu Phe Phe
385                 390                 395                 400

Tyr Cys Asn Thr Thr Arg Leu Phe Asn Asn Asn Ala Thr Glu Asp Glu
                405                 410                 415

Thr Ile Thr Leu Pro Cys Arg Ile Lys Gln Ile Ile Asn Met Trp Gln
            420                 425                 430

Gly Val Gly Arg Ala Met Tyr Ala Pro Pro Ile Ala Gly Asn Ile Thr
        435                 440                 445

Cys Lys Ser Asn Ile Thr Gly Leu Leu Leu Val Arg Asp Gly Gly Glu
450                 455                 460

Asp Asn Lys Thr Glu Glu Ile Phe Arg Pro Gly Gly Gly Asn Met Lys
465                 470                 475                 480

Asp Asn Trp Arg Ser Glu Leu Tyr Lys Tyr Lys Val Ile Glu Leu Lys
                485                 490                 495

Pro Leu Gly Ile Ala Pro Thr Gly Ala Lys Arg Arg Val Val Glu Arg
            500                 505                 510

Glu Lys Arg Ala Val Gly Ile Gly Ala Val Phe Leu Gly Phe Leu Gly
        515                 520                 525

Ala Ala Gly Ser Thr Met Gly Ala Ala Ser Leu Thr Leu Thr Val Gln
530                 535                 540

```
Ala Arg Gln Leu Leu Ser Ser Ile Val Gln Gln Gln Ser Asn Leu Leu
545                 550                 555                 560

Arg Ala Ile Glu Ala Gln Gln His Met Leu Gln Leu Thr Val Trp Gly
            565                 570                 575

Ile Lys Gln Leu Gln Thr Arg Val Leu Ala Ile Glu Arg Tyr Leu Lys
                580                 585                 590

Asp Gln Gln Leu Leu Gly Ile Trp Gly Cys Ser Gly Lys Leu Ile Cys
            595                 600                 605

Thr Thr Asn Val Pro Trp Asn Ser Ser Trp Ser Asn Lys Ser Gln Thr
610                 615                 620

Asp Ile Trp Asn Asn Met Thr Trp Met Glu Trp Asp Arg Glu Ile Ser
625                 630                 635                 640

Asn Tyr Thr Asp Thr Ile Tyr Arg Leu Leu Glu Asp Ser Gln Thr Gln
                645                 650                 655

Gln Glu Lys Asn Glu Lys Asp Leu Leu Ala Leu Asp Ser Trp Lys Asn
            660                 665                 670

Leu Trp Ser Trp Phe Asp Ile Ser Asn Trp Leu Trp Tyr Ile Lys Ser
            675                 680                 685

Gly Tyr Ile Pro Glu Ala Pro Arg Asp Gly Gln Ala Tyr Val Arg Lys
690                 695                 700

Asp Gly Glu Trp Val Leu Leu Ser Thr Phe Leu Asn Lys Leu Lys Ser
705                 710                 715                 720

Ser Ile Glu Ser Thr Asn Glu Ala Val Val Lys Leu Gln Glu Thr Ala
                725                 730                 735

Glu Lys Thr Val Tyr Val Leu Thr Ala Leu Gln
                740                 745

<210> SEQ ID NO 78
<211> LENGTH: 714
<212> TYPE: PRT
<213> ORGANISM: Artificial Sequence
<220> FEATURE:
<223> OTHER INFORMATION: Engineered HIV-1 clade C 1997 envelope
      glycoprotein ectodomain (gp140)-HR1Nipah fusion protein

<400> SEQUENCE: 78

Met Lys Phe Leu Val Asn Val Ala Leu Val Phe Met Val Val Tyr Ile
1               5                   10                  15

Ser Tyr Ile Tyr Ala Glu Asp His His His His His His Glu Asn Leu
            20                  25                  30

Tyr Phe Gln Gly Ala Glu Asn Leu Trp Val Gly Asn Met Trp Val Thr
        35                  40                  45

Val Tyr Tyr Gly Val Pro Val Trp Thr Asp Ala Lys Thr Thr Leu Phe
50                  55                  60

Cys Ala Ser Asp Thr Lys Ala Tyr Asp Arg Glu Val His Asn Val Trp
65                  70                  75                  80

Ala Thr His Ala Cys Val Pro Thr Asp Pro Asn Pro Gln Glu Ile Val
                85                  90                  95

Leu Glu Asn Val Thr Glu Asn Phe Asn Met Trp Lys Asn Asp Met Val
            100                 105                 110

Asp Gln Met His Glu Asp Ile Ile Ser Leu Trp Asp Gln Ser Leu Lys
        115                 120                 125

Pro Cys Val Lys Leu Thr Pro Leu Cys Val Thr Leu His Cys Thr Asn
    130                 135                 140

Ala Thr Phe Lys Asn Asn Val Thr Asn Asp Met Asn Lys Glu Ile Arg
145                 150                 155                 160
```

```
Asn Cys Ser Phe Asn Thr Thr Thr Glu Ile Arg Asp Lys Lys Gln Gln
                165                 170                 175

Gly Tyr Ala Leu Phe Tyr Arg Pro Asp Ile Val Leu Leu Lys Glu Asn
            180                 185                 190

Arg Asn Asn Ser Asn Asn Ser Glu Tyr Ile Leu Ile Asn Cys Asn Ala
                195                 200                 205

Ser Thr Ile Thr Gln Ala Cys Pro Lys Val Asn Phe Asp Pro Ile Pro
        210                 215                 220

Ile His Tyr Cys Ala Pro Ala Gly Tyr Ala Ile Leu Lys Cys Asn Asn
225                 230                 235                 240

Lys Thr Phe Ser Gly Lys Gly Pro Cys Asn Asn Val Ser Thr Val Gln
                245                 250                 255

Cys Thr His Gly Ile Lys Pro Val Val Ser Thr Gln Leu Leu Leu Asn
                260                 265                 270

Gly Ser Leu Ala Glu Lys Glu Ile Ile Ile Arg Ser Glu Asn Leu Thr
            275                 280                 285

Asp Asn Val Lys Thr Ile Ile Val His Leu Asn Lys Ser Val Glu Ile
        290                 295                 300

Val Cys Thr Arg Pro Asn Asn Asn Thr Arg Lys Ser Met Arg Ile Gly
305                 310                 315                 320

Pro Gly Gln Thr Phe Tyr Ala Thr Gly Asp Ile Ile Gly Asp Ile Arg
                325                 330                 335

Gln Ala Tyr Cys Asn Ile Ser Gly Ser Lys Trp Asn Glu Thr Leu Lys
                340                 345                 350

Arg Val Lys Glu Lys Leu Gln Glu Asn Tyr Asn Asn Lys Thr Ile
            355                 360                 365

Lys Phe Ala Pro Ser Ser Gly Gly Asp Leu Glu Ile Thr Thr His Ser
        370                 375                 380

Phe Asn Cys Arg Gly Glu Phe Phe Tyr Cys Asn Thr Thr Arg Leu Phe
385                 390                 395                 400

Asn Asn Asn Ala Thr Glu Asp Glu Thr Ile Thr Leu Pro Cys Arg Ile
                405                 410                 415

Lys Gln Ile Ile Asn Met Trp Gln Gly Val Gly Arg Ala Met Tyr Ala
                420                 425                 430

Pro Pro Ile Ala Gly Asn Ile Thr Cys Lys Ser Asn Ile Thr Gly Leu
            435                 440                 445

Leu Leu Val Arg Asp Gly Gly Glu Asp Asn Lys Thr Glu Glu Ile Phe
        450                 455                 460

Arg Pro Gly Gly Gly Asn Met Lys Asp Asn Trp Arg Ser Glu Leu Tyr
465                 470                 475                 480

Lys Tyr Lys Val Ile Glu Leu Lys Pro Leu Gly Ile Ala Pro Thr Gly
                485                 490                 495

Ala Lys Arg Arg Val Val Glu Arg Glu Lys Arg Ala Val Gly Ile Gly
                500                 505                 510

Ala Val Phe Leu Gly Phe Leu Gly Ala Ala Gly Ser Thr Met Gly Ala
            515                 520                 525

Ala Ser Leu Thr Leu Thr Val Gln Ala Arg Gln Leu Leu Ser Ser Ile
        530                 535                 540

Val Gln Gln Gln Ser Asn Leu Leu Arg Ala Ile Glu Ala Gln Gln His
545                 550                 555                 560

Met Leu Gln Leu Thr Val Trp Gly Ile Lys Gln Leu Gln Thr Arg Val
                565                 570                 575
```

Leu Ala Ile Glu Arg Tyr Leu Lys Asp Gln Gln Leu Leu Gly Ile Trp
            580                 585                 590

Gly Cys Ser Gly Lys Leu Ile Cys Thr Thr Asn Val Pro Trp Asn Ser
        595                 600                 605

Ser Trp Ser Asn Lys Ser Gln Thr Asp Ile Trp Asn Asn Met Thr Trp
610                 615                 620

Met Glu Trp Asp Arg Glu Ile Ser Asn Tyr Thr Asp Thr Ile Tyr Arg
625                 630                 635                 640

Leu Leu Glu Asp Ser Gln Thr Gln Gln Glu Lys Asn Glu Lys Asp Leu
                645                 650                 655

Leu Ala Leu Asp Ser Trp Lys Asn Leu Trp Ser Trp Phe Asp Ile Ser
            660                 665                 670

Asn Trp Leu Trp Tyr Ile Lys Ser Asn Ile Asn Lys Leu Lys Ser Ser
        675                 680                 685

Ile Glu Ser Thr Asn Glu Ala Val Val Lys Leu Gln Glu Thr Ala Glu
690                 695                 700

Lys Thr Val Tyr Val Leu Thr Ala Leu Gln
705                 710

<210> SEQ ID NO 79
<211> LENGTH: 722
<212> TYPE: PRT
<213> ORGANISM: Artificial Sequence
<220> FEATURE:
<223> OTHER INFORMATION: Engineered Rhesus Rotavirus VP7-HR2HXB2 fusion
      protein

<400> SEQUENCE: 79

Met Arg Val Arg Gly Ile Gln Arg Asn Cys Gln His Leu Trp Arg Trp
1               5                   10                  15

Gly Thr Leu Ile Leu Gly Met Leu Met Ile Cys Ser Ala Glu Asp His
            20                  25                  30

His His His His Glu Asn Leu Tyr Phe Gln Gly Ala Glu Asn Leu
        35                  40                  45

Trp Val Gly Asn Met Trp Val Thr Val Tyr Tyr Gly Val Pro Val Trp
    50                  55                  60

Thr Asp Ala Lys Thr Thr Leu Phe Cys Ala Ser Asp Thr Lys Ala Tyr
65                  70                  75                  80

Asp Arg Glu Val His Asn Val Trp Ala Thr His Ala Cys Val Pro Thr
                85                  90                  95

Asp Pro Asn Pro Gln Glu Ile Val Leu Glu Asn Val Thr Glu Asn Phe
            100                 105                 110

Asn Met Trp Lys Asn Asp Met Val Asp Gln Met His Glu Asp Ile Ile
        115                 120                 125

Ser Leu Trp Asp Gln Ser Leu Lys Pro Cys Val Lys Leu Thr Pro Leu
    130                 135                 140

Cys Val Thr Leu His Cys Thr Asn Ala Thr Phe Lys Asn Asn Val Thr
145                 150                 155                 160

Asn Asp Met Asn Lys Glu Ile Arg Asn Cys Ser Phe Asn Thr Thr Thr
                165                 170                 175

Glu Ile Arg Asp Lys Lys Gln Gln Gly Tyr Ala Leu Phe Tyr Arg Pro
            180                 185                 190

Asp Ile Val Leu Leu Lys Glu Asn Arg Asn Asn Ser Asn Asn Ser Glu
        195                 200                 205

Tyr Ile Leu Ile Asn Cys Asn Ala Ser Thr Ile Thr Gln Ala Cys Pro
    210                 215                 220

-continued

```
Lys Val Asn Phe Asp Pro Ile Pro Ile His Tyr Cys Ala Pro Ala Gly
225                 230                 235                 240
Tyr Ala Ile Leu Lys Cys Asn Asn Lys Thr Phe Ser Gly Lys Gly Pro
            245                 250                 255
Cys Asn Asn Val Ser Thr Val Gln Cys Thr His Gly Ile Lys Pro Val
                260                 265                 270
Val Ser Thr Gln Leu Leu Leu Asn Gly Ser Leu Ala Glu Lys Glu Ile
            275                 280                 285
Ile Ile Arg Ser Glu Asn Leu Thr Asp Asn Val Lys Thr Ile Ile Val
        290                 295                 300
His Leu Asn Lys Ser Val Glu Ile Val Cys Thr Arg Pro Asn Asn Asn
305                 310                 315                 320
Thr Arg Lys Ser Met Arg Ile Gly Pro Gly Gln Thr Phe Tyr Ala Thr
                325                 330                 335
Gly Asp Ile Ile Gly Asp Ile Arg Gln Ala Tyr Cys Asn Ile Ser Gly
            340                 345                 350
Ser Lys Trp Asn Glu Thr Leu Lys Arg Val Lys Glu Lys Leu Gln Glu
        355                 360                 365
Asn Tyr Asn Asn Lys Thr Ile Lys Phe Ala Pro Ser Ser Gly Gly
370                 375                 380
Asp Leu Glu Ile Thr Thr His Ser Phe Asn Cys Arg Gly Glu Phe Phe
385                 390                 395                 400
Tyr Cys Asn Thr Thr Arg Leu Phe Asn Asn Asn Ala Thr Glu Asp Glu
                405                 410                 415
Thr Ile Thr Leu Pro Cys Arg Ile Lys Gln Ile Ile Asn Met Trp Gln
            420                 425                 430
Gly Val Gly Arg Ala Met Tyr Ala Pro Pro Ile Ala Gly Asn Ile Thr
        435                 440                 445
Cys Lys Ser Asn Ile Thr Gly Leu Leu Leu Val Arg Asp Gly Gly Glu
    450                 455                 460
Asp Asn Lys Thr Glu Glu Ile Phe Arg Pro Gly Gly Gly Asn Met Lys
465                 470                 475                 480
Asp Asn Trp Arg Ser Glu Leu Tyr Lys Tyr Lys Val Ile Glu Leu Lys
                485                 490                 495
Pro Leu Gly Ile Ala Pro Thr Gly Ala Lys Arg Arg Val Val Glu Arg
            500                 505                 510
Glu Lys Arg Ala Val Gly Ile Gly Ala Val Phe Leu Gly Phe Leu Gly
        515                 520                 525
Ala Ala Gly Ser Thr Met Gly Ala Ala Ser Leu Thr Leu Thr Val Gln
    530                 535                 540
Ala Arg Gln Leu Leu Ser Ser Ile Val Gln Gln Ser Asn Leu Leu
545                 550                 555                 560
Arg Ala Ile Glu Ala Gln Gln His Met Leu Gln Leu Thr Val Trp Gly
                565                 570                 575
Ile Lys Gln Leu Gln Thr Arg Val Leu Ala Ile Glu Arg Tyr Leu Lys
            580                 585                 590
Asp Gln Gln Leu Leu Gly Ile Trp Gly Cys Ser Gly Lys Leu Ile Cys
        595                 600                 605
Thr Thr Asn Val Pro Trp Asn Ser Ser Trp Ser Asn Lys Ser Gln Thr
    610                 615                 620
Asp Ile Trp Asn Asn Met Thr Trp Met Glu Trp Asp Arg Glu Ile Ser
625                 630                 635                 640
```

```
Asn Tyr Thr Asp Thr Ile Tyr Arg Leu Leu Glu Asp Ser Gln Thr Gln
                645                 650                 655

Gln Glu Lys Asn Glu Lys Asp Leu Leu Ala Leu Asp Ser Trp Lys Asn
            660                 665                 670

Leu Trp Ser Trp Phe Asp Ile Ser Asn Trp Leu Trp Tyr Ile Lys Ser
        675                 680                 685

Asn Ile Asn Lys Leu Lys Ser Ser Ile Glu Ser Thr Asn Glu Ala Val
    690                 695                 700

Val Lys Leu Gln Glu Thr Ala Glu Lys Thr Val Tyr Val Leu Thr Ala
705                 710                 715                 720

Leu Gln

<210> SEQ ID NO 80
<211> LENGTH: 282
<212> TYPE: PRT
<213> ORGANISM: Artificial Sequence
<220> FEATURE:
<223> OTHER INFORMATION: CR6261 ScFv (for bacterial expression)

<400> SEQUENCE: 80

Met Glu Val Gln Leu Val Glu Ser Gly Ala Glu Val Lys Lys Pro Gly
1               5                   10                  15

Ser Ser Val Lys Val Ser Cys Lys Ala Ser Gly Gly Pro Phe Arg Ser
            20                  25                  30

Tyr Ala Ile Ser Trp Val Arg Gln Ala Pro Gly Gln Gly Pro Glu Trp
        35                  40                  45

Met Gly Gly Ile Ile Pro Ile Phe Gly Thr Thr Lys Tyr Ala Pro Lys
    50                  55                  60

Phe Gln Gly Arg Val Thr Ile Thr Ala Asp Asp Phe Ala Gly Thr Val
65                  70                  75                  80

Tyr Met Glu Leu Ser Ser Leu Arg Ser Glu Asp Thr Ala Met Tyr Tyr
                85                  90                  95

Cys Ala Lys His Met Gly Tyr Gln Val Arg Glu Thr Met Asp Val Trp
            100                 105                 110

Gly Lys Gly Thr Thr Val Thr Val Ser Ser Gly Gly Gly Gly Ser Gly
        115                 120                 125

Gly Gly Ser Gly Gly Gly Ser Gln Ser Val Leu Thr Gln Pro
    130                 135                 140

Pro Ser Val Ser Ala Ala Pro Gly Gln Lys Val Thr Ile Ser Cys Ser
145                 150                 155                 160

Gly Ser Ser Ser Asn Ile Gly Asn Asp Tyr Val Ser Trp Tyr Gln Gln
                165                 170                 175

Leu Pro Gly Thr Ala Pro Lys Leu Leu Ile Tyr Asp Asn Asn Lys Arg
            180                 185                 190

Pro Ser Gly Ile Pro Asp Arg Phe Ser Gly Ser Lys Ser Gly Thr Ser
        195                 200                 205

Ala Thr Leu Gly Ile Thr Gly Leu Gln Thr Gly Asp Glu Ala Asn Tyr
    210                 215                 220

Tyr Cys Ala Thr Trp Asp Arg Arg Pro Thr Ala Tyr Val Val Phe Gly
225                 230                 235                 240

Gly Gly Thr Lys Leu Thr Val Leu Gly Ala Ala Gly Gln Pro Lys
                245                 250                 255

Ala Ala Pro Ser Val Thr Leu Phe Pro Pro Ser Ser Glu Glu Leu Gln
            260                 265                 270

Arg Gly Ala Ala His His His His His His
```

275                 280

<210> SEQ ID NO 81
<211> LENGTH: 301
<212> TYPE: PRT
<213> ORGANISM: Artificial Sequence
<220> FEATURE:
<223> OTHER INFORMATION: CR6261 scFv (for mammalian expression)

<400> SEQUENCE: 81

Met Asp Ala Met Lys Arg Gly Leu Cys Cys Val Leu Leu Leu Cys Gly
1               5                   10                  15

Ala Val Phe Val Ser Pro Ser Gln Ser Val Leu Thr Gln Pro Pro Ser
            20                  25                  30

Val Ser Ala Ala Pro Gly Gln Lys Val Thr Ile Ser Cys Ser Gly Ser
        35                  40                  45

Ser Ser Asn Ile Gly Asn Asp Tyr Val Ser Trp Tyr Gln Gln Leu Pro
    50                  55                  60

Gly Thr Ala Pro Lys Leu Leu Ile Tyr Asp Asn Asn Lys Arg Pro Ser
65                  70                  75                  80

Gly Ile Pro Asp Arg Phe Ser Gly Ser Lys Ser Gly Thr Ser Ala Thr
                85                  90                  95

Leu Gly Ile Thr Gly Leu Gln Thr Gly Asp Glu Ala Asn Tyr Tyr Cys
            100                 105                 110

Ala Thr Trp Asp Arg Arg Pro Thr Ala Tyr Val Val Phe Gly Gly Gly
        115                 120                 125

Thr Lys Leu Thr Val Leu Gly Ala Ala Gly Gln Pro Lys Ala Ala
    130                 135                 140

Pro Ser Val Thr Leu Phe Pro Pro Ser Ser Glu Glu Leu Gln Gly Gly
145                 150                 155                 160

Ser Gly Gly Ser Gly Gly Ser Gly Gly Ser Glu Val Gln Leu Val Glu
                165                 170                 175

Ser Gly Ala Glu Val Lys Lys Pro Gly Ser Ser Val Lys Val Ser Cys
            180                 185                 190

Lys Ala Ser Gly Gly Pro Phe Arg Ser Tyr Ala Ile Ser Trp Val Arg
        195                 200                 205

Gln Ala Pro Gly Gln Gly Pro Glu Trp Met Gly Gly Ile Ile Pro Ile
    210                 215                 220

Phe Gly Thr Thr Lys Tyr Ala Pro Lys Phe Gln Gly Arg Val Thr Ile
225                 230                 235                 240

Thr Ala Asp Asp Phe Ala Gly Thr Val Tyr Met Glu Leu Ser Ser Leu
                245                 250                 255

Arg Ser Glu Asp Thr Ala Met Tyr Tyr Cys Ala Lys His Met Gly Tyr
            260                 265                 270

Gln Val Arg Glu Thr Met Asp Val Trp Gly Lys Gly Thr Thr Val Thr
        275                 280                 285

Val Ser Ser Arg Gly Ala Ala His His His His His
    290                 295                 300

<210> SEQ ID NO 82
<211> LENGTH: 244
<212> TYPE: PRT
<213> ORGANISM: Artificial Sequence
<220> FEATURE:
<223> OTHER INFORMATION: CR6261 Lignt Chain (Fab)

<400> SEQUENCE: 82

```
Met Asp Ala Met Lys Arg Gly Leu Cys Cys Val Leu Leu Leu Cys Gly
1               5                   10                  15

Ala Val Phe Val Ser Pro Ser Gln Ser Val Leu Thr Gln Pro Pro Ser
            20                  25                  30

Val Ser Ala Ala Pro Gly Gln Lys Val Thr Ile Ser Cys Ser Gly Ser
        35                  40                  45

Ser Ser Asn Ile Gly Asn Asp Tyr Val Ser Trp Tyr Gln Gln Leu Pro
50                  55                  60

Gly Thr Ala Pro Lys Leu Leu Ile Tyr Asp Asn Asn Lys Arg Pro Ser
65                  70                  75                  80

Gly Ile Pro Asp Arg Phe Ser Gly Ser Lys Ser Gly Thr Ser Ala Thr
                85                  90                  95

Leu Gly Ile Thr Gly Leu Gln Thr Gly Asp Glu Ala Asn Tyr Tyr Cys
            100                 105                 110

Ala Thr Trp Asp Arg Arg Pro Thr Ala Tyr Val Val Phe Gly Gly Gly
            115                 120                 125

Thr Lys Leu Thr Val Leu Gly Ala Ala Ala Gly Gln Pro Lys Ala Ala
        130                 135                 140

Pro Ser Val Thr Leu Phe Pro Pro Ser Ser Glu Glu Leu Gln Ala Asn
145                 150                 155                 160

Lys Ala Thr Leu Val Cys Leu Ile Ser Asp Phe Tyr Pro Gly Ala Val
                165                 170                 175

Thr Val Ala Trp Lys Ala Asp Ser Ser Pro Val Lys Ala Gly Val Glu
            180                 185                 190

Thr Thr Thr Pro Ser Lys Gln Ser Asn Asn Lys Tyr Ala Ala Ser Ser
        195                 200                 205

Tyr Leu Ser Leu Thr Pro Glu Gln Trp Lys Ser His Arg Ser Tyr Ser
210                 215                 220

Cys Gln Val Thr His Glu Gly Ser Thr Val Glu Lys Thr Val Ala Pro
225                 230                 235                 240

Thr Glu Cys Ser

<210> SEQ ID NO 83
<211> LENGTH: 249
<212> TYPE: PRT
<213> ORGANISM: Artificial Sequence
<220> FEATURE:
<223> OTHER INFORMATION: CR6261 Heavy Chain (Fab)

<400> SEQUENCE: 83

Met Asp Ala Met Lys Arg Gly Leu Cys Cys Val Leu Leu Leu Cys Gly
1               5                   10                  15

Ala Val Phe Val Ser Pro Ser Glu Val Gln Leu Val Glu Ser Gly Ala
            20                  25                  30

Glu Val Lys Lys Pro Gly Ser Ser Val Lys Val Ser Cys Lys Ala Ser
        35                  40                  45

Gly Gly Pro Phe Arg Ser Tyr Ala Ile Ser Trp Val Arg Gln Ala Pro
50                  55                  60

Gly Gln Gly Pro Glu Trp Met Gly Gly Ile Ile Pro Ile Phe Gly Thr
65                  70                  75                  80

Thr Lys Tyr Ala Pro Lys Phe Gln Gly Arg Val Thr Ile Thr Ala Asp
                85                  90                  95

Asp Phe Ala Gly Thr Val Tyr Met Glu Leu Ser Ser Leu Arg Ser Glu
            100                 105                 110

Asp Thr Ala Met Tyr Tyr Cys Ala Lys His Met Gly Tyr Gln Val Arg
```

-continued

```
            115                 120                 125
Glu Thr Met Asp Val Trp Gly Lys Gly Thr Thr Val Thr Val Ser Ser
        130                 135                 140

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Ser Leu Gly Thr Gln Thr
    210                 215                 220

Tyr Ile Cys Asn Val Asn His Lys Pro Ser Asn Thr Lys Val Asp Lys
225                 230                 235                 240

Arg Val Glu Pro Lys Ser Cys Asp Lys
                245
```